US012760294B2

(12) United States Patent
Amiram et al.

(10) Patent No.: US 12,760,294 B2
(45) Date of Patent: Oct. 13, 2026

(54) MUTANT AMINOACYL-TRNA SYNTHETASES

(71) Applicant: B. G. NEGEV TECHNOLOGIES AND APPLICATIONS LTD., AT BEN-GURION UNIVERSITY, Beer Sheva (IL)

(72) Inventors: Miriam Amiram, Beer Sheva (IL); Sigal Gelkop, Yeruham (IL); Bar Israeli, Yanuv (IL); Daniela Strugach, Ashdod (IL)

(73) Assignee: B. G. NEGEV TECHNOLOGIES AND APPLICATIONS LTD., AT BEN-GURION UNIVERSITY, Beer Sheva (IL)

( * ) Notice: Subject to any disclaimer, the term of this patent is extended or adjusted under 35 U.S.C. 154(b) by 1029 days.

(21) Appl. No.: 17/892,163

(22) Filed: Aug. 22, 2022

(65) Prior Publication Data

US 2023/0313168 A1 Oct. 5, 2023

Related U.S. Application Data

(63) Continuation of application No. PCT/IL2021/050194, filed on Feb. 18, 2021.

(60) Provisional application No. 62/978,895, filed on Feb. 20, 2020.

(51) Int. Cl.
*C12N 9/00* (2006.01)

(52) U.S. Cl.
CPC .............. *C12N 9/93* (2013.01); *C12Y 601/01* (2013.01)

(58) Field of Classification Search
CPC ........................................................ C12N 9/93
See application file for complete search history.

(56) References Cited

U.S. PATENT DOCUMENTS

| | | | | |
|---|---|---|---|---|
| 2008/0241903 | A1* | 10/2008 | Schultz | C12N 15/67 435/325 |
| 2012/0058949 | A1 | 3/2012 | Kaufer | |
| 2013/0244245 | A1 | 9/2013 | Schultz | |
| 2016/0355552 | A1* | 12/2016 | Fasan | C40B 50/06 |
| 2018/0214462 | A1 | 8/2018 | Friedman | |

FOREIGN PATENT DOCUMENTS

| | | | |
|---|---|---|---|
| CN | 102888387 | A | 1/2013 |
| EP | 2128246 | B1 | 3/2014 |
| WO | 2015054587 | A1 | 4/2015 |
| WO | 2015120287 | A2 | 8/2015 |
| WO | 2018116293 | A1 | 6/2018 |

OTHER PUBLICATIONS

Bar-Klein G, Cacheaux LP, Kamintsky L, Prager O, Weissberg I, Schoknecht K, Cheng P, Kim SY, Wood L, Heinemann U, Kaufer D, Friedman A. Losartan prevents acquired epilepsy via TGF-ß signaling suppression. Ann Neurol. Jun. 2014;75(6):864-75. doi: 10.1002/ana.24147. Epub May 28, 2014. PMID: 24659129; PMCID: PMC4077937.

Klee R, Töllner K, Rankovic V, Römermann K, Schidlitzki A, Bankstahl M, Löscher W. Network pharmacology for antiepileptogenesis: Tolerability of multitargeted drug combinations in nonepileptic vs. post-status epilepticus mice. Epilepsy Res. Dec. 2015;118:34-48. doi: 10.1016/j.eplepsyres.2015.11.003. Epub Nov. 10, 2015. PMID: 26600369.

A. Lavin Communications & About American Associates, Ben-Gurion University of the Negev. (Jun. 1, 2019). BGU's Drug Combo Therapy Protects Blood-Brain Barrier [Press release]. https://americansforbgu.org/bgus-drug-combo-therapy-protects-blood-brain-barrier/.

Israel21c Staff. (May 19, 2019). Novel combination therapy treats neurological disorders. Israel21C. https://www.israel21c.org/novel-combination-therapy-treats-neurological-disorders/#:~:text=The%20therapy%20combines%20two%20FDA,system%20to%20enter%20the%20brain.

Van Vliet EA, Aronica E, Gorter JA. Role of blood-brain barrier in temporal lobe epilepsy and pharmacoresistance. Neuroscience. Sep. 26, 2014;277:455-73. doi: 10.1016/j.neuroscience.2014.07.030. Epub Jul. 28, 2014. PMID: 25080160.

Benicky, J., Sánchez-Lemus, E., Pavel, J. et al. Anti-Inflammatory Effects of Angiotensin Receptor Blockers in the Brain and the Periphery. Cell Mol Neurobiol 29, 781-792 (2009). https://doi.org/10.1007/s10571-009-9368-4.

Cacheaux, L., Ivens, S., David, Y., Lakhter, A., Bar-Klein, G., Shapira, M., . . . Kaufer, D. (2009). Transcriptome profiling reveals TGF-beta signaling involvement in epileptogenesis. The Journal of Neuroscience I: The Official Journal of the Society for Neuroscience, 29(28), 8927-8935. https://doi.org/10.1523/JNEUROSCI.0430-09.2009.

Chassidim, Y., Vazana, U., Prager, O., Veksler, R., Bar-Klein, G., Schoknecht, K., . . . Shelef, I. (2014). Analyzing the blood-brain barrier: The benefits of medical imaging in research and clinical practice. Seminars in Cell & Developmental Biology, 38, 43-52. https://doi.org/10.1016/j.semcdb.2014.11.007.

Chassidim, Y., Veksler, R., Lublinsky, S., Pell, G., Friedman, A., & Shelef, I. (2013). Quantitative imaging assessment of blood-brain barrier permeability in humans. Fluids and Barriers of the CNS, 10(1). https://doi.org/10.1186/2045-8118-10-9.

Schoknecht, K., Prager, O., Vazana, U., Kamintsky, L., Harhausen, D., Zille, M., . . . Friedman, A. (2014). Monitoring stroke progression: in vivo imaging of cortical perfusion, blood-brain barrier permeability and cellular damage in the rat photothrombosis model. Journal of Cerebral Blood Flow and Metabolism I: Official Journal of the International Society of Cerebral Blood Flow and Metabolism, 34(201024), 1791-1801. https://doi.org/10.1038/jcbfm.2014.147.

(Continued)

*Primary Examiner* — Suzanne M Noakes
(74) *Attorney, Agent, or Firm* — The Roy Gross Law Firm, LLC; Roy Gross

(57) ABSTRACT

Mutant aminoacyl-tRNA synthetase (aaRS) proteins are provided. Nucleic acid molecules encoding the mutant aaRSs, orthogonal translation systems comprising the mutant aaRSs or nucleic acid molecules, cells comprising the orthogonal translation systems, as well as methods of using same are also provided.

18 Claims, 66 Drawing Sheets
(45 of 66 Drawing Sheet(s) Filed in Color)

Specification includes a Sequence Listing.

(56) References Cited

OTHER PUBLICATIONS

Vazana, U., Veksler, R., Pell, G. S., Prager, O., Fassler, M., Chassidim, Y., . . . Friedman, A. (2016). Glutamate-Mediated Blood-Brain Barrier Opening: Implications for Neuroprotection and Drug Delivery. The Journal of Neuroscience, 36(29), 7727-7739. https://doi.org/10.1523/JNEUROSCI.0587-16.2016.
Walther, T., Olah, L., Harms, C., Maul, B., Bader, M., Hortnagl, H., . . . Mies, G. (2002). Ischemic injury in experimental stroke depends on angiotensin II. The FASEB Journal, 16(2), 169-176. https://doi.org/10.1096/fj.01-0601com.
Weissberg I, Wood L, Kamintsky L, Vazquez O, Milikovsky DZ, Alexander A, Oppenheim H, Ardizzone C, Becker A, Frigerio F, Vezzani A, Buckwalter MS, Huguenard JR, Friedman A, Kaufer D. Albumin induces excitatory synaptogenesis through astrocytic TGF-β/ALK5 signaling in a model of acquired epilepsy following blood-brain barrier dysfunction. Neurobiol Dis. Jun. 2015;78:115-25. doi: 10.1016/j.nbd.2015.02.029. Epub Mar. 30, 2015. PMID: 25836421; PMCID: PMC4426044.
Prager O, Kamintsky L, Hasam-Henderson LA, Schoknecht K, Wuntke V, Papageorgiou I, Swolinsky J, Muoio V, Bar-Klein G, Vazana U, Heinemann U, Friedman A, Kovács R. Seizure-induced microvascular injury is associated with impaired neurovascular coupling and blood-brain barrier dysfunction. Epilepsia. Feb. 2019;60(2):322-336. doi: 10.1111/epi.14631. Epub Jan. 4, 2019. PMID: 30609012.
Buttler L, Jordão MT, Fragas MG, Ruggeri A, Ceroni A, Michelini LC. Maintenance of Blood-Brain Barrier Integrity in Hypertension: A Novel Benefit of Exercise Training for Autonomic Control. Front Physiol. Dec. 12, 2017;8:1048. doi: 10.3389/fphys.2017.01048. PMID: 29311978; PMCID: PMC5733101.
Amiram M, Haimovich AD, Fan C, Wang YS, Aerni HR, Ntai I, Moonan DW, Ma NJ, Rovner AJ, Hong SH, Kelleher NL, Goodman AL, Jewett MC, Söll D, Rinehart J, Isaacs FJ. Evolution of translation machinery in recoded bacteria enables multi-site incorporation of nonstandard amino acids. Nat Biotechnol. Dec. 2015;33(12):1272-1279. doi: 10.1038/nbt.3372. Epub Nov. 16, 2015. PMID: 26571098; PMCID: PMC4784704.
L. A. Strzegowski, M. B. Martinez, D. C. Gowda, D. W. Urry, and D. A. Tirrell. Photomodulation of the inverse temperature transition of a modified elastin poly(pentapeptide). Journal of the American Chemical Society 1994 116 (2), 813-814 DOI: 10.1021/ja00081a070.
Alonso, M., Reboto, V., Guiscardo, L., San Martín, A., & Rodríguez-Cabello, J. C. (2000). Spiropyran Derivative of an Elastin-like Bioelastic Polymer: Photoresponsive Molecular Machine to Convert Sunlight into Mechanical Work. Macromolecules, 33(26), 9480-9482. doi:10.1021/ma001348h.
Knie C, Utecht M, Zhao F, Kulla H, Kovalenko S, Brouwer AM, Saalfrank P, Hecht S, Bléger D. ortho-Fluoroazobenzenes: visible light switches with very long-Lived Z isomers. Chemistry. Dec. 8, 2014;20(50):16492-501. doi: 10.1002/chem.201404649. Epub Oct. 28, 2014. PMID: 25352421.
Bose M, Groff D, Xie J, Brustad E, Schultz PG. The incorporation of a photoisomerizable amino acid into proteins in *E. coli*. J Am Chem Soc. Jan. 18, 2006;128(2):388-9. doi: 10.1021/ja055467u. PMID: 16402807.
Arranz-Gibert P, Vanderschuren K, Isaacs FJ. Next-generation genetic code expansion. Curr Opin Chem Biol. Oct. 2018;46:203-211. doi: 10.1016/j.cbpa.2018.07.020. Epub Jul. 30, 2018. PMID: 30072242; PMCID: PMC6748649.
Kuru E, Määttälä RM, Noguera K, Stork DA, Narasimhan K, Rittichier J, Wiegand D, Church GM. Release Factor Inhibiting Antimicrobial Peptides Improve Nonstandard Amino Acid Incorporation in Wild-type Bacterial Cells. ACS Chem Biol. Jul. 17, 2020;15(7):1852-1861. doi: 10.1021/acschembio.0c00055. Epub Jun. 30, 2020. PMID: 32603088.
Johnson JA, Lu YY, Van Deventer JA, Tirrell DA. Residue-specific incorporation of non-canonical amino acids into proteins: recent developments and applications. Curr Opin Chem Biol. Dec. 2010;14(6):774-80. doi: 10.1016/j.cbpa.2010.09.013. Epub Nov. 9, 2010. PMID: 21071259; PMCID: PMC3008400.
Foley TL, Burkart MD. Site-specific protein modification: advances and applications. Curr Opin Chem Biol. Feb. 2007;11(1):12-9. doi: 10.1016/j.cbpa.2006.11.036. Epub Dec. 26, 2006. PMID: 17189712.
Deiters A, Schultz PG. In vivo incorporation of an alkyne into proteins in *Escherichia coli*. Bioorg Med Chem Lett. Mar. 1, 2005;15(5):1521-4. doi: 10.1016/j.bmcl.2004.12.065. PMID: 15713420.
Milles S, Tyagi S, Banterle N, Koehler C, VanDelinder V, Plass T, Neal AP, Lemke EA. Click strategies for single-molecule protein fluorescence. J Am Chem Soc. Mar. 21, 2012;134(11):5187-95. doi: 10.1021/ja210587q. Epub Mar. 5, 2012. PMID: 22356317.
Jao CY, Salic A. Exploring RNA transcription and turnover in vivo by using click chemistry. Proc Natl Acad Sci U S A. Oct. 14, 2008;105(41): 15779-84. doi: 10.1073/pnas.0808480105. Epub Oct. 7, 2008. PMID: 18840688; PMCID: PMC2572917.
Hassouneh W, Christensen T, Chilkoti A. Elastin-like polypeptides as a purification tag for recombinant proteins. Curr Protoc Protein Sci. Aug. 2010;Chapter 6:6.11.1-6.11.16. doi: 10.1002/0471140864.ps0611s61. PMID: 20814933; PMCID: PMC3076942.
Despanie J, Dhandhukia JP, Hamm-Alvarez SF, Mackay JA. Elastin-like polypeptides: Therapeutic applications for an emerging class of nanomedicines. J Control Release. Oct. 28, 2016;240:93-108. doi: 10.1016/j.jconrel.2015.11.010. Epub Nov. 11, 2015. PMID: 26578439; PMCID: PMC5767577.
Israeli, B., Vaserman, L., & Amiram, M. (2019). Multi-Site Incorporation of Nonstandard Amino Acids into Protein-Based Biomaterials. Israel Journal of Chemistry. doi:10.1002/ijch.201900043.
Search Report for PCT/IL2021/050194 Mailed May 27, 2021; Competed May 30, 2021 6 pages.
Written Opinion for PCT/IL2021/050194 Mailed May 27, 2021; Competed May 30, 2021 7 pages.

* cited by examiner

| position | 32 | 65 | 107 | 108 | 109 | 158 | 159 | 162 | 167 |
|---|---|---|---|---|---|---|---|---|---|
| Annotation | | | | | | | | | |
| **WT-MjTyrRS** | **Y** | **L** | **E** | **F** | **Q** | **D** | **I** | **L** | **A** |
| Mut1-RS | L | L | E | F | Q | S | M | K | H |
| Mut2-RS | L | V | E | F | Q | G | A | E | H |
| Mut3-RS | T | V | A | Y | M | G | C | R | D |
| Mut4-RS | L | V | E | F | Q | G | M | S | H |
| Mut5-RS | L | V | E | F | Q | G | Y | C | Y |

Figure 1A

| position | | Mutation sites: | | | | | | | | |
|---|---|---|---|---|---|---|---|---|---|---|
| | | 32 | 65 | 107 | 108 | 109 | 158 | 159 | 162 | 167 |
| | WT MjTYRRS | Y | L | E | F | Q | D | I | L | A |
| AzoRS variants | Mut 1 | L | V | E | F | Q | G | Y | S | F |
| | Mut 2 | G | V | E | F | Q | G | Y | S | F |
| | Mut 3 | L | V | S | V | S | G | Y | S | F |
| | Mut 4 | L | V | N | V | L | G | Y | S | F |
| | Mut 5 | L | V | D | F | Q | G | Y | S | F |
| | Mut 6 | L | V | S | V | C | G | Y | S | F |
| | Mut 7 | G | V | E | F | Q | G | Y | R | A |
| | Mut 8 | L | G | D | R | M | G | Y | S | F |

Figure 1B

| | 1 | 2 | 3 |
|---|---|---|---|
| PSS composition (trans->cis, cis->trans) | (78%, 76%) | (62%, 61%) | (91%, 84%) |
| λtrans->cis, λcis->trans (used in this study) | (365, 405) | (530, 405) | (530, 405) |

Figure 23

| *MW* | Expression strain | ELP(10Tyrosine)-GFP | ELP(10pPR)-GFP |
|---|---|---|---|
| *Expected* | - | 39769.61 | 40151.61 |
| *Found* | BL21 | 39803.11 | 40153.79 |
| | C321. ΔRF1 | 39850.45 | 40217.83 |

Figure 24A

| Sequence (SEQ ID NO:) | Instances of peptide sequenced | % of peptides | MH+ [Da] | ΔM [ppm] | XCorr |
|---|---|---|---|---|---|
| VPGAGVPGpPRGVPGVGK (53) | 148 | 87 | 1448.788 | -1.05 | 4.21 |
| VPGAGVPGYGVPGVGK (54) | 6 | 4 | 1410.771 | -2.14 | 3.69 |
| VPGAGVPGQGVPGVGK (55) | 6 | 4 | 1375.769 | -0.17 | 3.84 |
| VPGAGVPGWGVPGVGK (56) | 3 | 2 | 1433.774 | -10.79 | 3.58 |
| VPGAGVPGFGVPGVGK (57) | 3 | 2 | 1394.790 | 8.1 | 4.24 |
| VPGAGVPGPGVPGVGK (58) | 2 | 1 | 1344.763 | -0.39 | 3.78 |
| VPGAGVPGIGVPGVGK (59) | 2 | 1 | 1360.793 | -1.23 | 2.43 |

Figure 24B

| Sequence (SEQ ID NO:) | Instances of peptide sequenced | % of peptides | MH+ [Da] | ΔM [ppm] | XCorr |
|---|---|---|---|---|---|
| VPGAGVPGpPRGVPGVGK (53) | 151 | 88 | 1448.789 | 0.13 | 4 |
| VPGAGVPGYGVPGVGK (54) | 8 | 5 | 1410.773 | -0.49 | 3.92 |
| VPGAGVPGQGVPGVGK (55) | 4 | 2 | 1375.772 | 1.7 | 3.66 |
| VPGAGVPGPGVPGVGK (58) | 3 | 2 | 1344.764 | 0.43 | 3.32 |
| VPGAGVPGIGVPGVGK (59) | 2 | 1 | 1360.793 | -1.14 | 3.76 |
| VPGAGVPGFGVPGVGK (57) | 2 | 1 | 1394.778 | -0.92 | 3.97 |
| VPGAGVPGWGVPGVGK (56) | 1 | 1 | 1433.777 | -8.84 | 2.48 |

Figure 24C

| Sequence (SEQ ID NO:) | Instances of peptide sequenced | % of peptides | MH+ [Da] | ΔM [ppm] | XCorr |
|---|---|---|---|---|---|
| VPGAGVPGpPRGVPGVGK (53) | 158 | 93 | 1448.793 | 2.41 | 3.68 |
| VPGAGVPGYGVPGVGK (54) | 10 | 6 | 1410.774 | -0.41 | 3.73 |
| VPGAGVPGFGVPGVGK (57) | 2 | 1 | 1394.783 | 2.67 | 3.48 |

Figure 24D

| Sequence (SEQ ID NO:) | Instances of peptide sequenced | % of peptides | MH+ [Da] | ΔM [ppm] | XCorr |
|---|---|---|---|---|---|
| VPGAGVPGpPRGVPGVGK (53) | 133 | 85 | 1448.789 | -0.04 | 4.14 |
| VPGAGVPGYGVPGVGK (54) | 15 | 10 | 1410.774 | 0.11 | 3.69 |
| VPGAGVPGQGVPGVGK (55) | 4 | 3 | 1375.769 | 0.01 | 3.49 |
| VPGAGVPGPGVPGVGK (58) | 2 | 1 | 1344.763 | -0.48 | 2.44 |
| VPGAGVPGFGVPGVGK (57) | 2 | 1 | 1394.780 | 0.57 | 3.36 |
| VPGAGVPGWGVPGVGK (56) | 1 | 1 | 1433.786 | -2.62 | 3.24 |

Figure 24E

| Sequence (SEQ ID NO:) | Instances of peptide sequenced | % of peptides | MH+ [Da] | ΔM [ppm] | XCorr |
|---|---|---|---|---|---|
| VPGAGVPGpPRGVPGVGK (53) | 150 | 88 | 1448.789 | -0.29 | 4.09 |
| VPGAGVPGYGVPGVGK (54) | 17 | 10 | 1410.770 | -2.83 | 3.61 |
| VPGAGVPGQGVPGVGK (55) | 2 | 1 | 1375.770 | 0.72 | 3.16 |
| VPGAGVPGFGVPGVGK (57) | 1 | 1 | 1394.784 | 3.54 | 3.76 |
| VPGAGVPGPGVPGVGK (58) | 1 | 1 | 1344.763 | -0.39 | 3.48 |

Figure 24F

| Sequence (SEQ ID NO:) | Instances of peptide sequenced | % of peptides | MH+ [Da] | ΔM [ppm] | XCorr |
|---|---|---|---|---|---|
| VPGAGVPGpPRGVPGVGK (53) | 129 | 72 | 1448.791 | 1.23 | 4.04 |
| VPGAGVPGYGVPGVGK (54) | 40 | 22 | 1410.773 | -0.67 | 3.8 |
| VPGAGVPGQGVPGVGK (55) | 4 | 2 | 1375.769 | -0.43 | 3.31 |
| VPGAGVPGPGVPGVGK (58) | 2 | 1 | 1344.763 | -0.57 | 3.48 |
| VPGAGVPGIGVPGVGK (59) | 2 | 1 | 1360.793 | -1.5 | 2.24 |
| VPGAGVPGFGVPGVGK (57) | 2 | 1 | 1394.777 | -1.71 | 4.12 |
| VPGAGVPGWGVPGVGK (56) | 1 | 1 | 1433.787 | -2.28 | 2.79 |

Figure 24G

| Sequence | Instances of peptide sequenced | % of peptides | MH+ [Da] | ΔM [ppm] | XCorr |
|---|---|---|---|---|---|
| VPGAGVPGpPRGVPGVGK (53) | 139 | 94 | 1448.786 | -2.56 | 4.39 |
| VPGAGVPGYGVPGVGK (54) | 6 | 4 | 1410.772 | -1.19 | 4.18 |
| VPGAGVPGQGVPGVGK (55) | 2 | 1 | 1375.769 | -0.61 | 3.51 |
| VPGAGVPGFGVPGVGK (57) | 1 | 1 | 1394.777 | -1.44 | 3.88 |

Figure 24H

1. Expression of ELP(30TAG)$_{MS}$ using 5 mM pPR.

| Sequence (SEQ ID NO:) | Instances of peptide sequenced | % of peptides | MH+ [Da] | ΔM [ppm] | XCorr |
|---|---|---|---|---|---|
| VPGAGVPGpPRGVPGVGK (53) | 123 | 92 | 1448.79 | 0.81 | 3.95 |
| VPGAGVPGYGVPGVGK (54) | 9 | 7 | 1410.774 | 0.11 | 4.16 |
| VPGAGVPGFGVPGVGK (57) | 1 | 1 | 1394.78 | 0.57 | 3.97 |

2. Expression of ELP(30TAG)$_{MS}$ using 2 mM pPR.

| Sequence (SEQ ID NO:) | Instances of peptide sequenced | % of peptides | MH+ [Da] | ΔM [ppm] | XCorr |
|---|---|---|---|---|---|
| VPGAGVPGpPRGVPGVGK (53) | 152 | 82 | 1448.790 | 0.64 | 4.08 |
| VPGAGVPGYGVPGVGK (54) | 27 | 15 | 1410.774 | 0.28 | 3.88 |
| VPGAGVPGQGVPGVGK (55) | 3 | 2 | 1375.770 | 0.28 | 4.22 |
| VPGAGVPGDGVPGVGK (60) | 2 | 1 | 1362.738 | 0.47 | 3.61 |
| VPGAGVPGFGVPGVGK (57) | 1 | 1 | 1394.779 | -0.22 | 3.31 |
| VPGAGVPGPGVPGVGK (58) | 1 | 1 | 1344.765 | 1.24 | 3.15 |

3. Expression of ELP(30TAG)$_{MS}$ using 1mM pPR.

| Sequence (SEQ ID NO:) | Instances of peptide sequenced | % of peptides | MH+ [Da] | ΔM [ppm] | XCorr |
|---|---|---|---|---|---|
| VPGAGVPGpPRGVPGVGK (53) | 310 | 64 | 1448.799 | 6.71 | 4.26 |
| VPGAGVPGYGVPGVGK (54) | 153 | 32 | 1410.784 | 6.86 | 4.48 |
| VPGAGVPGQGVPGVGK (55) | 10 | 2 | 1375.781 | 8.88 | 4.2 |
| VPGAGVPGPGVPGVGK (58) | 4 | 1 | 1344.765 | 0.88 | 3.42 |
| VPGAGVPGWGVPGVGK (56) | 4 | 1 | 1433.777 | -9.35 | 3.86 |
| VPGAGVPGFGVPGVGK (57) | 2 | ~0 | 1394.785 | 4.24 | 4.13 |
| VPGAGVPGCGVPGVGK (61) | 1 | ~0 | 1350.733 | 9.55 | 2.29 |

Figure 24I

| Sequence (SEQ ID NO:) | Instances of peptide sequenced | % of peptides | MH+ [Da] | ΔM [ppm] | XCorr |
|---|---|---|---|---|---|
| VPGAGVPGpFRGVPGVGK (53) | 244 | 36 | 1448.790 | 0.72 | 4.36 |
| VPGAGVPGYGVPGVGK (54) | 210 | 31 | 1410.776 | 1.32 | 4.41 |
| VPGAGVPGFGVPGVGK (57) | 200 | 29 | 1394.782 | 1.79 | 4.31 |
| VPGAGVPGQGVPGVGK (55) | 18 | 3 | 1375.768 | -0.88 | 4.29 |
| VPGAGVPGWGVPGVGK (56) | 6 | 1 | 1433.774 | -11.05 | 3.79 |
| VPGAGVPGPGVPGVGK (58) | 3 | ~0 | 1344.764 | 0.52 | 3.51 |
| VPGAGVPGIGVPGVGK (59) | 2 | ~0 | 1360.795 | 0.3 | 3.87 |
| VPGAGVPGSGVPGVGK (62) | 1 | ~0 | 1334.740 | -2.14 | 3.7 |

Figure 24J

1. Sequence and signal intensities of identified high-scored peptides.

| Sequence (SEQ ID NO:) | Instances of peptide sequenced | MH+ [Da] | ΔM [ppm] | XCorr | # missed cleavages |
|---|---|---|---|---|---|
| YVYGSEFQLDKDYTLNVYR (63) | 2 | 2373.143 | 1.19 | 5.35 | 1 |
| FGGDLTVNSYEELESLFK (64) | 6 | 2047.987 | 0.68 | 4.84 | 0 |
| NTSEHSEEELR (65) | 2 | 1419.696 | -0.36 | 4.42 | 0 |
| LKNAVAEELIK (66) | 3 | 1227.731 | 0.08 | 3.65 | 1 |
| GNFIAVDDSPEEIR (67) | 3 | 1561.75 | 0.44 | 3.53 | 0 |
| SALIGFEPSGK (68) | 2 | 1105.588 | -0.83 | 3.2 | 0 |
| mIDLQNAGFDHILLADLHAYLNQK (69) | 1 | 2858.514 | 0.5 | 3.13 | 0 |
| MIDLQNAGFDHILLADLHAYLNQK (70) | 1 | 2842.524 | 2.22 | 3 | 0 |
| YFLEYPLTIK (71) | 3 | 1286.703 | -0.06 | 2.63 | 0 |
| YVYGSEFQLDK (72) | 2 | 1348.642 | -0.34 | 2.41 | 0 |
| GELDEIRK (73) | 3 | 959.5151 | -0.66 | 2.23 | 1 |
| GVDVHVGGMEQR (74) | 3 | 1283.616 | -0.03 | 2.12 | 0 |

m = indicates oxidation of methionine.

2. Sequence coverage map of Mut1-RS, including only high-scored peptides (highlighted green). Sequence coverage was determined to be ~45.7%. Sequence coverage of Mut1-RS including medium- and low-scoring peptides was determined to be 69.93%.

MDEFEMIKRNTSEHSEEELREVLKKDEKSALIGFEPSGKIHLGHYLQIKKMIDLQNAGFDHILL
ADLHAYLNQKGELDEIRKGDYNKKVFEAMGLKAKYVYGSEFQLDKDYTLNVYRLALKTTL
KRARRSMELIAREDENPKVAEVIYPIMQVNSMHYKGVDVHVGGMEQRKIHMLARELLPKKV
VCIHNPVLTGLDGEGKMSSSKGNFIAVDDSPEEIRAKIKKAYCPAGVVEGNPIMEIAKYFLEYPL
TIKGPEKFGGDLTVNSYEELESLFKNKELHPMRLKNAVAEELIKILEPIRKRL (SEQ ID NO: 2)

Figure 25

| *aaRS* | Protein construct | % labeled cells | Average fluorescence/cell |
|---|---|---|---|
| *Parent-pPR-RS* | ELP(1TAG) | 25.28 | 0.37 ± 0.14 |
| | ELP(10TAG) | 26.65 | 0.56 ± 0.28 |
| *Mut1-RS* | ELP(1TAG) | 46.72 | 1.13 ± 0.15 |
| | ELP(10TAG) | 90.44 | 2.64 ± 0.34 |

SEQUENCE LISTING

```
Sequence total quantity: 74
SEQ ID NO: 1            moltype = AA  length = 306
FEATURE                 Location/Qualifiers
source                  1..306
                        mol_type = protein
                        organism = Methanocaldococcus jannaschii
SEQUENCE: 1
MDEFEMIKRN TSEIISEEEL REVLKKDEKS AYIGFEPSGK IHLGHYLQIK KMIDLQNAGF  60
DIIILLADLH AYLNQKGELD EIRKIGDYNK KVFEAMGLKA KYVYGSEFQL DKDYTLNVYR  120
LALKTTLKRA RRSMELIARE DENPKVAEVI YPIMQVNDIH YLGVDVAVGG MEQRKIHMLA  180
RELLPKKVVC IHNPVLTGLD GEGKMSSSKG NFIAVDDSPE EIRAKIKKAY CPAGVVEGNP  240
IMEIAKYFLE YPLTIKRPEK FGGDLTVNSY EELESLFKNK ELHPMDLKNA VAEELIKILE  300
PIRKRL                                                             306

SEQ ID NO: 2            moltype = AA  length = 306
FEATURE                 Location/Qualifiers
REGION                  1..306
                        note = Synthetic
source                  1..306
                        mol_type = protein
                        organism = synthetic construct
SEQUENCE: 2
MDEFEMIKRN TSEIISEEEL REVLKKDEKS ALIGFEPSGK IHLGHYLQIK KMIDLQNAGF  60
DIIILLADLH AYLNQKGELD EIRKIGDYNK KVFEAMGLKA KYVYGSEFQL DKDYTLNVYR  120
LALKTTLKRA RRSMELIARE DENPKVAEVI YPIMQVNSMH YKGVDVHVGG MEQRKIHMLA  180
RELLPKKVVC IHNPVLTGLD GEGKMSSSKG NFIAVDDSPE EIRAKIKKAY CPAGVVEGNP  240
IMEIAKYFLE YPLTIKGPEK FGGDLTVNSY EELESLFKNK ELHPMRLKNA VAEELIKILE  300
PIRKRL                                                             306

SEQ ID NO: 3            moltype = AA  length = 306
FEATURE                 Location/Qualifiers
REGION                  1..306
                        note = Synthetic
source                  1..306
                        mol_type = protein
                        organism = synthetic construct
SEQUENCE: 3
MDEFEMIKRN TSEIISEEEL REVLKKDEKS ALIGFEPSGK IHLGHYLQIK KMIDLQNAGF  60
DIIIVLADLH AYLNQKGELD EIRKIGDYNK KVFEAMGLKA KYVYGSEFQL DKDYTLNVYR  120
LALKTTLKRA RRSMELIARE DENPKVAEVI YPIMQVNGAH YEGVDVHVGG MEQRKIHMLA  180
RELLPKKVVC IHNPVLTGLD GEGKMSSSKG NFIAVDDSPE EIRAKIKKAY CPAGVVEGNP  240
IMEIAKYFLE YPLTIKGPEK FGGDLTVNSY EELESLFKNK ELHPMRLKNA VAEELIKILE  300
PIRKRL                                                             306

SEQ ID NO: 4            moltype = AA  length = 306
FEATURE                 Location/Qualifiers
REGION                  1..306
                        note = Synthetic
source                  1..306
                        mol_type = protein
                        organism = synthetic construct
SEQUENCE: 4
MDEFEMIKRN TSEIISEEEL REVLKKDEKS ATIGFEPSGK IHLGHYLQIK KMIDLQNAGF  60
DIIIVLADLH AYLNQKGELD EIRKIGDYNK KVFEAMGLKA KYVYGSAYML DKDYTLNVYR  120
LALKTTLKRA RRSMELIARE DENPKVAEVI YPIMQVNGCH YRGVDVDVGG MEQRKIHMLA  180
RELLPKKVVC IHNPVLTGLD GEGKMSSSKG NFIAVDDSPE EIRAKIKKAY CPAGVVEGNP  240
IMEIAKYFLE YPLTIKGPEK FGGDLTVNSY EELESLFKNK ELHPMRLKNA VAEELIKILE  300
PIRKRL                                                             306

SEQ ID NO: 5            moltype = AA  length = 306
FEATURE                 Location/Qualifiers
REGION                  1..306
                        note = Synthetic
source                  1..306
                        mol_type = protein
                        organism = synthetic construct
SEQUENCE: 5
MDEFEMIKRN TSEIISEEEL REVLKKDEKS ALIGFEPSGK IHLGHYLQIK KMIDLQNAGF  60
DIIIVLADLH AYLNQKGELD EIRKIGDYNK KVFEAMGLKA KYVYGSEFQL DKDYTLNVYR  120
LALKTTLKRA RRSMELIARE DENPKVAEVI YPIMQVNGMH YSGVDVHVGG MEQRKIHMLA  180
RELLPKKVVC IHNPVLTGLD GEGKMSSSKG NFIAVDDSPE EIRAKIKKAY CPAGVVEGNP  240
```

```
IMEIAKYFLE YPLTIKGPEK FGGDLTVNSY EELESLFKNK ELHPMRLKNA VAEELIKILE  300
PIRKRL                                                             306

SEQ ID NO: 6           moltype = AA  length = 306
FEATURE                Location/Qualifiers
REGION                 1..306
                       note = Synthetic
source                 1..306
                       mol_type = protein
                       organism = synthetic construct
SEQUENCE: 6
MDEFEMIKRN TSEIISEEEL REVLKKDEKS ALIGFEPSGK IHLGHYLQIK KMIDLQNAGF  60
DIIIVLADLH AYLNQKGELD EIRKIGDYNK KVFEAMGLKA KYVYGSEFQL DKDYTLNVYR  120
LALKTTLKRA RRSMELIARE DENPKVAEVI YPIMQVNGYH YCGVDVYVGG MEQRKIHMLA  180
RELLPKKVVC IHNPVLTGLD GEGKMSSSKG NFIAVDDSPE EIRAKIKKAY CPAGVVEGNP  240
IMEIAKYFLE YPLTIKGPEK FGGDLTVNSY EELESLFKNK ELHPMRLKNA VAEELIKILE  300
PIRKRL                                                             306

SEQ ID NO: 7           moltype = DNA  length = 920
FEATURE                Location/Qualifiers
misc_feature           1..920
                       note = Synthetic
source                 1..920
                       mol_type = other DNA
                       organism = synthetic construct
SEQUENCE: 7
atggacgaat ttgaaatgat aaagagaaac acatctgaaa ttatcagcga ggaagagtta  60
agagaggttt taaaaaaaga tgaaaaatct gctctgatag gttttgaacc aagtggtaaa  120
atacatttag ggcattatct ccaaataaaa aagatgattg atttacaaaa tgctggattt  180
gatataatta tattgttggc tgatttacac gcctatttaa accagaaagg agagttggat  240
gagattagaa aaataggaga ttataacaaa aaagtttttg aagcaatggg gttaaaggca  300
aaatatgttt atggaagtga attccagctt gataaggatt atacactgaa tgtctataga  360
ttggctttaa aaactacctt aaaaagagca agaaggagta tggaacttat agcaagagag  420
gatgaaaatc caaaggttgc tgaagttatc tatccaataa tgcaggttaa ttctatgcat  480
tataagggcg ttgatgttca tgttggaggg atggagcaga gaaaaataca catgttagca  540
agggagcttt taccaaaaaa ggttgtttgt attcacaacc ctgtcttaac gggtttggat  600
ggagaaggaa agatgagttc ttcaaaaggg aattttatag ctgttgatga ctctccagaa  660
gagattaggg ctaagataaa gaaagcatac tgcccagctg gagttgttga aggaaatcca  720
ataatggaga tagctaaata cttccttgaa tatcctttaa ccataaaagg gccagaaaaa  780
tttggtggag atttgacagt taatagctat gaggagttag agagtttatt taaaaataag  840
gaattgcatc caatgcgctt aaaaaatgct gtagctgaag aacttataaa gattttagag  900
ccaattagaa agagattata                                              920

SEQ ID NO: 8           moltype = DNA  length = 920
FEATURE                Location/Qualifiers
misc_feature           1..920
                       note = Synthetic
source                 1..920
                       mol_type = other DNA
                       organism = synthetic construct
SEQUENCE: 8
atggacgaat ttgaaatgat aaagagaaac acatctgaaa ttatcagcga ggaagagtta  60
agagaggttt taaaaaaaga tgaaaaatct gctctgatag gttttgaacc aagtggtaaa  120
atacatttag ggcattatct ccaaataaaa aagatgattg atttacaaaa tgctggattt  180
gatataatta tagttttggc tgatttacac gcctatttaa accagaaagg agagttggat  240
gagattagaa aaataggaga ttataacaaa aaagtttttg aagcaatggg gttaaaggca  300
aaatatgttt atggaagtga attccagctt gataaggatt atacactgaa tgtctataga  360
ttggctttaa aaactacctt aaaaagagca agaaggagta tggaacttat agcaagagag  420
gatgaaaatc caaaggttgc tgaagttatc tatccaataa tgcaggttaa tggggctcat  480
tatgagggcg ttgatgttca tgttggaggg atggagcaga gaaaaataca catgttagca  540
agggagcttt taccaaaaaa ggttgtttgt attcacaacc ctgtcttaac gggtttggat  600
ggagaaggaa agatgagttc ttcaaaaggg aattttatag ctgttgatga ctctccagaa  660
gagattaggg ctaagataaa gaaagcatac tgcccagctg gagttgttga aggaaatcca  720
ataatggaga tagctaaata cttccttgaa tatcctttaa ccataaaagg gccagaaaaa  780
tttggtggag atttgacagt taatagctat gaggagttag agagtttatt taaaaataag  840
gaattgcatc caatgcgctt aaaaaatgct gtagctgaag aacttataaa gattttagag  900
ccaattagaa agagattata                                              920

SEQ ID NO: 9           moltype = DNA  length = 920
FEATURE                Location/Qualifiers
misc_feature           1..920
                       note = Synthetic
source                 1..920
                       mol_type = other DNA
                       organism = synthetic construct
SEQUENCE: 9
atggacgaat ttgaaatgat aaagagaaac acatctgaaa ttatcagcga ggaagagtta  60
agagaggttt taaaaaaaga tgaaaaatct gctactatag ggtttgaacc aagtggtaaa  120
atacatttag ggcattatct ccaaataaaa aagatgattg atttacaaaa tgctggattt  180
```

```
gatataatta tagttttggc tgatttacac gcctatttaa accagaaagg agagttggat  240
gagattagaa aaataggaga ttataacaaa aaagtttttg aagcaatggg gttaaaggca  300
aaatatgttt atggaagtgc gtatatgctt gataaggatt atacactgaa tgtctataga  360
ttggctttaa aaactacctt aaaaagagca agaaggagta tggaacttat agcaagagag  420
gatgaaaatc caaaggttgc tgaagttatc tatcccataa tgcaggttaa tggttgtcat  480
tataggggcg ttgatgttga tgttggaggg atggagcaga gaaaaataca catgttagca  540
agggagcttt taccaaaaaa ggttgtttgt attcacaacc ctgtcttaac gggtttggat  600
ggagaaggaa agatgagttc ttcaaaaggg aattttatag ctgttgatga ctctccagaa  660
gagattaggg ctaagataaa gaaagcatac tgcccagctg gagttgttga aggaaatcca  720
ataatggaga tagctaaata cttccttgaa tatcctttaa ccataaaagg gccagaaaaa  780
tttggtggag atttgacagt taatagctat gaggagttag agagtttatt taaaaataag  840
gaattgcatc caatgcgctt aaaaaatgct gtagctgaag aacttataaa gattttagag  900
ccaattagaa agagattata                                               920

SEQ ID NO: 10          moltype = DNA  length = 920
FEATURE                Location/Qualifiers
misc_feature           1..920
                       note = Synthetic
source                 1..920
                       mol_type = other DNA
                       organism = synthetic construct
SEQUENCE: 10
atggacgaat ttgaaatgat aaagagaaac acatctgaaa ttatcagcga ggaagagtta  60
agagaggttt taaaaaaaga tgaaaaatct gctctgatag gttttgaacc aagtggtaaa  120
atacatttag ggcattatct ccaaataaaa aagatgattg atttacaaaa tgctggattt  180
gatataatta tagttttggc tgatttacac gcctatttaa accagaaagg agagttggat  240
gagattagaa aaataggaga ttataacaaa aaagtttttg aagcaatggg gttaaaggca  300
aaatatgttt atggaagtga attccagctt gataaggatt atacactgaa tgtctataga  360
ttggctttaa aaactacctt aaaaagagca agaaggagta tggaacttat agcaagagag  420
gatgaaaatc caaaggttgc tgaagttatc tatccaataa tgcaggttaa tggtatgcat  480
tattcgggcg ttgatgttca tgttggaggg atggagcaga gaaaaataca catgttagca  540
agggagcttt taccaaaaaa ggttgtttgt attcacaacc ctgtcttaac gggtttggat  600
ggagaaggaa agatgagttc ttcaaaaggg aattttatag ctgttgatga ctctccagaa  660
gagattaggg ctaagataaa gaaagcatac tgcccagctg gagttgttga aggaaatcca  720
ataatggaga tagctaaata cttccttgaa tatcctttaa ccataaaagg gccagaaaaa  780
tttggtggag atttgacagt taatagctat gaggagttag agagtttatt taaaaataag  840
gaattgcatc caatgcgctt aaaaaatgct gtagctgaag aacttataaa gattttagag  900
ccaattagaa agagattata                                               920

SEQ ID NO: 11          moltype = DNA  length = 920
FEATURE                Location/Qualifiers
misc_feature           1..920
                       note = Synthetic
source                 1..920
                       mol_type = other DNA
                       organism = synthetic construct
SEQUENCE: 11
atggacgaat ttgaaatgat aaagagaaac acatctgaaa ttatcagcga ggaagagtta  60
agagaggttt taaaaaaaga tgaaaaatct gctctgatag gttttgaacc aagtggtaaa  120
atacatttag ggcattatct ccaaataaaa aagatgattg atttacaaaa tgctggattt  180
gatataatta tagttttggc tgatttacac gcctatttaa accagaaagg agagttggat  240
gagattagaa aaataggaga ttataacaaa aaagtttttg aagcaatggg gttaaaggca  300
aaatatgttt atggaagtga attccagctt gataaggatt atacactgaa tgtctataga  360
ttggctttaa aaactacctt aaaaagagca agaaggagta tggaacttat agcaagagag  420
gatgaaaatc caaaggttgc tgaagttatc tatccaataa tgcaggttaa tgggtatcat  480
tattgtggcg ttgatgttta tgttggaggg atggagcaga gaaaaataca catgttagca  540
agggagcttt taccaaaaaa ggttgtttgt attcacaacc ctgtcttaac gggtttggat  600
ggagaaggaa agatgagttc ttcaaaaggg aattttatag ctgttgatga ctctccagaa  660
gagattaggg ctaagataaa gaaagcatac tgcccagctg gagttgttga aggaaatcca  720
ataatggaga tagctaaata cttccttgaa tatcctttaa ccataaaagg gccagaaaaa  780
tttggtggag atttgacagt taatagctat gaggagttag agagtttatt taaaaataag  840
gaattgcatc caatgcgctt aaaaaatgct gtagctgaag aacttataaa gattttagag  900
ccaattagaa agagattata                                               920

SEQ ID NO: 12          moltype = AA  length = 306
FEATURE                Location/Qualifiers
REGION                 1..306
                       note = Synthetic
source                 1..306
                       mol_type = protein
                       organism = synthetic construct
SEQUENCE: 12
MDEFEMIKRN TSEIISEEEL REVLKKDEKS ALIGFEPSGK IHLGHYLQIK KMIDLQNAGF  60
DIIIVLADLH AYLNQKGELD EIRKIGDYNK KVFEAMGLKA KYVYGSEFQL DKDYTLNVYR  120
LALKTTLKRA RRSMELIARE DENPKVAEVI YPIMQVNGYH YSGVDVFVGG MEQRKIHMLA  180
RELLPKKVVC IHNPVLTGLD GEGKMSSSKG NFIAVDDSPE EIRAKIKKAY CPAGVVEGNP  240
IMEIAKYFLE YPLTIKGPEK FGGDLTVNSY EELESLFKNK ELHPMRLKNA VAEELIKILE  300
PIRKRL                                                              306
```

```
SEQ ID NO: 13          moltype = AA  length = 306
FEATURE                Location/Qualifiers
REGION                 1..306
                       note = Synthetic
source                 1..306
                       mol_type = protein
                       organism = synthetic construct
SEQUENCE: 13
MDEFEMIKRN TSEIISEEEL REVLKKDEKS AGIGFEPSGK IHLGHYLQIK KMIDLQNAGF  60
DIIIVLADLH AYLNQKGELD EIRKIGDYNK KVFEAMGLKA KYVYGSEFQL DKDYTLNVYR  120
LALKTTLKRA RRSMELIARE DENPKVAEVI YPIMQVNGYH YSGVDVFVGG MEQRKIHMLA  180
RELLPKKVVC IHNPVLTGLD GEGKMSSSKG NFIAVDDSPE EIRAKIKKAY CPAGVVEGNP  240
IMEIAKYFLE YPLTIKGPEK FGGDLTVNSY EELESLFKNK ELHPMRLKNA VAEELIKILE  300
PIRKRL                                                             306

SEQ ID NO: 14          moltype = AA  length = 306
FEATURE                Location/Qualifiers
REGION                 1..306
                       note = Synthetic
source                 1..306
                       mol_type = protein
                       organism = synthetic construct
SEQUENCE: 14
MDEFEMIKRN TSEIISEEKL REVLKKDEKS ALIGFEPSGK IHLGHYLQIK KMIDLQNAGF  60
DIIIVLADLH AYLNQKGELD EIRKIGDYNK KVFEAMGLKA KYVYGSSVSL DKDYTLNVYR  120
LALKTTLKRA RRSMELIARE DENPKVAEVI YPIMQVNGYH YSGVDVFVGG MEQRKIHMLA  180
RELLPKKVVC IHNPVLTGLD GEGKMSSSKG NFIAVDDSPE EIRAKIKKAY CPAGVVEGNP  240
IMEIAKYFLE YPLTIKGPEK FGGDLTVNSY EELESLFKNK ELHPMRLKNA VAEELIKILE  300
PIRKRL                                                             306

SEQ ID NO: 15          moltype = AA  length = 306
FEATURE                Location/Qualifiers
REGION                 1..306
                       note = Synthetic
source                 1..306
                       mol_type = protein
                       organism = synthetic construct
SEQUENCE: 15
MDEFEMIKRN TSEIISEEEL REVLKKDEKS ALIGFEPSGK IHLGHYLQIK KMIDLQNAGF  60
DIIIVLADLH AYLNQKGELD EIRKIGDYNK KVFEAMGLKA KYVYGSNVLL DKDYTLNVYR  120
LALKTTLKRA RRSMELIARE DENPKVAEVI YPIMQVNGYH YSGVDVFVGG MEQRKIHMLA  180
RELLPKKVVC IHNPVLTGLD GEGKMSSSKG NFIAVDDSPE EIRAKIKKAY CPAGVVEGNP  240
IMEIAKYFLE YPLTIKGPEK FGGDLTVNSY EELESLFKNK ELHPMRLKNA VAEELIKILE  300
PIRKRL                                                             306

SEQ ID NO: 16          moltype = AA  length = 306
FEATURE                Location/Qualifiers
REGION                 1..306
                       note = Synthetic
source                 1..306
                       mol_type = protein
                       organism = synthetic construct
SEQUENCE: 16
MDEFEMIKRN TSEIISEEEL REVLKKDEKS ALIGFEPSGK IHLGHYLQIK KMIDLQNAGF  60
DIIIVLADLH AYLNQKGELD EIRKIGDYNK KVFEAMGLKA KYVYGSDFQL DKDYTLNVYR  120
LALKTTLKRA RRSMELIARE DENPKVAEVI YPIMQVNGYH YSGVDVFVGG MEQRKIHMLA  180
RELLPKKVVC IHNPVLTGLD GEGKMSSSKG NFIAVDDSPE EIRAKIKKAY CPAGVVEGNP  240
IMEIAKYFLE YPLTIKGPEK FGGDLTVNSY EELESLFKNK ELHPMRLKNA VAEELIKILE  300
PIRKRL                                                             306

SEQ ID NO: 17          moltype = AA  length = 306
FEATURE                Location/Qualifiers
REGION                 1..306
                       note = Synthetic
source                 1..306
                       mol_type = protein
                       organism = synthetic construct
SEQUENCE: 17
MDEFEMIKRN TSEIISEEEL REVLKKDEKS ALIGFEPSGK IHLGHYLQIK KMIDLQNAGF  60
DIIIVLADLH AYLNQKGELD EIRKIGDYNK KVFEAMGLKA KYVYGSSVCL DKDYTLNVYR  120
LALKTTLKRA RRSMELIARE DENPKVAEVI YPIMQVNGYH YSGVDVFVGG MEQRKIHMLA  180
RELLPKKVVC IHNPVLTGLD GEGKMSSSKG NFIAVDDSPE EIRAKIKKAY CPAGVVEGNP  240
IMEIAKYFLE YPLTIKGPEK FGGDLTVNSY EELESLFKNK ELHPMRLKNA VAEELIKILE  300
PIRKRL                                                             306

SEQ ID NO: 18          moltype = AA  length = 306
FEATURE                Location/Qualifiers
REGION                 1..306
                       note = Synthetic
```

```
source                 1..306
                       mol_type = protein
                       organism = synthetic construct
SEQUENCE: 18
MDEFEMIKRN TSEIISEEEL REVLKKDEKS AGIGFEPSGK IHLGHYLQIK KMIDLQNAGF  60
DIIIVLADLH AYLNQKGELD EIRKIGDYNK KVFEAMGLKA KYVYGSEFQL DKDYTLNVYR  120
LALKTTLKRA RRSMELIARE DENPKVAEVI YPIMQVNGYH YRGVDVAVGG MEQRKIHMLA  180
RELLPKKVVC IHNPVLTGLD GEGKMSSSKG NFIAVDDSPE EIRAKIKKAY CPAGVVEGNP  240
IMEIAKYFLE YPLTIKGPEK FGGDLTVNSY EELESLFKNK ELHPMRLKNA VAEELIKILE  300
PIRKRL                                                            306

SEQ ID NO: 19          moltype = AA  length = 306
FEATURE                Location/Qualifiers
REGION                 1..306
                       note = Synthetic
source                 1..306
                       mol_type = protein
                       organism = synthetic construct
SEQUENCE: 19
MDEFEMIKRN TSEIISEEEL REVLKKDEKS ALIGFEPSGK IHLGHYLQIK KMIDLQNAGF  60
DIIIGLADLH AYLNQKGELD EIRKIGDYNK KVFEAMGLKA KYVYGSDRML DKDYTLNVYR  120
LALKTTLKRA RRSMELIARE DENPKVAEVI YPIMQVNGYH YSGVDVFVGG MEQRKIHMLA  180
RELLPKKVVC IHNPVLTGLD GEGKMSSSKG NFIAVDDSPE EIRAKIKKAY CPAGVVEGNP  240
IMEIAKYFLE YPLTIKGPEK FGGDLTVNSY EELESLFKNK ELHPMRLKNA VAEELIKILE  300
PIRKRL                                                            306

SEQ ID NO: 20          moltype = DNA  length = 920
FEATURE                Location/Qualifiers
misc_feature           1..920
                       note = Synthetic
source                 1..920
                       mol_type = other DNA
                       organism = synthetic construct
SEQUENCE: 20
atggacgaat ttgaaatgat aaagagaaac acatctgaaa ttatcagcga ggaagagtta  60
agagaggttt taaaaaaaga tgaaaaatct gctctgatag gttttgaacc aagtggtaaa  120
atacatttag ggcattatct ccaaataaaa aagatgattg atttacaaaa tgctggattt  180
gatataatta tagttttggc tgatttacac gcctatttaa accagaaagg agagttggat  240
gagattagaa aaataggaga ttataacaaa aaagtttttg aagcaatggg gttaaaggca  300
aaatatgttt atggaagtga attccagctt gataaggatt atacactgaa tgtctataga  360
ttggctttaa aaactacctt aaaaagagca agaaggagta tggaacttat agcaagagag  420
gatgaaaatc caaaggttgc tgaagttatc tatccaataa tgcaggttaa tggttatcat  480
tattcgggcg ttgatgtttt tgttggaggg atggagcaga gaaaaataca catgttagca  540
agggagcttt taccaaaaaa ggttgtttgt attcacaacc ctgtcttaac gggtttggat  600
ggagaaggaa agatgagttc ttcaaaaggg aattttatag ctgttgatga ctctccagaa  660
gagattaggg ctaagataaa gaaagcatac tgcccagctg gagttgttga aggaaatcca  720
ataatggaga tagctaaata cttccttgaa tatcctttaa ccataaaagg gccagaaaaa  780
tttggtggag atttgacagt taatagctat gaggagttag agagtttatt taaaaataag  840
gaattgcatc caatgcgctt aaaaaatgct gtagctgaag aacttataaa gattttagag  900
ccaattagaa agagattata                                             920

SEQ ID NO: 21          moltype = DNA  length = 920
FEATURE                Location/Qualifiers
misc_feature           1..920
                       note = Synthetic
source                 1..920
                       mol_type = other DNA
                       organism = synthetic construct
SEQUENCE: 21
atggacgaat ttgaaatgat aaagagaaac acatctgaaa ttatcagcga ggaagagtta  60
agagaggttt taaaaaaaga tgaaaaatct gctgggatag gttttgaacc aagtggtaaa  120
atacatttag ggcattatct ccaaataaaa aagatgattg atttacaaaa tgctggattt  180
gatataatta tagttttggc tgatttacac gcctatttaa accagaaagg agagttggat  240
gagattagaa aaataggaga ttataacaaa aaagtttttg aagcaatggg gttaaaggca  300
aaatatgttt atggaagtga attccagctt gataaggatt atacactgaa tgtctataga  360
ttggctttaa aaactacctt aaaaagagca agaaggagta tggaacttat agcaagagag  420
gatgaaaatc caaaggttgc tgaagttatc tatccaataa tgcaggttaa tggttatcat  480
tattcgggcg ttgatgtttt tgttggaggg atggagcaga gaaaaataca catgttagca  540
agggagcttt taccaaaaaa ggttgtttgt attcacaacc ctgtcttaac gggtttggat  600
ggagaaggaa agatgagttc ttcaaaaggg aattttatag ctgttgatga ctctccagaa  660
gagattaggg ctaagataaa gaaagcatac tgcccagctg gagttgttga aggaaatcca  720
ataatggaga tagctaaata cttccttgaa tatcctttaa ccataaaagg gccagaaaaa  780
tttggtggag atttgacagt taatagctat gaggagttag agagtttatt taaaaataag  840
gaattgcatc caatgcgctt aaaaaatgct gtagctgaag aacttataaa gattttagag  900
ccaattagaa agagattata                                             920

SEQ ID NO: 22          moltype = DNA  length = 920
FEATURE                Location/Qualifiers
misc_feature           1..920
```

```
                        note = Synthetic
source                  1..920
                        mol_type = other DNA
                        organism = synthetic construct
SEQUENCE: 22
atggacgaat ttgaaatgat aaagagaaac acatctgaaa ttatcagcga ggaagagtta  60
agagaggttt taaaaaaaga tgaaaaatct gctctgatag gttttgaacc aagtggtaaa  120
atacatttag ggcattatct ccaaataaaa aagatgattg atttacaaaa tgctggattt  180
gatataatta tagttttggc tgatttacac gcctatttaa accagaaagg agagttggat  240
gagattagaa aaataggaga ttataacaaa aaagtttttg aagcaatggg gttaaaggca  300
aaatatgttt atggaagtag tgtttctctt gataaggatt atacactgaa tgtctataga  360
ttggctttaa aaactacctt aaaaagagca agaaggagta tggaacttat agcaagagag  420
gatgaaaatc caaaggttgc tgaagttatc tatccaataa tgcaggttaa tggttatcat  480
tattcgggcg ttgatgtttt tgttggaggg atggagcaga gaaaaataca catgttagca  540
agggagcttt taccaaaaaa ggttgtttgt attcacaacc ctgtcttaac gggtttggat  600
ggagaaggaa agatgagttc ttcaaaaggg aattttatag ctgttgatga ctctccagaa  660
gagattaggg ctaagataaa gaaagcatac tgcccagctg gagttgttga aggaaatcca  720
ataatggaga tagctaaata cttccttgaa tatcctttaa ccataaaagg gccagaaaaa  780
tttggtggag atttgacagt taatagctat gaggagttag agagtttatt taaaaataag  840
gaattgcatc caatgcgctt aaaaaatgct gtagctgaag aacttataaa gattttagag  900
ccaattagaa agagattata                                               920

SEQ ID NO: 23           moltype = DNA  length = 920
FEATURE                 Location/Qualifiers
misc_feature            1..920
                        note = Synthetic
source                  1..920
                        mol_type = other DNA
                        organism = synthetic construct
SEQUENCE: 23
atggacgaat ttgaaatgat aaagagaaac acatctgaaa ttatcagcga ggaagagtta  60
agagaggttt taaaaaaaga tgaaaaatct gctctgatag gttttgaacc aagtggtaaa  120
atacatttag ggcattatct ccaaataaaa aagatgattg atttacaaaa tgctggattt  180
gatataatta tagttttggc tgatttacac gcctatttaa accagaaagg agagttggat  240
gagattagaa aaataggaga ttataacaaa aaagtttttg aagcaatggg gttaaaggca  300
aaatatgttt atggaagtaa tgttttgctt gataaggatt atacactgaa tgtctataga  360
ttggctttaa aaactacctt aaaaagagca agaaggagta tggaacttat agcaagagag  420
gatgaaaatc caaaggttgc tgaagttatc tatccaataa tgcaggttaa tggttatcat  480
tattcgggcg ttgatgtttt tgttggaggg atggagcaga gaaaaataca catgttagca  540
agggagcttt taccaaaaaa ggttgtttgt attcacaacc ctgtcttaac gggtttggat  600
ggagaaggaa agatgagttc ttcaaaaggg aattttatag ctgttgatga ctctccagaa  660
gagattaggg ctaagataaa gaaagcatac tgcccagctg gagttgttga aggaaatcca  720
ataatggaga tagctaaata cttccttgaa tatcctttaa ccataaaagg gccagaaaaa  780
tttggtggag atttgacagt taatagctat gaggagttag agagtttatt taaaaataag  840
gaattgcatc caatgcgctt aaaaaatgct gtagctgaag aacttataaa gattttagag  900
ccaattagaa agagattata                                               920

SEQ ID NO: 24           moltype = DNA  length = 920
FEATURE                 Location/Qualifiers
misc_feature            1..920
                        note = Synthetic
source                  1..920
                        mol_type = other DNA
                        organism = synthetic construct
SEQUENCE: 24
atggacgaat ttgaaatgat aaagagaaac acatctgaaa ttatcagcga ggaagagtta  60
agagaggttt taaaaaaaga tgaaaaatct gctctgatag gttttgaacc aagtggtaaa  120
atacatttag ggcattatct ccaaataaaa aagatgattg atttacaaaa tgctggattt  180
gatataatta tagttttggc tgatttacac gcctatttaa accagaaagg agagttggat  240
gagattagaa aaataggaga ttataacaaa aaagtttttg aagcaatggg gttaaaggca  300
aaatatgttt atggaagtga tttccagctt gataaggatt atacactgaa tgtctataga  360
ttggctttaa aaactacctt aaaaagagca agaaggagta tggaacttat agcaagagag  420
gatgaaaatc caaaggttgc tgaagttatc tatccaataa tgcaggttaa tggttatcat  480
tattcgggcg ttgatgtttt tgttggaggg atggagcaga gaaaaataca catgttagca  540
agggagcttt taccaaaaaa ggttgtttgt attcacaacc ctgtcttaac gggtttggat  600
ggagaaggaa agatgagttc ttcaaaaggg aattttatag ctgttgatga ctctccagaa  660
gagattaggg ctaagataaa gaaagcatac tgcccagctg gagttgttga aggaaatcca  720
ataatggaga tagctaaata cttccttgaa tatcctttaa ccataaaagg gccagaaaaa  780
tttggtggag atttgacagt taatagctat gaggagttag agagtttatt taaaaataag  840
gaattgcatc caatgcgctt aaaaaatgct gtagctgaag aacttataaa gattttagag  900
ccaattagaa agagattata                                               920

SEQ ID NO: 25           moltype = DNA  length = 920
FEATURE                 Location/Qualifiers
misc_feature            1..920
                        note = Synthetic
source                  1..920
                        mol_type = other DNA
                        organism = synthetic construct
```

```
SEQUENCE: 25
atggacgaat ttgaaatgat aaagagaaac acatctgaaa ttatcagcga ggaagagtta  60
agagaggttt taaaaaaaga tgaaaaatct gctctgatag gttttgaacc aagtggtaaa  120
atacatttag ggcattatct ccaaataaaa aagatgattg atttacaaaa tgctggattt  180
gatataatta tagttttggc tgatttacac gcctatttaa accagaaagg agagttggat  240
gagattagaa aaataggaga ttataacaaa aaagtttttg aagcaatggg gttaaaggca  300
aaatatgttt atggaagttc tgtgtgtctt gataaggatt atacactgaa tgtctataga  360
ttggctttaa aaactacctt aaaaagagca agaaggagta tggaacttat agcaagagag  420
gatgaaaatc caaaggttgc tgaagttatc tatccaataa tgcaggttaa tggttatcat  480
tattcgggcg ttgatgtttt tgttggaggg atggagcaga gaaaaataca catgttagca  540
agggagcttt taccaaaaaa ggttgtttgt attcacaacc ctgtcttaac gggtttggat  600
ggagaaggaa agatgagttc ttcaaaaggg aattttatag ctgttgatga ctctccagaa  660
gagattaggg ctaagataaa gaaagcatac tgcccagctg gagttgttga aggaaatcca  720
ataatggaga tagctaaata cttccttgaa tatcctttaa ccataaaagg gccagaaaaa  780
tttggtggag atttgacagt taatagctat gaggagttag agagtttatt taaaaataag  840
gaattgcatc caatgcgctt aaaaaatgct gtagctgaag aacttataaa gattttagag  900
ccaattagaa agagattata                                              920

SEQ ID NO: 26          moltype = DNA  length = 920
FEATURE                Location/Qualifiers
misc_feature           1..920
                       note = Synthetic
source                 1..920
                       mol_type = other DNA
                       organism = synthetic construct
SEQUENCE: 26
atggacgaat ttgaaatgat aaagagaaac acatctgaaa ttatcagcga ggaagagtta  60
agagaggttt taaaaaaaga tgaaaaatct gctgggatag ggtttgaacc aagtggtaaa  120
atacatttag ggcattatct ccaaataaaa aagatgattg atttacaaaa tgctggattt  180
gatataatta tagttttggc tgatttacac gcctatttaa accagaaagg agagttggat  240
gagattagaa aaataggaga ttataacaaa aaagtttttg aagcaatggg gttaaaggca  300
aaatatgttt atggaagtga attccagctt gataaggatt atacactgaa tgtctataga  360
ttggctttaa aaactacctt aaaaagagca agaaggagta tggaacttat agcaagagag  420
gatgaaaatc caaaggttgc tgaagttatc tatccaataa tgcaggttaa tgggtatcat  480
tataggggcg ttgatgttgc ggttggaggg atggagcaga gaaaaataca catgttagca  540
agggagcttt taccaaaaaa ggttgtttgt attcacaacc ctgtcttaac gggtttggat  600
ggagaaggaa agatgagttc ttcaaaaggg aattttatag ctgttgatga ctctccagaa  660
gagattaggg ctaagataaa gaaagcatac tgcccagctg gagttgttga aggaaatcca  720
ataatggaga tagctaaata cttccttgaa tatcctttaa ccataaaagg gccagaaaaa  780
tttggtggag atttgacagt taatagctat gaggagttag agagtttatt taaaaataag  840
gaattgcatc caatgcgctt aaaaaatgct gtagctgaag aacttataaa gattttagag  900
ccaattagaa agagattata                                              920

SEQ ID NO: 27          moltype = DNA  length = 920
FEATURE                Location/Qualifiers
misc_feature           1..920
                       note = Synthetic
source                 1..920
                       mol_type = other DNA
                       organism = synthetic construct
SEQUENCE: 27
atggacgaat ttgaaatgat aaagagaaac acatctgaaa ttatcagcga ggaagagtta  60
agagaggttt taaaaaaaga tgaaaaatct gctctgatag gttttgaacc aagtggtaaa  120
atacatttag ggcattatct ccaaataaaa aagatgattg atttacaaaa tgctggattt  180
gatataatta taggtttggc tgatttacac gcctatttaa accagaaagg agagttggat  240
gagattagaa aaataggaga ttataacaaa aaagtttttg aagcaatggg gttaaaggca  300
aaatatgttt atggaagtga taggatgctt gataaggatt atacactgaa tgtctataga  360
ttggctttaa aaactacctt aaaaagagca agaaggagta tggaacttat agcaagagag  420
gatgaaaatc caaaggttgc tgaagttatc tatccaataa tgcaggttaa tggttatcat  480
tattcgggcg ttgatgtttt tgttggaggg atggagcaga gaaaaataca catgttagca  540
agggagcttt taccaaaaaa ggttgtttgt attcacaacc ctgtcttaac gggtttggat  600
ggagaaggaa agatgagttc ttcaaaaggg aattttatag ctgttgatga ctctccagaa  660
gagattaggg ctaagataaa gaaagcatac tgcccagctg gagttgttga aggaaatcca  720
ataatggaga tagctaaata cttccttgaa tatcctttaa ccataaaagg gccagaaaaa  780
tttggtggag atttgacagt taatagctat gaggagttag agagtttatt taaaaataag  840
gaattgcatc caatgcgctt aaaaaatgct gtagctgaag aacttataaa gattttagag  900
ccaattagaa agagattata                                              920

SEQ ID NO: 28          moltype = AA  length = 306
FEATURE                Location/Qualifiers
REGION                 1..306
                       note = Synthetic
source                 1..306
                       mol_type = protein
                       organism = synthetic construct
SEQUENCE: 28
MDEFEMIKRN TSEIISEEEL REVLKKDEKS AYIGFEPSGK IHLGHYLQIK KMIDLQNAGF  60
DIIILLADLH AYLNQKGELD EIRKIGDYNK KVFEAMGLKA KYVYGSEFQL DKDYTLNVYR  120
LALKTTLKRA RRSMELIARE DENPKVAEVI YPIMQVNDIH YLGVDVAVGG MEQRKIHMLA  180
```

```
RELLPKKVVC IHNPVLTGLD GEGKMSSSKG NFIAVDDSPE EIRAKIKKAY CPAGVVEGNP  240
IMEIAKYFLE YPLTIKGPEK FGGDLTVNSY EELESLFKNK ELHPMRLKNA VAEELIKILE  300
PIRKRL                                                            306

SEQ ID NO: 29         moltype = AA  length = 239
FEATURE               Location/Qualifiers
REGION                1..239
                      note = Synthetic
source                1..239
                      mol_type = protein
                      organism = synthetic construct
SEQUENCE: 29
SKGEELFTGV VPILVELDGD VNGHKFSVRG EGEGDATNGK LTLKFICTTG KLPVPWPTLV  60
TTLTYGVQCF SRYPDHMKRH DFFKSAMPEG YVQERTISFK DDGTYKTRAE VKFEGDTLVN  120
RIELKGIDFK EDGNILGHKL EYNFNSHNVY ITADKQKNGI KANFKIRHNV EDGSVQLADH  180
YQQNTPIGDG PVLLPDNHYL STQSVLSKDP NEKRDHMVLL EFVTAAGITH GMDELYKGS   239

SEQ ID NO: 30         moltype = AA  length = 248
FEATURE               Location/Qualifiers
REGION                1..248
                      note = Synthetic
VARIANT               150
                      note = X - azobenzene-containing unnatural amino acid
VARIANT               181
                      note = X - azobenzene-containing unnatural amino acid
source                1..248
                      mol_type = protein
                      organism = synthetic construct
SEQUENCE: 30
SKGEELFTGV VPILVELDGD VNGHKFSVSG EGEGDATYGK LTLKFICTTG KLPVPWPTLV  60
TTLTYGVQCF SRYPDHMKQH DFFKSAMPEG YVQERTIFFK DDGNYKTRAE VKFEGDTLVN  120
RIELKGIDFK EDGNILGHKL EYNYNSHNVX IMADKQKNGI KVNFKIRHNI EDGSVQLADH  180
XQQNTPIGDG PVLLPDNHYL STQSKLSKDP NEKRDHMVLL EFVTAAGITL GMDELYKGSS  240
HHHHHHGG                                                          248

SEQ ID NO: 31         moltype = AA  length = 399
FEATURE               Location/Qualifiers
REGION                1..399
                      note = Synthetic
VARIANT               19
                      note = X - azobenzene-containing unnatural amino acid
VARIANT               34
                      note = X - azobenzene-containing unnatural amino acid
VARIANT               49
                      note = X - azobenzene-containing unnatural amino acid
VARIANT               64
                      note = X -azobenzene-containing unnatural amino acid
VARIANT               79
                      note = X - azobenzene-containing unnatural amino acid
VARIANT               94
                      note = X - azobenzene-containing unnatural amino acid
VARIANT               109
                      note = X - azobenzene-containing unnatural amino acid
VARIANT               124
                      note = X - azobenzene-containing unnatural amino acid
VARIANT               139
                      note = X - azobenzene-containing unnatural amino acid
VARIANT               154
                      note = X - azobenzene-containing unnatural amino acid
source                1..399
                      mol_type = protein
                      organism = synthetic construct
SEQUENCE: 31
SKGPGVPGGG VPGAGVPGXG VPGGGVPGAG VPGXGVPGGG VPGAGVPGXG VPGGGVPGAG  60
VPGXGVPGGG VPGAGVPGXG VPGGGVPGAG VPGXGVPGGG VPGAGVPGXG VPGGGVPGAG  120
VPGXGVPGGG VPGAGVPGXG VPGGGVPGAG VPGXGPGGGG SKGEELFTGV VPILVELDGD  180
VNGHKFSVRG EGEGDATNGK LTLKFICTTG KLPVPWPTLV TTLTYGVQCF SRYPDHMKRH  240
DFFKSAMPEG YVQERTISFK DDGTYKTRAE VKFEGDTLVN RIELKGIDFK EDGNILGHKL  300
EYNFNSHNVY ITADKQKNGI KANFKIRHNV EDGSVQLADH YQQNTPIGDG PVLLPDNHYL  360
STQSVLSKDP NEKRDHMVLL EFVTAAGITH GMDELYKGS                        399

SEQ ID NO: 32         moltype = AA  length = 399
FEATURE               Location/Qualifiers
REGION                1..399
                      note = Synthetic
VARIANT               19
                      note = X - azobenzene-containing unnatural amino acid
VARIANT               49
                      note = X - azobenzene-containing unnatural amino acid
```

```
VARIANT                79
                       note = X - azobenzene-containing unnatural amino acid
VARIANT                109
                       note = X - azobenzene-containing unnatural amino acid
VARIANT                139
                       note = X - azobenzene-containing unnatural amino acid
source                 1..399
                       mol_type = protein
                       organism = synthetic construct
SEQUENCE: 32
SKGPGVPGGG VPGAGVPGXG VPGGGVPGAG VPGYGVPGGG VPGAGVPGXG VPGGGVPGAG  60
VPGYGVPGGG VPGAGVPGXG VPGGGVPGAG VPGYGVPGGG VPGAGVPGXG VPGGGVPGAG  120
VPGYGVPGGG VPGAGVPGXG VPGGGVPGAG VPGYGPGGGG SKGEELFTGV VPILVELDGD  180
VNGHKFSVRG EGEGDATNGK LTLKFICTTG KLPVPWPTLV TTLTYGVQCF SRYPDHMKRH  240
DFFKSAMPEG YVQERTISFK DDGTYKTRAE VKFEGDTLVN RIELKGIDFK EDGNILGHKL  300
EYNFNSHNVY ITADKQKNGI KANFKIRHNV EDGSVQLADH YQQNTPIGDG PVLLPDNHYL  360
STQSVLSKDP NEKRDHMVLL EFVTAAGITH GMDELYKGS                         399

SEQ ID NO: 33          moltype = AA  length = 399
FEATURE                Location/Qualifiers
REGION                 1..399
                       note = Synthetic
VARIANT                79
                       note = X - azobenzene-containing unnatural amino acid
source                 1..399
                       mol_type = protein
                       organism = synthetic construct
SEQUENCE: 33
SKGPGVPGGG VPGAGVPGYG VPGGGVPGAG VPGYGVPGGG VPGAGVPGYG VPGGGVPGAG  60
VPGYGVPGGG VPGAGVPGXG VPGGGVPGAG VPGYGVPGGG VPGAGVPGYG VPGGGVPGAG  120
VPGYGVPGGG VPGAGVPGYG VPGGGVPGAG VPGYGPGGGG SKGEELFTGV VPILVELDGD  180
VNGHKFSVRG EGEGDATNGK LTLKFICTTG KLPVPWPTLV TTLTYGVQCF SRYPDHMKRH  240
DFFKSAMPEG YVQERTISFK DDGTYKTRAE VKFEGDTLVN RIELKGIDFK EDGNILGHKL  300
EYNFNSHNVY ITADKQKNGI KANFKIRHNV EDGSVQLADH YQQNTPIGDG PVLLPDNHYL  360
STQSVLSKDP NEKRDHMVLL EFVTAAGITH GMDELYKGS                         399

SEQ ID NO: 34          moltype = AA  length = 303
FEATURE                Location/Qualifiers
REGION                 1..303
                       note = Synthetic
VARIANT                145
                       note = X - azobenzene-containing unnatural amino acid
VARIANT                295
                       note = X - azobenzene-containing unnatural amino acid
source                 1..303
                       mol_type = protein
                       organism = synthetic construct
SEQUENCE: 34
GVPGGGVPGA GVPGGGVPGA GVPGGGVPGA GVPGGGVPGA GVPGGGVPGA GVPGGGVPGA  60
GVPGGGVPGA GVPGGGVPGA GVPGGGVPGA GVPGGGVPGA GVPGGGVPGA GVPGGGVPGA  120
GVPGGGVPGA GVPGGGVPGA GVPGXGVPGA GVPGGGVPGA GVPGGGVPGA GVPGGGVPGA  180
GVPGGGVPGA GVPGGGVPGA GVPGGGVPGA GVPGGGVPGA GVPGGGVPGA GVPGGGVPGA  240
GVPGGGVPGA GVPGGGVPGA GVPGGGVPGA GVPGGGVPGA GVPGGGVPGA GVPGXGVPGA  300
GGY                                                                303

SEQ ID NO: 35          moltype = AA  length = 303
FEATURE                Location/Qualifiers
REGION                 1..303
                       note = Synthetic
VARIANT                50
                       note = X - azobenzene-containing unnatural amino acid
VARIANT                100
                       note = X - azobenzene-containing unnatural amino acid
VARIANT                150
                       note = X - azobenzene-containing unnatural amino acid
VARIANT                200
                       note = X - azobenzene-containing unnatural amino acid
VARIANT                250
                       note = X - azobenzene-containing unnatural amino acid
VARIANT                300
                       note = X - azobenzene-containing unnatural amino acid
source                 1..303
                       mol_type = protein
                       organism = synthetic construct
SEQUENCE: 35
GVPGGGVPGA GVPGGGVPGA GVPGGGVPGA GVPGGGVPGA GVPGGGVPGX GVPGGGVPGA  60
GVPGGGVPGA GVPGGGVPGA GVPGGGVPGA GVPGGGVPGX GVPGGGVPGA GVPGGGVPGA  120
GVPGGGVPGA GVPGGGVPGA GVPGGGVPGX GVPGGGVPGA GVPGGGVPGA GVPGGGVPGA  180
GVPGGGVPGA GVPGGGVPGX GVPGGGVPGA GVPGGGVPGA GVPGGGVPGA GVPGGGVPGA  240
```

```
GVPGGGVPGX GVPGGGVPGA GVPGGGVPGA GVPGGGVPGA GVPGGGVPGA GVPGGGVPGX  300
GGY                                                                303

SEQ ID NO: 36           moltype = AA  length = 503
FEATURE                 Location/Qualifiers
REGION                  1..503
                        note = Synthetic
VARIANT                 50
                        note = X - azobenzene-containing unnatural amino acid
VARIANT                 100
                        note = X - azobenzene-containing unnatural amino acid
VARIANT                 150
                        note = X - azobenzene-containing unnatural amino acid
VARIANT                 200
                        note = X - azobenzene-containing unnatural amino acid
VARIANT                 250
                        note = X - azobenzene-containing unnatural amino acid
VARIANT                 300
                        note = X - azobenzene-containing unnatural amino acid
VARIANT                 350
                        note = X - azobenzene-containing unnatural amino acid
VARIANT                 400
                        note = X - azobenzene-containing unnatural amino acid
VARIANT                 450
                        note = X - azobenzene-containing unnatural amino acid
VARIANT                 500
                        note = X - azobenzene-containing unnatural amino acid
source                  1..503
                        mol_type = protein
                        organism = synthetic construct
SEQUENCE: 36
GVPGGGVPGA GVPGGGVPGA GVPGGGVPGA GVPGGGVPGA GVPGGGVPGX GVPGGGVPGA  60
GVPGGGVPGA GVPGGGVPGA GVPGGGVPGA GVPGGGVPGX GVPGGGVPGA GVPGGGVPGA  120
GVPGGGVPGA GVPGGGVPGA GVPGGGVPGX GVPGGGVPGA GVPGGGVPGA GVPGGGVPGA  180
GVPGGGVPGA GVPGGGVPGX GVPGGGVPGA GVPGGGVPGA GVPGGGVPGA GVPGGGVPGA  240
GVPGGGVPGX GVPGGGVPGA GVPGGGVPGA GVPGGGVPGA GVPGGGVPGA GVPGGGVPGX  300
GVPGGGVPGA GVPGGGVPGA GVPGGGVPGA GVPGGGVPGA GVPGGGVPGX GVPGGGVPGA  360
GVPGGGVPGA GVPGGGVPGA GVPGGGVPGA GVPGGGVPGX GVPGGGVPGA GVPGGGVPGA  420
GVPGGGVPGA GVPGGGVPGA GVPGGGVPGX GVPGGGVPGA GVPGGGVPGA GVPGGGVPGA  480
GVPGGGVPGA GVPGGGVPGX GGY                                          503

SEQ ID NO: 37           moltype = AA  length = 324
FEATURE                 Location/Qualifiers
REGION                  1..324
                        note = Synthetic
VARIANT                 26
                        note = X - azobenzene-containing unnatural amino acid
VARIANT                 58
                        note = X - azobenzene-containing unnatural amino acid
VARIANT                 90
                        note = X - azobenzene-containing unnatural amino acid
VARIANT                 122
                        note = X - azobenzene-containing unnatural amino acid
VARIANT                 154
                        note = X - azobenzene-containing unnatural amino acid
VARIANT                 186
                        note = X - azobenzene-containing unnatural amino acid
VARIANT                 218
                        note = X - azobenzene-containing unnatural amino acid
VARIANT                 250
                        note = X - azobenzene-containing unnatural amino acid
VARIANT                 282
                        note = X - azobenzene-containing unnatural amino acid
VARIANT                 314
                        note = X - azobenzene-containing unnatural amino acid
source                  1..324
                        mol_type = protein
                        organism = synthetic construct
SEQUENCE: 37
GVPGAGVPGG GVPGAGKVPG GGVPGXGVPG GGKVPGAGVP GGGVPGAGKV PGGGVPGXGV  60
PGGGKVPGAG VPGGGVPGAG KVPGGGVPGX GVPGGGKVPG AGVPGGGVPG AGKVPGGGVP  120
GXGVPGGGKV PGAGVPGGGV PGAGKVPGGG VPGXGVPGGG KVPGAGVPGG GVPGAGKVPG  180
GGVPGXGVPG GGKVPGAGVP GGGVPGAGKV PGGGVPGXGV PGGGKVPGAG VPGGGVPGAG  240
KVPGGGVPGX GVPGGGKVPG AGVPGGGVPG AGKVPGGGVP GXGVPGGGKV PGAGVPGGGV  300
PGAGKVPGGG VPGXGVPGGG KGGY                                         324

SEQ ID NO: 38           moltype = AA  length = 303
FEATURE                 Location/Qualifiers
REGION                  1..303
```

```
                         note = Synthetic
source                   1..303
                         mol_type = protein
                         organism = synthetic construct
SEQUENCE: 38
GVPGGGVPGA GVPGGGVPGA GVPGGGVPGA GVPGGGVPGA GVPGGGVPGA GVPGGGVPGA  60
GVPGGGVPGA GVPGGGVPGA GVPGGGVPGA GVPGGGVPGA GVPGGGVPGA GVPGGGVPGA  120
GVPGGGVPGA GVPGGGVPGA GVPGGGVPGA GVPGGGVPGA GVPGGGVPGA GVPGGGVPGA  180
GVPGGGVPGA GVPGGGVPGA GVPGGGVPGA GVPGGGVPGA GVPGGGVPGA GVPGGGVPGA  240
GVPGGGVPGA GVPGGGVPGA GVPGGGVPGA GVPGGGVPGA GVPGGGVPGA GVPGGGVPGA  300
GGY                                                                303

SEQ ID NO: 39            moltype = DNA  length = 90
FEATURE                  Location/Qualifiers
misc_feature             1..90
                         note = Synthetic
misc_feature             1..2
                         note = phosphorothioate bonds
misc_difference          42..43
                         note = n is a, c, g, or t
misc_difference          48..49
                         note = n is a, c, g, or t
source                   1..90
                         mol_type = other DNA
                         organism = synthetic construct
SEQUENCE: 39
aagagttaag agaggtttta aaaaaagatg aaaaatctgc tnnkatannk tttgaaccaa  60
gtggtaaaat acatttaggg cattatctcc                                   90

SEQ ID NO: 40            moltype = DNA  length = 90
FEATURE                  Location/Qualifiers
misc_feature             1..90
                         note = Synthetic
misc_feature             1..2
                         note = phosphorothioate bonds
misc_difference          42..43
                         note = n is a, c, g, or t
misc_difference          48..49
                         note = n is a, c, g, or t
source                   1..90
                         mol_type = other DNA
                         organism = synthetic construct
SEQUENCE: 40
agatgattga tttacaaaat gctggatttg atataattat annkttgnnk gatttacacg  60
cctatttaaa ccagaaagga gagttggatg                                   90

SEQ ID NO: 41            moltype = DNA  length = 90
FEATURE                  Location/Qualifiers
misc_feature             1..90
                         note = Synthetic
misc_feature             1..2
                         note = phosphorothioate bonds
misc_difference          45..46
                         note = n is a, c, g, or t
misc_difference          48..49
                         note = n is a, c, g, or t
misc_difference          51..52
                         note = n is a, c, g, or t
source                   1..90
                         mol_type = other DNA
                         organism = synthetic construct
SEQUENCE: 41
tttttgaagc aatggggtta aaggcaaaat atgtttatgg aagtnnknnk nnkcttgata  60
aggattatac actgaatgtc tatagattgg                                   90

SEQ ID NO: 42            moltype = DNA  length = 90
FEATURE                  Location/Qualifiers
misc_feature             1..90
                         note = Synthetic
misc_feature             1..2
                         note = phosphorothioate bonds
misc_difference          70..71
                         note = n is a, c, g, or t
source                   1..90
                         mol_type = other DNA
                         organism = synthetic construct
SEQUENCE: 42
aaaagagcaa gaaggagtat ggaacttata gcaagagagg atgaaaatcc aaaggttgct  60
gaagttatcn nkccaataat gcaggttaat                                   90
```

```
SEQ ID NO: 43          moltype = DNA  length = 90
FEATURE                Location/Qualifiers
misc_feature           1..90
                       note = Synthetic
misc_difference        19..20
                       note = n is a, c, g, or t
misc_difference        22..23
                       note = n is a, c, g, or t
misc_difference        31..32
                       note = n is a, c, g, or t
misc_difference        46..47
                       note = n is a, c, g, or t
source                 1..90
                       mol_type = other DNA
                       organism = synthetic construct
misc_feature           1..2
                       note = phosphorothioate bonds
SEQUENCE: 43
ccaataatgc aggttaatnn knnkcattat nnkggcgttg atgttnnkgt tggagggatg  60
gagcagagaa aaatacacat gttagcaagg                                    90

SEQ ID NO: 44          moltype = AA  length = 16
FEATURE                Location/Qualifiers
REGION                 1..16
                       note = Synthetic
SITE                   9
                       note = X - azobenzene-uAA
source                 1..16
                       mol_type = protein
                       organism = synthetic construct
SEQUENCE: 44
VPGGGVPGXG VPGGGK                                                   16

SEQ ID NO: 45          moltype = AA  length = 16
FEATURE                Location/Qualifiers
REGION                 1..16
                       note = Synthetic
source                 1..16
                       mol_type = protein
                       organism = synthetic construct
SEQUENCE: 45
VPGGGVPGQG VPGGGK                                                   16

SEQ ID NO: 46          moltype = AA  length = 16
FEATURE                Location/Qualifiers
REGION                 1..16
                       note = Synthetic
source                 1..16
                       mol_type = protein
                       organism = synthetic construct
SEQUENCE: 46
VPGGGVPGPG VPGGGK                                                   16

SEQ ID NO: 47          moltype = AA  length = 16
FEATURE                Location/Qualifiers
REGION                 1..16
                       note = Synthetic
source                 1..16
                       mol_type = protein
                       organism = synthetic construct
SEQUENCE: 47
VPGGGVPGYG VPGGGK                                                   16

SEQ ID NO: 48          moltype = AA  length = 16
FEATURE                Location/Qualifiers
REGION                 1..16
                       note = Synthetic
source                 1..16
                       mol_type = protein
                       organism = synthetic construct
SEQUENCE: 48
VPGGGVPGLG VPGGGK                                                   16

SEQ ID NO: 49          moltype = AA  length = 16
FEATURE                Location/Qualifiers
REGION                 1..16
                       note = Synthetic
source                 1..16
```

```
                        mol_type = protein
                        organism = synthetic construct
SEQUENCE: 49
VPGGGVPGFG VPGGGK                                                    16

SEQ ID NO: 50           moltype = AA  length = 16
FEATURE                 Location/Qualifiers
REGION                  1..16
                        note = Synthetic
SITE                    9
                        note = X - azobenzene-uAA
source                  1..16
                        mol_type = protein
                        organism = synthetic construct
SEQUENCE: 50
VPGGGVPGXG VPGGGK                                                    16

SEQ ID NO: 51           moltype = AA  length = 16
FEATURE                 Location/Qualifiers
REGION                  1..16
                        note = Synthetic
source                  1..16
                        mol_type = protein
                        organism = synthetic construct
SEQUENCE: 51
VPGGGVPGQG VPGGGK                                                    16

SEQ ID NO: 52           moltype = AA  length = 16
FEATURE                 Location/Qualifiers
REGION                  1..16
                        note = Synthetic
source                  1..16
                        mol_type = protein
                        organism = synthetic construct
SEQUENCE: 52
VPGGGVPGYG VPGGGK                                                    16

SEQ ID NO: 53           moltype = AA  length = 16
FEATURE                 Location/Qualifiers
REGION                  1..16
                        note = Synthetic
SITE                    9
                        note = X - pPR
source                  1..16
                        mol_type = protein
                        organism = synthetic construct
SEQUENCE: 53
VPGAGVPGXG VPGVGK                                                    16

SEQ ID NO: 54           moltype = AA  length = 16
FEATURE                 Location/Qualifiers
REGION                  1..16
                        note = Synthetic
source                  1..16
                        mol_type = protein
                        organism = synthetic construct
SEQUENCE: 54
VPGAGVPGYG VPGVGK                                                    16

SEQ ID NO: 55           moltype = AA  length = 16
FEATURE                 Location/Qualifiers
REGION                  1..16
                        note = Synthetic
source                  1..16
                        mol_type = protein
                        organism = synthetic construct
SEQUENCE: 55
VPGAGVPGQG VPGVGK                                                    16

SEQ ID NO: 56           moltype = AA  length = 16
FEATURE                 Location/Qualifiers
REGION                  1..16
                        note = Synthetic
source                  1..16
                        mol_type = protein
                        organism = synthetic construct
SEQUENCE: 56
VPGAGVPGWG VPGVGK                                                    16
```

```
SEQ ID NO: 57          moltype = AA  length = 16
FEATURE                Location/Qualifiers
REGION                 1..16
                       note = Synthetic
source                 1..16
                       mol_type = protein
                       organism = synthetic construct
SEQUENCE: 57
VPGAGVPGFG VPGVGK                                              16

SEQ ID NO: 58          moltype = AA  length = 16
FEATURE                Location/Qualifiers
REGION                 1..16
                       note = Synthetic
source                 1..16
                       mol_type = protein
                       organism = synthetic construct
SEQUENCE: 58
VPGAGVPGPG VPGVGK                                              16

SEQ ID NO: 59          moltype = AA  length = 16
FEATURE                Location/Qualifiers
REGION                 1..16
                       note = Synthetic
source                 1..16
                       mol_type = protein
                       organism = synthetic construct
SEQUENCE: 59
VPGAGVPGIG VPGVGK                                              16

SEQ ID NO: 60          moltype = AA  length = 16
FEATURE                Location/Qualifiers
REGION                 1..16
                       note = Synthetic
source                 1..16
                       mol_type = protein
                       organism = synthetic construct
SEQUENCE: 60
VPGAGVPGDG VPGVGK                                              16

SEQ ID NO: 61          moltype = AA  length = 16
FEATURE                Location/Qualifiers
REGION                 1..16
                       note = Synthetic
source                 1..16
                       mol_type = protein
                       organism = synthetic construct
SEQUENCE: 61
VPGAGVPGCG VPGVGK                                              16

SEQ ID NO: 62          moltype = AA  length = 16
FEATURE                Location/Qualifiers
REGION                 1..16
                       note = Synthetic
source                 1..16
                       mol_type = protein
                       organism = synthetic construct
SEQUENCE: 62
VPGAGVPGSG VPGVGK                                              16

SEQ ID NO: 63          moltype = AA  length = 19
FEATURE                Location/Qualifiers
REGION                 1..19
                       note = Synthetic
source                 1..19
                       mol_type = protein
                       organism = synthetic construct
SEQUENCE: 63
YVYGSEFQLD KDYTLNVYR                                           19

SEQ ID NO: 64          moltype = AA  length = 18
FEATURE                Location/Qualifiers
REGION                 1..18
                       note = Synthetic
source                 1..18
                       mol_type = protein
                       organism = synthetic construct
SEQUENCE: 64
FGGDKTVNSY EELESLFK                                            18
```

```
SEQ ID NO: 65          moltype = AA  length = 13
FEATURE                Location/Qualifiers
REGION                 1..13
                       note = Synthetic
source                 1..13
                       mol_type = protein
                       organism = synthetic construct
SEQUENCE: 65
NTTSEIISEE ELR                                                    13

SEQ ID NO: 66          moltype = AA  length = 11
FEATURE                Location/Qualifiers
REGION                 1..11
                       note = Synthetic
source                 1..11
                       mol_type = protein
                       organism = synthetic construct
SEQUENCE: 66
LKNAVAEELI K                                                      11

SEQ ID NO: 67          moltype = AA  length = 14
FEATURE                Location/Qualifiers
REGION                 1..14
                       note = Synthetic
source                 1..14
                       mol_type = protein
                       organism = synthetic construct
SEQUENCE: 67
GNFIAVDDSP EEIR                                                   14

SEQ ID NO: 68          moltype = AA  length = 11
FEATURE                Location/Qualifiers
REGION                 1..11
                       note = Synthetic
source                 1..11
                       mol_type = protein
                       organism = synthetic construct
SEQUENCE: 68
SALIGFEPSG K                                                      11

SEQ ID NO: 69          moltype = AA  length = 25
FEATURE                Location/Qualifiers
REGION                 1..25
                       note = Synthetic
MOD_RES                1
                       note = Oxidated methionine
source                 1..25
                       mol_type = protein
                       organism = synthetic construct
SEQUENCE: 69
MIDLQNAGFD IIILLADLHA YLNQK                                       25

SEQ ID NO: 70          moltype = AA  length = 25
FEATURE                Location/Qualifiers
REGION                 1..25
                       note = Synthetic
source                 1..25
                       mol_type = protein
                       organism = synthetic construct
SEQUENCE: 70
MIDLQNAGFD IIILLADLHA YLNQK                                       25

SEQ ID NO: 71          moltype = AA  length = 10
FEATURE                Location/Qualifiers
REGION                 1..10
                       note = Synthetic
source                 1..10
                       mol_type = protein
                       organism = synthetic construct
SEQUENCE: 71
YFLEYPLTIK                                                        10

SEQ ID NO: 72          moltype = AA  length = 11
FEATURE                Location/Qualifiers
REGION                 1..11
                       note = Synthetic
source                 1..11
                       mol_type = protein
```

-continued

```
                         organism = synthetic construct
SEQUENCE: 72
YVYGSEFQLD K                                                     11

SEQ ID NO: 73            moltype = AA  length = 8
FEATURE                  Location/Qualifiers
REGION                   1..8
                         note = Synthetic
source                   1..8
                         mol_type = protein
                         organism = synthetic construct
SEQUENCE: 73
GELDEIRK                                                         8

SEQ ID NO: 74            moltype = AA  length = 12
FEATURE                  Location/Qualifiers
REGION                   1..12
                         note = Synthetic
source                   1..12
                         mol_type = protein
                         organism = synthetic construct
SEQUENCE: 74
GVDVHVGGME QR                                                    12
```

MUTANT AMINOACYL-TRNA SYNTHETASES

CROSS-REFERENCE TO RELATED APPLICATIONS

This application is a bypass continuation of PCT Patent Application No. PCT/IL2021/050194 having International filing date of Feb. 18, 2021, which claims the benefit of priority to U.S. Provisional Application No. 62/978,895 titled "MUTANT AMINOACYL-TRNA SYNTHETASES" filed Feb. 20, 2020, the contents of which are all incorporate herein by reference in their entirety.

REFERENCE TO AN ELECTRONIC SEQUENCE LISTING

The contents of the electronic sequence listing (BGU-P-098-US.xml; Size: 139,200 bytes; and Date of Creation: Jun. 20, 2023) is herein incorporated by reference in its entirety.

FIELD OF INVENTION

The present invention is in the field of artificial amino acid incorporation.

BACKGROUND OF THE INVENTION

Site-specific modification of proteins is a powerful means for investigation and manipulation of the properties of proteins, and has been utilized for a variety of applications, such as fluorescent labeling, analysis of structure and functions, and manipulation of the chemical, biological, and pharmacological properties of target molecules. Beyond single-site modifications, multi-site modifications have been demonstrated to extend and further exploit the potential of such applications, for example for direct polymerization of target proteins, site-specific conjugation of single protein to multiple ligands, and increased performance in analytical chemistry assays.

Traditional methods for protein modification via the chemically reactive cysteine and lysine residues often result in heterogenous product, may disturb the proper folding and function of the modified protein, or may require additional mutations to the protein to achieve single-site modification. In contrast, site-specific introduction of small bio-orthogonal groups to proteins followed by a chemo-selective reaction, does not require the introduction of additional mutations, enables site-selection to minimize interference with the folding and function of the protein, and results in homogenously modified product.

One of the most commonly utilized bio-orthogonal reactions is the copper catalyzed azide-alkyne cycloaddition (CuAAC), which has been employed in a variety of applications, such as modifying and labeling nucleic acids, viruses and proteins both in-vitro and in-vivo. In addition to bio-orthogonality, reactions of this family are rapid, regioselective, and result in high yields of the conjugated product. However, CuAAC bioconjugation application in living systems is hindered due to the Cu(I)-induced generation of reactive oxygen species (ROS) with consequent cellular toxicity. Several methodologies have addressed this limitation by using different ligands to reduce the Cu-mediated toxicity to cells, by utilizing an azide probe that contains an internal copper-chelating moiety, or by using strained alkynes which obviate the need for copper catalysts. However, unlike azides and alkynes, the azide probes with internal copper chelating moiety and strained alkynes are large structures, therefore they may interfere with the function of the labeled protein. In addition, the strain promoted azide-alkyne cycloaddition (SPAAC) is a much slower reaction than the CuAAC and is not strictly bio-orthogonal and regioselective.

As a pre-requisite for site-specific conjugation via CuAAC, an alkyne or azide group must be site-specifically incorporated into the protein. This can be achieved using several methodologies including enzymatic or chemical modification of selected residues (typically post-protein purification), or by incorporation of unnatural amino acids (uAAs) that bear an alkyne or an azide group. Several studies describe the incorporation of such uAAs by substitution of a natural amino acid with a close synthetic analog in auxotrophic strain, which has been used for labeling in various organisms. However, while this method has been applied in various organisms, growth defects due to amino acid substitution, relatively low aminoacylation of the endogenous tRNA with the uAA, compared to the natural amino acid limit the yield of the target protein. In addition, this method replaces all instances of the relevant natural amino acid with the uAA, and therefore is not site specific. Alternatively, uAAs can be incorporated site specifically via codon reassignment or frameshift codons by using orthogonal translation systems (OTSs) consisting of an aminoacyl tRNA synthetase (aaRS), which is able to charge only a cognate tRNA that is not aminoacylated by endogenous aaRSs. Typically, a TAG stop codon (transcribed to UAG during mRNA synthesis) is assigned to the uAA.

Genetic code expansion to integrate light sensitive moieties into proteins. Generally, there are three common classes of light-responsive moieties that are used to impart light-responsive behavior for biopolymers: (1) fusion to a genetically encoded light-responsive protein, however the main drawback is lack of generality, (2) incorporation of an irreversible photolabile group, and (3) incorporation of a reversible photoswitchable group. Among the third group molecules, azobenzenes, a class of molecules known to undergo reversible light-based isomerization, are the most robust and commonly used photoswitches. Upon irradiation with light of the appropriate wavelength (λtrans→cis), the azobenzene molecule undergoes a dramatic switch from the trans to the cis configuration (shortening by at least ~3.5 Å), with a concomitant change from a hydrophobic to a hydrophilic (polar) molecule (~3 Debyes). Importantly, this process is reversible, and with time or upon irradiation with a second, different, wavelength within the blue light range (λcis→trans), the azobenzene molecule relaxes back to the trans configuration.

Incorporation of azobenzene into a polypeptide chain can be mediated by incorporation of azobenzene-containing non-standard amino acid (nsAA), using expanded genetic code method as is used for the alkyne or azide groups. This expansion has enabled template-based incorporation of >100 nsAAs containing diverse chemical groups including post-translational modifications, photocaged amino acids, bio-orthogonal reactive groups, and spectroscopic labels. However, with respect to light-responsive nsAA only incorporation of a single nsAA into a single protein has ever been successfully achieved.

Several challenges have limited genetic code modification-based integration of nsAA technology to in some applications only one instance, or in others a few instances, of site-specific uAA incorporation per protein. Improved translation systems that can circumvent these limitations and improved nsAA integration technology are greatly needed.

SUMMARY OF THE INVENTION

The present invention provides mutant aminoacyl-tRNA synthetase (aaRS) proteins. Nucleic acid molecules encoding the mutant aaRSs are provided. Orthogonal translation systems comprising the mutant aaRSs or the nucleic acid molecules are provided. Cells comprising the orthogonal translation systems, mutant aaRSs or nucleic acid molecules are provided. Methods of using the mutant aaRSs, nucleic acid molecules, orthogonal translation systems and cells are also provided.

According to a first aspect, there is provided a mutant aminoacyl-tRNA synthetase (aaRS) comprising an amino acid sequence of an aaRS comprising at least one amino acid mutation selected from the group consisting of: tyrosine 32 mutated to leucine, tyrosine 32 mutated to threonine; leucine 65 mutated to valine; glutamic acid 107 mutated to alanine; phenylalanine 108 mutated to tyrosine; glutamine 109 mutated to methionine; aspartic acid 158 mutated to serine; aspartic acid 158 mutated to glycine; isoleucine 159 mutated to alanine; isoleucine 159 mutated to methionine; isoleucine 159 mutated to cysteine; isoleucine 159 mutated to tyrosine; leucine 162 mutated to glutamic acid; leucine 162 mutated to lysine; leucine 162 mutated to valine; leucine 162 mutated to arginine; leucine 162 mutated to serine; leucine 162 mutated to cysteine; alanine 167 mutated to histidine, alanine 167 mutated to aspartic acid and alanine 167 mutated to tyrosine.

According to some embodiments, the mutant is selected from the group consisting of:

a) a mutant comprising tyrosine 32 mutated to leucine, aspartic acid 158 mutated to serine, isoleucine 159 mutated to methionine, leucine 162 mutated to lysine, and alanine 167 mutated to histidine;
b) a mutant comprising tyrosine 32 mutated to leucine, leucine 65 mutated to valine, aspartic acid 158 mutated to glycine, isoleucine 159 mutated to alanine, leucine 162 mutated to glutamic acid, and alanine 167 mutated to histidine;
c) a mutant comprising alanine 32 mutated to threonine, leucine 65 mutated to valine, glutamic acid 107 mutated to alanine, phenylalanine 108 mutated to tyrosine, glutamine 109 mutated to methionine, aspartic acid 158 mutated to glycine, isoleucine 159 mutated to cysteine, leucine 162 mutated to arginine, and alanine 167 mutated to aspartic acid;
d) a mutant comprising tyrosine 32 mutated to leucine, leucine 65 mutated to valine, aspartic acid 158 mutated to glycine, isoleucine 159 mutated to methionine, leucine 162 mutated to serine, and alanine 167 mutated to histidine; and
e) a mutant comprising tyrosine 32 mutated to leucine, leucine 65 mutated to valine, aspartic acid 158 mutated to glycine, isoleucine 159 mutated to tyrosine, alanine 162 mutated to cysteine, and alanine 167 mutated to tyrosine.

According to some embodiments, the mutant aaRS comprises an amino acid sequence selected from: SEQ ID NO: 2, SEQ ID NO: 3, SEQ ID NO: 4, SEQ ID NO: 5 and SEQ ID NO: 6.

According to another aspect, there is provided a mutant aminoacyl-tRNA synthetase (aaRS) comprising an amino acid sequence of an aaRS comprising at least one amino acid mutation selected from the group consisting of: tyrosine 32 mutated to leucine, tyrosine 32 mutated to glycine; leucine 65 mutated to valine; leucine 65 mutated to glycine; glutamic acid 107 mutated to serine; glutamic acid 107 mutated to asparagine; glutamic acid 107 mutated to aspartic acid; phenylalanine 108 mutated to valine; phenylalanine 108 mutated to arginine; glutamine 109 mutated to methionine; glutamine 109 mutated to serine; glutamine 109 mutated to leucine; and glutamine 109 mutated to cysteine; aspartic acid 158 mutated to glycine; isoleucine 159 mutated to tyrosine; leucine 162 mutated to serine; leucine 162 mutated to arginine; and alanine 167 mutated to phenylalanine.

According to some embodiments, the mutant aaRS of the invention comprises:

a) aspartic acid 158 mutated to glycine;
b) isoleucine 159 mutated to tyrosine; and
c) leucine 162 mutated to serine or leucine 162 mutated to arginine.

According to some embodiments, the mutant aaRS of the invention further comprises alanine 167 mutated to phenylalanine.

According to some embodiments, the mutant aaRS of the invention further comprises tyrosine 32 mutated to leucine or tyrosine 32 mutated to glycine.

According to some embodiments, the mutant aaRS of the invention further comprises leucine 65 mutated to valine or leucine 65 mutated to glycine.

According to some embodiments, the mutant is selected from the group consisting of:

a) a mutant comprising tyrosine 32 mutated to leucine, lysine 65 mutated to valine; aspartic acid 158 mutated to glycine; isoleucine 159 mutated to tyrosine; leucine 162 mutated to serine; and alanine 167 mutated to phenylalanine;
b) a mutant comprising tyrosine 32 mutated to glycine, lysine 65 mutated to valine; aspartic acid 158 mutated to glycine; isoleucine 159 mutated to tyrosine; leucine 162 mutated to serine; and alanine 167 mutated to phenylalanine;
c) a mutant comprising tyrosine 32 mutated to leucine, lysine 65 mutated to valine; glutamic acid 107 mutated to serine, phenylalanine 108 mutated to valine, glutamine 109 mutated to serine; aspartic acid 158 mutated to glycine; isoleucine 159 mutated to tyrosine; leucine 162 mutated to serine; and alanine 167 mutated to phenylalanine;
d) a mutant comprising tyrosine 32 mutated to leucine, lysine 65 mutated to valine; glutamic acid 107 mutated to asparagine, phenylalanine 108 mutated to valine, glutamine 109 mutated to leucine; aspartic acid 158 mutated to glycine; isoleucine 159 mutated to tyrosine; leucine 162 mutated to serine; and alanine 167 mutated to phenylalanine;
e) a mutant comprising tyrosine 32 mutated to leucine, lysine 65 mutated to valine; glutamic acid 107 mutated to aspartic acid, aspartic acid 158 mutated to glycine; isoleucine 159 mutated to tyrosine; leucine 162 mutated to serine; and alanine 167 mutated to phenylalanine;
f) a mutant comprising tyrosine 32 mutated to leucine, lysine 65 mutated to valine; glutamic acid 107 mutated to serine, phenylalanine 108 mutated to valine, glutamine 109 mutated to cysteine; aspartic acid 158 mutated to glycine; isoleucine 159 mutated to tyrosine; leucine 162 mutated to serine; and alanine 167 mutated to phenylalanine;
g) a mutant comprising tyrosine 32 mutated to leucine, lysine 65 mutated to valine; aspartic acid 158 mutated to glycine; isoleucine 159 mutated to tyrosine; and leucine 162 mutated to arginine; and h) a mutant comprising tyrosine 32 mutated to leucine, lysine 65 mutated to glycine; glutamic acid 107 mutated to aspartic acid, phenylalanine 108 mutated to arginine, glutamine 109 mutated to methionine; aspartic acid 158 mutated to glycine; isoleucine 159 mutated to tyrosine; leucine 162 mutated to serine; and alanine 167 mutated to phenylalanine.

According to some embodiments, the mutant comprises an amino acid sequence selected from: SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19.

According to some embodiments, the amino acid sequence of an aaRS is SEQ ID NO: 1.

According to some embodiments, mutant aaRS of the invention further comprises a mutation of arginine 257 to glycine, a mutation of aspartic acid 286 to arginine or both.

According to another aspect, there is provided a nucleic acid molecule comprising a coding region encoding a mutant aaRS of the invention.

According to some embodiments, the coding region comprises a nucleic acid sequence selected from SEQ ID NO: 7, SEQ ID NO: 8, SEQ ID NO: 9, SEQ ID NO: 10, SEQ ID NO: 11, SEQ ID NO: 20, SEQ ID NO: 21, SEQ ID NO: 22, SEQ ID NO: 23, SEQ ID NO: 24; SEQ ID NO: 25, SEQ ID NO: 26, and SEQ ID NO: 27.

According to some embodiments, the coding region is operably linked to at least one regulatory element configured to express the coding region in a target cell.

According to another aspect, there is provided an orthogonal translation system, comprising, a) a mutant aaRS of the invention, or a nucleic acid molecule of the invention, and
b) an orthogonal tRNA compatible with the mutant aaRS and comprising an anticodon that corresponds to a stop codon.

According to some embodiments, orthogonal translation system of the invention further comprises a non-standard amino acid (nsAA) recognized by the mutant aaRS.

According to some embodiments, the nsAA is an unnatural amino acid (uAA).

According to some embodiments, the uAA comprises a biorthogonal chemical moiety.

According to some embodiments, the mutant aaRS is the mutant aaRS of the invention and the uAA comprises an azide or an alkyne group.

According to some embodiments, the mutant aaRS is the mutant aaRS of the invention and the uAA comprises an azobenzene group.

According to some embodiments, the nsAA is a modified phenylalanine.

According to some embodiments, the modified phenylalanine is 4-propargyloxy-L-phenylalanine (pPR).

According to some embodiments, the uAA comprising an azobenzene group is selected from phenylalanine-4'-azobenzene (AzoPhe). tri-fluorinated azobenzene (Azo3F), and tetra-ortho-fluorinated azobenzene (Azo4F) amino acids.

According to some embodiments, the stop codon is a TAG stop codon.

According to another aspect, there is provided a cell comprising an orthogonal translation system of the invention.

According to some embodiments, the cell of the invention further comprises an expression vector comprising an open reading frame (ORF) comprising at least one of the stop codons within the open reading frame.

According to some embodiments, the ORF comprises a plurality of stop codons.

According to some embodiments, the ORF comprises at least 10 stop codons.

According to some embodiments, the ORF is operatively linked to at least one regulatory element capable of inducing expression of the ORF within the cell.

According to some embodiments, the cell is devoid of native TAG stop codons and does not express release factor 1 (RF1).

According to some embodiments, the cell comprises RF1 and at least one native TAG stop codon.

According to another aspect, there is provided a method of producing a protein comprising a nsAA, the method comprising introducing into a cell an expression vector comprising an open reading frame encoding the protein wherein the open reading frame comprises a stop codon, wherein the cell comprises an orthogonal translation system of the invention.

According to some embodiments, the method of the invention is for labeling the protein, and the method further comprises converting the nsAA into a detectably labeled amino acid and wherein the mutant aaRS is the mutant aaRS of the invention.

According to some embodiments, the converting comprises addition of a detectable moiety by Click chemistry.

According to some embodiments, the method of the invention is for producing a light-responsive protein, wherein the mutant aaRS is the mutant aaRS of the invention.

According to another aspect, there is provided a protein comprising a nsAA produced by a method of the invention.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-C: (1A) A table depicting amino acid substitutions present in mutant aminoacyl tRNA synthetases capable of incorporating alkyne-containing non-standard amino acids. The mutation sites are with respect to a *M. janaschii* tyrosyl-tRNA synthetase. (1B) A table depicting amino acid substitutions present in mutant aminoacyl tRNA synthetases capable of incorporating azobenzene-containing non-standard amino acids. The mutation sites are with respect to a wild-type *M. janaschii* tyrosyl-tRNA synthetase. (1C) Production of GFP(3TAG) by chromosomally integrated parent and evolved aaRS variants in *E. coli* strain C321.ΔRF1.

FIG. 23: Expected and experimental molecular weights of ELP(10TAG)-GFP by MALDI-TOF mass spectrometry analysis. Molecular weights (Da) calculated based on doubly charged proteins. pPR-bearing proteins were expressed by Mut1-RS.

FIGS. 24A-J: Sequence and signal intensities of peptides identified LC-MS of tryptic fragments. (24A) ELP(10TAG)-GFP MS, expressed by parent pPR-RS in the C321.ΔRF1 strain. (24B) ELP(10TAG)-GFP MS, expressed by parent pPR-RS in the BL21 strain. (24C) ELP(10TAG)-GFP MS, expressed by Mut1-RS in the C321.ΔRF1 using 1 mM pPR. (24D) ELP(10TAG)-GFP MS, expressed by Mut1-RS in the C321.ΔRF1 using 0.25 mM pPR. (24E) ELP(10TAG)-GFP MS, expressed by Mut1-RS in the BL21 *E. coli* strain using 1 mM pPR. (24F) ELP(10TAG)-GFP MS, expressed by Mut1-RS in the BL21 *E. coli* strain using 0.25 mM pPR. (24G) ELP(10TAG)-GFP MS, expressed by Mut2-RS in the C321.ΔRF1 using 1 mM pPR. (24H) ELP(30TAG) MS, expressed in the C321.ΔRF1 by Mut1-RS, using different pPR concentrations. (24I) ELP(30TAG)MS, expressed by Mut2-RS in the C321.ΔRF1, using 1 mM pPR. (24J) Identification of Mut1-RS in the fluorescent band following in-vivo click reaction in C321.ΔRF1 and in-gel trypsin digestion.

FIG. 25: Fluorescent quantification of microscopy images.

DETAILED DESCRIPTION OF THE INVENTION

Figure 1C:
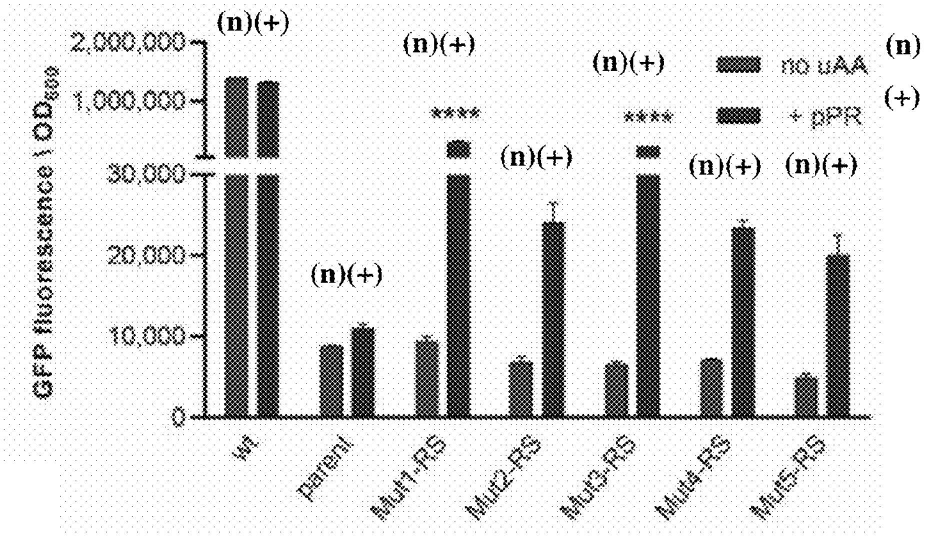

The present invention provides, in some embodiments, mutant aminoacyl-tRNA synthetase (aaRS) proteins. Nucleic acid molecules encoding the mutant aaRSs are also provided, as are orthogonal translation systems comprising the mutant aaRSs or nucleic acid molecules and cells comprising the orthogonal translation system. Methods of use are also provided.

The present invention is based on the surprising development of highly efficient aaRS variants capable of multi-site incorporation of uAAs in a genomically recoded organism (GRO) that lacks all native TAG codons as well as the associated release factor (RF1). Surprisingly some new aaRS variants were even functional in wild-type cells. The toolbox for multi-site and site-selective protein labeling has thus been greatly expanded via evolution of efficient aaRS variants for the multi-site incorporation of the alkyne-bearing uAA, 4-propargyloxy-L-phenylalanine (pPR), azobenzene-bearing phenylalanine-4'-azobenzene (AzoPhe), tri-fluorinated azobenzene (Azo3F) and tetra-ortho-fluorinated azobenzene (Azo4F). While OTSs have been previously developed, they are suitable for single-site pPR incorporation per-protein generally. For example previous attempts to incorporate pPR found proteins harboring a single pPR were expressed by the system in only moderate yields (<20% or ~42% of wild-type proteins in *E. coli* cell free protein synthesis, depending on the position for uAA incorporation in the protein). The newly evolved aaRS variants are capable of incorporating up to 10 or 30 instances of the uAA in a single protein, in both the commonly used, non-recoded *E. coli* strain BL21 and the GRO, respectively. Further, it is shown herein that multi-site incorporation of uAAs in proteins allows rapid, robust, and non-toxic fluorescent labeling of these proteins or generation of light responsive polymers in vivo. Not only that, but there is shown herein the genetic encoding of light-responsive phase transition and self-assembly of a PBB using photo-switchable uAAs. In particular, azobenzene-containing ELPs with a predetermined number of azobenzenes, incorporated at specific positions, were generated. This allowed for manipulation of the transition temperature of the ELP and control of the ELP's self-assembly and geometry. Finally, light-responsive nanostructures were engineered by incorporating azobenzene-uAAs in the hydrophobic segment of ELP diblock co-polymers.

Mutant aaRS

By a first aspect, the present invention provides a mutant aminoacyl-tRNA synthetase (aaRS).

In some embodiments, the mutant aaRS comprises an amino acid sequence of an aaRS comprising at least one amino acid mutation. In some embodiments, the mutant aaRS comprises at least 1, 2, 3, 4, 5, 6, 7, 8, 9, 10 or 11 mutations. In some embodiments, the mutant aaRS comprises 2 mutations. In some embodiments, the mutant aaRS comprises 5 mutations. In some embodiments, the mutant aaRS comprises 6 mutations. In some embodiments, the mutant aaRS comprises 7 mutations. In some embodiments, the mutant aaRS comprises 8 mutations. In some embodiments, the mutant aaRS comprises 9 mutations. In some embodiments, the mutant aaRS comprises 11 mutations.

As used herein, the term "mutation" refers to any mutation such as can be introduced into an amino acid sequence or into a nucleic acid sequence by any method known in the art. In some embodiments, a mutation is a deletion. In some embodiments, is an insertion. In some embodiments, a mutation is a substitution. In some embodiments, a mutation is a conversion of one amino acid to another. In some embodiments, a mutation is a conversion of one nucleotide to another. In some embodiments, a mutation is a conversion of a plurality of nucleotides to other nucleotides. In some embodiments, a mutation introduced into a nucleic acid sequence when translated, results in a mutant amino acid sequence. In some embodiments, the mutation is not a silent mutation.

In some embodiments, the mutation increases the incorporation rate of a non-standard amino acid (nsAA) into a protein. In some embodiments, the mutation increases the rate of recognition of the aaRS of its cognate tRNA. In some embodiments, the mutation increases the rate of recognition of the aaRS of an orthogonal tRNA. In some embodiments, the mutation increases the rate of recognition of an amino acid. In some embodiments, the mutation increases the rate of recognition of the aaRS of its cognate amino acid. In some embodiments, the mutation increases the rate of recognition of the aaRS of an orthogonal amino acid.

In some embodiments, the amino acid is a non-standard amino acid (nsAA). In some embodiments, the nsAA is an unnatural amino acid (uAA). In some embodiments, a nsAA is a uAA. In some embodiments, the amino acid is an orthogonal amino acid. In some embodiments, the amino acid is a non-naturally occurring amino acid. In some embodiments, the amino acid is a man-made amino acid.

The term "unnatural amino acid" as used herein refers to any amino acid that is not genetically encoded for in an organism. The term "unnatural amino acid" as used herein refers to an amino acid that that is not inherently present within the organism. This refers to any amino acid other than the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. Examples of unnatural amino acids are common in the art.

Methods of generating mutations are well-described in the art and include, but are not limited to, site-directed mutagenesis, nucleotide excision, nucleotide addition, clustered regularly interspaced short palindromic repeats (CRISPR), transcription activator-like effector nuclease (TALEN), multiplexed automated genome engineering (MAGE) and polymerase chain reaction (PCR) with mutation generating primers or probes.

Aminoacyl-tRNA synthetase is a well-known protein that catalyzes the attachment of amino acids to the 3' end of their cognate tRNAs. In some embodiments, the aaRS is an archaeal aaRS. In some embodiments, the aaRS is a *Methanocaldococcus jannaschii* (Mj) protein. In some embodiments, the aaRS is a Mj aaRS. Mj is also known as *Methanococcus jannaschii*. In some embodiments, the aaRS recognizes a tRNA molecule. In some embodiments, the aaRS transfers an amino acid to the tRNA molecule. In some embodiments, the aaRS transfers an amino acid to the tRNA molecule. In some embodiments, the aaRS transfers an amino acid derived molecule to the tRNA molecule. In some embodiments, the aaRS is an orthogonal aaRS (o-aaRS). In some embodiments, the aaRS is a uAA-specific o-aaRS. As used herein the term "uAA-specific o-aaRS" refers to an orthogonal amino-acyl-tRNA synthetase that recognizes only the uAA and the tRNA of the system or cell of the invention.

In some embodiments, the amino acid derived molecule is a non-standard amino acid (nsAA). In some embodiments, the nsAA is an unnatural amino acid (uAA). In some embodiments, the uAA is a D amino acid or an L amino acid. In some embodiments, the uAA is a D amino acid. In some embodiments, the uAA is an L amino acid. In some embodiments, the uAA is an azide- or an alkyne-containing amino acid. In some embodiments, the uAA is an azide containing amino acid. In some embodiments, the uAA is an alkyne containing amino acid. In some embodiments, the uAA is an azobenzene-containing amino acid. In some embodiments, the uAA is a modified phenylalanine. In some embodiments, the modified phenylalanine is 4-propargyloxy-L-phenylalanine (pPR). In some embodiments, the modified phenylalanine is phenylalanine-4'-azobenzene (AzoPhe). In some embodiments, the azobenzene-containing amino acid is AzoPhe or tri-fluorinated azobenzene (Azo3F). In some embodiments, the azobenzene-containing amino acid is AzoPhe, Azo3F or tetra-ortho-fluorinated azobenzene (Azo4F). In some embodiments, the azobenzene-containing amino acid is AzoPhe. In some embodiments, the azobenzene-containing amino acid is Azo3F. In some embodiments, the azobenzene-containing amino acid is Azo4F. In some embodiments, the aaRS transfers 4-propargyloxy-L-phenylalanine (pPR) to the tRNA molecule. In some embodiments, the aaRS transfers phenylalanine-4'-azobenzene (AzoPhe), tri-fluorinated azobenzene (Azo3F) or tetra-ortho-fluorinated azobenzene (Azo4F) to the tRNA molecule. In some embodiments, the aaRS transfers phenylalanine-4'-azobenzene (AzoPhe) to the tRNA molecule. In some embodiments, the aaRS transfers tri-fluorinated azobenzene (Azo3F) to the tRNA molecule. In some embodiments, the aaRS transfers tetra-ortho-fluorinated azobenzene (Azo4F) to the tRNA molecule.

In some embodiments, the tRNA molecule is an orthogonal tRNA (o-tRNA). In some embodiments, the tRNA molecule comprises a stop anticodon. In some embodiments the tRNA molecule comprises an amber anticodon. In some embodiments, the aaRS does not recognize a canonical tRNA in a cell. In some embodiments, the canonical tRNA comprises an anticodon with complementarity to a tyrosine codon. In some embodiments, the cell is a target cell. In some embodiments, the cell is a cell comprising the mutant aaRs. In some embodiments, the cell is a bacterial cell. In some embodiments, the cell is an *Escherichia coli* cell. In some embodiments, the cell is selected from a bacterium, an *Escherichia coli* cell, a eukaryotic cell, a yeast cell. a fungal cell, a plant cell, an animal cell.

The term "orthogonal" as used herein refers to molecules (e.g., "orthogonal tRNA synthetase" and "orthogonal tRNA" pairs) that can process information in parallel with wild-type molecules (e.g., tRNA synthetases and tRNAs), but that do not engage in crosstalk with the wild-type molecules of a cell. As a non-limiting example, the orthogonal tRNA synthetase preferentially aminoacylates a complementary orthogonal tRNA (O-tRNA), but no other cellular tRNAs, with a non-canonical amino acid (e.g., Propargyl-l-Lysine), and the orthogonal tRNA is a substrate for the orthogonal synthetase but is not substantially aminoacylated by any endogenous tRNA synthetases. In some embodiments, orthogonal is with respect to a target cell. In some embodiments, the target cell is a cell of the invention.

In the context of tRNAs and aminoacyl-tRNA synthetases, the term "orthogonal" refers to an inability or reduced efficiency, e.g., less than 20% efficiency, less than 10% efficiency, less than 5% efficiency, or less than 1% efficiency, of an O-tRNA to function with an endogenous tRNA synthetase (RS) compared to an endogenous tRNA to function with the endogenous tRNA synthetase, or of O-tRNA synthetase (O-RS) to function with an endogenous tRNA compared to an endogenous tRNA synthetase to function with the endogenous tRNA. For a non-limiting example, an O-tRNA in a cell is aminoacylated by any endogenous RS of the cell with reduced or even zero efficiency, when compared to aminoacylation of an endogenous tRNA by the endogenous RS. In another non-limiting example, an O-tRNA synthetase aminoacylates any endogenous tRNA a cell of interest with reduced or even zero efficiency, as compared to aminoacylation of the endogenous tRNA by an endogenous RS.

In some embodiments, the O-tRNA anticodon loop recognizes a codon, which is not recognized by endogenous tRNAs, on the mRNA and incorporates the UAA at this site in the polypeptide, details of which are further described, for example, in U.S. Pat. No. 2006/0160175, which is hereby incorporated by reference in its entirety. For a non-limiting example, the unique codon may include nonsense codons, such as, stop codons, four or more base codons, rare codons, codons derived from natural or unnatural base pairs and/or the like. In some embodiments, the unique codon is the TAG stop codon.

As used herein, aaRS recognition of a tRNA molecule refers to the association of an aaRS with a specific tRNA molecule including but not limited to contact at the anticodon or the acceptor stem of the tRNA molecule. As used herein, transfer to a tRNA molecule, refers to the process by which an amino acid or an amino acid derived molecule is associated with an aaRS or a mutant aaRS and moved onto the 3'-hydroxyl group on the CCA tail of the tRNA molecule. The process is also referred to in the art as "charging the tRNA molecule".

As used herein, the term "canonical" describes an endogenous molecule that is present in a cell without any transgenic manipulation to the cell or to the progenitors of the cell.

In some embodiments, the aaRS into which the mutation is introduced comprises or consists of the amino acid sequence

```
                                      (SEQ ID NO: 1)
MDEFEMIKRNTSEIISEEELREVLKKDEKSAYIGFEPSGKIHLGHYLQIK

KMIDLQNAGFDIIILLADLHAYLNQKGELDEIRKIGDYNKKVFEAMGLKA

KYVYGSEFQLDKDYTLNVYRLALKTTLKRARRSMELIAREDENPKVAEVI

YPIMQVNDIHYLGVDVAVGGMEQRKIHMLARELLPKKVVCIHNPVLTGLD

GEGKMSSSKGNFIAVDDSPEEIRAKIKKAYCPAGVVEGNPIMEIAKYFLE

YPLTIKRPEKFGGDLTVNSYEELESLFKNKELHPMDLKNAVAEELIKILE

PIRKRL
```

or a sequence with at least 95% identity thereto. In some embodiments, an amino acid sequence of Mj aaRS consists of SEQ ID NO: 1. In some embodiments, an amino acid sequence of wild-type aaRS comprises or consists of SEQ ID NO: 1 or a sequence with 95% identity thereto. In some embodiments, an amino acid sequence of aaRS comprises or consists of SEQ ID NO: 1 or a sequence with 95% identity thereto. In some embodiments, the an amino acid sequence of a non-mutant aaRS comprises or consists of SEQ ID NO: 1 or a sequence with 95% identity thereto. In some embodiments, the amino acid numbering provided herein is with respect to the sequence of SEQ ID NO: 1. In some embodiments, SEQ ID NO:1 comprises a wildtype sequence for an aaRS and the isolated peptide is a mutant aaRS.

In some embodiments, the mutation is selected from the group consisting of: tyrosine 32 mutated to leucine, tyrosine 32 mutated to threonine; leucine 65 mutated to valine; glutamic acid 107 mutated to alanine; phenylalanine 108 mutated to tyrosine; glutamine 109 mutated to methionine; aspartic acid 158 mutated to serine; aspartic acid 158 mutated to glycine; isoleucine 159 mutated to alanine; isoleucine 159 mutated to methionine; isoleucine 159 mutated to cysteine; isoleucine 159 mutated to tyrosine; leucine 162 mutated to glutamic acid; leucine 162 mutated to lysine; leucine 162 mutated to valine; leucine 162 mutated to arginine; leucine 162 mutated to serine; leucine 162 mutated to cysteine; alanine 167 mutated to histidine, alanine 167 mutated to aspartic acid and alanine 167 mutated to tyrosine.

In some embodiments the mutation is tyrosine 32 mutated to leucine, or threonine. In some embodiments the mutation is tyrosine 32 mutated to leucine. In some embodiments the mutation is tyrosine 32 mutated to threonine. In some embodiments the mutation is leucine 65 mutated to valine. In some embodiments, the mutation is glutamic acid 107 mutated to alanine. In some embodiments, the mutation is phenylalanine 108 mutated to tyrosine. In some embodiments, the mutation is glutamine 109 mutated to methionine. In some embodiments, the mutation is aspartic acid 158 mutated to serine, or glycine. In some embodiments, the mutation is aspartic acid 158 mutated to serine. In some embodiments, the mutation is aspartic acid 158 mutated to glycine. In some embodiments, the mutation is isoleucine 159 mutated to alanine, methionine, cysteine, or tyrosine. In some embodiments, the mutation is isoleucine 159 mutated to alanine. In some embodiments, the mutation is isoleucine 159 mutated to methionine. In some embodiments, the mutation is isoleucine 159 mutated to cysteine. In some embodiments, the mutation is isoleucine 159 mutated to tyrosine. In some embodiments, the mutation is leucine 162 mutated to glutamic acid, lysine, valine, arginine, serine or cysteine. In some embodiments, the mutation is leucine 162 mutated to glutamic acid. In some embodiments, the mutation is leucine 162 mutated to lysine. In some embodiments, the mutation is leucine 162 mutated to valine. In some embodiments, the mutation is leucine 162 mutated to arginine. In some embodiments, the mutation is leucine 162 mutated to serine. In some embodiments, the mutation is leucine 162 mutated to cysteine. In some embodiments, the mutation is alanine 167 mutated to histidine, aspartic acid or tyrosine. In some embodiments, the mutation is alanine 167 mutated to histidine. In some embodiments, the mutation is alanine 167 mutated to aspartic acid. In some embodiments, the mutation is alanine 167 mutated to tyrosine. It will be understood by a skilled artisan that any combination of the above recited mutations is envisioned and may be present in the mutant aaRS of the invention.

In some embodiments, the mutation is selected from the group consisting of: tyrosine 32 mutated to leucine, tyrosine 32 mutated to glycine; leucine 65 mutated to valine; leucine 65 mutated to glycine; glutamic acid 107 mutated to serine; glutamic acid 107 mutated to asparagine; glutamic acid 107 mutated to aspartic acid; phenylalanine 108 mutated to valine; phenylalanine 108 mutated to arginine; glutamine 109 mutated to methionine; glutamine 109 mutated to serine; glutamine 109 mutated to leucine; and glutamine 109 mutated to cysteine; aspartic acid 158 mutated to glycine; isoleucine 159 mutated to tyrosine; leucine 162 mutated to serine; leucine 162 mutated to arginine; and alanine 167 mutated to phenylalanine.

In some embodiments, the mutation is selected from the group consisting of: tyrosine 32 mutated to leucine, tyrosine 32 mutated to threonine; tyrosine 32 mutated to glycine; leucine 65 mutated to valine; leucine 65 mutated to glycine; glutamic acid 107 mutated to alanine; glutamic acid 107 mutated to serine; glutamic acid 107 mutated to asparagine; glutamic acid 107 mutated to aspartic acid; phenylalanine 108 mutated to tyrosine; phenylalanine 108 mutated to valine; phenylalanine 108 mutated to arginine; glutamine 109 mutated to methionine; glutamine 109 mutated to serine; glutamine 109 mutated to leucine; and glutamine 109 mutated to cysteine; aspartic acid 158 mutated to serine; aspartic acid 158 mutated to glycine; isoleucine 159 mutated to alanine; isoleucine 159 mutated to methionine; isoleucine 159 mutated to cysteine; isoleucine 159 mutated to tyrosine; leucine 162 mutated to glutamic acid; leucine 162 mutated to lysine; leucine 162 mutated to valine; leucine 162 mutated to arginine; leucine 162 mutated to serine; leucine 162 mutated to cysteine; alanine 167 mutated to histidine, alanine 167 mutated to aspartic acid, alanine 167 mutated to phenylalanine and alanine 167 mutated to tyrosine.

In some embodiments, the mutation is tyrosine 32 mutated to leucine or glycine. In some embodiments, the mutation is tyrosine 32 mutated to leucine. In some embodiments, the mutation is tyrosine 32 mutated to glycine. In some embodiments, the mutation is leucine 65 mutated to valine or glycine. In some embodiments, the mutation is leucine 65 mutated to valine. In some embodiments, the mutation is leucine 65 mutated to glycine. In some embodiments, the mutation is glutamic acid 107 mutated to serine, asparagine or aspartic acid. In some embodiments, the mutation is glutamic acid 107 mutated to serine. In some embodiments, the mutation is glutamic acid 107 mutated to asparagine. In some embodiments, the mutation is glutamic acid 107 mutated to aspartic acid. In some embodiments, the mutation is phenylalanine 108 mutated to arginine. In some embodiments, the mutation is glutamine 109 mutated to methionine, serine, leucine or cysteine. In some embodiments, the mutation is glutamine 109 mutated to methionine. In some embodiments, the mutation is glutamine 109 mutated to serine. In some embodiments, the mutation is glutamine 109 mutated to leucine. In some embodiments, the mutation is glutamine 109 mutated to cysteine. In some embodiments, the mutation is aspartic acid 158 mutated to glycine. In some embodiments, the mutation is isoleucine 159 mutated to tyrosine. In some embodiments, the mutation is leucine 162 mutated to serine or arginine. In some embodiments, the mutation is leucine 162 mutated to serine. In some embodiments, the mutation is leucine 162 mutated to arginine. In some embodiments, the mutation is alanine 167 mutated to phenylalanine.

In some embodiments, the mutant aaRS comprises aspartic acid 158 mutated to glycine, and isoleucine 159 mutated to tyrosine. In some embodiments, the mutant aaRS comprises aspartic acid 158 mutated to glycine, isoleucine 159 mutated to tyrosine and leucine 162 mutated to serine or arginine. In some embodiments, the mutant aaRS comprises aspartic acid 158 mutated to glycine, isoleucine 159 mutated to tyrosine and leucine 162 mutated to serine. In some embodiments, the mutant aaRS comprises aspartic acid 158 mutated to glycine, isoleucine 159 mutated to tyrosine and leucine 162 mutated to arginine.

In some embodiments, the mutant aaRS comprises aspartic acid 158 mutated to glycine, isoleucine 159 mutated to tyrosine, leucine 162 mutated to serine or arginine, and alanine 167 mutated to phenylalanine. In some embodiments, the mutant aaRS comprises aspartic acid 158 mutated to glycine, isoleucine 159 mutated to tyrosine, leucine 162 mutated to serine or arginine, and tyrosine 32 mutated to leucine or glycine. In some embodiments, the mutant aaRS comprises aspartic acid 158 mutated to glycine, isoleucine 159 mutated to tyrosine, leucine 162 mutated to serine or arginine, and tyrosine 32 mutated to leucine. In some embodiments, the mutant aaRS comprises aspartic acid 158 mutated to glycine, isoleucine 159 mutated to tyrosine, leucine 162 mutated to serine or arginine, and tyrosine 32 mutated to glycine. In some embodiments, the mutant aaRS comprises aspartic acid 158 mutated to glycine, isoleucine 159 mutated to tyrosine, leucine 162 mutated to serine or arginine, and leucine 65 mutated to valine or glycine. In some embodiments, the mutant aaRS comprises aspartic acid 158 mutated to glycine, isoleucine 159 mutated to tyrosine, leucine 162 mutated to serine or arginine, and leucine 65 mutated to valine. In some embodiments, the mutant aaRS comprises aspartic acid 158 mutated to glycine, isoleucine 159 mutated to tyrosine, leucine 162 mutated to serine or arginine, and leucine 65 mutated to glycine.

In some embodiments, the mutant aaRS comprises aspartic acid 158 mutated to glycine, isoleucine 159 mutated to tyrosine, leucine 162 mutated to serine or arginine, alanine 167 mutated to phenylalanine, and tyrosine 32 mutated to leucine or glycine. In some embodiments, the mutant aaRS comprises aspartic acid 158 mutated to glycine, isoleucine 159 mutated to tyrosine, leucine 162 mutated to serine or arginine, alanine 167 mutated to phenylalanine, and tyrosine 32 mutated to leucine. In some embodiments, the mutant aaRS comprises aspartic acid 158 mutated to glycine, isoleucine mutated to tyrosine, leucine 162 mutated to serine or arginine, alanine 167 mutated to phenylalanine, and tyrosine 32 mutated to glycine. In some embodiments, the mutant aaRS comprises aspartic acid 158 mutated to glycine, isoleucine mutated to tyrosine, leucine 162 mutated to serine or arginine, alanine 167 mutated to phenylalanine, and leucine 65 mutated to valine or glycine. In some embodiments, the mutant aaRS comprises aspartic acid 158 mutated to glycine, isoleucine mutated to tyrosine, leucine 162 mutated to serine or arginine, alanine 167 mutated to phenylalanine, and leucine 65 mutated to valine. In some embodiments, the mutant aaRS comprises aspartic acid 158 mutated to glycine, isoleucine mutated to tyrosine, leucine 162 mutated to serine or arginine, alanine 167 mutated to phenylalanine, and leucine 65 mutated to glycine. In some embodiments, the mutant aaRS comprises aspartic acid 158 mutated to glycine, isoleucine 159 mutated to tyrosine, leucine 162 mutated to serine or arginine, tyrosine 32 mutated to leucine or glycine and leucine 65 mutated to valine or glycine. In some embodiments, the mutant aaRS comprises aspartic acid 158 mutated to glycine, isoleucine 159 mutated to tyrosine, leucine 162 mutated to serine or arginine, tyrosine 32 mutated to leucine or glycine and leucine 65 mutated to valine. In some embodiments, the mutant aaRS comprises aspartic acid 158 mutated to glycine, isoleucine 159 mutated to tyrosine, leucine 162 mutated to serine or arginine, tyrosine 32 mutated to leucine or glycine and leucine 65 mutated to glycine. In some embodiments, the mutant aaRS comprises aspartic acid 158 mutated to glycine, isoleucine 159 mutated to tyrosine, leucine 162 mutated to serine or arginine, tyrosine 32 mutated to leucine and leucine 65 mutated to valine or glycine. In some embodiments, the mutant aaRS comprises aspartic acid 158 mutated to glycine, isoleucine 159 mutated to tyrosine, leucine 162 mutated to serine or arginine, tyrosine 32 mutated to glycine and leucine 65 mutated to valine or glycine. In some embodiments, the mutant aaRS comprises aspartic acid 158 mutated to glycine, isoleucine 159 mutated to tyrosine, leucine 162 mutated to serine or arginine, tyrosine 32 mutated to leucine and leucine 65 mutated to valine. In some embodiments, the mutant aaRS comprises aspartic acid 158 mutated to glycine, isoleucine 159 mutated to tyrosine, leucine 162 mutated to serine or arginine, tyrosine 32 mutated to leucine and leucine 65 mutated to glycine. In some embodiments, the mutant aaRS comprises aspartic acid 158 mutated to glycine, isoleucine 159 mutated to tyrosine, leucine 162 mutated to serine or arginine, tyrosine 32 mutated to glycine and leucine 65 mutated to valine. In some embodiments, the mutant aaRS comprises aspartic acid 158 mutated to glycine, isoleucine 159 mutated to tyrosine, leucine 162 mutated to serine or arginine, tyrosine 32 mutated to glycine and leucine 65 mutated to glycine.

In some embodiments, the aaRS further comprises mutation of arginine 257 to glycine, mutation of aspartic acid 286 to arginine, or both. In some embodiments, the aaRS further comprises mutation of arginine 257 to glycine. In some embodiments, the aaRS further comprises mutation of aspartic acid 286 to arginine. In some embodiments, the aaRS further comprises mutation of both arginine 257 to glycine and aspartic acid 286 to arginine. In some embodiments, SEQ ID NO:1 further comprises these two known mutations. In some embodiments, the sequence into which the mutations of the invention are introduced comprises or consists of (SEQ ID NO: 28)

MDEFEMIKRNTSEIISEEELREVLKKDEKSAYIGFEPSGKIHLGHYLQIK

KMIDLQNAGFDIIILLADLHAYLNQKGELDEIRKIGDYNKKVFEAMGLKA

KYVYGSEFQLDKDYTLNVYRLALKTTLKRARRSMELIAREDENPKVAEVI

YPIMQVNDIHYLGVDVAVGGMEQRKIHMLARELLPKKVVCIHNPVLTGLD

GEGKMSSSKGNFIAVDDSPEEIRAKIKKAYCPAGVVEGNPIMEIAKYFLE

YPLTIKGPEKFGGDLTVNSYEELESLFKNKELHPMRLKNAVAEELIKILE

PIRKRL or a sequence with 95% identity thereto. In some embodiments, the sequence into which the mutations of the invention are introduced consists of SEQ ID NO: 28.

In some embodiments, the mutant aaRS comprises tyrosine 32 mutated to leucine, aspartic acid 158 mutated to serine, isoleucine 159 mutated to methionine, leucine 162 mutated to lysine, alanine 167 mutated to histidine, arginine 257 mutated to glycine, and aspartic acid 286 mutated to arginine. In some embodiments, the mutant aaRS comprises or consists of the amino acid sequence (SEQ ID NO: 2)

MDEFEMIKRNTSEIISEEELREVLKKDEKSALIGFEPSGKIHLGHYLQIK

KMIDLQNAGFDIIILLADLHAYLNQKGELDEIRKIGDYNKKVFEAMGLKA

KYVYGSEFQLDKDYTLNVYRLALKTTLKRARRSMELIAREDENPKVAEVI

YPIMQVNSMHYKGVDVHVGGMEQRKIHMLARELLPKKVVCIHNPVLTGLD

GEGKMSSSKGNFIAVDDSPEEIRAKIKKAYCPAGVVEGNPIMEIAKYFLE

YPLTIKGPEKFGGDLTVNSYEELESLFKNKELHPMRLKNAVAEELIKILE

PIRKRL, or a fragment, a derivative or analog thereof. In some embodiments, the mutant aaRS comprises or consists of the amino acid sequence of SEQ ID NO: 2.

In some embodiments, the mutant aaRS comprises: tyrosine 32 mutated to leucine, leucine 65 mutated to valine, aspartic acid 158 mutated to glycine, isoleucine 159 mutated to alanine, leucine 162 mutated to glutamic acid, alanine 167 mutated to histidine, arginine 257 mutated to glycine, and aspartic acid 286 mutated to arginine. In some embodiments, the mutant aaRS comprises or consists of the amino acid sequence:

(SEQ ID NO: 3)

MDEFEMIKRNTSEIISEEELREVLKKDEKSALIGFEPSGKIHLGHYLQIK

KMIDLQNAGFDIIIVLADLHAYLNQKGELDEIRKIGDYNKKVFEAMGLKA

KYVYGSEFQLDKDYTLNVYRLALKTTLKRARRSMELIAREDENPKVAEVI

YPIMQVNGAHYEGVDVHVGGMEQRKIHMLARELLPKKVVCIHNPVLTGLD

GEGKMSSSKGNFIAVDDSPEEIRAKIKKAYCPAGVVEGNPIMEIAKYFLE

YPLTIKGPEKFGGDLTVNSYEELESLFKNKELHPMRLKNAVAEELIKILE

PIRKRL, or a fragment, a derivative or analog thereof. In some embodiments, the mutant aaRS comprises or consists of the amino acid sequence of SEQ ID NO: 3.

In some embodiments, the mutant aaRS comprises: tyrosine 32 mutated to threonine, leucine 65 mutated to valine, glutamic acid 107 mutated to alanine, phenylalanine 108 mutated to tyrosine, glutamine 109 mutated to methionine, aspartic acid 158 mutated to glycine, isoleucine 159 mutated to cysteine, leucine 162 mutated to arginine, alanine 167 mutated to aspartic acid, arginine 257 mutated to glycine and aspartic acid 286 mutated to arginine. In some embodiments, the mutant aaRS comprises or consists of the amino acid sequence:

(SEQ ID NO: 4)

MDEFEMIKRNTSEIISEEELREVLKKDEKSATIGFEPSGKIHLGHYLQIK

KMIDLQNAGFDIIIVLADLHAYLNQKGELDEIRKIGDYNKKVFEAMGLKA

KYVYGSAYMLDKDYTLNVYRLALKTTLKRARRSMELIAREDENPKVAEVI

YPIMQVNGCHYRGVDVDVGGMEQRKIHMLARELLPKKVVCIHNPVLTGLD

GEGKMSSSKGNFIAVDDSPEEIRAKIKKAYCPAGVVEGNPIMEIAKYFLE

YPLTIKGPEKFGGDLTVNSYEELESLFKNKELHPMRLKNAVAEELIKILE

PIRKRL, or a fragment, a derivative or analog thereof. In some embodiments, the mutant aaRS comprises or consists of the amino acid sequence of SEQ ID NO: 4.

In some embodiments, the mutant aaRS comprises: tyrosine 32 mutated to leucine, leucine 65 mutated to valine, aspartic acid 158 mutated to glycine, isoleucine 159 mutated to methionine; leucine 162 mutated to serine, alanine 167 mutated to histidine, arginine 257 mutated to glycine and aspartic acid 286 mutated to arginine. In some embodiments, the mutant aaRS comprises or consists of the amino acid sequence:

(SEQ ID NO: 5)

MDEFEMIKRNTSEIISEEELREVLKKDEKSALIGFEPSGKIHLGHYLQ

IKKMIDLQNAGFDIIIVLADLHAYLNQKGELDEIRKIGDYNKKVFEAM

GLKAKYVYGSEFQLDKDYTLNVYRLALKTTLKRARRSMELIAREDENP

KVAEVIYPIMQVNGMHYSGVDVHVGGMEQRKIHMLARELLPKKVVCIH

NPVLTGLDGEGKMSSSKGNFIAVDDSPEEIRAKIKKAYCPAGVVEGNP

IMEIAKYFLEYPLTIKGPEKFGGDLTVNSYEELESLFKNKELHPMRLK

NAVAEELIKILEPIRKRL, or a fragment, a derivative or analog thereof. In some embodiments, the mutant aaRS comprises or consists of the amino acid sequence of SEQ ID NO: 5.

In some embodiments, the mutant aaRS comprises: tyrosine 32 mutated to leucine, leucine 65 mutated to valine, aspartic acid 158 mutated to glycine, isoleucine 159 mutated to tyrosine, leucine 162 mutated to cysteine, alanine 167 mutated to tyrosine, arginine 257 mutated to glycine, and aspartic acid 286 mutated to arginine. In some embodiments, the mutant aaRS comprises or consists of the amino acid sequence:

(SEQ ID NO: 6)

MDEFEMIKRNTSEIISEEELREVLKKDEKSALIGFEPSGKIHLGHYLQ

IKKMIDLQNAGFDIIIVLADLHAYLNQKGELDEIRKIGDYNKKVFEAM

GLKAKYVYGSEFQLDKDYTLNVYRLALKTTLKRARRSMELIAREDENP

KVAEVIYPIMQVNGYHYCGVDVYVGGMEQRKIHMLARELLPKKVVCIH

-continued

```
NPVLTGLDGEGKMSSSKGNFIAVDDSPEEIRAKIKKAYCPAGVVEGNP

IMEIAKYFLEYPLTIKGPEKFGGDLTVNSYEELESLFKNKELHPMRLK

NAVAEELIKILEPIRKRL,
```

or a fragment, a derivative or an analog thereof. In some embodiments, the mutant aaRS comprises or consists of the amino acid sequence of SEQ ID NO: 6.

In some embodiments, the mutant aaRS comprises: tyrosine 32 mutated to leucine, lysine 65 mutated to valine; aspartic acid 158 mutated to glycine; isoleucine 159 mutated to tyrosine; leucine 162 mutated to serine; and alanine 167 mutated to phenylalanine. In some embodiments, the mutant aaRS comprises or consists of the amino acid sequence:

```
                                    (SEQ ID NO: 12)
MDEFEMIKRNTSEIISEEELREVLKKDEKSALIGFEPSGKIHLGHYLQ

IKKMIDLQNAGFDIIIVLADLHAYLNQKGELDEIRKIGDYNKKVFEAM

GLKAKYVYGSEFQLDKDYTLNVYRLALKTTLKRARRSMELIAREDENP

KVAEVIYPIMQVNGYHYSGVDVFVGGMEQRKIHMLARELLPKKVVCIH

NPVLTGLDGEGKMSSSKGNFIAVDDSPEEIRAKIKKAYCPAGVVEGNP

IMEIAKYFLEYPLTIKGPEKFGGDLTVNSYEELESLFKNKELHPMRLK

NAVAEELIKILEPIRKRL
```

or a fragment, a derivative or an analog thereof. In some embodiments, the mutant aaRS comprises or consists of the amino acid sequence of SEQ ID NO: 12.

In some embodiments, the mutant aaRS comprises: tyrosine 32 mutated to glycine, lysine 65 mutated to valine; aspartic acid 158 mutated to glycine; isoleucine 159 mutated to tyrosine; leucine 162 mutated to serine; and alanine 167 mutated to phenylalanine. In some embodiments, the mutant aaRS comprises or consists of the amino acid sequence:

```
                                    (SEQ ID NO: 13)
MDEFEMIKRNTSEIISEEELREVLKKDEKSAGIGFEPSGKIHLGHYLQ

IKKMIDLQNAGFDIIIVLADLHAYLNQKGELDEIRKIGDYNKKVFEAM

GLKAKYVYGSEFQLDKDYTLNVYRLALKTTLKRARRSMELIAREDENP

KVAEVIYPIMQVNGYHYSGVDVFVGGMEQRKIHMLARELLPKKVVCIH

NPVLTGLDGEGKMSSSKGNFIAVDDSPEEIRAKIKKAYCPAGVVEGNP

IMEIAKYFLEYPLTIKGPEKFGGDLTVNSYEELESLFKNKELHPMRLK

NAVAEELIKILEPIRKRL
```

or a fragment, a derivative or an analog thereof. In some embodiments, the mutant aaRS comprises or consists of the amino acid sequence of SEQ ID NO: 13.

In some embodiments, the mutant aaRS comprises: tyrosine 32 mutated to leucine, lysine 65 mutated to valine; glutamic acid 107 mutated to serine, phenylalanine 108 mutated to valine, glutamine 109 mutated to serine; aspartic acid 158 mutated to glycine; isoleucine 159 mutated to tyrosine; leucine 162 mutated to serine; and alanine 167 mutated to phenylalanine. In some embodiments, the mutant aaRS comprises or consists of the amino acid sequence:

```
                                    (SEQ ID NO: 14)
MDEFEMIKRNTSEIISEEKLREVLKKDEKSALIGFEPSGKIHLGHYLQ

IKKMIDLQNAGFDIIIVLADLHAYLNQKGELDEIRKIGDYNKKVFEAM

GLKAKYVYGSSVSLDKDYTLNVYRLALKTTLKRARRSMELIAREDENP

KVAEVIYPIMQVNGYHYSGVDVFVGGMEQRKIHMLARELLPKKVVCIH

NPVLTGLDGEGKMSSSKGNFIAVDDSPEEIRAKIKKAYCPAGVVEGNP

IMEIAKYFLEYPLTIKGPEKFGGDLTVNSYEELESLFKNKELHPMRLK

NAVAEELIKILEPIRKRL
```

or a fragment, a derivative or an analog thereof. In some embodiments, the mutant aaRS comprises or consists of the amino acid sequence of SEQ ID NO: 14.

In some embodiments, the mutant aaRS comprises: tyrosine 32 mutated to leucine, lysine 65 mutated to valine; glutamic acid 107 mutated to asparagine, phenylalanine 108 mutated to valine, glutamine 109 mutated to leucine; aspartic acid 158 mutated to glycine; isoleucine 159 mutated to tyrosine; leucine 162 mutated to serine; and alanine 167 mutated to phenylalanine. In some embodiments, the mutant aaRS comprises or consists of the amino acid sequence:

```
                                    (SEQ ID NO: 15)
MDEFEMIKRNTSEIISEEELREVLKKDEKSALIGFEPSGKIHLGHYLQ

IKKMIDLQNAGFDIIIVLADLHAYLNQKGELDEIRKIGDYNKKVFEAM

GLKAKYVYGSNVLLDKDYTLNVYRLALKTTLKRARRSMELIAREDENP

KVAEVIYPIMQVNGYHYSGVDVFVGGMEQRKIHMLARELLPKKVVCIH

NPVLTGLDGEGKMSSSKGNFIAVDDSPEEIRAKIKKAYCPAGVVEGNP

IMEIAKYFLEYPLTIKGPEKFGGDLTVNSYEELESLFKNKELHPMRLK

NAVAEELIKILEPIRKRL
```

or a fragment, a derivative or an analog thereof. In some embodiments, the mutant aaRS comprises or consists of the amino acid sequence of SEQ ID NO: 15.

In some embodiments, the mutant aaRS comprises: tyrosine 32 mutated to leucine, lysine 65 mutated to valine; glutamic acid 107 mutated to aspartic acid, aspartic acid 158 mutated to glycine; isoleucine 159 mutated to tyrosine; leucine 162 mutated to serine; and alanine 167 mutated to phenylalanine. In some embodiments, the mutant aaRS comprises or consists of the amino acid sequence:

```
                                    (SEQ ID NO: 16)
MDEFEMIKRNTSEIISEEELREVLKKDEKSALIGFEPSGKIHLGHYLQ

IKKMIDLQNAGFDIIIVLADLHAYLNQKGELDEIRKIGDYNKKVFEAM

GLKAKYVYGSDFQLDKDYTLNVYRLALKTTLKRARRSMELIAREDENP

KVAEVIYPIMQVNGYHYSGVDVFVGGMEQRKIHMLARELLPKKVVCIH

NPVLTGLDGEGKMSSSKGNFIAVDDSPEEIRAKIKKAYCPAGVVEGNP

IMEIAKYFLEYPLTIKGPEKFGGDLTVNSYEELESLFKNKELHPMRLK

NAVAEELIKILEPIRKRL
```

or a fragment, a derivative or an analog thereof. In some embodiments, the mutant aaRS comprises or consists of the amino acid sequence of SEQ ID NO: 16.

In some embodiments, the mutant aaRS comprises: tyrosine 32 mutated to leucine, lysine 65 mutated to valine; glutamic acid 107 mutated to serine, phenylalanine 108 mutated to valine, glutamine 109 mutated to cysteine; aspartic acid 158 mutated to glycine; isoleucine 159 mutated to tyrosine; leucine 162 mutated to serine; and alanine 167 mutated to phenylalanine. In some embodiments, the mutant aaRS comprises or consists of the amino acid sequence:

(SEQ ID NO: 17)
MDEFEMIKRNTSEIISEEELREVLKKDEKSALIGFEPSGKIHLGHYLQ

IKKMIDLQNAGFDIIIVLADLHAYLNQKGELDEIRKIGDYNKKVFEAM

GLKAKYVYGSSVCLDKDYTLNVYRLALKTTLKRARRSMELIAREDENP

KVAEVIYPIMQVNGYHYSGVDVFVGGMEQRKIHMLARELLPKKVVCIH

NPVLTGLDGEGKMSSSKGNFIAVDDSPEEIRAKIKKAYCPAGVVEGNP

IMEIAKYFLEYPLTIKGPEKFGGDLTVNSYEELESLFKNKELHPMRLK

NAVAEELIKILEPIRKRL or a fragment, a derivative or an analog thereof. In some embodiments, the mutant aaRS comprises or consists of the amino acid sequence of SEQ ID NO: 17.

In some embodiments, the mutant aaRS comprises: tyrosine 32 mutated to glycine, lysine 65 mutated to valine; aspartic acid 158 mutated to glycine; isoleucine 159 mutated to tyrosine; and leucine 162 mutated to arginine. In some embodiments, the mutant aaRS comprises or consists of the amino acid sequence:

(SEQ ID NO: 18)
MDEFEMIKRNTSEIISEEELREVLKKDEKSAGIGFEPSGKIHLGHYLQ

IKKMIDLQNAGFDIIIVLADLHAYLNQKGELDEIRKIGDYNKKVFEAM

GLKAKYVYGSEFQLDKDYTLNVYRLALKTTLKRARRSMELIAREDENP

KVAEVIYPIMQVNGYHYRGVDVAVGGMEQRKIHMLARELLPKKVVCIH

NPVLTGLDGEGKMSSSKGNFIAVDDSPEEIRAKIKKAYCPAGVVEGNP

IMEIAKYFLEYPLTIKGPEKFGGDLTVNSYEELESLFKNKELHPMRLK

NAVAEELIKILEPIRKRL or a fragment, a derivative or an analog thereof. In some embodiments, the mutant aaRS comprises or consists of the amino acid sequence of SEQ ID NO: 18.

In some embodiments, the mutant aaRS comprises: tyrosine 32 mutated to leucine, lysine 65 mutated to glycine; glutamic acid 107 mutated to aspartic acid, phenylalanine 108 mutated to arginine, glutamine 109 mutated to methionine; aspartic acid 158 mutated to glycine; isoleucine 159 mutated to tyrosine; leucine 162 mutated to serine; and alanine 167 mutated to phenylalanine. In some embodiments, the mutant aaRS comprises or consists of the amino acid sequence:

(SEQ ID NO: 19)
MDEFEMIKRNTSEIISEEELREVLKKDEKSALIGFEPSGKIHLGHYLQ

IKKMIDLQNAGFDIIIGLADLHAYLNQKGELDEIRKIGDYNKKVFEAM

GLKAKYVYGSDRMLDKDYTLNVYRLALKTTLKRARRSMELIAREDENP

KVAEVIYPIMQVNGYHYSGVDVFVGGMEQRKIHMLARELLPKKVVCIH

-continued

NPVLTGLDGEGKMSSSKGNFIAVDDSPEEIRAKIKKAYCPAGVVEGNP

IMEIAKYFLEYPLTIKGPEKFGGDLTVNSYEELESLFKNKELHPMRLK

NAVAEELIKILEPIRKRL or a fragment, a derivative or an analog thereof. In some embodiments, the mutant aaRS comprises or consists of the amino acid sequence of SEQ ID NO: 19.

In some embodiments, the fragment, derivative or analog comprises at least one of the recited mutations. In some embodiments, the fragment, derivative or analog is an active fragment, derivative or analog. In some embodiments, active refers to possessing an aaRS activity. In some embodiments, the aaRS activity is the ability to catalyzes the attachment of an amino acid to its cognate tRNA. In some embodiments, the aaRS activity is the ability to recognize an amino acid. In some embodiments, the aaRS activity is the ability to recognize a tRNA. In some embodiments, the aaRS activity is the ability to transfer an amino acid to a tRNA.

The term "derivative" as used herein, refers to any polypeptide that is based off the polypeptide of the invention and still comprises the recited mutations. A derivative is not merely a fragment of the polypeptide, nor does it need to have amino acids replaced or removed (an analog), rather it may have additional modification made to the polypeptide, such as post-translational modification. Further, a derivative may be a derivative of a fragment of the polypeptide of the invention. In some embodiments, a derivative of a sequence comprises at least 70, 75, 80, 85, 90, 92, 93, 95, 97, 99 or 100% identity to that sequence. Each possibility represents a separate embodiment of the invention. In some embodiments, a derivative of a sequence comprises at least 90% identity to that sequence. In some embodiments, a derivative of a sequence comprises at least 95% identity to that sequence. In some embodiments, a derivative of a sequence comprises at least 97% identity to that sequence. In some embodiments, a derivative of a sequence comprises at least 99% identity to that sequence.

In some embodiments, a fragment comprises at least 50, 100, 150, 200, or 250 amino acids of the aaRS. Each possibility represents a separate embodiment of the invention. In some embodiments, a fragment is a functional fragment. In some embodiments, a fragment comprises at least 50 amino acids of the aaRS. In some embodiments, a fragment comprises at least 100 amino acids of the aaRS.

In some embodiments, the fragment is a portion of the polypeptide comprises any one of a leucine at position 32, a threonine at position 32, a valine at position 65, an alanine at position 107, a tyrosine at position 108, a methionine at position 109, a serine at position 158, a glycine at position 158, an alanine at position 159, a methionine at position 159, a cysteine at position 159, a tyrosine at position 159, a glutamic acid at position 162, a lysine at position 162, a valine at position 162, an arginine at position 162, a serine at position 162, a cysteine at position 162, a histidine at position 167, an aspartic acid at position 167, and a tyrosine at position 167. Such a fragment will still be recognizable as being from the polypeptide of the invention, and as such will be at least 10 amino acids in length. As such, any fragment of the isolated polypeptide of the invention will still comprise at least 10, at least 20, at least 30, at least 40, at least 50, at least 80, or at least 100 amino acids surrounding position 32, position 65, position 107, position 108, position 109, position 158, position 159, position 162, or position 167 of the polypeptide. Each possibility represents a separate embodiment of the present invention.

In some embodiments, the fragment is a portion of the polypeptide comprises any one of a leucine at position 32, a glycine at position 32, a valine at position 65, a glycine at position 65, a serine at position 107, an asparagine at position 107, a aspartic acid at position 107, a valine at position 108, a arginine at position 108, a methionine at position 109, a serine at position 109, a leucine at position 109, a cysteine at position 109, a glycine at position 158, a tyrosine at position 159, a an alanine at position 162, a serine at position 162, and a phenylalanine at position 167. Such a fragment will still be recognizable as being from the polypeptide of the invention, and as such will be at least 10 amino acids in length. As such, any fragment of the isolated polypeptide of the invention will still comprise at least 10, at least 20, at least 30, at least 40, at least 50, at least 80, or at least 100 amino acids surrounding position 32, position 65, position 107, position 108, position 109, position 158, position 159, position 162, or position 167 of the polypeptide. Each possibility represents a separate embodiment of the present invention.

As used herein, the term "analog" includes any peptide having an amino acid sequence substantially identical to one of the sequences specifically shown herein in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. Each possibility represents a separate embodiment of the present invention.

In some embodiments, the mutant aaRS comprises or consists of an amino acid sequence selected from: SEQ ID NO: 2, SEQ ID NO: 3, SEQ ID NO: 4, SEQ ID NO: 5 and SEQ ID NO: 6. In some embodiments, the mutant aaRS comprises or consists of an amino acid sequence selected from: SEQ ID NO: 2, SEQ ID NO: 3, SEQ ID NO: 4, SEQ ID NO: 5 and SEQ ID NO: 6 or a fragment, analog or derivative thereof. In some embodiments, the mutant aaRS consists of an amino acid sequence selected from: SEQ ID NO: 2, SEQ ID NO: 3, SEQ ID NO: 4, SEQ ID NO: 5 and SEQ ID NO: 6. In some embodiments, the mutant aaRS consists of an amino acid sequence selected from: SEQ ID NO: 2, SEQ ID NO: 3, SEQ ID NO: 4, SEQ ID NO: 5 and SEQ ID NO: 6 or a fragment, analog or derivative thereof.

In some embodiments, the mutant aaRS comprises or consists of an amino acid sequence selected from: SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19. In some embodiments, the mutant aaRS comprises or consists of an amino acid sequence selected from: SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19 or a fragment, analog or derivative thereof. In some embodiments, the mutant aaRS consists of an amino acid sequence selected from: SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19. In some embodiments, the mutant aaRS consists of an amino acid sequence selected from: SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19 or a fragment, analog or derivative thereof.

By another aspect, the present invention provides an isolated polypeptide, comprising or consisting of an amino acid sequence selected from SEQ ID NO: 2, SEQ ID NO: 3, SEQ ID NO: 4, SEQ ID NO: 5 SEQ ID NO: 6, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19.

As used herein, the terms "peptide", "polypeptide" and "protein" are used interchangeably to refer to a polymer of amino acid residues. In some embodiment, the peptides, polypeptides and proteins described herein have modifications rendering them more stable while in the body, more capable of penetrating into cells or capable of eliciting a more potent effect than previously described. In some embodiment, the terms "peptide", "polypeptide" and "protein" apply to naturally occurring amino acid polymers. In another embodiment, the terms "peptide", "polypeptide" and "protein" apply to amino acid polymers in which one or more amino acid residue is an artificial chemical analogue of a corresponding naturally occurring amino acid.

As used herein, the term "isolated polypeptide" refers to a peptide that is essentially free from contaminating cellular components, such as carbohydrate, lipid, or other proteinaceous impurities associated with the peptide in nature. Typically, a preparation of isolated peptide contains the peptide in a highly-purified form, i.e., at least about 80% pure, at least about 90% pure, at least about 95% pure, greater than 95% pure, or greater than 99% pure. Each possibility represents a separate embodiment of the invention.

Nucleic Acid Molecules

In another aspect, there is provided a nucleic acid molecule encoding a mutant aaRS of the invention, or a fragment, a derivative or an analog thereof.

In another aspect, there is provided a nucleic acid molecule comprising a coding region encoding a mutant aaRS of the invention, or a fragment, a derivative or an analog thereof.

In some embodiments, the nucleic acid molecule encodes a mutant aaRS of the invention. In some embodiments, the nucleic acid molecule comprises a coding region encoding a mutant aaRS of the invention.

In some embodiments, the nucleic acid molecule is selected from DNA, RNA, cDNA, genomic DNA (gDNA), vector DNA, vector RNA, LNA, PNA and a combination thereof. In some embodiments, the nucleic acid molecule is DNA. In some embodiments, the nucleic acid molecule is RNA. In some embodiments, the nucleic acid molecule is cDNA. In some embodiments, the nucleic acid molecule is gDNA. In some embodiments, the nucleic acid molecule is LNA. In some embodiments, the nucleic acid molecule is PNA. In some embodiments, the nucleic acid molecule is a hybrid molecule comprising more than one type of nucleic acid.

As used herein, the phrases "coding sequence" and "coding region" are interchangeable and refer to the region that when translated results in the production of an expression product, such as a polypeptide, protein, or enzyme, and specifically the mutant aaRS. In some embodiments, the coding region is operably linked to at least one regulatory element. In some embodiments, the regulatory element is configured to express the coding region in a target cell. In some embodiments, the regulatory element is configured to express a protein encoded by the coding region in a target cell. In some embodiments, the regulatory element is a promoter. In some embodiments, the regulatory element is an enhancer. In some embodiments, the regulatory element is a silencer. The term "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). In some embodiments, expression of the coding region refers to a state in which mRNA is transcribed from the coding region acting as a template. In some embodiments, expression of the coding region refers to a state in which polypeptide is translated from the mRNA transcribed from the coding region.

The term "promoter" as used herein refers to a group of transcriptional control modules that are clustered around the initiation site for an RNA polymerase i.e., RNA polymerase II. Promoters are composed of discrete functional modules, each consisting of approximately 7-20 bp of DNA, and containing one or more recognition sites for transcriptional activator or repressor proteins. In some embodiments, nucleic acid sequences are transcribed by RNA polymerase II (RNAP II and Pol II). RNAP II is an enzyme found in eukaryotic cells. It catalyzes the transcription of DNA to synthesize precursors of mRNA and most snRNA and microRNA.

In some embodiments, the nucleic acid molecule is a vector. In some embodiments, the vector is a DNA vector. In some embodiments, the vector is an RNA vector. In some embodiments, the vector is an expression vector. In some embodiments, the expression vector is configured for expression in a bacterial cell. In some embodiments, the expression vector is configured for expression in a mammalian cell. In some embodiments, the expression vector is configured for expression in a target cell.

Expressing of a gene or protein within a cell is well known to one skilled in the art. It can be carried out by, among many methods, transfection, viral infection, or direct alteration of the cell's genome. In some embodiments, the gene is in an expression vector such as plasmid or viral vector.

In some embodiments, the vector is introduced into a cell by standard methods including electroporation (e.g., as described in From et al., Proc. Natl. Acad. Sci. USA 82, 5824 (1985)), Heat shock, infection by viral vectors, high velocity ballistic penetration by small particles with the nucleic acid either within the matrix of small beads or particles, or on the surface (Klein et al., Nature 327. 70-73 (1987)), and/or the like. A vector of the invention may be introduced into a target cell by any method known in the art, including but not limited to those provided herein. In some embodiments, the introducing produces a cell of the invention.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

A vector nucleic acid sequence generally contains at least an origin of replication for propagation in a cell and optionally additional elements, such as a heterologous polynucleotide sequence, expression control element (e.g., a promoter, enhancer), selectable marker (e.g., antibiotic resistance), poly-Adenine sequence.

The vector may be a DNA plasmid delivered via non-viral methods or via viral methods. The viral vector may be a retroviral vector, a herpesviral vector, an adenoviral vector, an adeno-associated viral vector or a poxviral vector. The promoters may be active in mammalian cells. The promoters may be a viral promoter.

In some embodiments, mammalian expression vectors include, but are not limited to, pcDNA3, pcDNA3.1 (±), pGL3, pZeoSV2(±), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors, which offer advantages such as lateral infection and targeting specificity, are used for in vivo expression. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

A person with skill in the art will appreciate that a gene or protein can also be expressed from a nucleic acid construct administered to the individual employing any suitable mode of administration, described hereinabove (i.e., in vivo gene therapy). In one embodiment, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex vivo gene therapy).

In some embodiments, a sequence of the nucleic acid molecule comprises or consists of the sequence:

```
                                          (SEQ ID NO: 7)
ATGGACGAATTTGAAATGATAAAGAGAAACACATCTGAAATTATCAGC

GAGGAAGAGTTAAGAGAGGTTTTAAAAAAAGATGAAAAATCTGCTCTG

ATAGGTTTTGAACCAAGTGGTAAAATACATTTAGGGCATTATCTCCAA

ATAAAAAAGATGATTGATTTACAAAATGCTGGATTTGATATAATTATA

TTGTTGGCTGATTTACACGCCTATTTAAACCAGAAAGGAGAGTTGGAT

GAGATTAGAAAAATAGGAGATTATAACAAAAAAGTTTTTGAAGCAATG

GGGTTAAAGGCAAAATATGTTTATGGAAGTGAATTCCAGCTTGATAAG

GATTATACACTGAATGTCTATAGATTGGCTTTAAAAACTACCTTAAAA

AGAGCAAGAAGGAGTATGGAACTTATAGCAAGAGAGGATGAAAATCCA

AAGGTTGCTGAAGTTATCTATCCAATAATGCAGGTTAATTCTATGCAT

TATAAGGGCGTTGATGTTCATGTTGGAGGGATGGAGCAGAGAAAAATA

CACATGTTAGCAAGGGAGCTTTTACCAAAAAAGGTTGTTTGTATTCAC

AACCCTGTCTTAACGGGTTTGGATGGAGAAGGAAAGATGAGTTCTTCA

AAAGGGAATTTTATAGCTGTTGATGACTCTCCAGAAGAGATTAGGGCT

AAGATAAAGAAAGCATACTGCCCAGCTGGAGTTGTTGAAGGAAATCCA

ATAATGGAGATAGCTAAATACTTCCTTGAATATCCTTTAACCATAAAA

GGGCCAGAAAAATTTGGTGGAGATTTGACAGTTAATAGCTATGAGGAG

TTAGAGAGTTTATTTAAAAATAAGGAATTGCATCCAATGCGCTTAAAA

AATGCTGTAGCTGAAGAACTTATAAAGATTTTAGAGCCAATTAGAAAG

AGATTATA.
```

In some embodiments, the sequence of the nucleic acid molecule comprises SEQ ID NO: 7. In some embodiments, the coding region of the nucleic acid molecule comprises or consists of SEQ ID NO: 7. In some embodiments, the coding region of the nucleic acid molecule consists of SEQ ID NO: 7.

In some embodiments, a sequence of the nucleic acid molecule comprises or consists of the sequence:

```
                                          (SEQ ID NO: 8)
ATGGACGAATTTGAAATGATAAAGAGAAACACATCTGAAATTATCAGC

GAGGAAGAGTTAAGAGAGGTTTTAAAAAAAGATGAAAAATCTGCTCTG

ATAGGTTTTGAACCAAGTGGTAAAATACATTTAGGGCATTATCTCCAA

ATAAAAAAGATGATTGATTTACAAAATGCTGGATTTGATATAATTATA

GTTTTGGCTGATTTACACGCCTATTTAAACCAGAAAGGAGAGTTGGAT

GAGATTAGAAAAATAGGAGATTATAACAAAAAAGTTTTTGAAGCAATG

GGGTTAAAGGCAAAATATGTTTATGGAAGTGAATTCCAGCTTGATAAG

GATTATACACTGAATGTCTATAGATTGGCTTTAAAAACTACCTTAAAA

AGAGCAAGAAGGAGTATGGAACTTATAGCAAGAGAGGATGAAAATCCA

AAGGTTGCTGAAGTTATCTATCCAATAATGCAGGTTAATGGGGCTCAT

TATGAGGGCGTTGATGTTCATGTTGGAGGGATGGAGCAGAGAAAAATA

CACATGTTAGCAAGGGAGCTTTTACCAAAAAAGGTTGTTTGTATTCAC

AACCCTGTCTTAACGGGTTTGGATGGAGAAGGAAAGATGAGTTCTTCA

AAAGGGAATTTTATAGCTGTTGATGACTCTCCAGAAGAGATTAGGGCT

AAGATAAAGAAAGCATACTGCCCAGCTGGAGTTGTTGAAGGAAATCCA

ATAATGGAGATAGCTAAATACTTCCTTGAATATCCTTTAACCATAAAA

GGGCCAGAAAAATTTGGTGGAGATTTGACAGTTAATAGCTATGAGGAG

TTAGAGAGTTTATTTAAAAATAAGGAATTGCATCCAATGCGCTTAAAA

AATGCTGTAGCTGAAGAACTTATAAAGATTTTAGAGCCAATTAGAAAG

AGATTATA.
```

In some embodiments, the sequence of the nucleic acid molecule comprises SEQ ID NO: 8. In some embodiments, the coding region of the nucleic acid molecule comprises or consists of SEQ ID NO: 8. In some embodiments, the coding region of the nucleic acid molecule consists of SEQ ID NO: 8.

In some embodiments, a sequence of the nucleic acid molecule comprises or consists of the sequence:

```
                                          (SEQ ID NO: 9)
ATGGACGAATTTGAAATGATAAAGAGAAACACATCTGAAATTATCAGC

GAGGAAGAGTTAAGAGAGGTTTTAAAAAAAGATGAAAAATCTGCTACT

ATAGGGTTTGAACCAAGTGGTAAAATACATTTAGGGCATTATCTCCAA

ATAAAAAAGATGATTGATTTACAAAATGCTGGATTTGATATAATTATA

GTTTTGGCTGATTTACACGCCTATTTAAACCAGAAAGGAGAGTTGGAT

GAGATTAGAAAAATAGGAGATTATAACAAAAAAGTTTTTGAAGCAATG

GGGTTAAAGGCAAAATATGTTTATGGAAGTGCGTATATGCTTGATAAG

GATTATACACTGAATGTCTATAGATTGGCTTTAAAAACTACCTTAAAA

AGAGCAAGAAGGAGTATGGAACTTATAGCAAGAGAGGATGAAAATCCA

AAGGTTGCTGAAGTTATCTATCCCATAATGCAGGTTAATGGTTGTCAT

TATAGGGGCGTTGATGTTGATGTTGGAGGGATGGAGCAGAGAAAAATA

CACATGTTAGCAAGGGAGCTTTTACCAAAAAAGGTTGTTTGTATTCAC
```

-continued

AACCCTGTCTTAACGGGTTTGGATGGAGAAGGAAAGATGAGTTCTTCA

AAAGGGAATTTTATAGCTGTTGATGACTCTCCAGAAGAGATTAGGGCT

AAGATAAAGAAAGCATACTGCCCAGCTGGAGTTGTTGAAGGAAATCCA

ATAATGGAGATAGCTAAATACTTCCTTGAATATCCTTTAACCATAAAA

GGGCCAGAAAAAATTTGGTGGAGATTTGACAGTTAATAGCTATGAGGAG

TTAGAGAGTTTATTTAAAAATAAGGAATTGCATCCAATGCGCTTAAAA

AATGCTGTAGCTGAAGAACTTATAAAGATTTTAGAGCCAATTAGAAAG

AGATTATA.

In some embodiments, the sequence of the nucleic acid molecule comprises SEQ ID NO: 9. In some embodiments, the coding region of the nucleic acid molecule comprises or consists of SEQ ID NO: 9. In some embodiments, the coding region of the nucleic acid molecule consists of SEQ ID NO: 9.

In some embodiments, a sequence of the nucleic acid molecule comprises or consists of the sequence:

(SEQ ID NO: 10)

ATGGACGAATTTGAAATGATAAAGAGAAACACATCTGAAATTATCAGC

GAGGAAGAGTTAAGAGAGGTTTTAAAAAAAGATGAAAAATCTGCTCTG

ATAGGTTTTGAACCAAGTGGTAAAATACATTTAGGGCATTATCTCCAA

ATAAAAAAGATGATTGATTTACAAAATGCTGGATTTGATATAATTATA

GTTTTGGCTGATTTACACGCCTATTTAAACCAGAAAGGAGAGTTGGAT

GAGATTAGAAAAATAGGAGATTATAACAAAAAAGTTTTTGAAGCAATG

GGGTTAAAGGCAAAATATGTTTATGGAAGTGAATTCCAGCTTGATAAG

GATTATACACTGAATGTCTATAGATTGGCTTTAAAAACTACCTTAAAA

AGAGCAAGAAGGAGTATGGAACTTATAGCAAGAGAGGATGAAAATCCA

AAGGTTGCTGAAGTTATCTATCCAATAATGCAGGTTAATGGTATGCAT

TATTCGGGCGTTGATGTTCATGTTGGAGGGATGGAGCAGAGAAAAATA

CACATGTTAGCAAGGGAGCTTTTACCAAAAAAGGTTGTTTGTATTCAC

AACCCTGTCTTAACGGGTTTGGATGGAGAAGGAAAGATGAGTTCTTCA

AAAGGGAATTTTATAGCTGTTGATGACTCTCCAGAAGAGATTAGGGCT

AAGATAAAGAAAGCATACTGCCCAGCTGGAGTTGTTGAAGGAAATCCA

ATAATGGAGATAGCTAAATACTTCCTTGAATATCCTTTAACCATAAAA

GGGCCAGAAAAATTTGGTGGAGATTTGACAGTTAATAGCTATGAGGAG

TTAGAGAGTTTATTTAAAAATAAGGAATTGCATCCAATGCGCTTAAAA

AATGCTGTAGCTGAAGAACTTATAAAGATTTTAGAGCCAATTAGAAAG

AGATTATA.

In some embodiments, the sequence of the nucleic acid molecule comprises SEQ ID NO: 10. In some embodiments, the coding region of the nucleic acid molecule comprises or consists of SEQ ID NO: 10. In some embodiments, the coding region of the nucleic acid molecule consists of SEQ ID NO: 10.

In some embodiments, a sequence of the nucleic acid molecule comprises or consists of the sequence:

(SEQ ID NO: 11)

ATGGACGAATTTGAAATGATAAAGAGAAACACATCTGAAATTATCAGC

GAGGAAGAGTTAAGAGAGGTTTTAAAAAAAGATGAAAAATCTGCTCTG

ATAGGTTTTGAACCAAGTGGTAAAATACATTTAGGGCATTATCTCCAA

ATAAAAAAGATGATTGATTTACAAAATGCTGGATTTGATATAATTATA

GTTTTGGCTGATTTACACGCCTATTTAAACCAGAAAGGAGAGTTGGAT

GAGATTAGAAAAATAGGAGATTATAACAAAAAAGTTTTTGAAGCAATG

GGGTTAAAGGCAAAATATGTTTATGGAAGTGAATTCCAGCTTGATAAG

GATTATACACTGAATGTCTATAGATTGGCTTTAAAAACTACCTTAAAA

AGAGCAAGAAGGAGTATGGAACTTATAGCAAGAGAGGATGAAAATCCA

AAGGTTGCTGAAGTTATCTATCCAATAATGCAGGTTAATGGGTATCAT

TATTGTGGCGTTGATGTTTATGTTGGAGGGATGGAGCAGAGAAAAATA

CACATGTTAGCAAGGGAGCTTTTACCAAAAAAGGTTGTTTGTATTCAC

AACCCTGTCTTAACGGGTTTGGATGGAGAAGGAAAGATGAGTTCTTCA

AAAGGGAATTTTATAGCTGTTGATGACTCTCCAGAAGAGATTAGGGCT

AAGATAAAGAAAGCATACTGCCCAGCTGGAGTTGTTGAAGGAAATCCA

ATAATGGAGATAGCTAAATACTTCCTTGAATATCCTTTAACCATAAAA

GGGCCAGAAAAATTTGGTGGAGATTTGACAGTTAATAGCTATGAGGAG

TTAGAGAGTTTATTTAAAAATAAGGAATTGCATCCAATGCGCTTAAAA

AATGCTGTAGCTGAAGAACTTATAAAGATTTTAGAGCCAATTAGAAAG

AGATTATA.

In some embodiments, the sequence of the nucleic acid molecule comprises SEQ ID NO: 11. In some embodiments, the coding region of the nucleic acid molecule comprises or consists of SEQ ID NO: 11. In some embodiments, the coding region of the nucleic acid molecule consists of SEQ ID NO: 11.

In some embodiments, a sequence of the nucleic acid molecule comprises or consists of the sequence:

(SEQ ID NO: 20)

ATGGACGAATTTGAAATGATAAAGAGAAACACATCTGAAATTATCAGCGA

GGAAGAGTTAAGAGAGGTTTTAAAAAAAGATGAAAAATCTGCTCTGATAG

GTTTTGAACCAAGTGGTAAAATACATTTAGGGCATTATCTCCAAATAAAA

AAGATGATTGATTTACAAAATGCTGGATTTGATATAATTATAGTTTTGGC

TGATTTACACGCCTATTTAAACCAGAAAGGAGAGTTGGATGAGATTAGAA

AAATAGGAGATTATAACAAAAAAGTTTTTGAAGCAATGGGGTTAAAGGCA

AAATATGTTTATGGAAGTGAATTCCAGCTTGATAAGGATTATACACTGAA

TGTCTATAGATTGGCTTTAAAAACTACCTTAAAAAGAGCAAGAAGGAGTA

TGGAACTTATAGCAAGAGAGGATGAAAATCCAAAGGTTGCTGAAGTTATC

TATCCAATAATGCAGGTTAATGGTTATCATTATTCGGGCGTTGATGTTTT

TGTTGGAGGGATGGAGCAGAGAAAAATACACATGTTAGCAAGGGAGCTTT

TACCAAAAAAGGTTGTTTGTATTCACAACCCTGTCTTAACGGGTTTGGAT

GGAGAAGGAAAGATGAGTTCTTCAAAAGGGAATTTTATAGCTGTTGATGAC

TCTCCAGAAGAGATTAGGGCTAAGATAAAGAAGCATACTGCCCAGCTGGA

-continued

GTTGTTGAAGGAAATCCAATAATGGAGATAGCTAAATACTTCCTTGAATA

TCCTTTAACCATAAAAGGGCCAGAAAAATTTGGTGGAGATTTGACAGTTA

ATAGCTATGAGGAGTTAGAGAGTTTATTTAAAAATAAGGAATTGCATCCA

ATGCGCTTAAAAAATGCTGTAGCTGAAGAACTTATAAAGATTTTAGAGCC

AATTAGAAAGAGATTATA.

In some embodiments, the sequence of the nucleic acid molecule comprises SEQ ID NO: 20. In some embodiments, the coding region of the nucleic acid molecule comprises or consists of SEQ ID NO: 20. In some embodiments, the coding region of the nucleic acid molecule consists of SEQ ID NO: 20.

In some embodiments, a sequence of the nucleic acid molecule comprises or consists of the sequence:

(SEQ ID NO: 21)

ATGGACGAATTTGAAATGATAAAGAGAAACACATCTGAAATTATCAGCGA

GGAAGAGTTAAGAGAGGTTTTAAAAAAAGATGAAAAATCTGCTGGGATAG

GTTTTGAACCAAGTGGTAAAATACATTTAGGGCATTATCTCCAAATAAAA

AAGATGATTGATTTACAAAATGCTGGATTTGATATAATTATAGTTTTGGC

TGATTTACACGCCTATTTAAACCAGAAAGGAGAGTTGGATGAGATTAGAA

AAATAGGAGATTATAACAAAAAAGTTTTTGAAGCAATGGGGTTAAAGGCA

AAATATGTTTATGGAAGTGAATTCCAGCTTGATAAGGATTATACACTGAA

TGTCTATAGATTGGCTTTAAAAACTACCTTAAAAAGAGCAAGAAGGAGTA

TGGAACTTATAGCAAGAGAGGATGAAAATCCAAAGGTTGCTGAAGTTATC

TATCCAATAATGCAGGTTAATGGTTATCATTATTCGGGCGTTGATGTTTT

TGTTGGAGGGATGGAGCAGAGAAAAATACACATGTTAGCAAGGGAGCTTT

TACCAAAAAAGGTTGTTTGTATTCACAACCCTGTCTTAACGGGTTTGGAT

GGAGAAGGAAAGATGAGTTCTTCAAAAGGGAATTTTATAGCTGTTGATGA

CTCTCCAGAAGAGATTAGGGCTAAGATAAAGAAAGCATACTGCCCAGCTG

GAGTTGTTGAAGGAAATCCAATAATGGAGATAGCTAAATACTTCCTTGAA

TATCCTTTAACCATAAAAGGGCCAGAAAAATTTGGTGGAGATTTGACAGT

TAATAGCTATGAGGAGTTAGAGAGTTTATTTAAAAATAAGGAATTGCATC

CAATGCGCTTAAAAAATGCTGTAGCTGAAGAACTTATAAAGATTTTAGAG

CCAATTAGAAAGAGATTATA.

In some embodiments, the sequence of the nucleic acid molecule comprises SEQ ID NO: 21. In some embodiments, the coding region of the nucleic acid molecule comprises or consists of SEQ ID NO: 21. In some embodiments, the coding region of the nucleic acid molecule consists of SEQ ID NO: 21.

In some embodiments, a sequence of the nucleic acid molecule comprises or consists of the sequence:

(SEQ ID NO: 22)

ATGGACGAATTTGAAATGATAAAGAGAAACACATCTGAAATTATCAGCGA

GGAAGAGTTAAGAGAGGTTTTAAAAAAAGATGAAAAATCTGCTCTGATAG

GTTTTGAACCAAGTGGTAAAATACATTTAGGGCATTATCTCCAAATAAAA

-continued

AAGATGATTGATTTACAAAATGCTGGATTTGATATAATTATAGTTTTGGC

TGATTTACACGCCTATTTAAACCAGAAAGGAGAGTTGGATGAGATTAGAA

AAATAGGAGATTATAACAAAAAAGTTTTTGAAGCAATGGGGTTAAAGGCA

AAATATGTTTATGGAAGTAGTGTTTCTCTTGATAAGGATTATACACTGAA

TGTCTATAGATTGGCTTTAAAAACTACCTTAAAAAGAGCAAGAAGGAGTA

TGGAACTTATAGCAAGAGAGGATGAAAATCCAAAGGTTGCTGAAGTTATC

TATCCAATAATGCAGGTTAATGGTTATCATTATTCGGGCGTTGATGTTTT

TGTTGGAGGGATGGAGCAGAGAAAAATACACATGTTAGCAAGGGAGCTTT

TACCAAAAAAGGTTGTTTGTATTCACAACCCTGTCTTAACGGGTTTGGAT

GGAGAAGGAAAGATGAGTTCTTCAAAAGGGAATTTTATAGCTGTTGATGA

CTCTCCAGAAGAGATTAGGGCTAAGATAAAGAAAGCATACTGCCCAGCTG

GAGTTGTTGAAGGAAATCCAATAATGGAGATAGCTAAATACTTCCTTGAA

TATCCTTTAACCATAAAAGGGCCAGAAAAATTTGGTGGAGATTTGACAGT

TAATAGCTATGAGGAGTTAGAGAGTTTATTTAAAAATAAGGAATTGCATC

CAATGCGCTTAAAAAATGCTGTAGCTGAAGAACTTATAAAGATTTTAGAG

CCAATTAGAAAGAGATTATA.

In some embodiments, the sequence of the nucleic acid molecule comprises SEQ ID NO: 22. In some embodiments, the coding region of the nucleic acid molecule comprises or consists of SEQ ID NO: 22. In some embodiments, the coding region of the nucleic acid molecule consists of SEQ ID NO: 22.

In some embodiments, a sequence of the nucleic acid molecule comprises or consists of the sequence:

(SEQ ID NO: 23)

ATGGACGAATTTGAAATGATAAAGAGAAACACATCTGAAATTATCAGCGA

GGAAGAGTTAAGAGAGGTTTTAAAAAAAGATGAAAAATCTGCTCTGATAG

GTTTTGAACCAAGTGGTAAAATACATTTAGGGCATTATCTCCAAATAAAA

AAGATGATTGATTTACAAAATGCTGGATTTGATATAATTATAGTTTTGGC

TGATTTACACGCCTATTTAAACCAGAAAGGAGAGTTGGATGAGATTAGAA

AAATAGGAGATTATAACAAAAAAGTTTTTGAAGCAATGGGGTTAAAGGCA

AAATATGTTTATGGAAGTAATGTTTTGCTTGATAAGGATTATACACTGAA

TGTCTATAGATTGGCTTTAAAAACTACCTTAAAAAGAGCAAGAAGGAGTA

TGGAACTTATAGCAAGAGAGGATGAAAATCCAAAGGTTGCTGAAGTTATC

TATCCAATAATGCAGGTTAATGGTTATCATTATTCGGGCGTTGATGTTTT

TGTTGGAGGGATGGAGCAGAGAAAAATACACATGTTAGCAAGGGAGCTTT

TACCAAAAAAGGTTGTTTGTATTCACAACCCTGTCTTAACGGGTTTGGAT

GGAGAAGGAAAGATGAGTTCTTCAAAAGGGAATTTTATAGCTGTTGATGA

CTCTCCAGAAGAGATTAGGGCTAAGATAAAGAAAGCATACTGCCCAGCTG

GAGTTGTTGAAGGAAATCCAATAATGGAGATAGCTAAATACTTCCTTGAA

-continued

```
TATCCTTTAACCATAAAAGGGCCAGAAAAATTTGGTGGAGATTTGACAGT

TAATAGCTATGAGGAGTTAGAGAGTTTATTTAAAAATAAGGAATTGCATC

CAATGCGCTTAAAAAATGCTGTAGCTGAAGAACTTATAAAGATTTTAGAG

CCAATTAGAAAGAGATTATA.
```

In some embodiments, the sequence of the nucleic acid molecule comprises SEQ ID NO: 23. In some embodiments, the coding region of the nucleic acid molecule comprises or consists of SEQ ID NO: 23. In some embodiments, the coding region of the nucleic acid molecule consists of SEQ ID NO: 23.

In some embodiments, a sequence of the nucleic acid molecule comprises or consists of the sequence:

```
                                      (SEQ ID NO: 24)
ATGGACGAATTTGAAATGATAAAGAGAAACACATCTGAAATTATCAGCGA

GGAAGAGTTAAGAGAGGTTTTAAAAAAAGATGAAAAATCTGCTCTGATAG

GTTTTGAACCAAGTGGTAAAATACATTTAGGGCATTATCTCCAAATAAAA

AAGATGATTGATTTACAAAATGCTGGATTTGATATAATTATAGTTTTGGC

TGATTTACACGCCTATTTAAACCAGAAAGGAGAGTTGGATGAGATTAGAA

AAATAGGAGATTATAACAAAAAAGTTTTTGAAGCAATGGGGTTAAAGGCA

AAATATGTTTATGGAAGTGATTTCCAGCTTGATAAGGATTATACACTGAA

TGTCTATAGATTGGCTTTAAAAACTACCTTAAAAAGAGCAAGAAGGAGTA

TGGAACTTATAGCAAGAGAGGATGAAAATCCAAAGGTTGCTGAAGTTATC

TATCCAATAATGCAGGTTAATGGTTATCATTATTCGGGCGTTGATGTTTT

TGTTGGAGGGATGGAGCAGAGAAAAATACACATGTTAGCAAGGGAGCTTT

TACCAAAAAAGGTTGTTTGTATTCACAACCCTGTCTTAACGGGTTTGGAT

GGAGAAGGAAAGATGAGTTCTTCAAAAGGGAATTTTATAGCTGTTGATGA

CTCTCCAGAAGAGATTAGGGCTAAGATAAAGAAAGCATACTGCCCAGCTG

GAGTTGTTGAAGGAAATCCAATAATGGAGATAGCTAAATACTTCCTTGAA

TATCCTTTAACCATAAAAGGGCCAGAAAAATTTGGTGGAGATTTGACAGT

TAATAGCTATGAGGAGTTAGAGAGTTTATTTAAAAATAAGGAATTGCATC

CAATGCGCTTAAAAAATGCTGTAGCTGAAGAACTTATAAAGATTTTAGAG

CCAATTAGAAAGAGATTATA.
```

In some embodiments, the sequence of the nucleic acid molecule comprises SEQ ID NO: 24. In some embodiments, the coding region of the nucleic acid molecule comprises or consists of SEQ ID NO: 24. In some embodiments, the coding region of the nucleic acid molecule consists of SEQ ID NO: 24.

In some embodiments, a sequence of the nucleic acid molecule comprises or consists of the sequence:

```
                                      (SEQ ID NO: 25)
ATGGACGAATTTGAAATGATAAAGAGAAACACATCTGAAATTATCAGCGA

GGAAGAGTTAAGAGAGGTTTTAAAAAAAGATGAAAAATCTGCTCTGATAG

GTTTTGAACCAAGTGGTAAAATACATTTAGGGCATTATCTCCAAATAAAA

AAGATGATTGATTTACAAAATGCTGGATTTGATATAATTATAGTTTTGGC
```

-continued

```
TGATTTACACGCCTATTTAAACCAGAAAGGAGAGTTGGATGAGATTAGAA

AAATAGGAGATTATAACAAAAAAGTTTTTGAAGCAATGGGGTTAAAGGCA

AAATATGTTTATGGAAGTTCTGTGTGTCTTGATAAGGATTATACACTGAA

TGTCTATAGATTGGCTTTAAAAACTACCTTAAAAAGAGCAAGAAGGAGTA

TGGAACTTATAGCAAGAGAGGATGAAAATCCAAAGGTTGCTGAAGTTATC

TATCCAATAATGCAGGTTAATGGTTATCATTATTCGGGCGTTGATGTTTT

TGTTGGAGGGATGGAGCAGAGAAAAATACACATGTTAGCAAGGGAGCTTT

TACCAAAAAAGGTTGTTTGTATTCACAACCCTGTCTTAACGGGTTTGGAT

GGAGAAGGAAAGATGAGTTCTTCAAAAGGGAATTTTATAGCTGTTGATGA

CTCTCCAGAAGAGATTAGGGCTAAGATAAAGAAAGCATACTGCCCAGCTG

GAGTTGTTGAAGGAAATCCAATAATGGAGATAGCTAAATACTTCCTTGAA

TATCCTTTAACCATAAAAGGGCCAGAAAAATTTGGTGGAGATTTGACAGT

TAATAGCTATGAGGAGTTAGAGAGTTTATTTAAAAATAAGGAATTGCATC

CAATGCGCTTAAAAAATGCTGTAGCTGAAGAACTTATAAAGATTTTAGAG

CCAATTAGAAAGAGATTATA.
```

In some embodiments, the sequence of the nucleic acid molecule comprises SEQ ID NO: 25. In some embodiments, the coding region of the nucleic acid molecule comprises or consists of SEQ ID NO: 25. In some embodiments, the coding region of the nucleic acid molecule consists of SEQ ID NO: 25.

In some embodiments, a sequence of the nucleic acid molecule comprises or consists of the sequence:

```
                                      (SEQ ID NO: 26)
ATGGACGAATTTGAAATGATAAAGAGAAACACATCTGAAATTATCAGCGA

GGAAGAGTTAAGAGAGGTTTTAAAAAAAGATGAAAAATCTGCTGGGATAG

GGTTTGAACCAAGTGGTAAAATACATTTAGGGCATTATCTCCAAATAAAA

AAGATGATTGATTTACAAAATGCTGGATTTGATATAATTATAGTTTTGGC

TGATTTACACGCCTATTTAAACCAGAAAGGAGAGTTGGATGAGATTAGAA

AAATAGGAGATTATAACAAAAAAGTTTTTGAAGCAATGGGGTTAAAGGCA

AAATATGTTTATGGAAGTGAATTCCAGCTTGATAAGGATTATACACTGAA

TGTCTATAGATTGGCTTTAAAAACTACCTTAAAAAGAGCAAGAAGGAGTA

TGGAACTTATAGCAAGAGAGGATGAAAATCCAAAGGTTGCTGAAGTTATC

TATCCAATAATGCAGGTTAATGGGTATCATTATAGGGGCGTTGATGTTGC

GGTTGGAGGGATGGAGCAGAGAAAAATACACATGTTAGCAAGGGAGCTTT

TACCAAAAAAGGTTGTTTGTATTCACAACCCTGTCTTAACGGGTTTGGAT

GGAGAAGGAAAGATGAGTTCTTCAAAAGGGAATTTTATAGCTGTTGATGA

CTCTCCAGAAGAGATTAGGGCTAAGATAAAGAAAGCATACTGCCCAGCTG

GAGTTGTTGAAGGAAATCCAATAATGGAGATAGCTAAATACTTCCTTGAA

TATCCTTTAACCATAAAAGGGCCAGAAAAATTTGGTGGAGATTTGACAGT

TAATAGCTATGAGGAGTTAGAGAGTTTATTTAAAAATAAGGAATTGCATC

CAATGCGCTTAAAAAATGCTGTAGCTGAAGAACTTATAAAGATTTTAGAG

CCAATTAGAAAGAGATTATA.
```

In some embodiments, the sequence of the nucleic acid molecule comprises SEQ ID NO: 26. In some embodiments, the coding region of the nucleic acid molecule comprises or consists of SEQ ID NO: 26. In some embodiments, the coding region of the nucleic acid molecule consists of SEQ ID NO: 26.

In some embodiments, a sequence of the nucleic acid molecule comprises or consists of the sequence:

(SEQ ID NO: 27)

```
ATGGACGAATTTGAAATGATAAAGAGAAACACATCTGAAATTATCAGCGA
GGAAGAGTTAAGAGAGGTTTTAAAAAAAGATGAAAAATCTGCTCTGATAG
GTTTTGAACCAAGTGGTAAAATACATTTAGGGCATTATCTCCAAATAAAA
AAGATGATTGATTTACAAAATGCTGGATTTGATATAATTATAGGTTTGGC
TGATTTACACGCCTATTTAAACCAGAAAGGAGAGTTGGATGAGATTAGAA
AAATAGGAGATTATAACAAAAAAGTTTTTGAAGCAATGGGGTTAAAGGCA
AAATATGTTTATGGAAGTGATAGGATGCTTGATAAGGATTATACACTGAA
TGTCTATAGATTGGCTTTAAAAACTACCTTAAAAAGAGCAAGAAGGAGTA
TGGAACTTATAGCAAGAGAGGATGAAAATCCAAAGGTTGCTGAAGTTATC
TATCCAATAATGCAGGTTAATGGTTATCATTATTCGGGCGTTGATGTTTT
TGTTGGAGGGATGGAGCAGAGAAAAATACACATGTTAGCAAGGGAGCTTT
TACCAAAAAAGGTTGTTTGTATTCACAACCCTGTCTTAACGGGTTTGGAT
GGAGAAGGAAAGATGAGTTCTTCAAAAGGGAATTTTATAGCTGTTGATGA
CTCTCCAGAAGAGATTAGGGCTAAGATAAAGAAAGCATACTGCCCAGCTG
GAGTTGTTGAAGGAAATCCAATAATGGAGATAGCTAAATACTTCCTTGAA
TATCCTTTAACCATAAAAGGGCCAGAAAAATTTGGTGGAGATTTGACAGT
TAATAGCTATGAGGAGTTAGAGAGTTTATTTAAAAATAAGGAATTGCATC
CAATGCGCTTAAAAAATGCTGTAGCTGAAGAACTTATAAAGATTTTAGAG
CCAATTAGAAAGAGATTATA.
```

In some embodiments, the sequence of the nucleic acid molecule comprises SEQ ID NO: 27. In some embodiments, the coding region of the nucleic acid molecule comprises or consists of SEQ ID NO: 27. In some embodiments, the coding region of the nucleic acid molecule consists of SEQ ID NO: 27.

In some embodiments, each of SEQ ID NO:7-11 comprises a coding sequence for a mutant aaRS. In some embodiments, each of 20-27 comprises a coding sequence for a mutant aaRS. In some embodiments, each of the nucleic acid molecules comprises a coding sequence coding for a mutant aaRS. It will be understood by a skilled artisan, that as the protein is the active molecule any substitution to the nucleic acid sequence that does not alter the protein encoded is also envisioned. As the codons for amino acids are degenerate, one codon may be switched for a synonymous codon.

In some embodiments, the coding region encodes a recombinant protein. In some embodiments, the recombinant protein is a mutant aaRS. As used herein, the term "recombinant protein" refers to a protein which is coded for by a recombinant DNA and is thus not naturally occurring. In some embodiments, the polypeptide is a recombinant protein. The term "recombinant DNA" refers to DNA molecules formed by laboratory methods of genetic recombination. Generally, this recombinant DNA is in the form of a vector used to express the recombinant protein in a cell.

In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid" which refers to a circular double stranded DNA loop into which additional DNA segments can be inserted, such as by standard molecular cloning techniques. Another type of vector, wherein virally-derived DNA or RNA sequences are present in the virus (e.g. retroviruses, replication defective retroviruses, adenoviruses, replication defective adenoviruses, and adeno-associated viruses). Viral vectors also include polynucleotides carried by a virus for transfecting into host cells. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". Common expression vectors of utility in recombinant DNA techniques are often in the form of plasmids.

Recombinant expression vectors can comprise a nucleic acid coding for the protein of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

A vector nucleic acid sequence generally contains at least an origin of replication for propagation in a cell and optionally additional elements, such as a heterologous polynucleotide sequence, expression control element (e.g., a promoter, enhancer), selectable marker (e.g., antibiotic resistance), poly-Adenine sequence.

Orthogonal Translation Systems

In another aspect, there is provided an orthogonal translation system, comprising:

a. a mutant aaRS of the invention or a nucleic acid molecule of the invention; and b. a tRNA compatible with the aaRS.

In some embodiments, the orthogonal translation system is configured for translation in a target cell. In some embodiments, the orthogonal translation system is configured for in vitro translation. In some embodiments, the orthogonal translation system is configured for administration to a subject. In some embodiments, the orthogonal translation system is configured for administration to a cell. In some embodiments, the orthogonal translation system is configured for transfection to a cell. In some embodiments, the orthogonal translation system comprises a mutant aaRS of the invention. In some embodiments, the orthogonal translation system comprises a nucleic acid molecule of the invention.

In some embodiments, the tRNA is an orthogonal tRNA. In some embodiments, the tRNA is a non-naturally occurring tRNA. In some embodiments, the tRNA is a Mj tRNA. In some embodiments, the Mj tRNA is the tRNA corresponding to a stop codon. In some embodiments, the tRNA corresponds to a stop codon. In some embodiments, the stop codon is a stop codon that is absent in a target cell. In some embodiments, the stop codon is a stop codon that is depleted in a target cell. In some embodiments, the tRNA is recognized by the aaRS. In some embodiments, the tRNA is compatible with the mutant aaRS. In some embodiments, the tRNA is recognized by the mutant aaRS. In some embodiments, the mutation does not affect the aaRS's recognition of the tRNA. In some embodiments, the mutation enhances the aaRS's recognition of the tRNA. In some embodiments, the tRNA comprises an anticodon. In some embodiments, the anticodon corresponds to a stop codon. In some embodiments, the anticodon recognizes a stop codon. In some embodiments, the anticodon anneals to a stop codon. In some embodiments, the stop codon is a TAG stop codon. In some embodiments, the stop codon is a TGA stop codon. In some embodiments, the stop codon is a TAA stop codon. In some embodiments, the stop codon is not a TGA stop codon. In some embodiments, the stop codon is not a TAA stop codon.

In some embodiments, the orthogonal translation system further comprises an nsAA. In some embodiments, the nsAA is a uAA. In some embodiments, the uAA comprises a chemical moiety. In some embodiments, the chemical moiety is a biorthogonal chemical moiety. In some embodiments, the uAA is not naturally found in a target cell. In some embodiments, the biorthogonal chemical moiety is not naturally found in a target cell. In some embodiments, the chemical moiety is an azide or an alkyne group. In some embodiments, the chemical moiety comprises an azide or an alkyne group. Unnatural amino acids comprising azide and/or alkyne groups are well known in the art and non-limiting example include 3-Azido-D alanine, 3-azido-L-alanine, 4-azido-D-homoalanine, 4-azido-L-homoalanaine, 5-azido-D-ornithine, 5-azido-L-ornithine, 6-azido-D lysine, 6-azido-L-lysine, Boc-(R)-4-(2-propynyl)-L-proline, Boc-propargyl-Glycine-OH, Fmoc-(S)-propargyl-alanine-OH, Fmoc-(R)-propargyl-alanine-OH, and pPR. In some embodiments, the chemical moiety is an azide group. In some embodiments, the chemical moiety is an alkyne group. In some embodiments, the chemical moiety is an azobenzene group. Unnatural amino acids comprising azobenzene groups are well known in the art and non-limiting example include 4,4'-AMPB, 3,3'-AMPB, 3,4'-AMPB, 3,3'-APB, AzoPhe, Azo3F and Azo4F. In some embodiments, the uAA is a modified phenylalanine. In some embodiments, the modified phenylalanine is selected from 4-propargyloxy-L-phenylalanine (pPR), and phenylalanine-4'-azobenzene (AzoPhe). In some embodiments, the modified phenylalanine is pPR. In some embodiments, the modified phenylalanine is AzoPhe. In some embodiments, a uAA comprising an azobenezene group is selected from AzoPhe, Azo3F and Azo4F. In some embodiments, Azo3F is 2,4,6-tri-fluorinated azobenzene. In some embodiments, a uAA comprising an azobenezene group is AzoPhe. In some embodiments, a uAA comprising an azobenezene group is Azo3F. In some embodiments, a uAA comprising an azobenezene group is Azo4F.

In some embodiments, the mutant aaRS comprises a mutation found in SEQ ID NO: 2-6 and the uAA comprises an azide or an alkyne group. In some embodiments, the mutant aaRS comprises a sequence of SEQ ID NO: 2-6 and the uAA comprises an azide or an alkyne group. In some embodiments, the mutant aaRS comprises a mutation found in SEQ ID NO: 12-19 and the uAA comprises an azobenzene group. In some embodiments, the mutant aaRS comprises a sequence of SEQ ID NO: 12-19 and the uAA comprises an azobenzene group.

Cells

In another aspect, there is provided a cell comprising a mutant aaRS of the invention.

In another aspect, there is provided a cell comprising a nucleic acid molecule of the invention.

In another aspect, there is provided a cell comprising an orthogonal translation system of the invention.

In some embodiments, the cell is a target cell. In some embodiments, the cell is a mammalian cell. In some embodiments, the cell is a bacterial cell. In some embodiments, the bacterium is *E. coli*. In some embodiments, the cell is not an archaeal cell. In some embodiments, the cell is an unmodified cell. In some embodiments, the cell is unmodified with the exception of the presence of a protein, nucleic acid or system of the invention. In some embodiments, the cell is a genetically modified cell.

In some embodiments, the genome of the cell is unmodified. In some embodiments, the genome of the cell is modified. In some embodiments, the cell is devoid of TAG stop codons. In some embodiments, the TAG stop codons are endogenous TAG stop codons. In some embodiments, the TAG stop codons are native TAG stop codons. In some embodiments, the cell is depleted of TAG stop codons. In some embodiments, depleted comprises at least 50, 60, 70, 75, 80, 90, 95, 97, 99 or 100% of the stop codons of the cell having been removed. Each possibility represents a separate embodiment of the invention. In some embodiments, the TAG stop codons are mutated to TGA or TAA stop codons. In some embodiments, the TAG stop codons are mutated to TGA stop codons. In some embodiments, the TAG stop codons are mutated to TAA stop codons. In some embodiments, the stop codon that is depleted or absent from the cell is the stop codon that corresponds to the anticodon loop of the tRNA.

In some embodiments, the cell is devoid of release factor 1 (RF1). In some embodiments, the cell does not express RF1. In some embodiments, the cell has decreased expression of RF1. In some embodiments, decreased is with respect to a wild-type cell. In some embodiments, decreased is with respect to a non-modified cell. In some embodiments, decreased is at least a 50, 60, 70, 75, 80, 90, 95, 97, 99 or 100% reduction in expression. Each possibility represents a separate embodiment of the invention. In some embodiments, the RF1 gene has been genomically ablated from the cell. In some embodiments, the cell is an RF1 knockout cell.

In some embodiments, the cell is a wild-type cell. In some embodiments, the cell expresses RF1. In some embodiments, the cell expresses RF1 at normal levels. In some embodiments, the cell comprises at least one TAG stop codon. In some embodiments, the cell comprises its natural content of TAG stop codons. In some embodiments, the cell does not comprise a TAG stop codon mutated to a TGA or TAA stop codon.

In some embodiments, the cell further comprises a vector comprising an open reading frame (ORF). In some embodiments, the ORF is a coding region. In some embodiments, the ORF comprises at least one stop codon within the open reading frame. In some embodiments, the stop codon is a stop codon that corresponds to the anticodon of the tRNA of the orthogonal translation system. In some embodiments, the at least one stop codon is not the last codon of the ORF. In some embodiments, at least one codon coding for an amino acid is present after the stop codon in the ORF. In some embodiments, the amino acid encoded after the stop codon is a natural amino acid. In some embodiments, the last codon of the ORF is a stop codon that does not correspond to the anticodon of the tRNA of the orthogonal translation system.

In some embodiments, the vector is an expression vector. In some embodiments, the vector is configured to express a protein encoded by the ORF in the cell. In some embodiments, the ORF is operatively linked to at least one regulatory element. In some embodiments, the regulatory element is configured to induce expression of the protein encoded by the ORF in the cell. In some embodiments, the regulatory element is capable of induce expression of the protein encoded by the ORF in the cell.

In some embodiments, the ORF comprises at least one stop codon. In some embodiments, the ORF comprises at least two stop codons. In some embodiments, the OFR comprises a plurality of stop codons. In some embodiments, the ORF comprises at least 1, 2, 3, 4, 5, 6, 7, 8, 9, 10, 11, 12, 13, 14, 15, 16, 17, 18, 19, 20, 25, 30, 35, 40, 45 or 50 stop codons. Each possibility represents a separate embodiment of the invention. In some embodiments, the ORF comprises at least 10 stop codons. In some embodiments, the ORF comprises at least 30 stop codons. It will be understood by a skilled artisan that the number of stop codons recited herein does not refer to the stop codon at the end of the ORF that is responsible for stopping translation. The stop codon at the end of the ORF that stops translation will not correspond to the anticodon of the tRNA of the orthogonal translation system.

In some embodiments, the ORF encodes a protein of interest. In some embodiments, the ORF encodes a protein to comprise an nsAA. In some embodiments, the protein of interest is a protein to be tagged. In some embodiments, the protein or interest is a protein to be made light responsive.

Methods of Use

In another aspect, there is provided a method of producing a protein comprising an nsAA, the method comprising introducing into a cell an expression vector comprising an ORF encoding the protein, wherein the ORF comprises at least one stop codon, and wherein the cell comprises an orthogonal translation system of the invention, thereby producing a protein comprising an nsAA.

In some embodiments, the protein is a target protein. In some embodiments, the expression vector comprising an ORF encoding the protein is an expression vector as described herein above. In some embodiments, the orthogonal translation system is an orthogonal translation system comprising a nsAA. In some embodiments, the cell comprises the nsAA. In some embodiments, the orthogonal translation system is compatible with the nsAA. In some embodiments, the tRNA of the orthogonal translation system is compatible with the nsAA. In some embodiments, the mutant aaRS of the orthogonal translation system is compatible with the nsAA.

In some embodiments, the method further comprises introducing the orthogonal translation system into the cell. In some embodiments, the method further comprises introducing the nsAA into the cell. In some embodiments, introducing comprises transfection. In some embodiments, introducing comprises nucleofection. In some embodiments, introducing comprises genomic alteration. In some embodiments, introducing comprises genome editing.

In some embodiments, the method is for labeling a protein. In some embodiments, the method is for labeling and the nsAA is an azide or alkyne group containing nsAA. In some embodiments, the method is for labeling and the mutant aaRS comprises a mutation found in SEQ ID NO: 2-6. In some embodiments, the method is for labeling and the mutant aaRS comprises a sequence of SEQ ID NO: 2-6.

In some embodiments, the method is for labeling and further comprises converting the nsAA into a detectably labeled amino acid. In some embodiments, converting comprises addition of a detectable moiety by Click chemistry. In some embodiments, the Click chemistry is copper-catalyzed Click chemistry. In some embodiments, the Click chemistry is not copper-catalyzed Click chemistry. In some embodiments, the Click chemistry comprises azide and/or alkene cycloaddition.

As used herein, a "detectable moiety" is any molecule or portion of a molecule that can be specifically detected by a method known in the art. Examples of detectable moieties include, but are not limited to fluorescent moieties, radioactive moieties, bulky groups, dyes, and a tag. The term "moiety", as used herein, relates to a part of a molecule that may include either whole functional groups or parts of functional groups as substructures. The term "moiety" further means part of a molecule that exhibits a particular set of chemical and/or pharmacologic characteristics which are similar to the corresponding molecule. In some embodiments, the detectable moiety is a fluorescent moiety.

In some embodiments, method is for producing a light-responsive protein. In some embodiments, a light-responsive protein is a light-sensitive protein. In some embodiments, the method is for producing a light-responsive protein and the nsAA comprises an azobenzene group. In some embodiments, the method is for producing a light-responsive protein and the mutant aaRS of the orthogonal translation system comprises a mutation found in SEQ ID NO: 12-19. In some embodiments, the method is for producing a light-responsive protein and the mutant aaRS of the orthogonal translation system comprises a sequence of SEQ ID NO: 12-19. In some embodiments, the method further comprises irradiating the produced protein with light.

By another aspect, there is provided a protein produced by a method of the invention.

By another aspect, there is provided a protein comprising a nsAA.

In some embodiments, the protein is a protein comprising a nsAA. In some embodiments, the protein is a light-responsive protein. In some embodiments, the protein is a light-sensitive protein. In some embodiments, the protein is an ELP. In some embodiments, the protein is a self-assembling protein. In some embodiments, the protein is a diblock. In some embodiments, the protein is a ELP diblock copolymer.

In some embodiments, the protein comprises at least one nsAA. In some embodiments, the protein comprises a plurality of nsAA. In some embodiments, the protein comprises at least 1, 2, 3, 4, 5, 6, 7, 8, 9, 10, 15, 20, 25, 30, 40, 50, 60, 70, 80, 90 or 100 nsAA. Each possibility represents a separate embodiment of the invention. In some embodiments, the protein comprises at least 5 nsAA. In some embodiments, the protein comprises at least 10 nsAA. In some embodiments, the protein comprises at least 15 nsAA. In some embodiments, the protein comprises at least 20 nsAA. In some embodiments, the protein comprises at least 30 nsAA. In some embodiments, the protein comprises at least 50 nsAA. In some embodiments, the protein comprises at least 100 nsAA.

In some embodiments, all the nsAA in the protein are the same nsAA. In some embodiments, the nsAA comprise at least two different nsAA. In some embodiments, the nsAA are present at predetermined positions in the protein. In some embodiments, at least one nsAA is inserted in a hydrophobic segment of an ELP diblock co-polymer. In some embodiments, all the nsAA are inserted in a hydrophobic segment of an ELP diblock co-polymer.

Unless otherwise indicated, the word "or" in the specification and claims is considered to be the inclusive "or" rather than the exclusive or, and indicates at least one of, or any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a", "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, "comprise", "include" and "have" and conjugates thereof, are used to indicate that the object or objects of the verb are not necessarily a complete listing of components, elements or parts of the subject or subjects of the verb.

Other terms as used herein are meant to be defined by their well-known meanings in the art.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

EXAMPLES

Generally, the nomenclature used herein, and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

Materials: The uAA para-propargyloxy-l-phenylalanine (pPR) was purchased from Chem-Impex and from Iris-biotech. For in-vivo click reaction DPBS (without calcium and magnesium) was purchased from Thermo-Fisher scientific, TAMRA-azide (azide fluor 545), sodium ascorbate, copper(II) sulfate pentahydrate (CuSO4) and Tris(3-hydroxypropyltriazolylmethyl)amine (THPTA) were purchased from Sigma-Aldrich, BugBuster protein extraction reagent was purchased from Merck.

The azobenzene-uAAs 1 and 2 were purchased from Giotto Biotech and the azobenzene-uAA 3 was purchased from Chiroblock. Restriction endonucleases and ligation enzymes were purchased from New England Biolabs. DNA amplification was performed using The KAPA2G Fast HotStart ReadyMix or the KAPA HiFi PCR kit (Roche). Plasmid purification was conducted with Plasmid HiYield mini-prep (RBC Bioscience) and the PCR/restriction product was purified using a HiYield gel/PCR extraction kit (RBC Bioscience). Ligation was performed using the Quick Ligation™ Kit or with the T4 DNA Ligase, both purchased from New England Biolabs. Ligation products were transformed into 5-alpha Competent *E. coli* (High Efficiency) or Stbl2 Competent *E. coli* (High Efficiency), purchased from New England Biolabs. SDS solution was purchased from Bio-Rad. Anhydrotetracycline hydrochloride was purchased from Sigma-Aldrich. C321.ΔA (Isaacs lab) and pEvol-pAzFRS.1.t1 were a gift from Farren Isaacs (Addgene plasmids #73581 and #73547). Isomerization experiments were performed with a 365 nm UV lamp (VL-6.LC, 12W, VILBER LOURMAT) and green, and blue mounted LEDs: (1) 405 nm, 1000 mW, 800 mA (M405L4, Thor-Labs) and (2) 530 nm, 350 mM (M530L3, Thor-Labs).

Diversification and selection of pPR-RS and AzoRS variants. AARS libraries were generated by MAGE-based diversification of previously isolated genomically integrated mutants, pAcF-RS.t1, pAcFRS.2.t1 and pAzFRS.2.t1. Prior to MAGE cycling, cultures were established by inoculating the liquid medium with a single bacterial colony or by adding 30 μl of a confluent liquid culture (1:100 dilution) at 34° C. to mid-logarithmic growth (OD at 600 nm of 0.6-0.7) in a shaking incubator. To induce expression of the lambdared recombination proteins cell cultures were shifted to 42° C. for 15 min and then immediately chilled on ice. In a 4° C. environment, 1 ml of cells was centrifuged at 15,000 g for 30 s. Supernatant medium was removed and cells were resuspended in milli-Q water. The cells were spun down, the supernatant was removed, and washing procedure was repeated. After a final 30 s spin, the supernatant was removed and MAGE oligos (5-6 μM in DNase-free water) were added to the cell pellet. MAGE oligos are known in the art, and are provided for example in Amiram et al., 2015, "Evolution of translation machinery in recoded bacteria enables multi-site incorporation of nonstandard amino acids", Nature Biotechnology, 22, 1272-1279, herein incorporated by reference in its entirety. The oligo-cell mixture was transferred to a pre-chilled 1 mm gap electroporation cuvette (Bio-Rad) and electroporated under the following parameters: 1.8 kV, 200 V and 25 mF. LB media (3 ml) was immediately added to the electroporated cells. The cells were recovered from electroporation and grown at 34° C. for 3-3.5 h. Once the cells reached mid-log stage, they were used in additional MAGE cycles, subjected to negative and positive selection cycles, or frozen for further use.

Both colE1 (negative) or SDS (positive) selections were optimized by testing LB broth containing various concentrations of colE1 or SDS before addition of cells. Control strains with or without the TolC gene were used to verify selection conditions. Growth curves of libraries and controls in both selection experiments were monitored in real-time using kinetic measurements of the OD (600 nm) on a shaking and incubating plate reader. Screening of improved pPR variants after rounds of diversification with MAGE and negative (using varying concentrations of colicin E1 in the absence of pPR) and positive (using varying concentrations of SDS in the presence of pPR) selection was performed by plating cells on LB plates supplement with proper antibiotics, 0.2% L-Arabinose, 60 ng/μl anhydrotetracycline, and pPR at a concentration of 1 mM. Colonies expressing high levels of GFP were selected and subjected to further analysis of GFP expression by intact cell fluorescence measurements in the presence or absence of pPR. The aaRS genes of the best-performing colonies were analyzed by Sanger sequencing.

Plasmid construction: Plasmids bearing GFP-based reporter genes were known in the art. Plasmids bearing the OTS variants for pPR incorporation were constructed by insertion of aaRS genes to a previously described plasmid harboring a p15A origin of replication and a chloramphenicol resistance marker. The gene encoding for the parent-pPR-RS OTS was chemically synthetized (IDT), and aaRS genes were PCR-amplified from chromosomal templates. All variants were inserted sequentially using the flanking restriction sites restriction sites BglII and SalI, to produce inducible expression under the control of araBAD promoter and the rrnB terminator. The second constitutive copy of the aaRS, typically found in the pEvol system was removed.

The GFP(2TAG) reporter gene was chemically synthesized (IDT), restricted with XhoI and HindIII restriction enzymes, and ligated to a similarly cut reporter plasmid. The $ELP_{60}$ genes were chemically synthesized as half-proteins, $ELP_{30}$ genes (GeneArt, Thermo Fisher), restricted with BseRI, and ligated sequentially using PreRDL, under the control of the pTac promoter in a pet24 modified vector (GeneScript). Plasmids bearing the OTS variants for azobenzene-uAA incorporation were constructed by inserting aaRS genes into a previously described plasmid (pEvol) harboring a p15A origin of replication and a chloramphenicol resistance marker. The gene encoding for the AzoRS OTS was synthetized (IDT), and the evolved genomic aaRS genes were PCR-amplified from chromosomal templates. All variants were inserted sequentially by using the flanking restriction sites BglII and SalI to obtain inducible expression under the control of the araBAD promoter and the rrnB terminator. The second constitutive copy of the aaRS typically found in the pEvol system was removed. Ligation was conducted with the Quick Ligation™ Kit (NEB©) and the ligation products were transformed into NEB® 5-alpha Competent *E. coli* (High Efficiency), later plated on LB-agar plates supplemented with chloramphenicol (25 μg $ml^{-1}$) and analyzed by Sanger sequencing.

Analysis of GFP expression by intact cell fluorescence measurements: For 96-well plate-based assays, strains harboring chromosomally integrated orthogonal translation systems and GFP reporter plasmids were inoculated from frozen stocks and grown to confluence overnight. Cultures were then inoculated at 1:15 dilution in 2×YT media supplemented with 30 g/ml kanamycin. For cells harboring plasmid-based orthogonal translation system and GFP reporter proteins, the media was also supplemented with 25 g/ml chloramphenicol. Cells and allowed to grow at 34° C. to an OD600 of 0.5-0.8 in a shaking plate incubator at 567 c.p.m. (~3 h). aaRS expression was then induced by the addition of 0.2% arabinose, GFP expression was induced by the addition of 60 ng/μl anhydrotetracycline, and the uAA was added at a concentration of 1 mM. For GFP activity assays in BL21 strain, inducers for aaRS and GFP expression were added immediately after inoculation in the plate. Cultures and inducers were added individually to each well. Cells were incubated at 34° C. overnight. Following expression, cells were centrifuged at 4,000 g for 5 min. Supernatant medium was removed and cells were resuspended in PBS. GFP fluorescence was measured on a Biotek spectrophotometric plate reader using excitation and emission wavelengths of 485 and 528 nm, respectively. Fluorescence signals were normalized by dividing the fluorescence counts by the OD600 reading.

Alternatively, Cultures were then inoculated at a 1:50 dilution in 2×YT medium supplemented with kanamycin (30 μg $ml^{-1}$). For cells harboring the plasmid-based orthogonal translation system and GFP reporter proteins, the media were also supplemented with chloramphenicol (25 μg $ml^{-1}$). Cells were allowed to grow at 34° C. to an $OD_{600}$ of 0.5-0.8 in a shaking plate incubator at 567 rpm (~3 h). The expression of aaRS was then induced by adding arabinose (0.2%); GFP expression was induced by adding anhydrotetracycline (60 ng $ml^{-1}$); and the uAA was added at a concentration of 0.25 mM. Following expression, the cells were centrifuged at 4,000 g for 5 min, the supernatant medium was removed, and the cells were resuspended in PBS. GFP fluorescence was measured on a Biotek spectrophotometric plate reader by using excitation and emission wavelengths of 485 nm and 528 nm, respectively. Fluorescence signals were normalized by dividing the fluorescence counts by the $OD_{600}$ reading.

ELP expression and purification: Before batch expression, starter cultures (1:25 v/v of final expression volume) of 2×YT media supplemented with 30 μg/ml kanamycin and 25 μg/ml chloramphenicol were inoculated with transformed cells from a fresh agar plate or from stocks stored at −80° C., and incubated overnight at 34° C. while shaking at 220 r.p.m. Cells were centrifuged at 4,000 g for 10 min, supernatant medium was removed and cells were resuspended in remaining media, and transferred to expression flasks (containing 2×YT media, antibiotics, 0.2% arabinose and the uAA). For the expression of ELP(10TAG)-GFP by Mut1-RS in the genomically recoded organism, cells were supplemented with 0.25 mM of the uAA. For expression of ELP(30TAG)-GFP or for expression in BL21, cells were supplemented with 1 mM uAA. Cells were incubated at 34° C. for 4-5 h and then reporter protein expression was induced with 60 μg/ml anhydrotetracycline. Cells were harvested 24 h after inoculation by centrifugation at 4,000 g for 30 min at 4° C. The cell pellet was resuspended by vortex in ~2 ml PBS buffer and stored at −80° C. or immediately purified. For purification, resuspended pellets were lysed by ultrasonic disruption (18 cycles of 10 s sonication separated by 40 s intervals). Poly(ethyleneimine) (0.2 ml of 10% solution) was added to each lysed suspension before centrifugation at 4,000 g for 15 min at 4° C. to separate cell debris from the soluble cell lysate. All ELP constructs were purified by a modified inverse transition cycling (ITC) protocol consisting of multiple "hot" and "cold" spins using sodium citrate to trigger the phase transition. Before purification, the soluble cell lysate was incubated for 1-2 min at 75° C. to denature native *E. coli* proteins. The cell lysate was then cooled on ice, centrifuged for 2 min at ~14,000 r.p.m and the pellet was discarded. For "hot" spins, the ELP phase transition was triggered by adding sodium citrate to the cell lysate or the product of a previous cycle of ITC at a final concentration of ~0.5 M. The solutions were then centrifuged at ~14,000 r.p.m for 2 min and the pellets were resuspended in PBS, followed by a 2 min "cold" spin performed without addition of sodium citrate to remove denatured contaminant. Additional rounds of ITC were carried out as needed, using a saturated solution of sodium citrate until sufficient purification was achieved.

Protein concentration was calculated by measuring the OD280 of purified protein according to the following extinction coefficients: Tyr (WT protein): 33,935, ELP(1pPR)-GFP: 33,645, ELP(5pPR)-GFP: 32,485, ELP(10pPR)-GFP: 31,035, based on extinction coefficient of pPR (1200 M·cm-1).

Alternatively, before batch expression, starter cultures (1:40 v/v of final expression volume) of 2×YT media, supplemented with kanamycin (30 μg ml$^{-1}$) and chloramphenicol (25 μg ml$^{-1}$), were inoculated with transformed cells from either a fresh agar plate or from stocks stored at −80° C., incubated overnight at 34° C. while shaking at 220 rpm, and transferred to expression flasks containing 2×YT media, antibiotics, arabinose (0.2%), and azobenzene-uAA (0.25 mM). For the expression of $ELP_{60}$(10TAG), $ELP_{60}$(6TAG), and $ELP_{60}$(2TAG) by AzoRS-4, the C321.ΔRF1 strain[40], supplemented with azobenzene-uAA (0.25 mM) and arabinose (0.2%), was incubated at 34° C. for 4-5 h and then protein expression was induced with isopropyl 0-d-1-thiogalactopyranoside (IPTG, 1 mM). The cells were harvested 24 h after inoculation by centrifugation at 4,000 g for 30 min at 4° C. The cell pellet was then resuspended by vortex in milli-Q water (~4 ml) and either stored at −80° C. or purified immediately. For purification, resuspended pellets were lysed by ultrasonic disruption (18 cycles of 10 s sonication, separated by 40 s intervals of rest). Poly(ethyleneimine) was added (0.2 ml of a 10% solution) to each lysed suspension before centrifugation at 4,000 g for 15 min at 4° C. to separate cell debris from the soluble cell lysate. All ELP constructs were purified by a modified inverse transition cycling (ITC) protocol[20b] consisting of multiple "hot" and "cold" spins by using sodium chloride to trigger the phase transition. Before purification, the soluble cell lysate was incubated for 1-2 min at 42-55° C. to denature the native *E. coli* proteins. The cell lysate was then cooled on ice, centrifuged for 2 min at ~14,000 rpm, and the pellet was discarded. For "hot" spins, the ELP phase transition was triggered by adding sodium chloride to the cell lysate or to the product of a previous cycle of ITC at a final concentration of ~5 M. The solutions were then centrifuged at ~14,000 rpm for 10 min and the pellets were resuspended in milli-Q water, after which a 2 min "cold" spin was performed without sodium chloride to remove denatured contaminant. Additional rounds of ITC were conducted as needed using a saturated solution of sodium chloride until sufficient purification was achieved.

Protein concentrations were calculated by measuring the $OD_{280}$ of the purified protein according to the following extinction coefficients: $ELP_{60}$(tyrosine×10): 16,390, $ELP_{60}$(1×10): 26,900, $ELP_{60}$(1×6): 16,736, and $ELP_{60}$(2×10): 6,572, based on the extinction coefficient of 1 (2,541 M cm$^{-1}$); $ELP_{60}$(2×10): 41590, $ELP_{60}$(2×6): 25550, and $ELP_{60}$(2×10): 9510, based on the extinction coefficient of 2 (4010 M cm$^{-1}$); and $ELP_{60}$(3×10): 79122, $ELP_{60}$(3×6): 74546, and $ELP_{60}$(3×10): 25482, based on the extinction coefficient of 3 (123250 M cm$^{-1}$).

Intact mass measurements: Intact mass measurements of the proteins were performed using the MALDI-TOF instrument (MALDI-TOF/TOF autoflex speed), at the Ilse Katz Institute for Nanoscale Science and Technology (Ben-Gurion University of the Negev). Spectrum analysis was performed by the Flexanalysis software.

In-vivo click reaction: Before the reaction, ELP(1TAG) and ELP(10TAG), (both without GFP) were expressed in the genomically recoded organism or in the BL21 strain, by the parent-pPR-RS or evolved Mut1-RS. Starter cultures of 2×YT media supplemented with 30 μg/ml kanamycin and 25 μg/ml chloramphenicol were inoculated with transformed cells from a fresh agar plate or from stocks stored at −80° C., and incubated overnight at 34° C. while shaking at 220 r.p.m. Cells were then inoculated in 2 ml 2×YT media, supplemented with antibiotics, 0.2% arabinose and 1 mM of the uAA. Cells were incubated at 34° C. for 4-5 h and then reporter protein expression was induced with 60 μg/ml anhydrotetracycline. When comparing the click reaction in the GRO and BL21, induction of all proteins was performed immediately after seeding. Cells were grown overnight, harvested by centrifugation at ~14,000 r.p.m for 2 min, resuspended in DPBS buffer and immediately used. Proteins were conjugated in-vivo to azide-fluor 545 (TAMRA azide). *E. coli* cells were added to a final OD600=1 in the reaction. Concentrations of other reagents in the reaction were as following: 2% v\v DMSO, 0.1 mM TAMRA, 0.5 mM THPTA premixed with 0.1 mM CuSO4 for 20 min, 2.5 mM sodium ascorbate. DPBS solution was added up to desired volume. Reaction was performed for 1 hour at 25° C., in a shaking incubator at 400 r.p.m in the dark. Cells were washed by cycles of 3 min centrifugation at ~14,000 r.p.m followed by pellet resuspension in PBS, until the supernatant was colorless. Cells were then lysed using BugBuster protein extraction reagent according to manufacturer's instructions, and lysed cells were centrifuged for 10 min at 4° C. to separate cell debris from soluble proteins. Laemmli sample buffer was added to the reaction, and denaturation was performed by heating at 100° C. for 5 min.

For in vitro click reaction performed on cell lysates, cells were lysed by BugBuster protein extraction reagent after protein expression and cell harvesting. Cell lysate, equivalent to final OD600=5.5 was added to the reaction. Final concentration for other reagents were as following: 50 μM TAMRA, 3 mM THPTA premixed for 20 min with 0.4 mM CuSO4, 5 mM sodium ascorbate. DPBS was added up to desired volume. Reaction was performed for 1 hour at 25° C., in a shaking incubator at 400 r.p.m in the dark. Laemmli sample buffer was added to supernatant, and denaturation was performed by heating at 100° C. for 5 min.

All clicked products were analyzed on SDS-PAGE until free TAMRA was eluted from the gel. In-gel fluorescence analysis was performed on the Typhoon FLA-9500, using 532 nm laser. Equal lysis of all samples was validated by Coomassie blue staining of the gel.

Phase transition analysis: To characterize the inverse transition temperature of ELP variants, the $OD_{600}$ of the ELP solution (in milli-Q water, unless otherwise noted) was monitored as a function of temperature, with heating and cooling performed at a rate of 1° C. $min^{-1}$ on a UV-vis spectrophotometer equipped with a multicell thermoelectric temperature controller (Thermo Scientific).

Dynamic light scattering (DLS) analysis: ELP self-assembly was analyzed using a Zetasizer Nano ZS (Malvern Pananalytical). For each sample, 12-17 acquisitions (determined automatically by the instrument) were obtained at 10° C. for single-block ELPs or at 1-2° C. increments from 18 to 50° C. for diblock ELPs. Populations comprising less than 1% of the total mass (by volume) were excluded from the analysis.

Circular Dichroism (CD) analysis: The secondary structure of ELPs was studied using an Jasco J-715 spectropolarimeter (Tokyo) equipped with a PTC-348WI temperature controller, using a 1-mm quartz cuvette instrument by scanning from 280 nm to 180 nm at either 10° C. or 30° C. Purified constructs were diluted to 7.5 μM in water. Data were considered for analysis whenever the Dynode voltage was below 800 V.

Transmission electron microscopy: TEM at cryogenic temperature (Cryo-TEM) was used for direct imaging of solutions and dispersions. Vitrified specimens were prepared on a copper grid coated with a perforated lacey carbon 300 mesh (Ted Pella Inc.). A typically 2.5μl drop from the solution was applied to the grid and blotted with a filter paper to form a thin liquid film of solution. The blotted sample were immediately plunged into liquid ethane at its freezing point (−183° C.). The procedure was performed automatically in the Plunger (Lieca EM GP). The vitrified specimens were then transferred into liquid nitrogen for storage. The samples were studied using a FEI Talos F200C TEM, at 200 kV maintained at −180° C.; and images are recorded on a FEI Ceta 16M camera (4 k×4 k CMOS sensor) at low dose conditions, to minimize electron beam radiation damage. The measurements were done at the Ilse Katz Institute for Nanoscale Science and Technology (Ben-Gurion University of the Negev).

Statistical analysis: Statistical analysis was performed using GraphPad Prism software. Significance is reported where P was found to be <0.05. For multiple comparisons, GFP production by each aaRS variant at the presence of the uAA was compared with GFP production by the parent-pPR-RS system, using ANOVA followed by Dunnett test, under the assumptions of Gaussian distribution and unequal variability of differences. For single comparison analysis, a one-tailed heteroscedastic t-test was performed. GFP production by each aaRS variant in the presence of azobenzene-uAAs was compared with GFP production by the AzoRS system using ANOVA followed by Dunnett's post-hoc test, assuming a Gaussian distribution and unequal variability of differences.

Example 1: Evolution and Performance of Chromosomally Integrated nsAA-RS Variants In order to improve multi-site pPR incorporation, a modified MAGE-based protein evolution strategy was employed to identify improved mutants of the *M. janaschii* tyrosyl-tRNA synthetase (MjTyrRS) that efficiently charge an amber suppressor tRNA with pPR in *Escherichia coli*. In brief, mutants of the MjTyrRS were subjected to 5 or 10 rounds of MAGE-based diversification followed by tolC-mediated (1) negative, (2) positive, and (3) negative selections (colicin E1 (ColE1)-mediated negative selection, or SDS-mediated positive selections cycles). Individual colonies harboring genomically integrated mutant aaRSs from the remaining orthogonal library were screened for increased GFP(3TAG) production in the presence of pPR to identify improved variants. The best performing variants in isolated colonies were analyzed by Sanger sequencing, to identify the resulting mutations in the aaRS sequence (FIG. 1A). A similar MAGE-based protein evolution strategy was also employed to identify mutants of the MjTyrRS that efficiently charge an amber suppressor tRNA with azide-containing nsAAs in *Escherichia coli*. The best performing variants in isolated colonies were analyzed by Sanger sequencing, to identify the resulting mutations in the aaRS sequence (FIG. 1B).

Figure 2A:
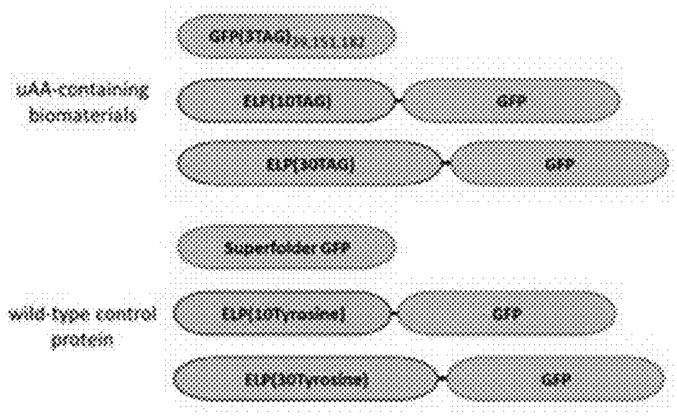
FIGS. 2A-Z: Multi-site incorporation of pPR by the parent translation systems and evolution of chromosomally integrated pPR-RS variants. (2A) Schematic illustration of reporter proteins for incorporation of 3, 10 and 30 unnatural amino acids (uAAs) and equivalent control wild-type (WT) proteins. (2B) GFP expression from WT GFP reporter, or from GFP(3TAG) ELP(10TAG)-GFP or ELP(30TAG)-GFP reporters produced by the parent pPR-RS, expressed by plasmid (P) or genomic integration (G). Red bars indicate addition of uAA (pPR), blue bars indicate no addition of uAA (pPR). (2C-E) Incorporation of (2C) 3, (2D) 10 and (2E) 30 pPRs in a single protein by evolved aaRS variants, expressed on a plasmid in C321.ΔRF1. *^<0.05, *^<0.0005, and **^<0.0001 indicate comparison of each evolved variant with the parent pPR-RS (2C-D) or with the wild-type protein (2E). n=3; error bars indicate S.D. (2F) Production of ELP(10TAG)-GFP by Mut1-RS and previously evolved aaRS variants, in the absence (red bars) and the presence of the respective uAAs, using the C321.ΔRF1 strain. (pPR for Mut1-RS, pAcF for pAcF-RS.2.t1, pAzF for pAzFRS.2.t1). n=3; error bars indicate s.d. (2G-N) Time-course kinetic analysis of GFP(3TAG) production by Mut1-RS and Mut2-RS expressed from multi-copy plasmids. (2G) production by Mut1-RS in C321.ΔRF1 and 2×YT media, (2H) production by Mut2-RS in C321.ΔRF1 and 2×YT media, (2I) production by Mut1-RS in C321.ΔRF1 and minimal media (MM), (2J) production by Mut2-RS in C321.ΔRF1 and minimal media, (2K) production by Mut1-RS in BL21 and 2×YT media, (2L) production by Mut2-RS in BL21 and 2×YT media, (2M) production by Mut1-RS in BL21 and minimal media, (2N) production by Mut2-RS in BL21 and minimal media. (2O-V) Time-course kinetic analysis of ELP(10TAG)-GFP production by Mut1-RS and Mut2-RS expressed from multi-copy plasmids. (2O) production by Mut1-RS in C321.ΔRF1 and 2×YT media, (2P) production by Mut2-RS in C321.ΔRF1 and 2×YT media, (2Q) production by Mut1-RS in C321.ΔRF1 and minimal media, (2R) production by Mut2-RS in C321.ΔRF1 and minimal media, (2S) production by Mut1-RS in BL21 and 2×YT media, (2T) production by Mut2-RS in BL21 and 2×YT media, (2U) production by Mut1-RS in BL21 and minimal media, (2V) production by Mut2-RS in BL21 and minimal media. (2W-Z) Time-course kinetic analysis of ELP(30TAG)-GFP production by Mut1-RS and Mut2-RS expressed from multi-copy plasmids. (2W) production by Mut1-RS in C321.ΔRF1 and 2×YT media, (2X) production by Mut2-RS in C321.ΔRF1 and 2×YT media, (2Y) production by Mut1-RS in C321.ΔRF1 and minimal media, (2Z) production by Mut2-RS in C321.ΔRF1 and minimal media. Fluorescence signals were normalized by dividing the fluorescence counts by the final OD600 reading. n=3. Note: error bars indicating s.d. may be too small to be visible.
Figure 2B:
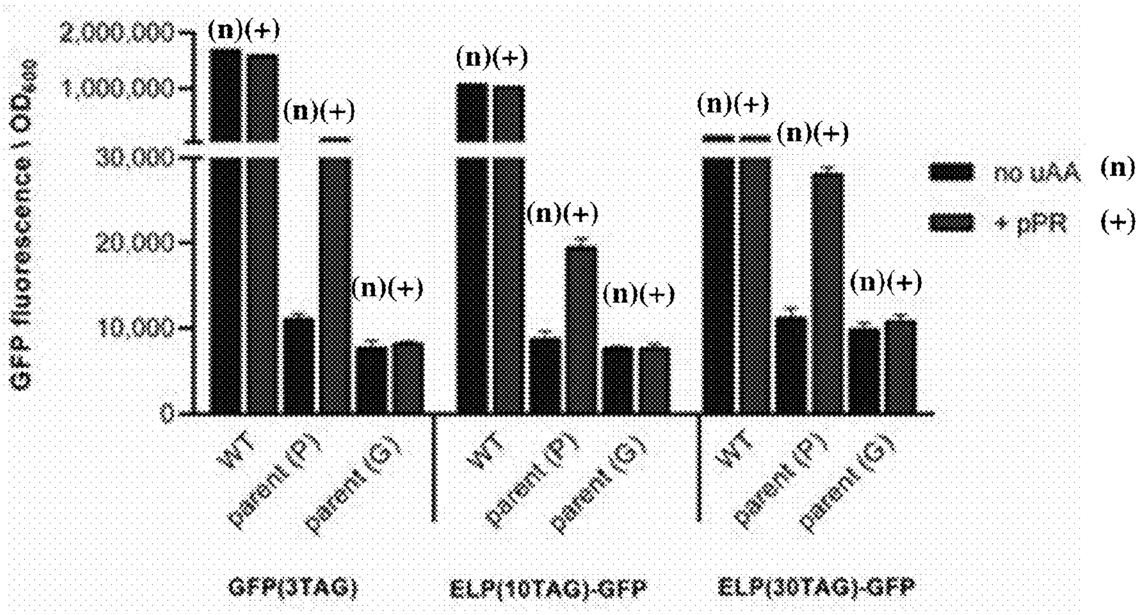

The ability of a previously-described pPR-RS (hereafter named "parent-pPR-RS") to incorporate 3-30 instances of the uAA per protein in the GRO was now characterized. Three reporter proteins for multi-site uAA incorporation were used: GFP(3TAG), ELP(10TAG)-GFP and ELP(30TAG)-GFP, and their WT protein controls (GFP WT, ELP(10Tyrosine)-GFP, ELP(30Tyrosine)-GFP) (FIG. 2A). A GFP fluorescence assay indicated that multi-site pPR incorporation by parent-pPR-RS, expressed from a multi-copy plasmid, in the GRO produced ~5%, ~2% and ~24.5% of pPR-containing GFP(3TAG), ELP(10TAG)-GFP and ELP(30TAG)-GFP, respectively, as compared to WT proteins (FIG. 2B). In addition, the inventors also compared the efficacy of the parent-pPR-RS, which was integrated into a permissive region in the GRO genome so that the aaRS is expressed from only a single chromosomal copy. As expected, the reduction in copy number caused by genomic integration of the OTS resulted in further decrease in protein yields, with ~0.5%, ~0.75% and ~9.4% production of GFP (3TAG), ELP(10TAG)-GFP and ELP(30TAG)-GFP, respectively, as compared with WT proteins (FIG. 2B).

Example 2: Efficient Multi-Site uAA Incorporation by Evolved pPR-RSs

Figure 2C:
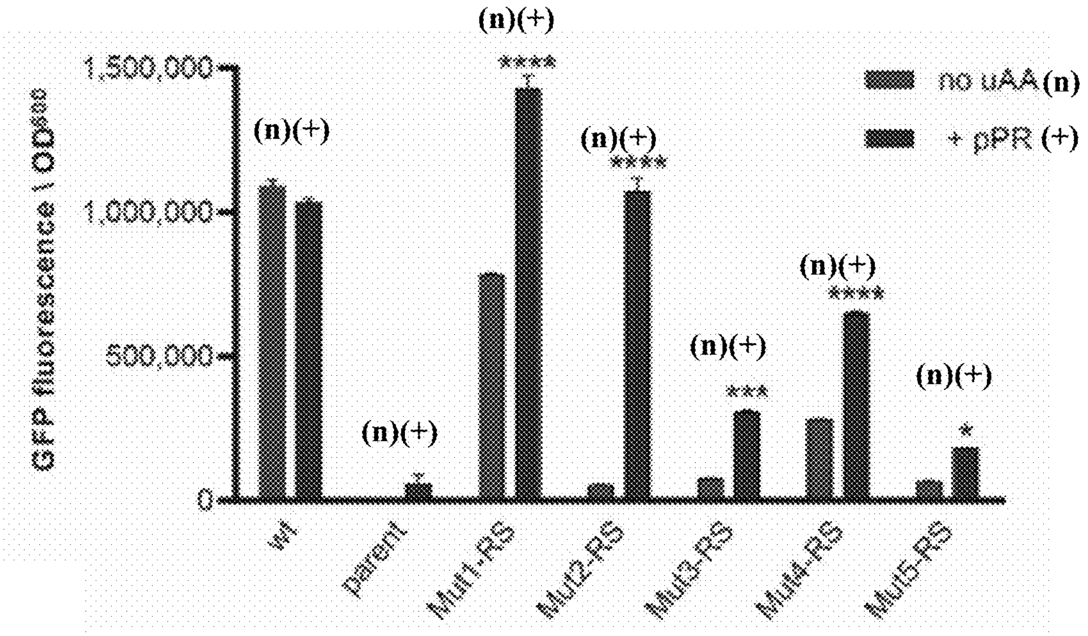
Figure 2D:
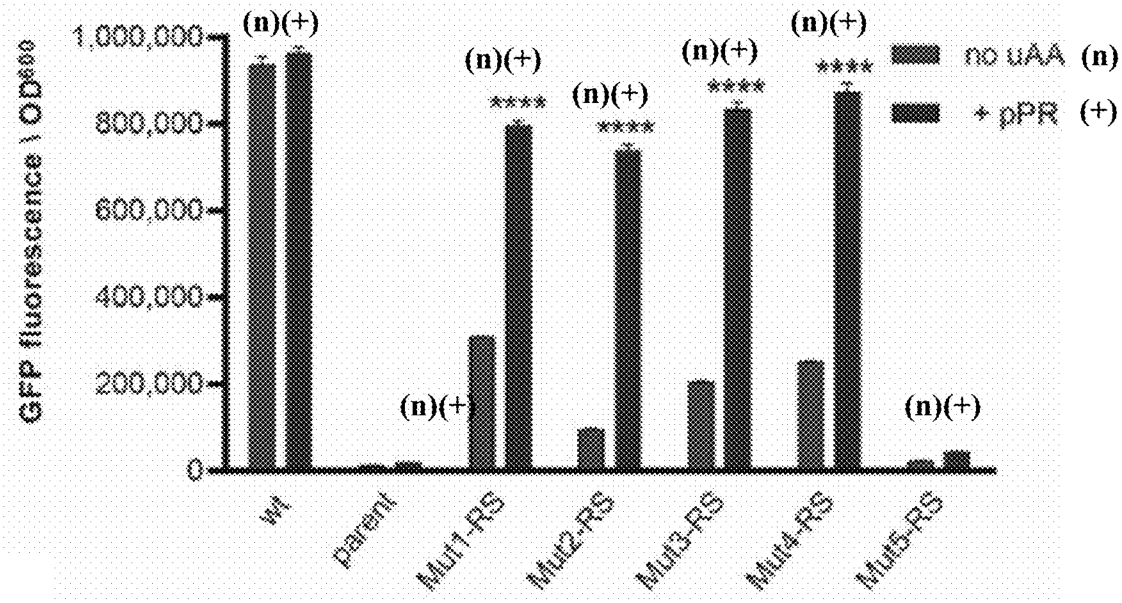
Figure 2E:
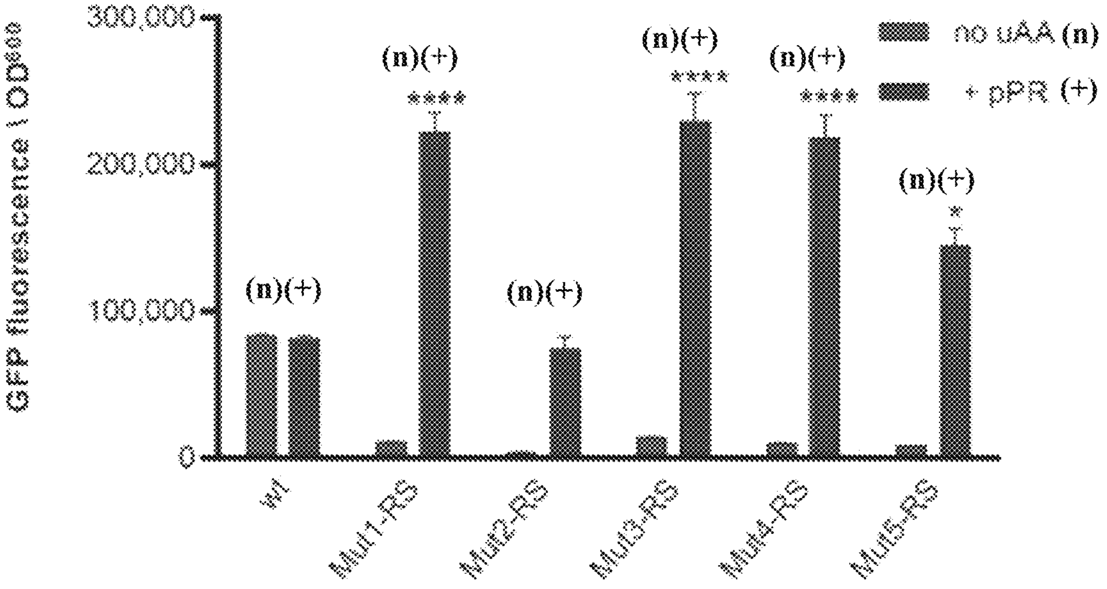
Figure 2F:
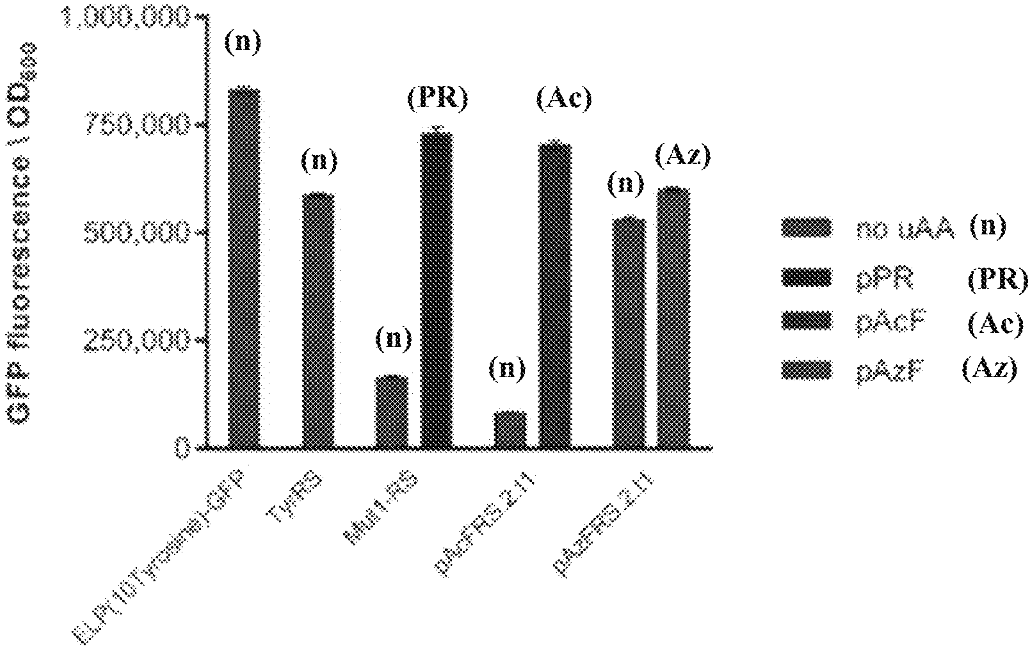
Figure 2G:
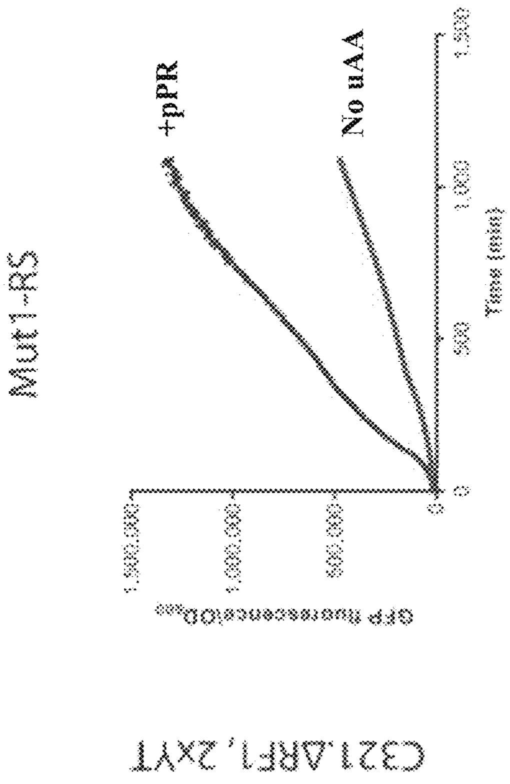
Figure 2H:
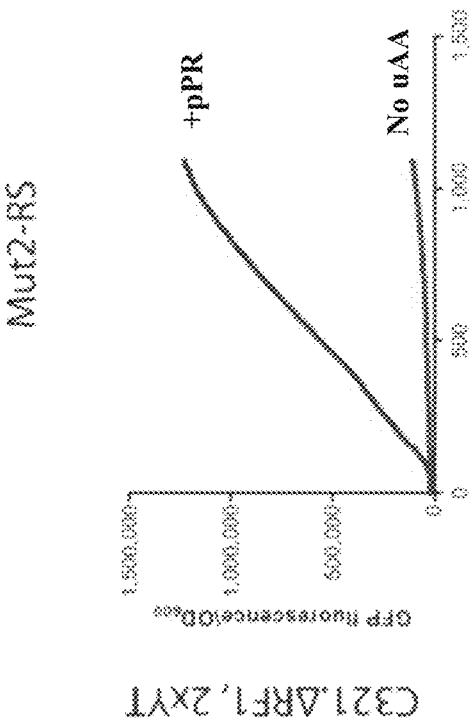
Figure 2I:
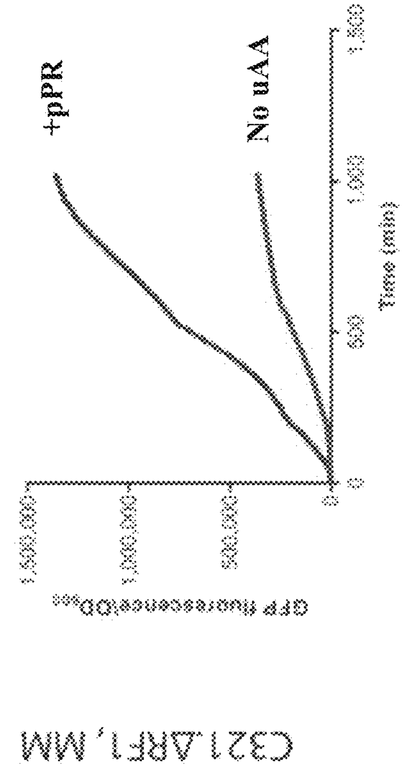
Figure 2J:
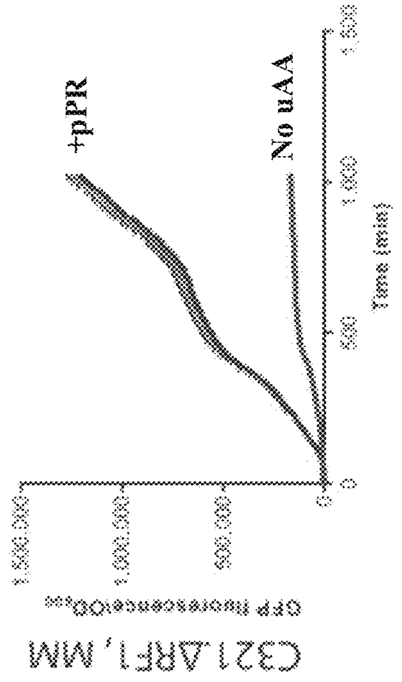
Figure 2K:
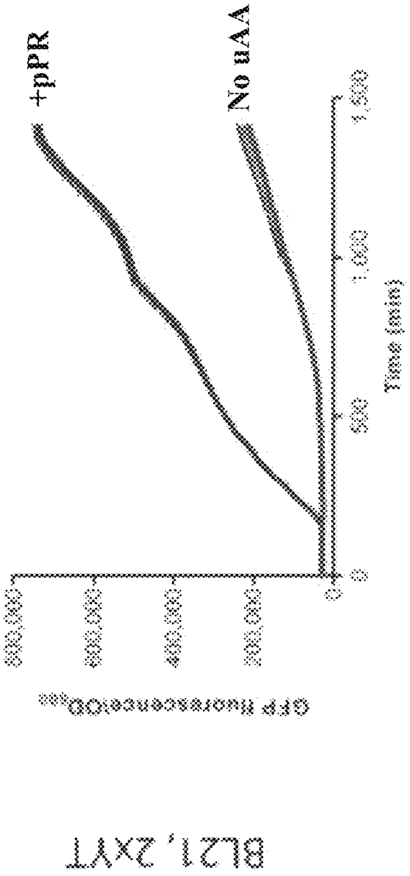
Figure 2L:
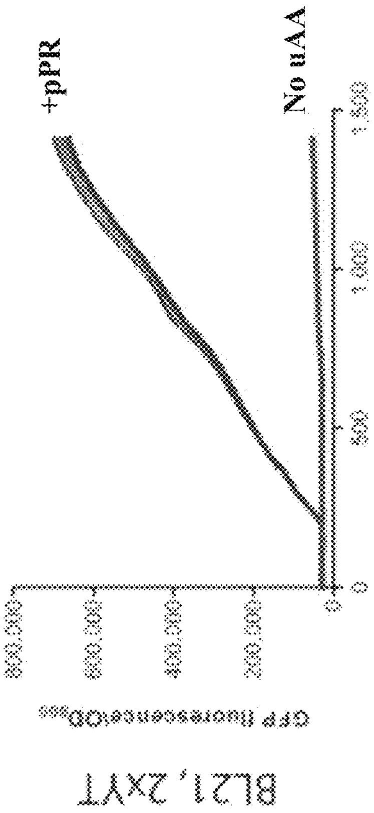
Figure 2M:
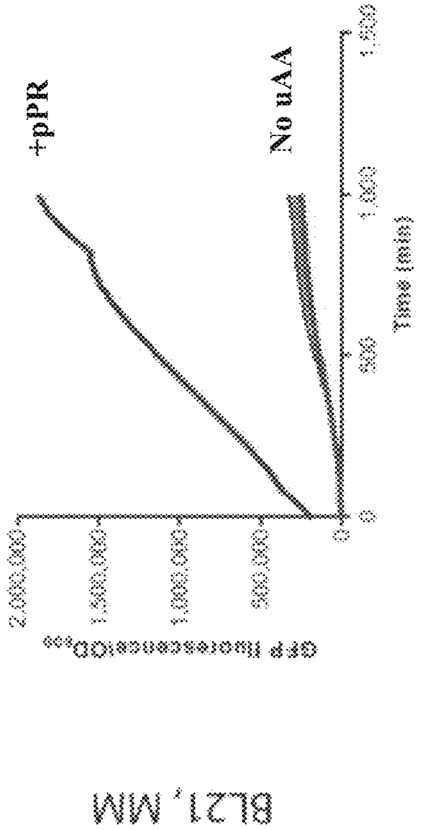
Figure 2N:
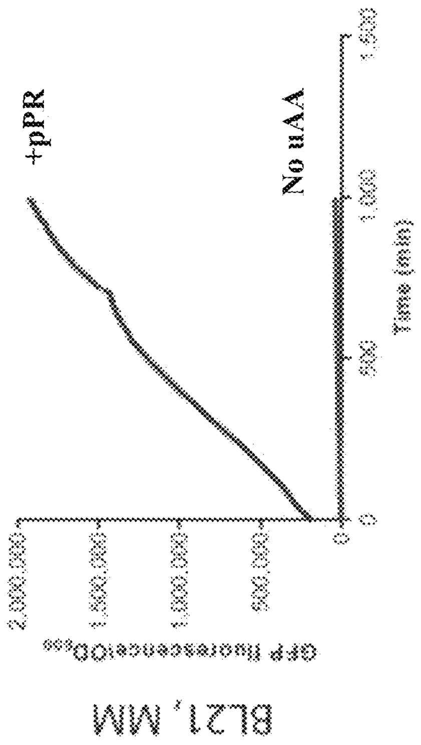
Figure 2O:
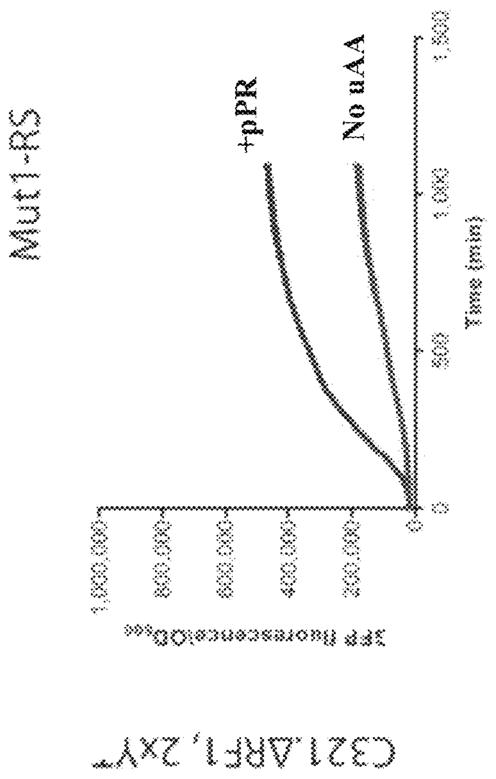
Figure 2P:
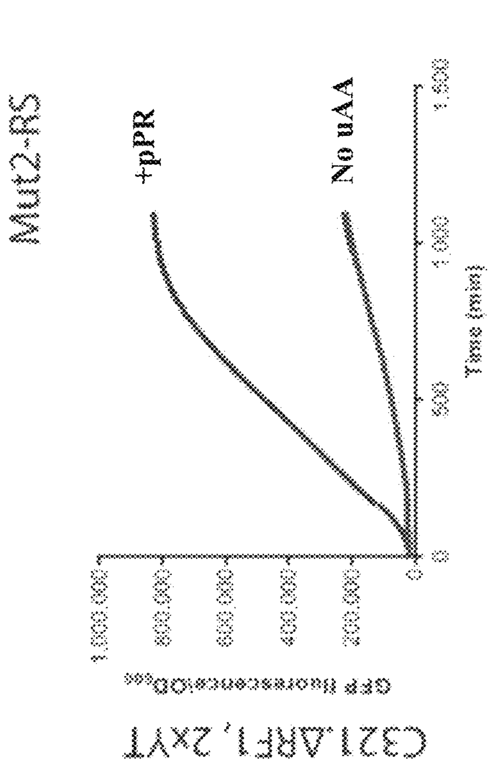
Figure 2Q:
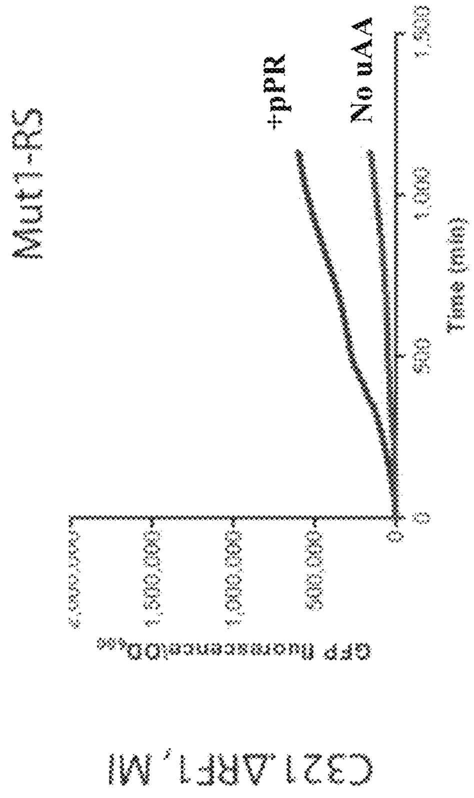
Figure 2R:
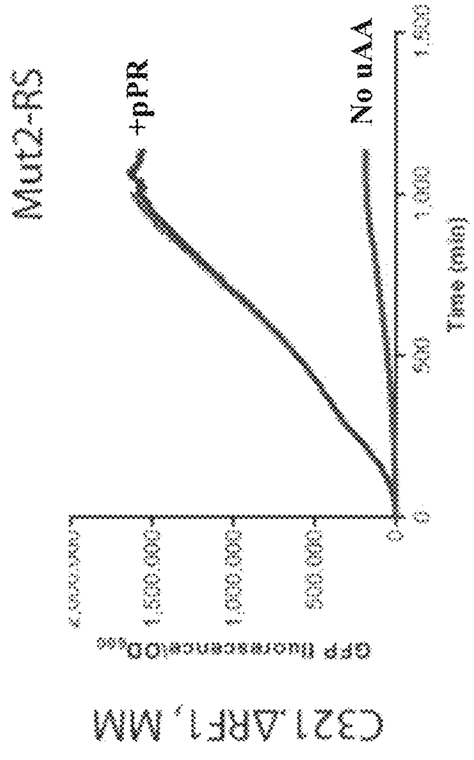
Figure 2T:
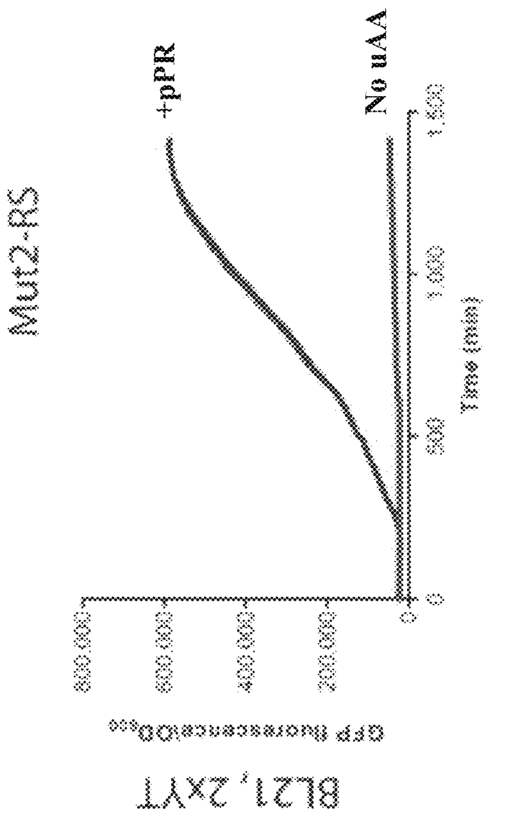
Figure 2V:
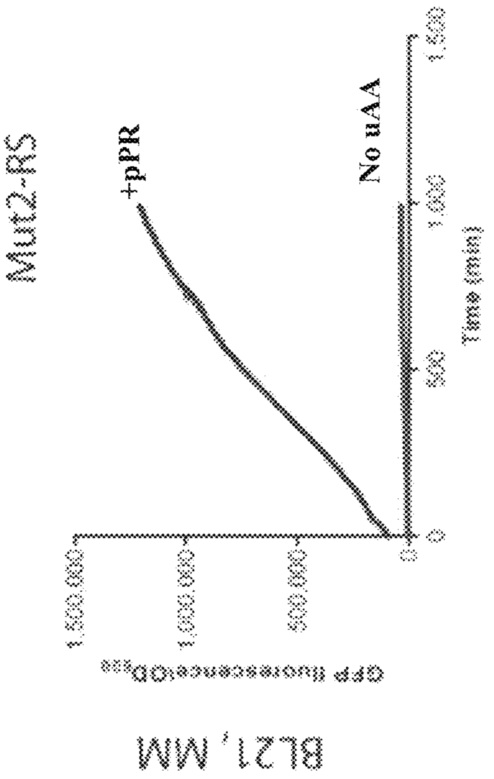
Figure 2S:
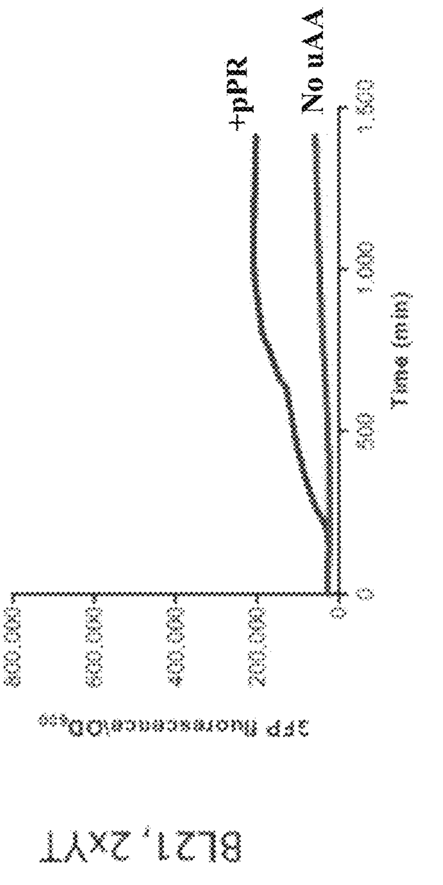
Figure 2U:
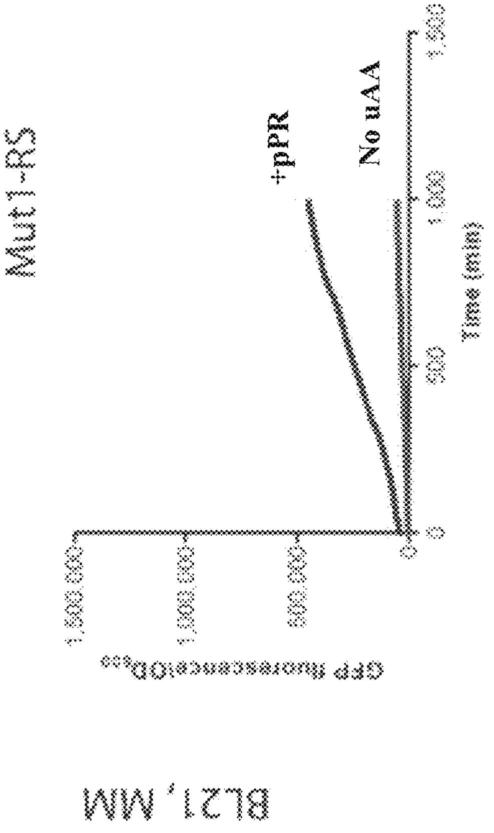
Figure 2X:
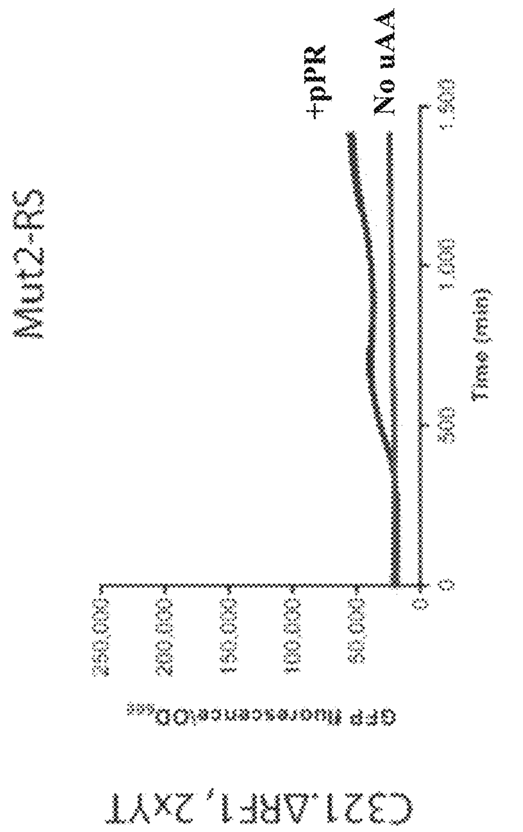
Figure 2Z:
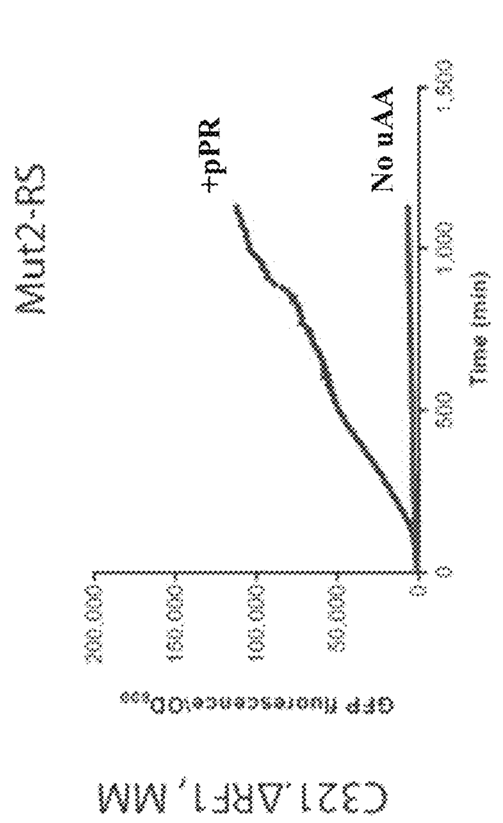
Figure 2W:
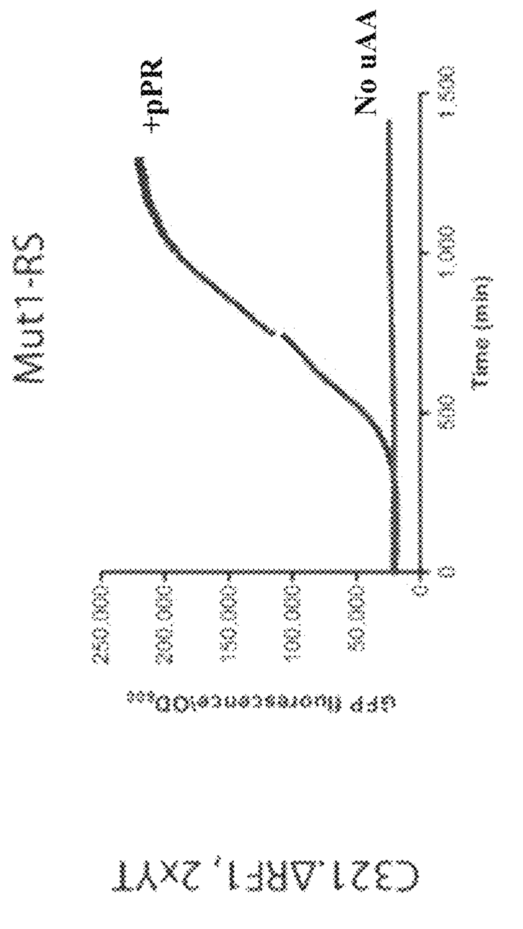
Figure 2Y:
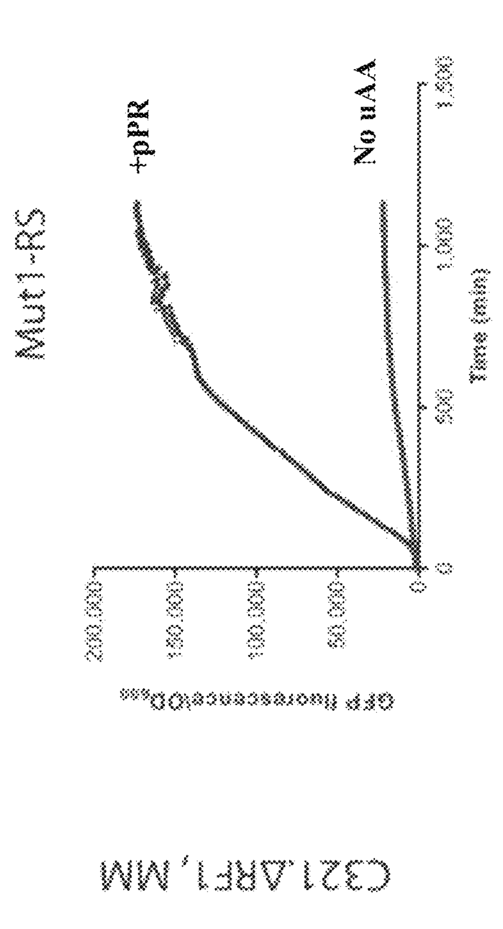
Figure 3A:
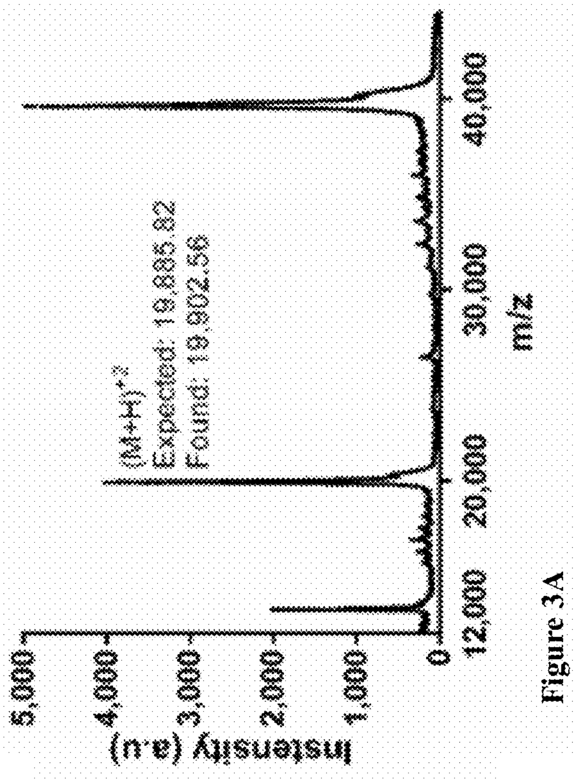
FIGS. 3A-D: MALDI-TOF analysis of WT ELP(10Tyrosine)-GFP protein expressed in (3A) BL21 and (3B) C321.ΔRF1, and ELP(10pPR)-GFP protein expressed by Mut1-RS in (3C) BL21 and (3D) C321.ΔRF1, respectively.
Figure 3B:
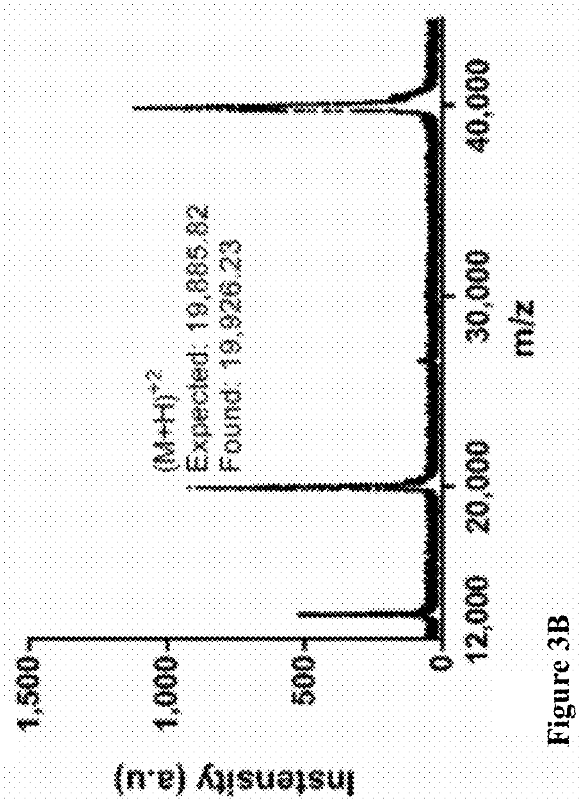
Figure 3C:
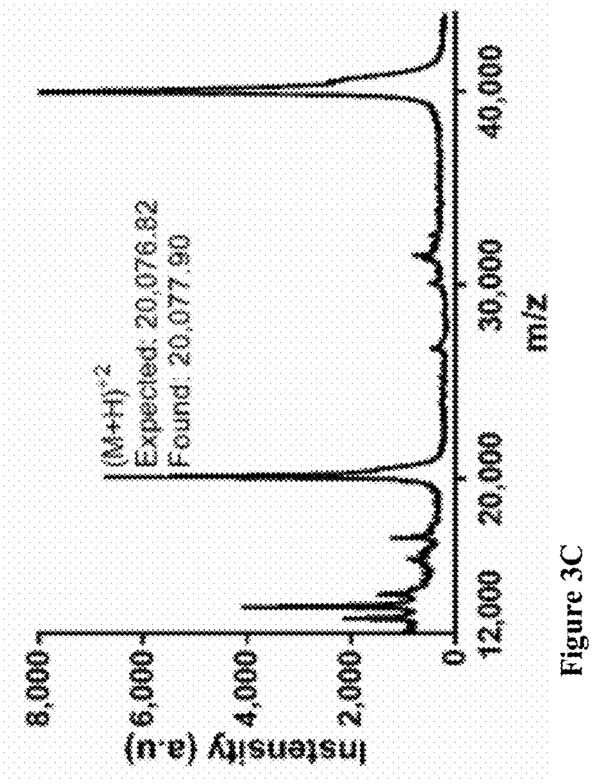
Figure 3D:
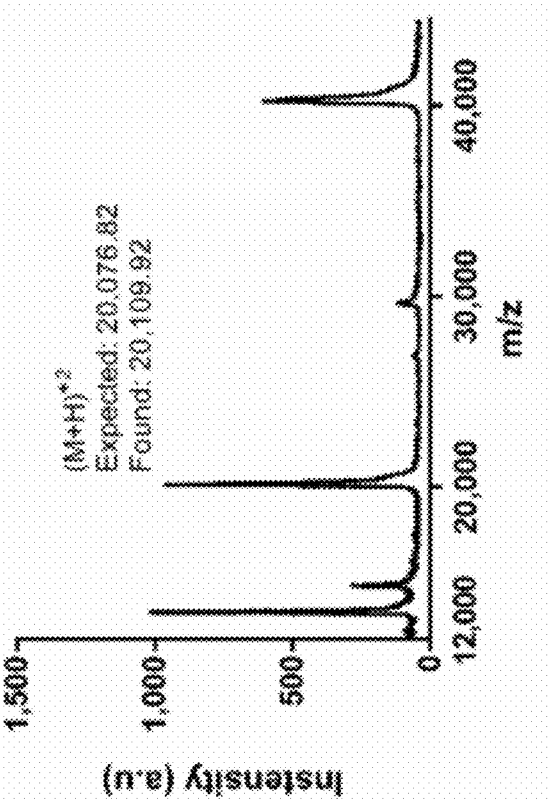

The evolved variants were now evaluated for multisite (3-30) pPR incorporation. C321.ΔRF1 was co-transformed with plasmids carrying the above-mentioned reporter proteins and episomal versions of each evolved pPR-RS variant. As expected, the expression of the evolved pPR-RSs from multi-copy plasmids led to higher protein production in the presence of pPR (FIG. 2C-E). Of note, only truncated ELP(30TAG)-GFP was produced by the parent pPR-RS in these conditions (FIG. 2B). Notably, when expressed from multi-copy plasmids in the absence of uAAs, most evolved variants showed increased protein production compared with the parent enzyme (FIG. 2C-E), in keeping with similar findings for other chromosomally evolved aaRSs (FIG. 2F). However, kinetic analysis demonstrated a reduced rate of AA incorporation in the absence of the uAA, which was also somewhat reduced when protein expression was induced in minimal medium (FIG. 2G-Z). Accurate incorporation of pPR was confirmed by intact mass analysis, as well as by LC-MS of tryptic fragments of ELP(10TAG)-GFPMS (~%^93 of the total ions by Mut1-RS, ~94^% of the total ions by Mut2-RS, and ~87^% of total ions produced by the parent-pPR-RS) and ELP(30TAG)MS (~64-92.5^% of the total ions, by Mut1-RS, depending on pPR concentration and ~36ˆ% of the total ions, by Mut2-RS using 1 mM pPR), with the latter methodology providing improved sensitivity of misincorporation events (FIG. 23, 24A, 24C, 24G-I, FIG. 3A-D). Therefore, it appears that the parent pPR-RS, Mut1-RS (which shows the highest level of background incorporation of all of the evolved variants), and Mut2-RS (which shows the lowest level of background incorporation of all of the evolved variants), all have similar fidelities when challenged to incorporate ten instances of pPR per protein. Likewise, when incorporating 30 pPR residues per protein, Mut1-RS shows higher fidelity than Mut2-RS, despite having higher background incorporation in the absence of pPR.

Figure 4A:
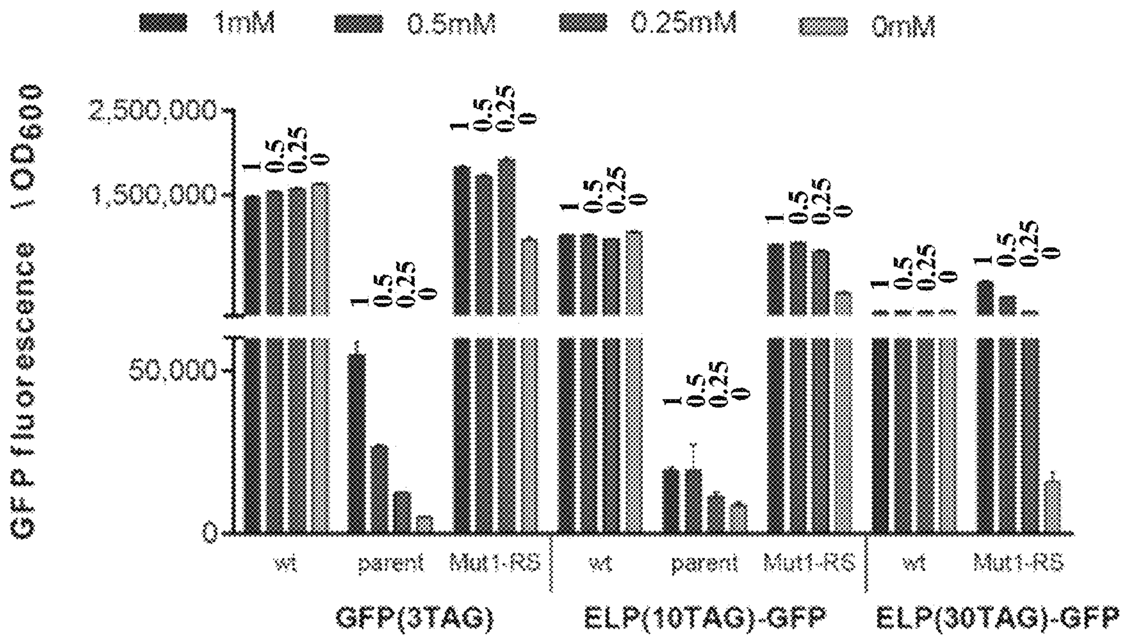
FIGS. 4A-B: (4A) Evaluation of pPR incorporation in the presence of standard (1 mM), twofold (0.5 mM) and fourfold (0.25 mM) reduced pPR concentrations. (4B) Multisite incorporation of pPR by Mut1-RS compared with the parent pPR-RS, in the BL21 and C321.ΔRF1 strains. n=3; error bars indicate S.D.

The best-performing variant, Mut1-RS (FIG. 1C), was further evaluated in the production of proteins with three to 30 instances of the uAA in the presence of twofold or fourfold reduced concentrations of pPR (1ˆˆmM is typically added to the growth medium; FIG. 4A). This analysis revealed that Mut1-RS is able to efficiently produce GFP (3TAG) and ELP(10TAG)-GFP in the presence of twofold or fourfold reduced pPR concentrations with only a minor loss of protein yield (0 to ~8ˆ%) and ~8ˆ% loss in pPR incorporation fidelity in the presence of fourfold reduced pPR concentrations (FIG. 24C-D). In contrast, production of ELP(30TAG)-GFP resulted in protein losses of ~40ˆ% and ~70ˆ% in the presence of two- or fourfold reduced pPR concentrations, respectively. Importantly, our evolved aaRS outperformed the parent synthetase by 20- to 200-fold improved protein yields at all pPR concentrations [except for ELP(30TAG)-GFP, which could not be produced by the parent in these conditions]. Small-batch expression of ELP (10TAG)-GFP and ELP(30TAG)-GFP produced using Mut1-RS in the C321.ΔRF1 strain was performed. Detected protein yields were 24.52±1.9 and 54.42±5.7ˆˆmg/L for ELP(10TAG)-GFP and ELP(30TAG)-GFP, respectively, when expressed with 1ˆˆmM pPR in the growth medium (compared with 8.98±0.88ˆˆmg/L and 14.97±0.85ˆˆmg/L, respectively, of the equivalent WT proteins).

Figure 4B:
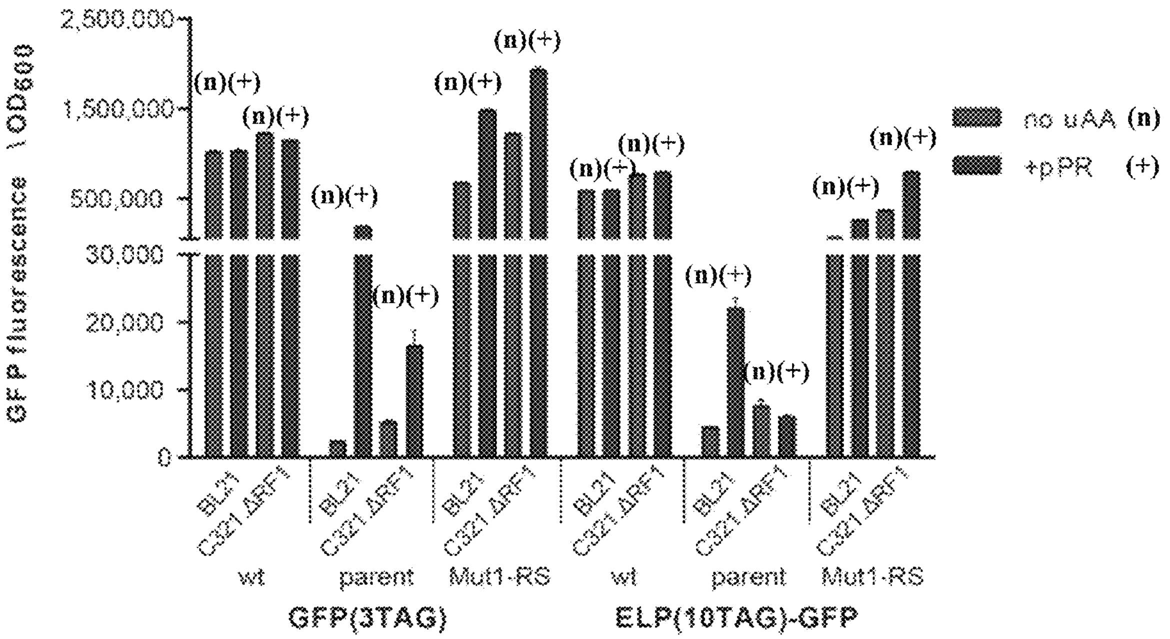

Given the high incorporation efficiency of the evolved pPR-RS variants in C321.ΔRF1, it was posited that they would also be capable of enhancing multisite pPR incorporation efficacy in non-recoded *E. coli*. To test this premise, the ability of Mut1-RS to incorporate three or ten pPR instances in a single protein was evaluated using the commonly utilized, non-recoded BL21 protein-expression strain. Fluorescence analysis of GFP(3TAG) and ELP(10TAG)-GFP expression by Mut1-RS in the BL21 strain showed production rates of ~140ˆ% and ~44ˆ%, respectively, compared to WT proteins (FIG. 4B). To determine protein yields and purity, a similar small-batch expression of ELP (10TAG)-GFP by using Mut1-RS in BL21 was performed. Protein yields were 6.33±0.2ˆˆmg/L by Mut1-RS (or ~50ˆ% of the equivalent WT protein, which expressed at 12.26±0.35ˆˆmg/L). Correct incorporation of pPR was confirmed by intact mass analysis (FIG. 23 and FIG. 3A-D) as well as by LC-MS of tryptic fragments (~88ˆ% and ~72ˆ% of the total ions by Mut1-RS when expressed using 1 and 0.25ˆˆmM pPR in the growth media, compared with ~88ˆ% of total ions produced by the parent-pPR-RS, using 1ˆˆmM pPR in the growth medium, FIG. 24B, 24E, 24F).

The above results should be viewed in the wider context of a number of previously reported findings, particularly the following: three uAAs were incorporated per protein at WT levels by using a partially recoded and RF-1 deficient BL21 strain (B-95.ΔA); incorporation of six uAAs yielded ~6-9ˆ% of WT proteins in the presence of release factor inhibitors; and proteins bearing ten uAAs were produced with yields of 3ˆ% compared to WT protein yields in an RF-1 deficient, non-recoded *E. coli* strain. It has also been previously reported that multisite incorporation can be achieved by AA replacement, but this method replaces all instances of the relevant natural amino acid with the uAA and, as such, is not site specific. It can therefore result in labeling in unintended sites in the target proteins and/or loss of function as a result of unintended AA to uAA substitutions. The methodology disclosed herein, based on high-efficiency evolved aaRS variants that facilitate the production of proteins with ten pPRs in high yields in the non-recoded BL21 strain, can therefore be used to complement AA substitution, recoding, or RF1 attenuation efforts. Although ELPs and GFP are well-expressed, soluble proteins, we expect that our evolved aaRSs will also enhance the expression of additional proteins bearing multiple pPR residues, albeit in varying degrees.

Figure 5A:
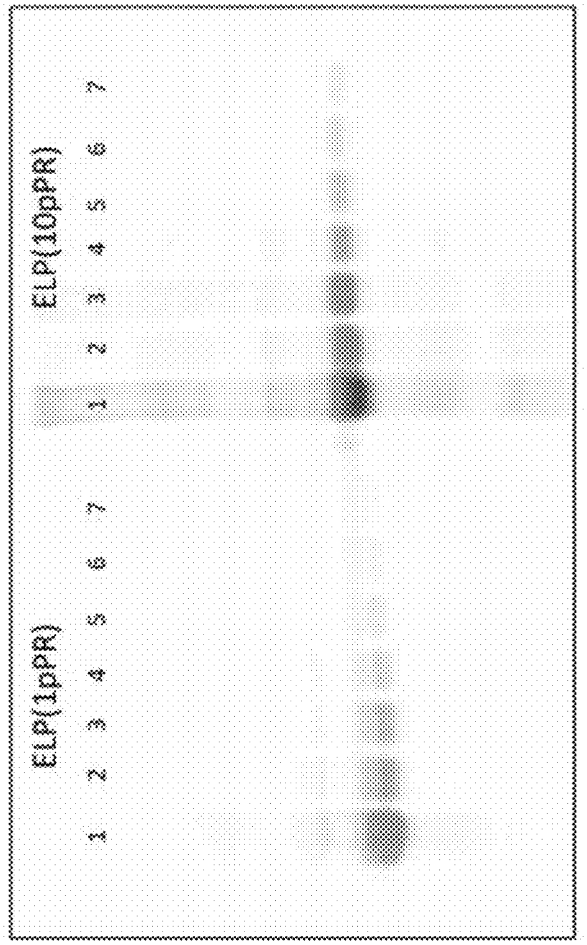
FIGS. 5A-E: (5A) In-gel fluorescence analysis of purified ELPs containing 1 or 10 instances of pPR conjugated to TAMRA-azide at various protein concentrations, namely: (1) 30 μM; (2) 6 μM; (3) 3 μM; (4) 1.5 μM; (5) 0.6 μM; (6) 0.33 μM; (7) 0.165 μM. (5B-E) TAMRA labeling of C321.ΔRF1 cells expressing (5B) ELP(1pPR) by the parentpPR-RS; (5C) ELP(1pPR) by Mut1-RS; (5D) ELP (10pPR) b the parent pPR-RS and (5E) ELP(10pPR) by the Mut1-RS. Percentage of labeled cells was calculated using ImageJ and is given for each image.
Figure 5B:
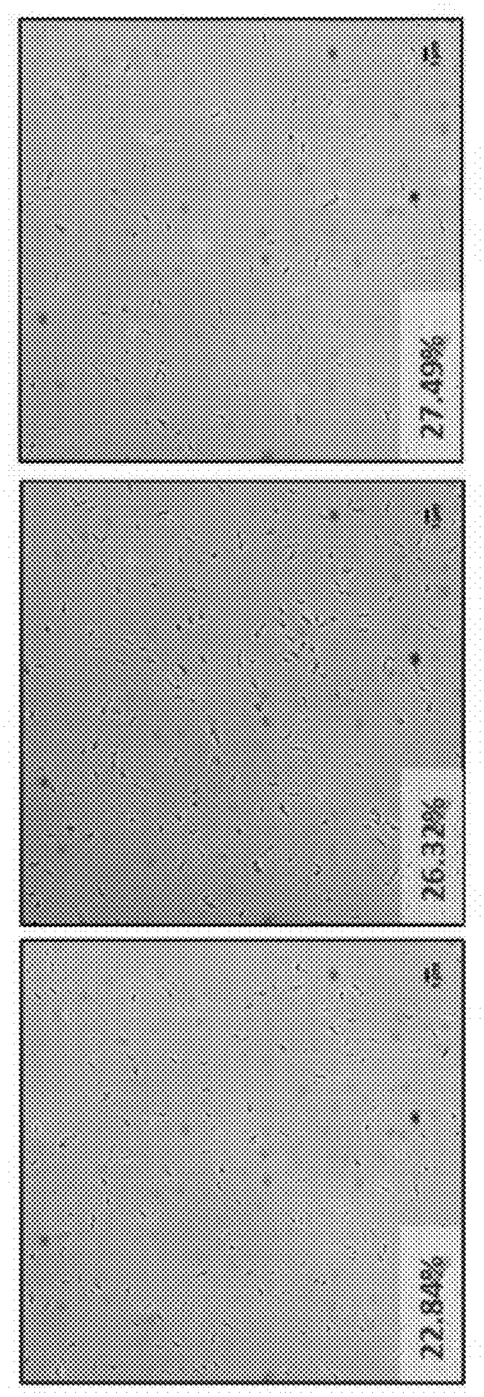
Figure 5C:
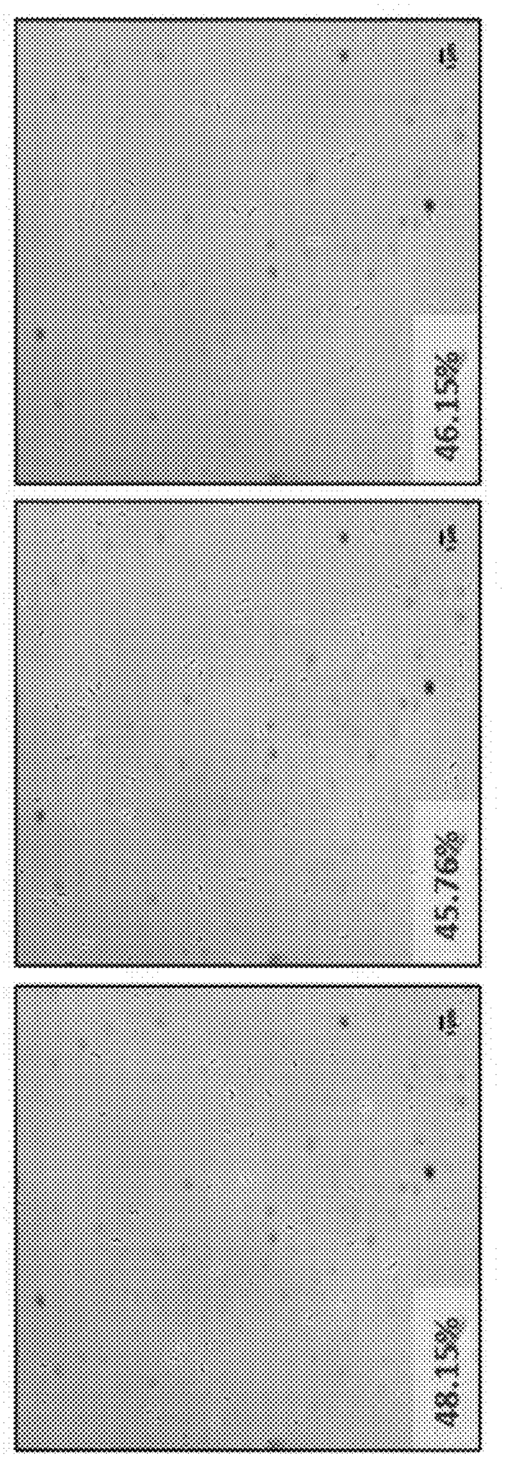
Figure 5D:
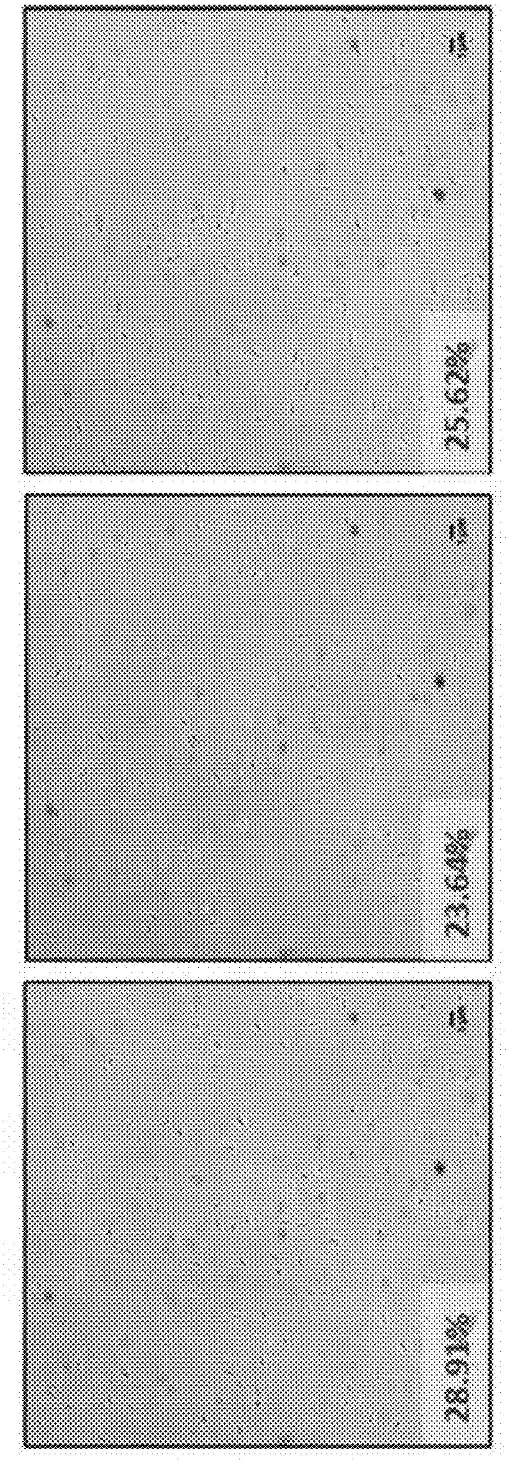
Figure 5E:
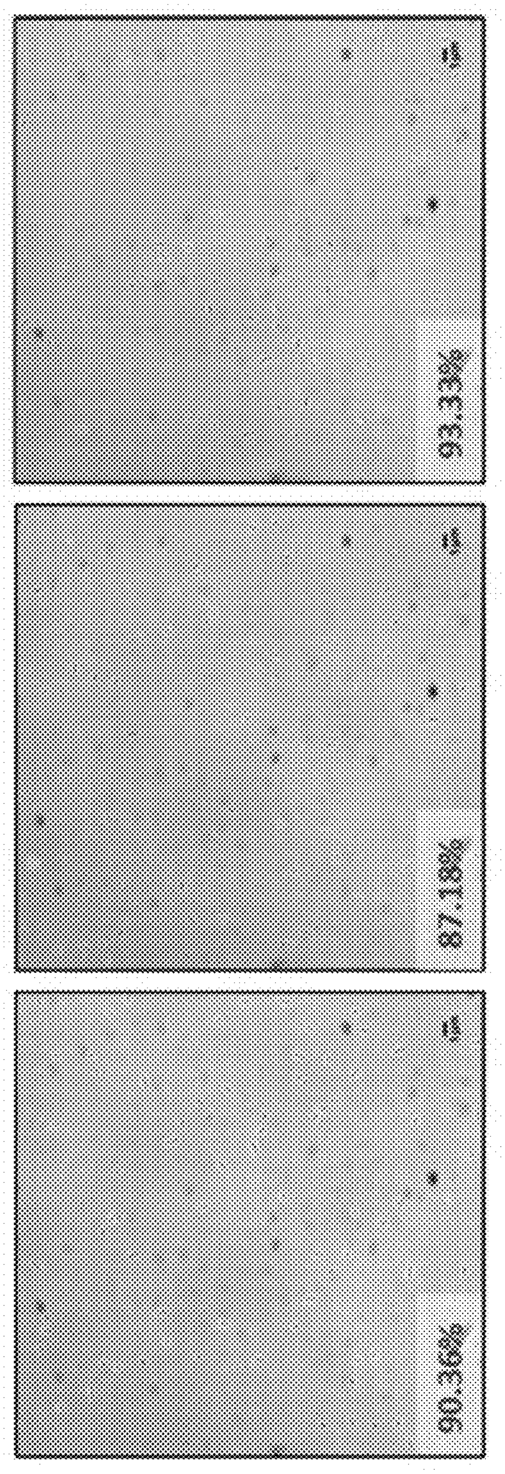
Figure 6A:
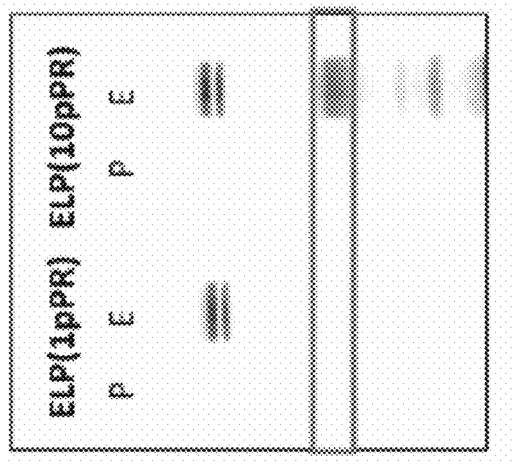
FIGS. 6A-F: Conjugation of multiple fluorophores to ELPs in bacteria. (6A) Conjugation of ELP(1TAG) and ELP(10TAG), produced by either the parent pPR-RS (P) or evolved Mut1-RS (E) in C321.ΔRF1. Conjugation of (6B) ELP(1TAG) and (6C) ELP(10TAG) produced by either the parent pPR-RS or Mut1-RS in BL21 compared to C321.ΔRF1. 1: parent-pPR-RS, BL21; 2: Mut1-RS, BL21; 3: parent pPR-RS, C321.ΔRF1; 4: Mut1-RS, C321.ΔRF1. (6D) In-vitro TAMRA labeling of cell lysates containing ELP(10pPR) expressed in BL21 strain by the (1) the parent pPR-RS or (2) Mut1-RS, or expressed in the C321.ΔRF1 strain by (3) parent pPR-RS or (4) Mut1-RS. (6E-F) Labeling of the OTS by conjugation of pPR to TAMRA. (6E) In-vivo and (6F) in-vitro fluorescent labeling of C321. (1)ΔRF1 cells harboring the Mut1-RS plasmid, (2) ΔRF1 cells harboring the Mut1-RS plasmid, with induction of the aaRS, and (3) ΔRF1 cells harboring both the Mut1-RS and ELP(10pPR) plasmids. A double-band (indicated by a red arrow) was detected when OTS was induced.
Figure 6B:
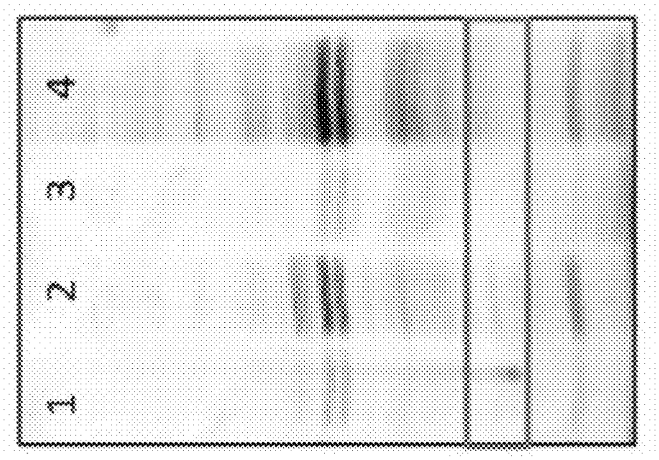
Figure 6C:
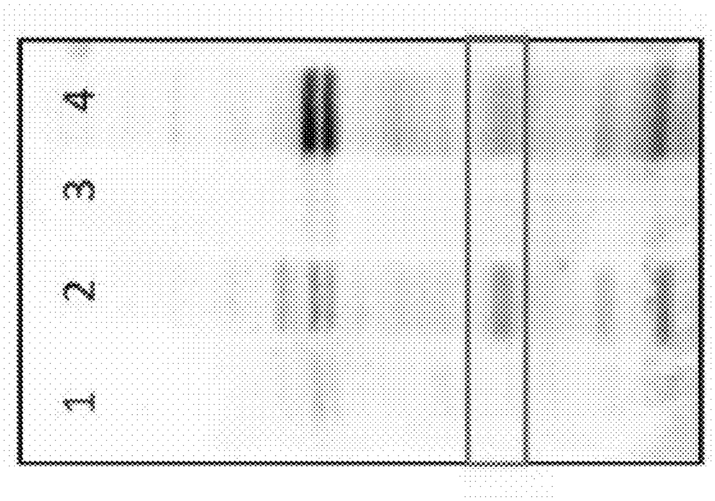
Figure 6D:
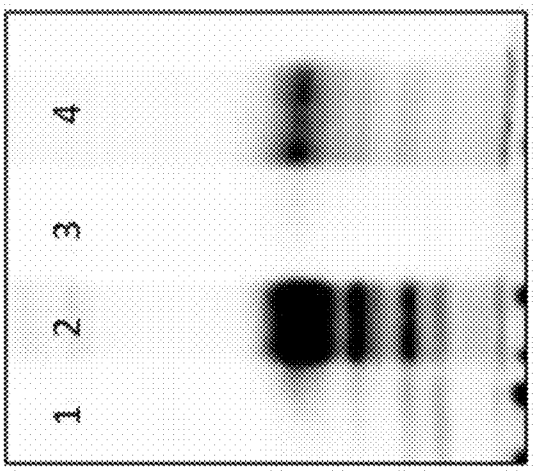

The next step in this study was to determine whether efficient multisite pPR incorporation could be exploited for the bioorthogonal fluorescent labeling of proteins in vitro and in bacteria. It was posited that the multiple conjugated fluorophores and increased target protein yields of the pPR incorporation method disclosed herein could improve the fluorescent signal that is generated following a click reaction of pPR-containing proteins with an azide-fluorescent molecule, thereby enabling short reaction times, lower Cu concentrations, and improved biocompatibility. First, the fluorescent signal generated upon conjugation of purified ELPs with one or ten instances of pPR expressed in C321.ΔRF1 by using Mut1-RS was compared. As expected, improved signals and an improved limit of detection were obtained for purified proteins harboring ten pPR instances compared to those with only a single pPR residue (FIG. 5A). To test whether this increase in signal strength also translated into an improved signal following a click reaction in bacteria, we conjugated TAMRA-azide fluor to the pPR-containing proteins expressed by either the parent-pPR-RS or the evolved Mut1-RS (following induction of protein expression) in the presence of 100ˆˆμM copper for (only) 1 hour at room temperature. At the end of the reaction, the cells were washed and then imaged by fluorescent microscopy to evaluate the labeling efficiency and to verify that the conjugation reaction had indeed occurred inside the cells. Analysis of the microscopy images indicated that ~90ˆ% of the bacteria were labeled by expression of ELP(10TAG) with Mut1-RS, as compared with ~25ˆ% labeled cells obtained by expression of ELP(1TAG) or ELP(10TAG) with parent pPR-RS, and that the fluorescence per cell increased by approximately five- to sevenfold using the former condition as compared to the latter (FIG. 5B-E, FIG. 25). In addition, the labeled cells were lysed, and the proteins were then resolved by SDS-PAGE and analyzed by in-gel fluorescence to image the TAMRA-labeled proteins. In keeping with the microscopy results, labeling in the bacteria resulted in a noticeable fluorescent band only for cells expressing the ELP(10pPR) proteins produced by the Mut1-RS, while all other conjugation reactions produced signals that were below the limit of detection under these conditions (FIG. 6A). Next, the identical labeling experiment was performed in the BL21 strain, which, as expected, returned similar results (FIG. 6B-C). Notably, a comparison of the size and number of labeled bands following labeling in the C321.ΔRF1 and in BL21 cells indicated that only the full-length protein was produced by Mut1-RS in both strains. However, a closer examination of the labeled products obtained after the more efficient in-vitro TAMRA labeling of the cell lysates indicated that various truncated proteins were also produced by the BL21 strain, presumably due to competition with RF-1, which remained present in this non-recoded strain. In-vitro TAMRA labeling of ELP (10pPR) also revealed that while Mut1-RS produced mainly the full-length protein, only short truncated proteins were visible by the parent-pPR-RS (FIG. 6D).

Figure 6E:
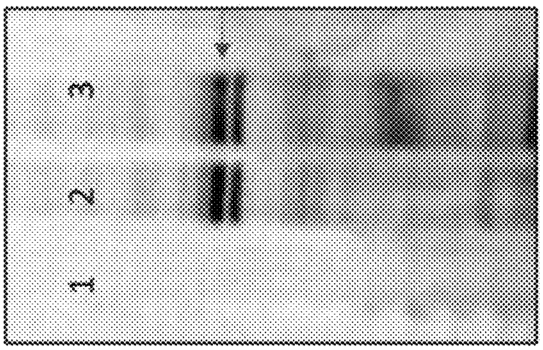
Figure 6F:
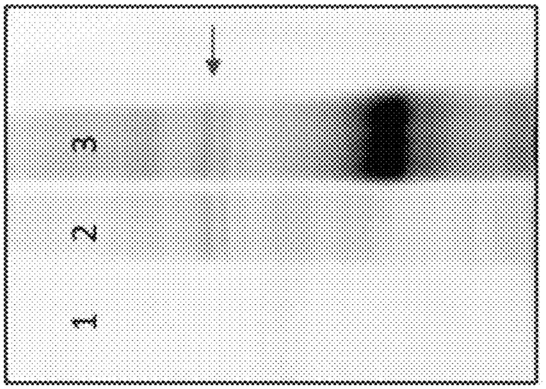

In addition to the expected fluorescent band of labeled ELP(10TAG), an additional, fluorescent double band was detected in all cells harboring the evolved pPR-RS (regardless of the reporter protein) in both *E. coli* strains. It was posited that the double bands represented the aminoacylated aaRS and aminoacylated aaRS-tRNA complex (~35 kDa), in which the complexed pPR was also fluorescently labeled by the TAMRA azide, as has previously been described in other cell types. As anticipated, transformation of C321.ΔRF1 with the Mut1-RS plasmid alone generated the same labeled double bands only when the expression of Mut1-RS was induced, and extraction of these bands from the gel, followed by tryptic digestion and LC-MS analysis, validated the presence of Mut1-RS, confirming the above premise (FIG. 6E-F, FIG. 24J).

Example 3: Evolved pPR-RSs Enable Rapid and Non-Toxic Protein Labeling In Vivo

Figure 7A:
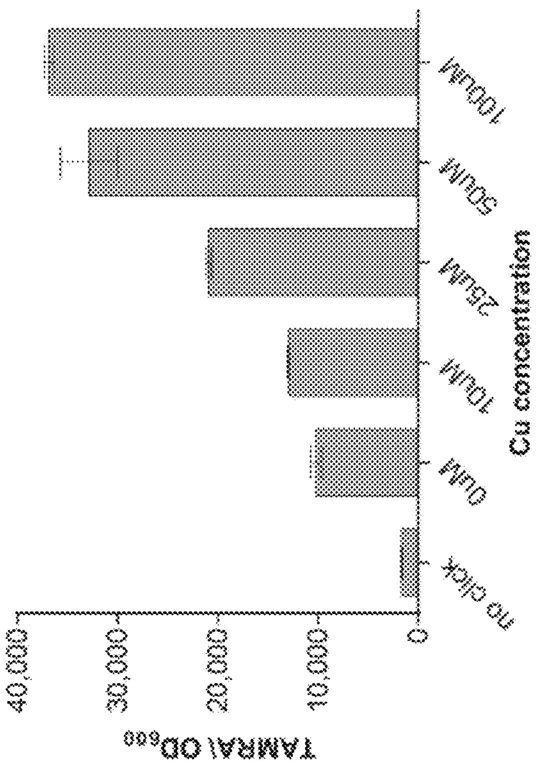
FIGS. 7A-B: (7A) Labeling efficiency of cells harboring ELP(10pPR) expressed by Mut1-RS in the presence of reduced copper concentrations. n=3; values are means s.d. (7B) Growth curves of C321.ΔRF1 cells following an in-vivo click reaction. n=3; values are means±s.d.
Figure 7B:
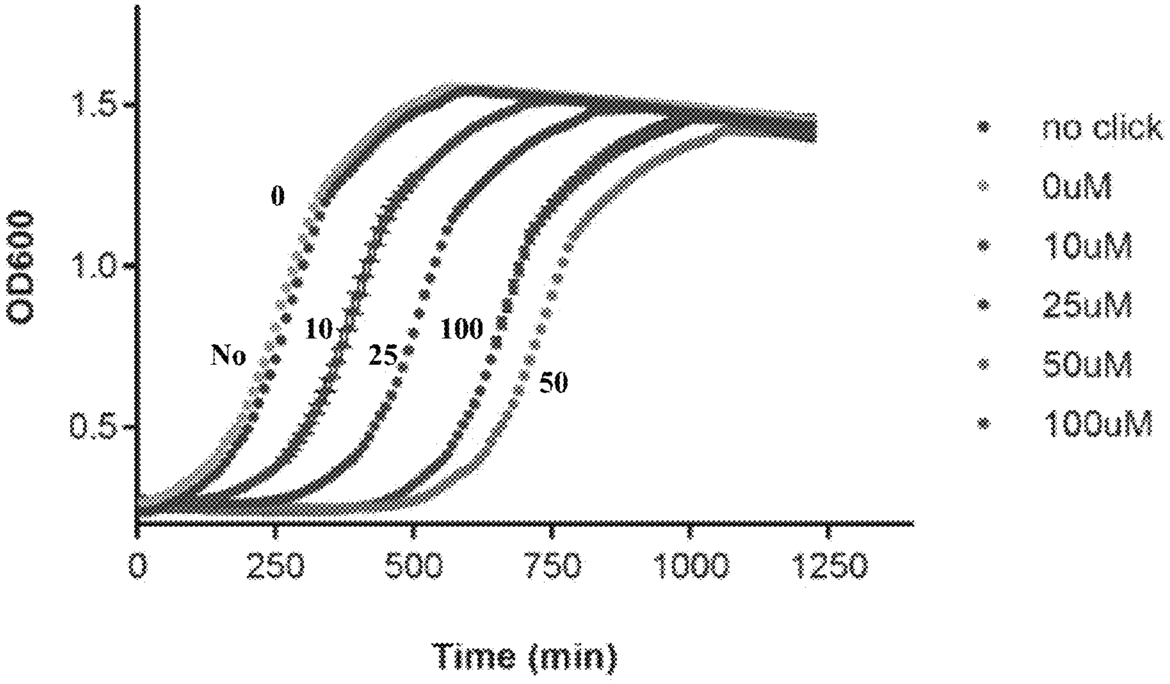

It is well known that the application of CuAAC bioconjugation in living systems is hindered due to the CuI-induced generation of reactive oxygen species (ROS), with consequent cellular toxicity. Therefore, the cell viability and the labeling efficiency of ELP(10TAG) produced by Mut1-RS was tested in the recoded *E. coli* in the presence of different copper concentrations. The efficiency of the evolved aaRS enabled labeling of ELP(10pPR) with a reduced copper concentration of 50 μM, without a significant decrease in labeling efficiency—evaluated as 56 and 35^% in the presence of 25 μM and 10 μM copper, respectively (FIG. 7A). These results exemplify the efficacy of multisite protein labeling for signal amplification when compared with those of previous studies, which reported extensive modification with 100^^μM or 1 mM copper (in an overnight reaction at 4^° C.) but a complete loss of labeling when the copper concentration was reduced to 10 μM. We then determined the effect of copper toxicity on the viability of C321.ΔRF1 in the presence of 10-100 μM copper. Growth curves indicated that although the lag phase for recovery was lengthened as the copper concentration increased, the cells were able to recover and reached an OD600 value similar to that of untreated cells in the stationary phase (FIG. 7B), in agreement with previous studies in mammalian and *E. coli* cells.

Several methodologies have described the use of Cu ligands to reduce Cu-mediated toxicity to cells by using an azide probe that contains an internal copper-chelating moiety or by using strained alkynes, which obviate the need for copper catalysts. However, unlike simple azides and alkynes, the azide probes that have an internal copper chelating moiety and the strained alkynes are large structures, and they might, therefore, interfere with the function of the labeled protein. Additional drawbacks of strain-promoted azide-alkyne cycloaddition (SPAAC) are that it is much slower than CuAAC and it is neither strictly bioorthogonal nor regioselective. Here it is shows herein that the incorporation of multiple alkyne instances in ELP can be used to generate an enhanced fluorescent signal at a reduced copper concentration.

Commonly used fluorescent labeling methods include fusion to GFP variants or to self-labeling enzymes (e.g., SNAP- and CLIP-tag and self-labeling tags (e.g., tetracysteine tag). However, these methods are limited, as the large size of the fused proteins (~20-27 kDa) may perturb the cellular localization, structure, or function of the fused protein, while the utilization of small, genetically encoded labeling tags often results in nonspecific staining of the membrane and hydrophobic pockets and thiols in off-target proteins. In contrast, it is shown herein that site-specific pPR incorporation in ELP-fusion proteins enables labeling at multiple, precise positions with minimal changes to the target protein sequence. Although other studies have demonstrated the detection of proteins that were each conjugated in vivo to a single fluorescent molecule, herein, the conjugation of a single TAMRA molecule failed to generate a detectable signal in a SDS-PAGE protein gel, under the examined conditions. This could be the result of comparatively lower expression levels of the target proteins (due to the proteins themselves, the strength of the promotor, or to other factors that affect expression) or of the moderate extinction coefficient and quantum yield of TAMRA compared to other fluorophores. The data nonetheless suggest that the ability to conjugate multiple fluorophores to the target protein can compensate for low protein expression or fluorophore properties.

This is the first study to use ELP fusion proteins as scaffolds for fluorophore conjugation sites. ELPs have already been successfully fused to a variety of proteins and typically do not reduce (and can even enhance) protein yields. Herein is shown that they can also enable the conjugation of multiple fluorophore labels while preventing or minimizing perturbation of proper protein folding or function, which can be caused by internal labeling. Herein, every third pentapeptide contained an X-guest residue that encoded for pPR, which resulted in a ~12 kDa ELP protein. Thus, the ability to precisely control the length, composition and number of sites for conjugation of the fluorescent molecules suggests that other (e.g., smaller) ELP fusions can also be used, and that the ELP-family can be exploited as valuable fusion partners, permitting site-specific conjugation of multiple fluorescent molecules for increased labeling efficiency and improved detection of the target proteins. Moreover, ELPs containing natural amino acids or uAAs have previously been designed and utilized for various applications, such as protein purification, hydrogel formation, drug delivery, tumor targeting and tissue engineering.

Example 4: Efficient Multi-Site AzoPhe Incorporation by Evolved nsAA-RS

Figure 8A:
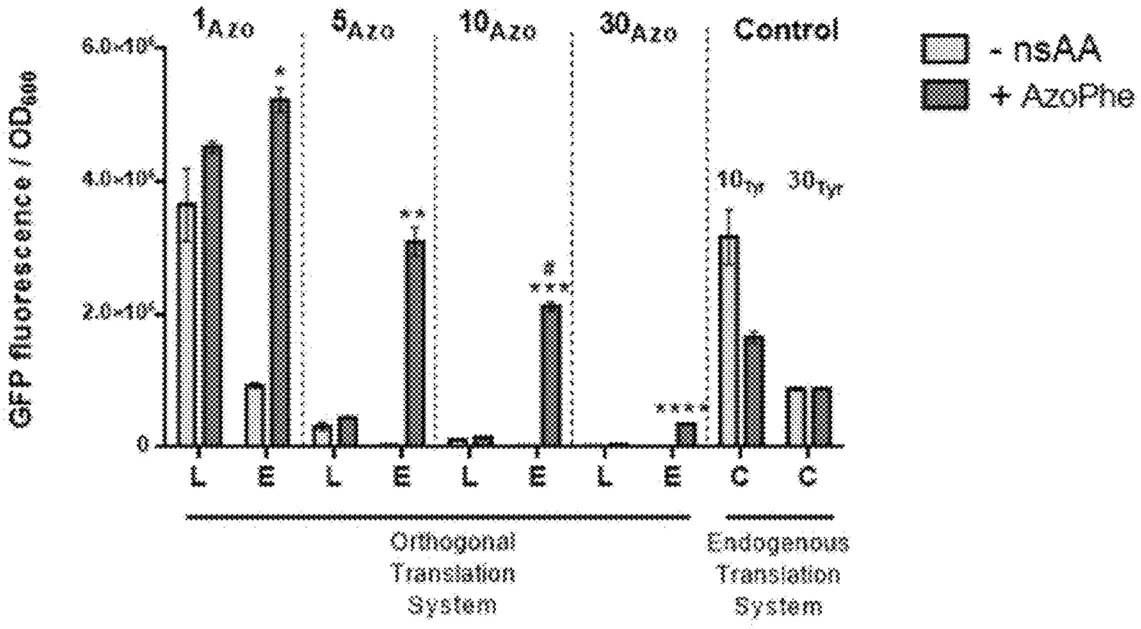
FIGS. 8A-D: Incorporation of phenylalanine-4'-azobenzene (AzoPhe) in expressed proteins. (8A) GFP expression in GRO from ELP(10Tyr or 30Tyr)-GFP reporters, or from ELP(1TAG, 5TAG, 10TAG or 30TAG)-GFP reporters produced by literary (L) or Mut7 aaRS. Red bars indicate addition of uAA (AzoPhe), grey bars indicate no addition of uAA. error bars; mean±standard error. *P<0.01 indicates comparison of literary aaRS with the evolved. #P<0.01 indicates comparison of evolved aaRS (10Azo) with the endogenous (10Tyr). (8B) Multi-site-specific incorporation of AzoPhe into E2(10TAG). Mass-spectrometry results (MALDI-TOF) of (top) E2 with 10 TAG, expressed with episomal evolved aaRS, in presence of AzoPhe, compared with (bottom) ELP (10Tyr). (8C). MALDI (z=2, z=3) spectra of purified proteins expressed in the GRO. ELP(Tyr)-GFP (Left), ELP(10pPR)-GFP (Right) The deviation from the theoretical MW is indicated. (8D). MALDI (z=2, z=3) spectra of purified proteins expressed in BL21 ELP(Tyr)-GFP (Left), ELP(10pPR)-GFP (Right) The deviation from the theoretical MW is indicated.
Figure 8B:
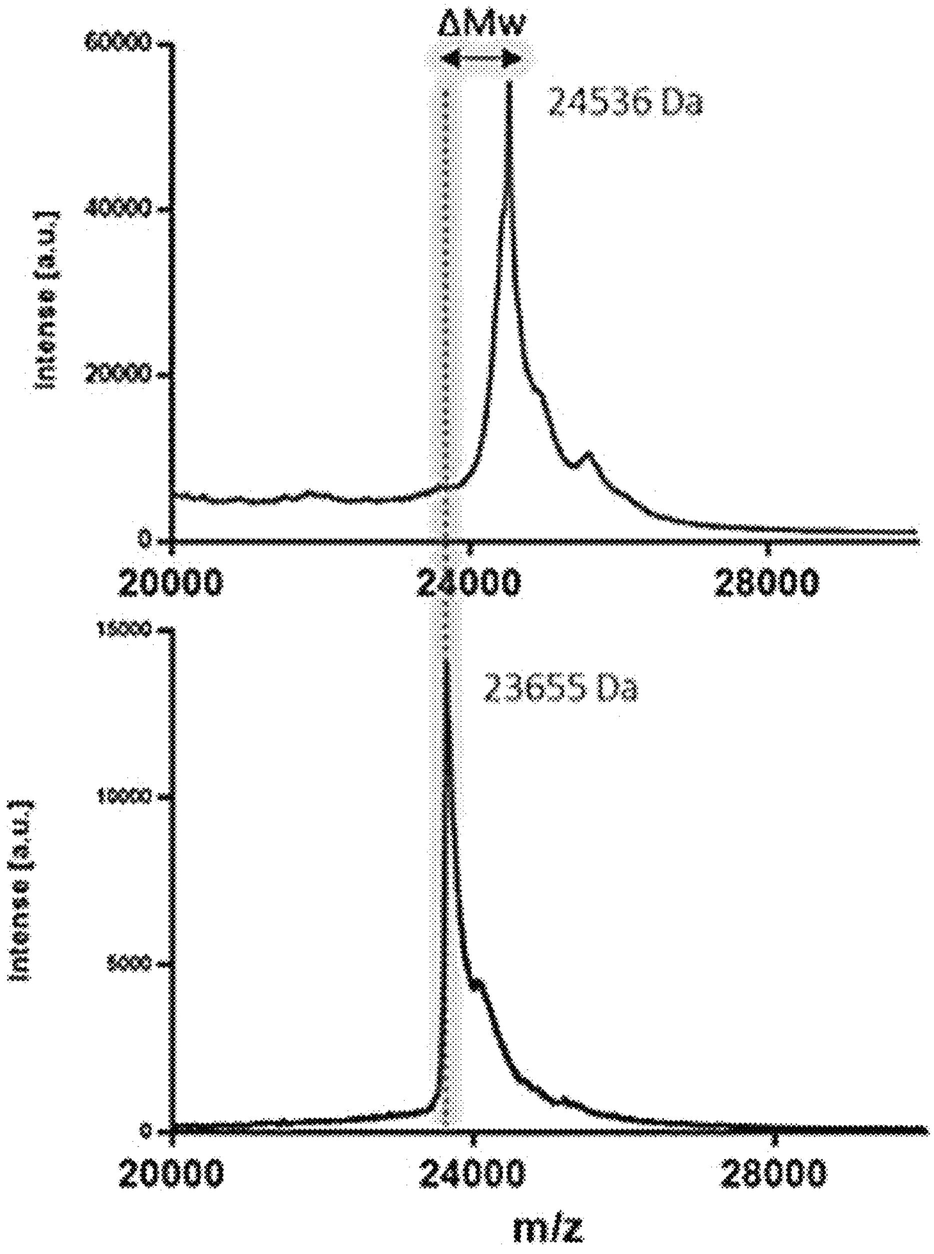
Figure 8C:
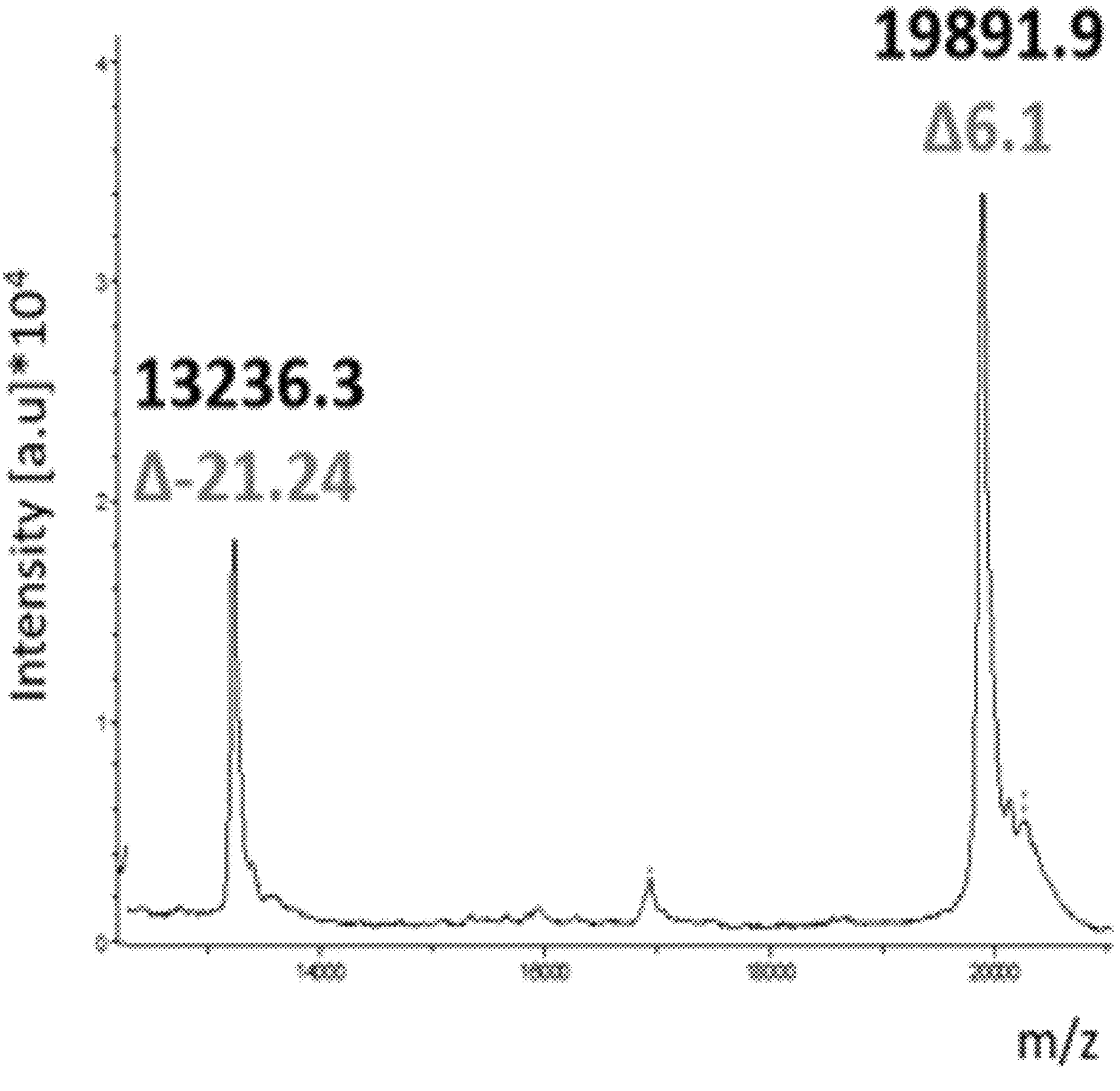
Figure 8C:
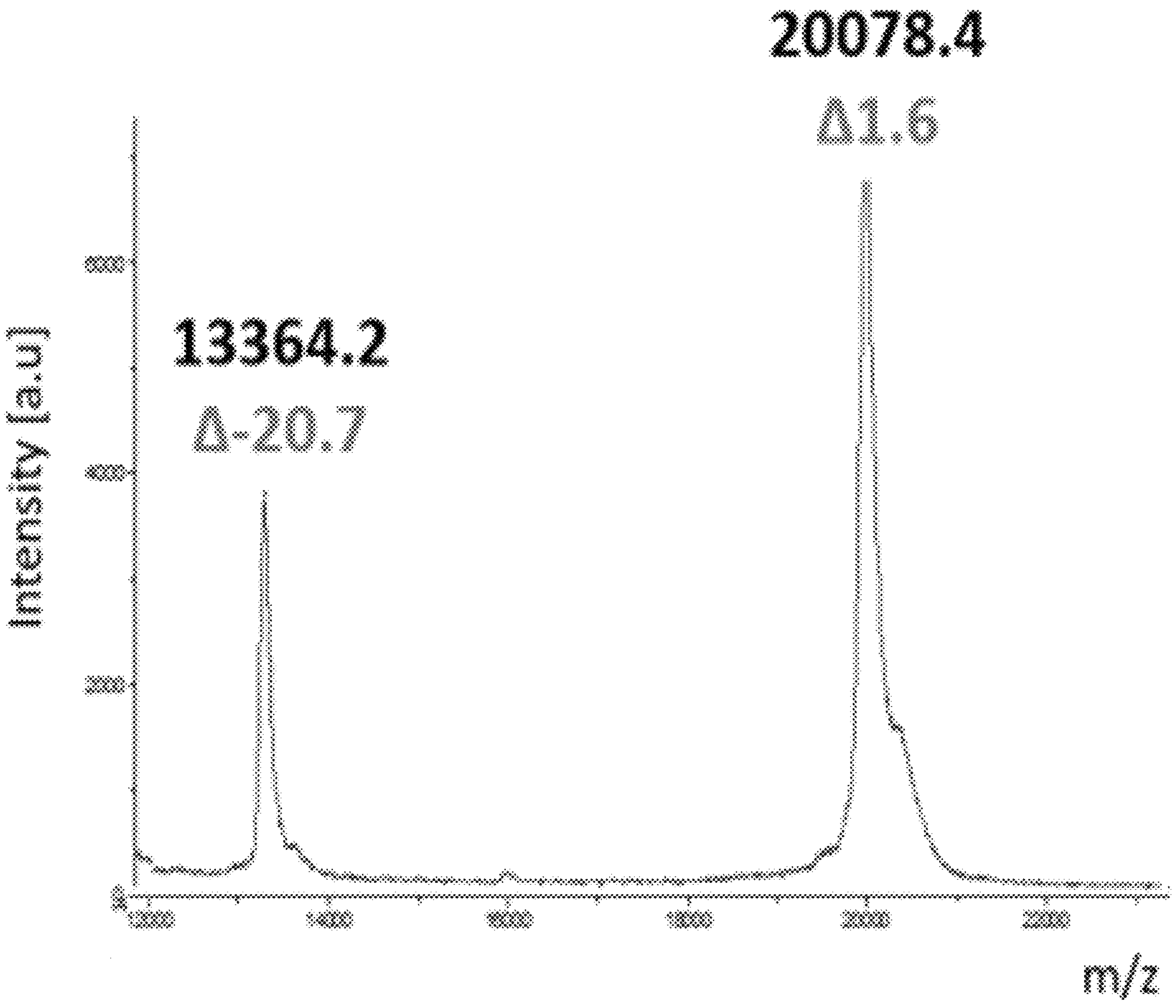
Figure 8D:
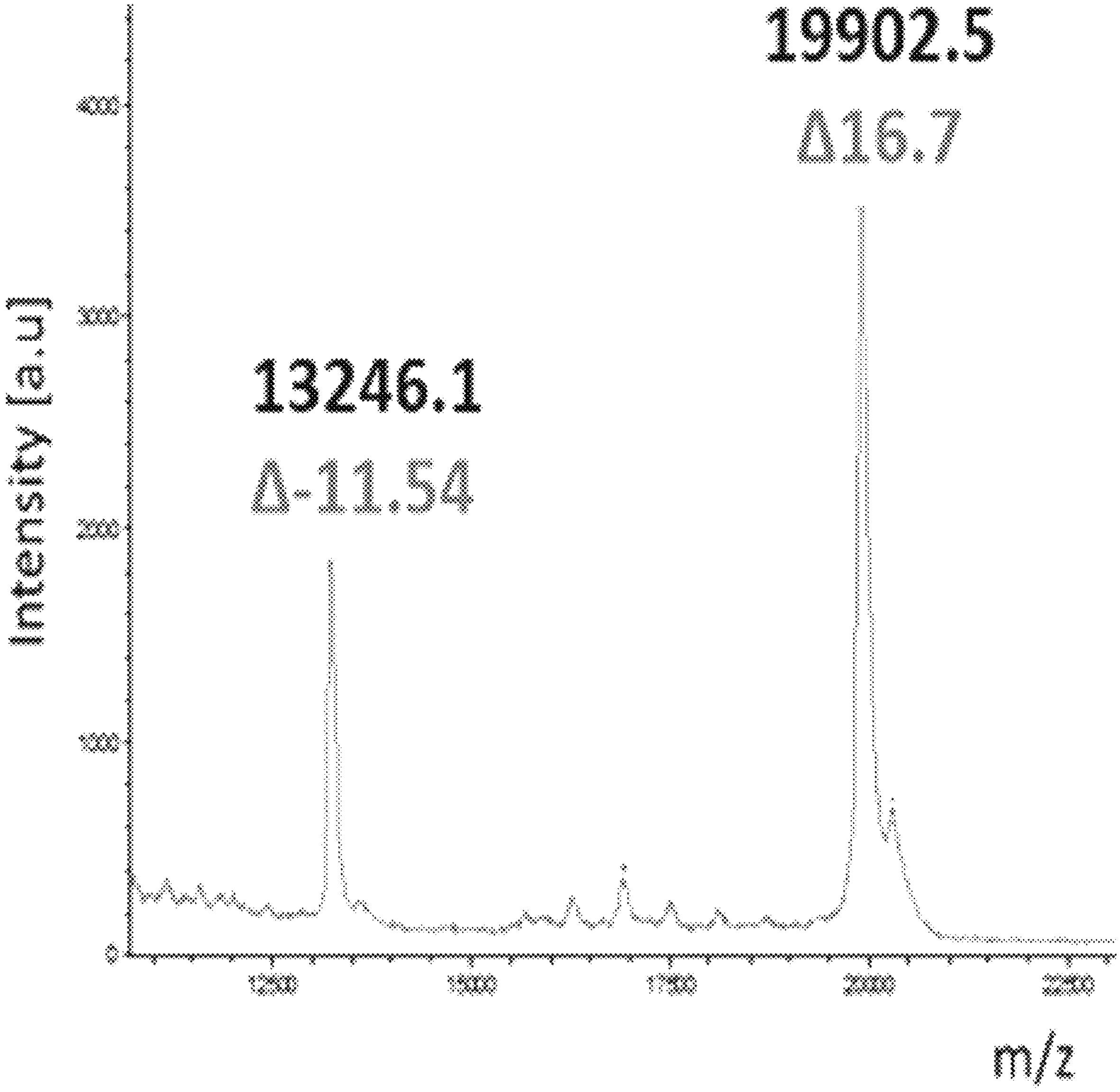
Figure 8D:
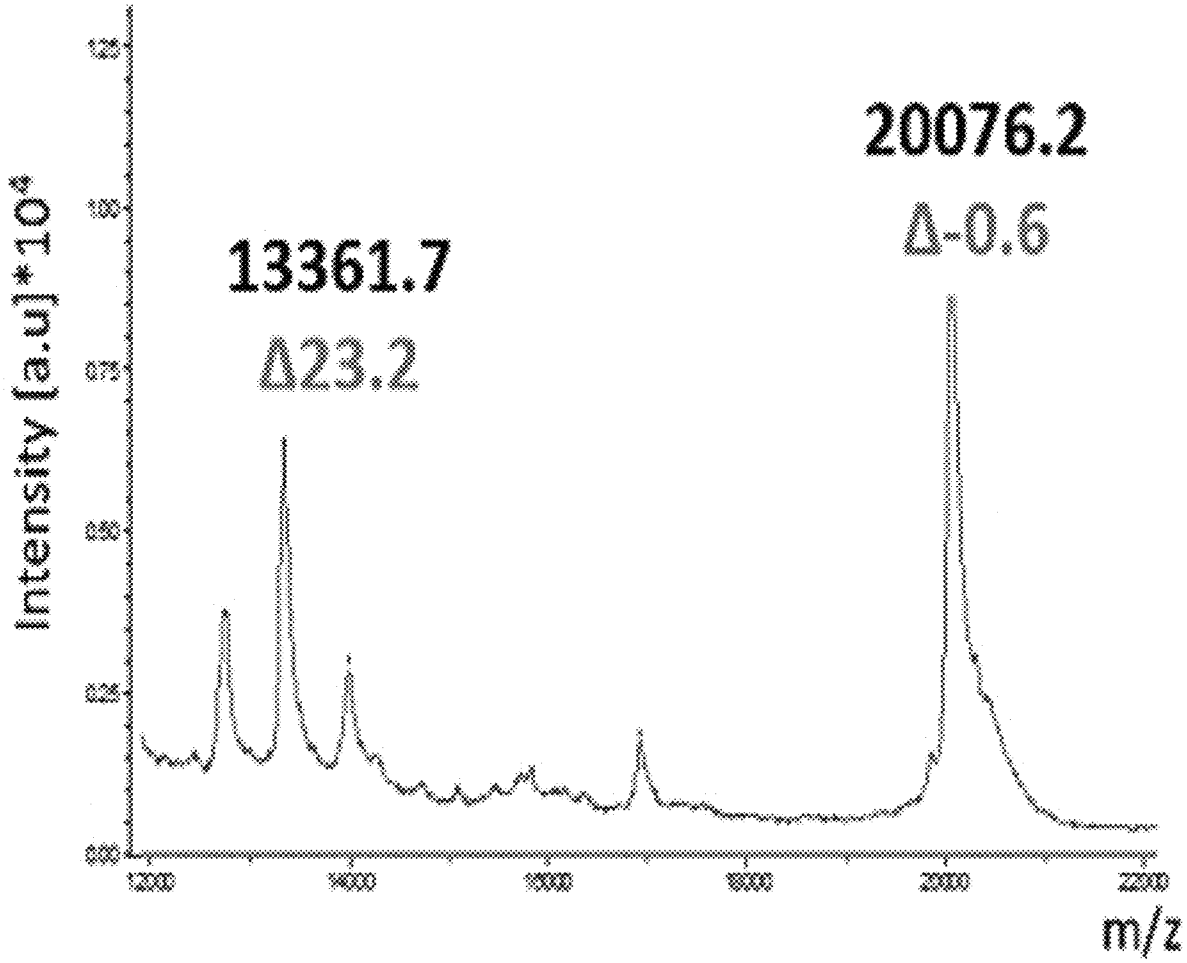

The performance of evolved nsAA-RSs was characterized for the ability to incorporate azobenzene-containing nsAA into proteins. Mutants are shown in FIG. 1B. To evaluate the mutants for multi-site (3-30) AzoPhe incorporation, a GRO was transfected with plasmids carrying the reporter proteins of elastin-like protein (ELP)-GFP fusion, whereby ELP coding sequence harbors 1, 5, 10 or 30 TAGs or WT equivalents (harboring 10 or 30 tyrosine substitutions), and episomal versions of one selected evolved AzoPhe-RS variant (Mut 7). Plate-based fluorescence analysis indicated that expression of the evolved nsAA-RS (AzoPhe-RS) from multi-copy plasmids lead to higher multi-site-specific incorporation in the presence of AzoPhe compared with the literary-RS and to the endogenous system of tyrosine with 10 TAGs (FIG. 8A).

Figure 9A:
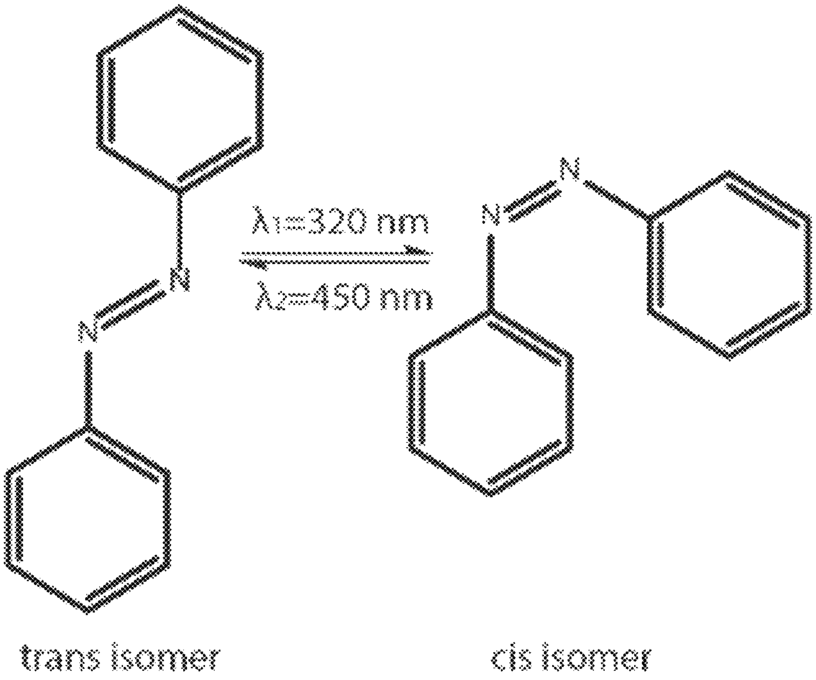
FIGS. 9A-G: (9A) Illustration of the reversible trans-to-cis isomerization of an azobenzene molecule. (9B) Illustrations and properties of azobenzene-uAAs 1, 2, and 3. (9C) Illustration of the mechanism for altering the Tt of the ELP by azobenzene isomerization. A change in the transition temperature by cis/trans isomerization generates a "window" in which isothermal (e.g., at T*), light-mediated change in ELP solubility can be achieved. (9D) Schematic illustration of reporter proteins for the incorporation of either 2 (GFP) or 1, 5, or 10 (ELP-GFP) uAAs at TAG codons. (9E-G) Incorporation of either (9E) 1, (9F) 5, or (9G) 10 instances of azobenzene-uAAs 1, 2, or 3 in a single ELP by the previously described AzoRS, expressed from a multi-copy plasmid. Error bars indicate SD (n=3).
Figure 9B:
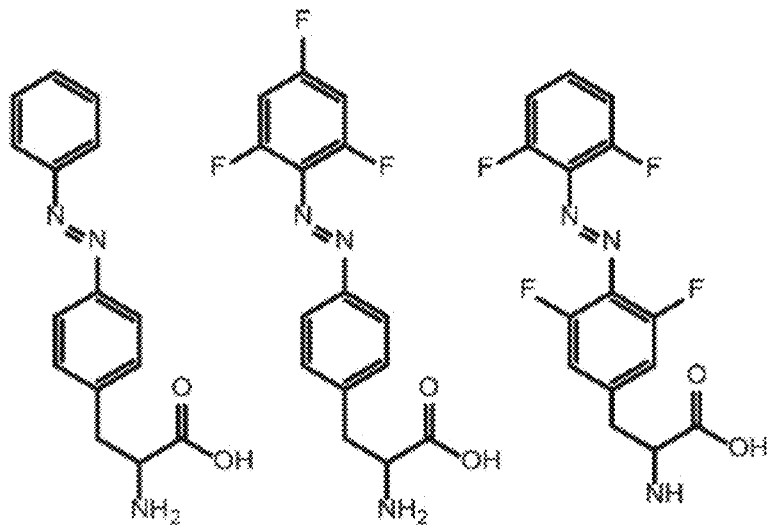
Figure 9C:
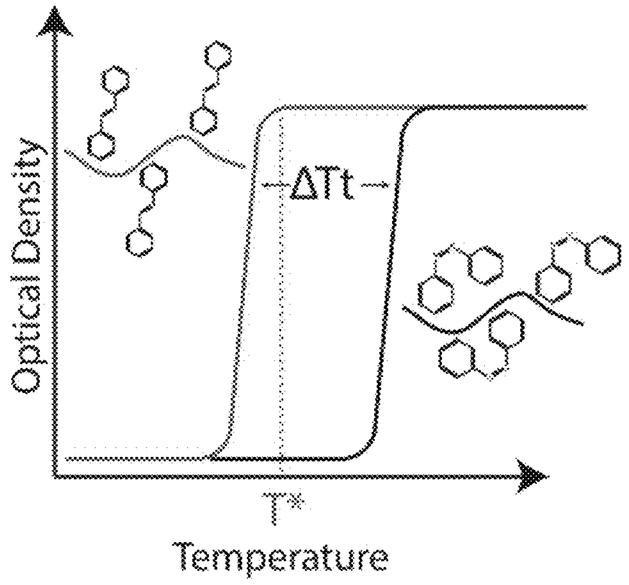
Figure 9D:
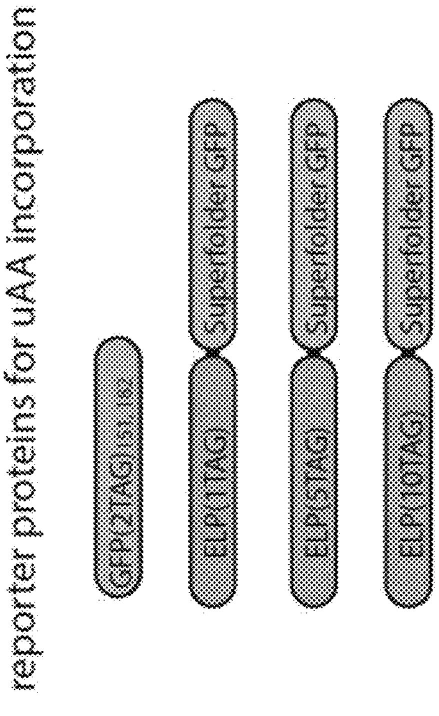
Figure 9E:
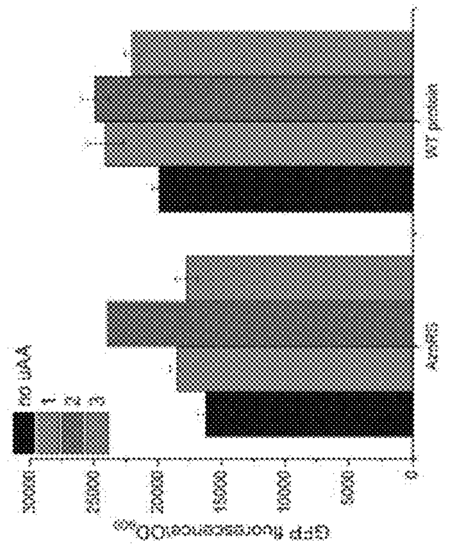
Figure 9F:
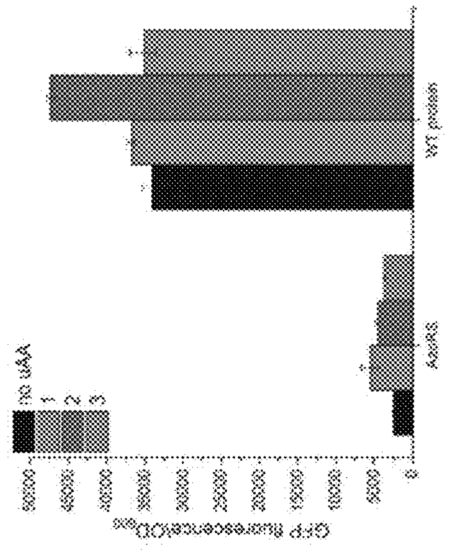
Figure 9G:
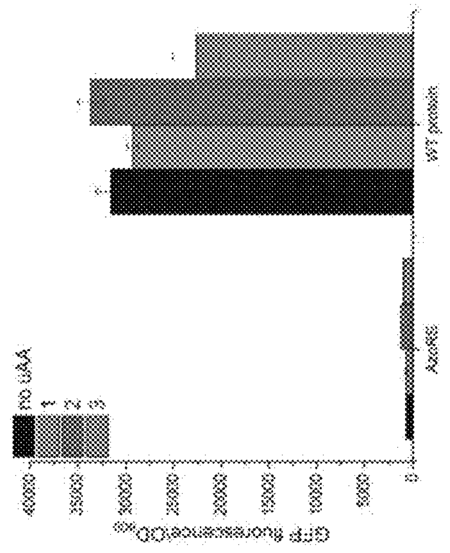

Next, the ability of the Azo-RS variant, to incorporate azobenzene uAAs 1, 2, or 3 (FIG. 9B; 1-10 instances per protein) in the *Escherichia coli* strain C321.ΔRF1, which lacks all the native TAG codons and their associated release factor (RF-1). To this end, the GFP- and ELP-based reporter proteins were utilized to indicate the multi-site incorporation of uAAs in the reassigned TAG codons GFP(2TAG), ELP (1TAG)-GFP, ELP(5TAG)-GFP, and ELP(10TAG)-GFP, which are identical to or slightly modified from previously described GFP and ELP-based reporter proteins for uAA incorporation (FIG. 9D, Table 1). A GFP fluorescence assay indicated that the multi-site incorporation of 1, 2, or 3 by AzoRS, when expressed from a multi-copy plasmid in C321.ΔRF1, produced up to ~96%, 14%, and ~4% of ELP(1TAG)-GFP, ELP(5TAG)-GFP, and ELP(10TAG)-GFP, respectively, as compared with control GFP and ELP proteins, which contained tyrosines incorporated by the wild-type MjTyrRS system (FIG. 9E-G).

Figure 10A:
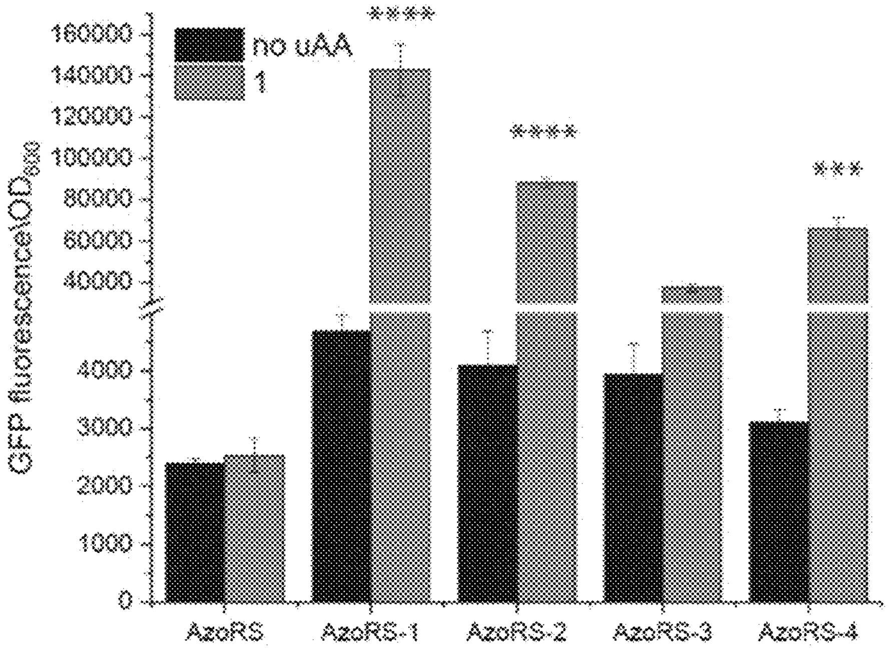
FIGS. 10A-D: (10A) Production of GFP(2TAG) by the previously described AzoRS and four evolved variants, expressed from a single chromosomal copy. (10B-D) Production of ELP-GFP fusion proteins containing either (10B) 1, (10C) 5, or (10D) 10 instances of the azobenzene-uAAs depicted in 10B and expressed by episomal versions of the previously described AzoRS, our evolved variants (AzoRS1-4), or MjTyrRS (producing tyrosine-containing control ELPs) in the C321.ΔRF1 strain. The level of GFP fluorescence indicates the production of the ELP-GFP fusion and, therefore, the efficiency of sAA incorporation. *P<0.05, P<0.001, *P<0.0005, ****P<0.0001 indicate comparison of each evolved variant with the AzoRS. n=3; error bars indicate s.d.
Figure 10B:
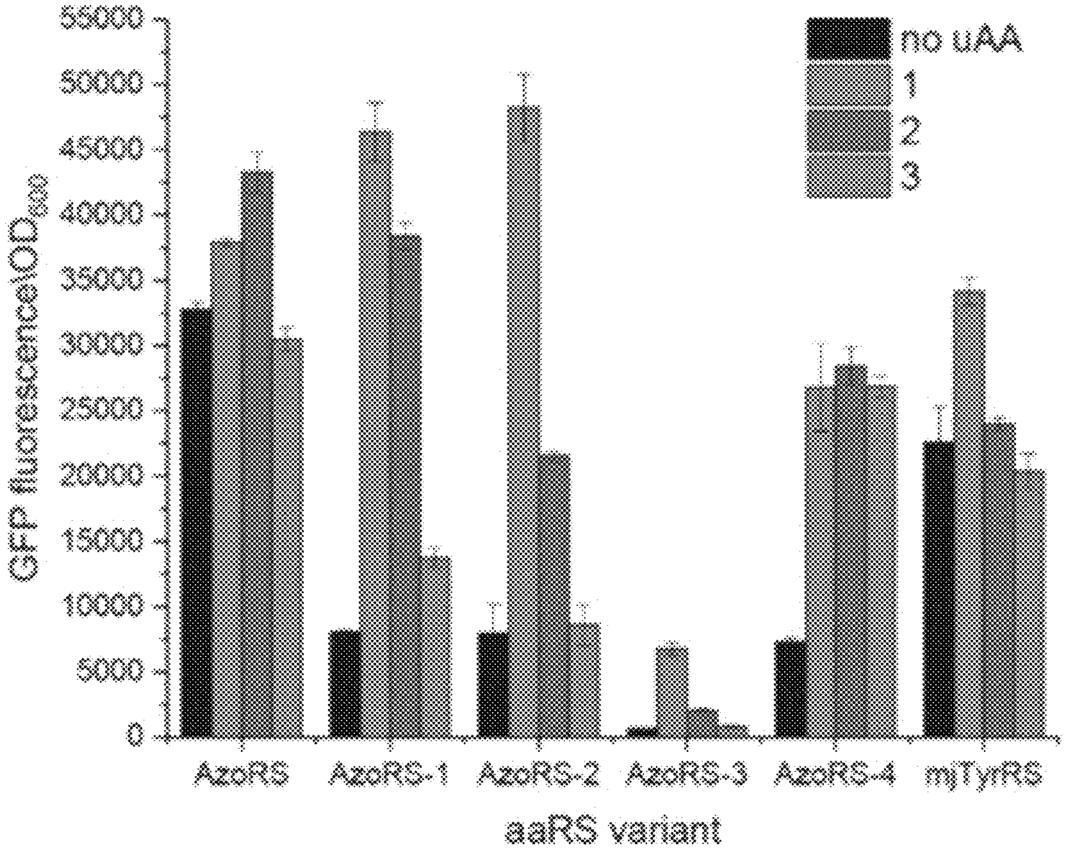
Figure 10C:
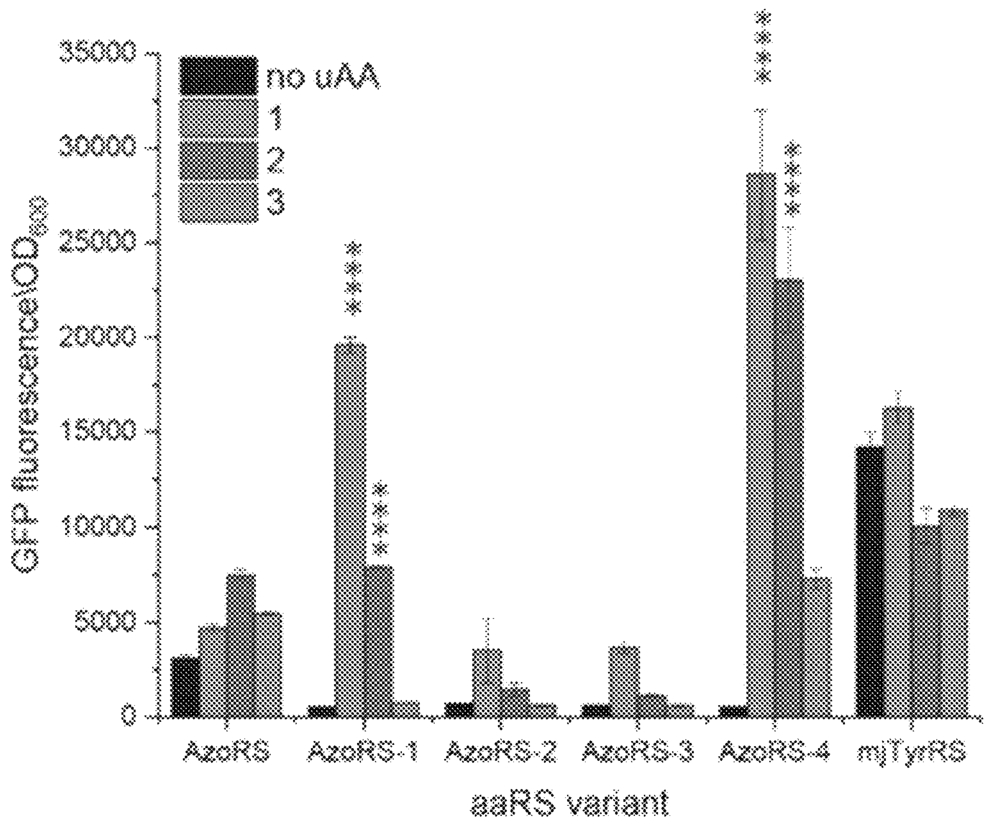
Figure 10D:
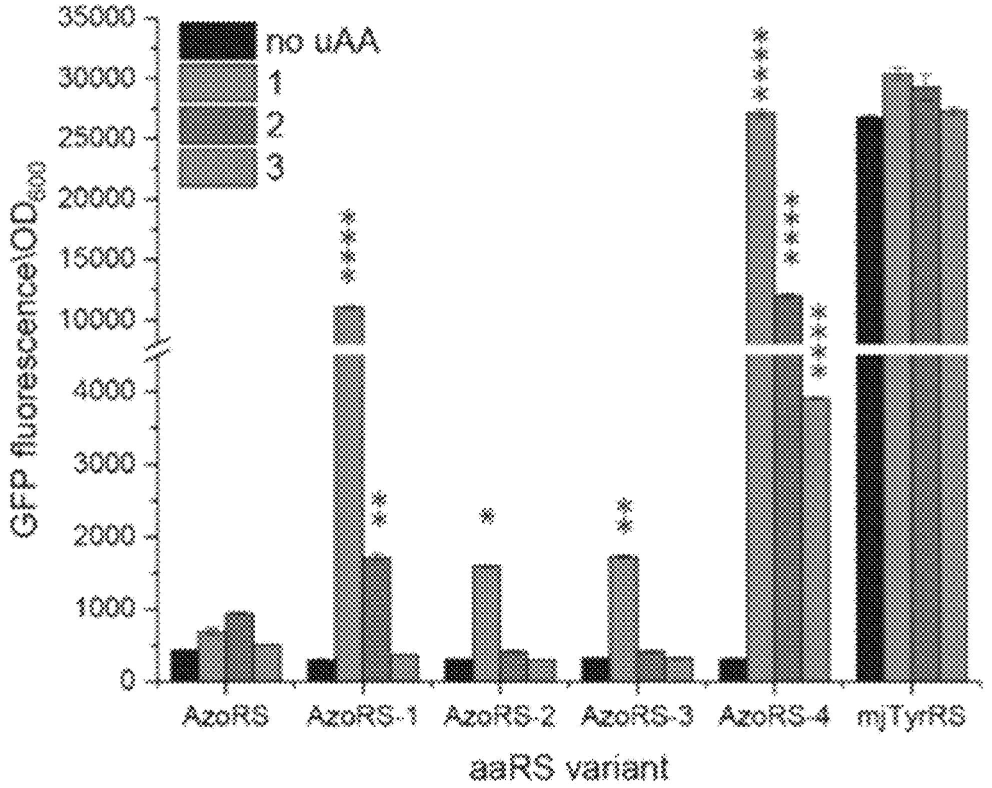

To enable the multi-site incorporation of azobenzene-uAAs, a modified protein-evolution strategy was used that was previously developed to identify improved MjTyrRS mutants, which can efficiently charge an amber suppressor tRNA with azobenzenes 1, 2, or 3 in C321.ΔRF1. Briefly, genomically integrated aaRS variants were subjected to 5-10 rounds of multiplex automated genome engineering (MAGE)-based diversification, using degenerate ssDNA oligonucleotides (Table 2), followed by successive tolC-mediated negative-positive-negative selection cycles (ColE1-mediated negative selection or SDS-mediated positive selection). The first (negative) selection cycle was used to eliminate non-orthogonal variants generated in the diversification process, which, even if rare, would otherwise be enriched in the subsequent positive selection cycle; the second (positive) selection cycle was used to enrich the efficient aaRS variants; and the third (negative) selection cycle was used to eliminate "cheater" non-orthogonal clones generated in response to the stress applied in the positive selection step. The production of GFP(2TAG) in the presence of 1 was used to evaluate activity in genomically integrated individual clones. Several improved variants were identified that, when expressed from a single chromosomal copy, were capable of 14-56-fold higher GFP(2TAG) production compared with the parent enzyme (FIG. 10A). After Sanger-sequencing all the evolved variants (Table 3), we evaluated them for the multi-site (1-10) incorporation of 1, 2, or 3 by co-transforming C321.ΔRF1 with plasmids carrying the above-mentioned reporter proteins and episomal versions of each evolved variant. As expected, the expression of the evolved aaRSs from multi-copy plasmids increased their ability to incorporate multiple (1, 5, or 10) azobenzene-uAAs. Notably, one of the evolved variants, designated AzoRS-4, increased the expression of ELP (10TAG)-GFP containing 1, 2, or 3, by ~40-, ~13-, and ~-7-fold, respectively, as compared with the abovementioned AzoRS (FIG. 10B-D). Although the substituents of 1, 2, and 3 differ only in hydrogen-to-fluorine substitutions, which are not expected to significantly alter the size of the azobenzene molecule, the efficiencies of incorporating these uAAs were different between the aaRS variants. Similar findings have been reported for other *Methanosarcina*-derived azobenzene aaRSs.

TABLE 1

GFP and ELP sequences

| Protein | Amino acid sequence (X denotes the TAG codon) (SEQ ID NO:) |
|---|---|
| GFP-WT | SKGEELFTGVVPILVELDGDVNGHKFSVRGE<br>GEGDATNGKLTLKFICTTGKLPVPWPTLVTT<br>LTYGVQCFSRYPDHMKRHDFFKSAMPEGYVQ<br>ERTISFKDDGTYKTRAEVKFEGDTLVNRIEL<br>KGIDFKEDGNILGHKLEYNFNSHNVYITADK<br>QKNGIKANFKIRHNVEDGSVQLADHYQQNTP<br>IGDGPVLLPDNHYLSTQSVLSKDPNEKRDHM<br>VLLEFVTAAGITHGMDELYKGS (29) |
| GFP(2TAG) | SKGEELFTGVVPILVELDGDVNGHKFSVSGE<br>GEGDATYGKLTLKFICTTGKLPVPWPTLVTT<br>LTYGVQCFSRYPDHMKQHDFFKSAMPEGYVQ<br>ERTIFFKDDGNYKTRAEVKFEGDTLVNRIEL<br>KGIDFKEDGNILGHKLEYNYNSHNVXIMADK<br>QKNGIKVNFKIRHNIEDGSVQLADHXQQNTP<br>IGDGPVLLPDNHYLSTQSKLSKDPNEKRDHM<br>VLLEFVTAAGITLGMDELYKGSSHHHHHHGG<br>(30) |
| ELP(10TAG)-GFP | SKGPG(VPGGGVPGAGVPGXG)$_{10}$PGGGG-<br>(GFP-WT) (31) |
| ELP(5TAG)-GFP | SKGPG(VPGGGVPGAGVPGXGVPGGGV<br>PGAGVPGYG)$_{5}$SPGGGG-(GFP-WT) (32) |
| ELP(1TAG)-GFP | SKGPG(VPGGGVPGAGVPGYG)$_{4}$(VPGGGVP<br>GAGVPGXG)$_{1}$(VPGGGVPGAGVPGYG)$_{5}$PGG<br>GG-(GFP-WT) (33) |
| ELP$_{60}$(2TAG) | G[(VPGGGVPGAG)$_{14}$<br>(VPGXGVPGAG)]$_{2}$GY (34) |
| ELP$_{60}$(6TAG) | G[(VPGGGVPGAG)$_{4}$<br>(VPGGGVPGXG)]$_{6}$GY (35) |
| ELP$_{60}$(10TAG | G[(VPGGGVPGAG)$_{4}$<br>(VPGGGVPGXG)]$_{10}$GY (36) |
| ELP$_{60}$(10TAG) | G[(VPGAGVPGGGVPGAG)<br>K(VPGGGVPGXGVPGGG)K]$_{10}$GGY<br>(37) |
| ELP$_{60}$WT | G(VPGGGVPGAG)$_{30}$GY (38) |

TABLE 2

Degenerate ssDNA MAGE oligonucleotides

| Targeted residues in the uAA binding | Oligonucleotide sequence (SEQ ID NO:) |
|---|---|
| L32, G34 | a*a*gagttaagagaggttt<br>taaaaaaagatgaaaaatct<br>gctnnkatannktttgaacc<br>aagtggtaaaatacatttag<br>ggcattatctcc (39) |
| L65, A67 | a*g*atgattgatttacaaa<br>atgctggatttgatataatt<br>atannkttgnnkgatttaca<br>cgcctatttaaaccagaaag<br>gagagttggatg (40) |
| E107, F108, Q109 | t*t*tttgaagcaatggggt<br>taaaggcaaaatatgtttat<br>ggaagtnnknnknnkcttga<br>taaggattatacactgaatg<br>tctatagattgg (41) |

TABLE 2-continued

| Degenerate ssDNA MAGE oligonucleotides | |
|---|---|
| Targeted residues in the uAA binding | Oligonucleotide sequence (SEQ ID NO:) |
| Y151 | a*a*aagagcaagaaggagt atggaacttatagcaagaga ggatgaaaatccaaaggttg ctgaagttatcnnkccaata atgcaggttaat (42) |
| G158, C159, R162, A167 | c*c*aataatgcaggttaat nnknnkcattatnnkggcgt tgatgttnnkgttggaggga tggagcagagaaaaatacac atgttagcaagg (43) |

Single-stranded DNA oligonucleotides with two phosphorothioate bonds at the 5' end (denoted by *) were purchased from Integrated DNA Technologies.
The degenerate base n represents all four bases, and k represents G/T.

TABLE 3

Annotations of specific mutations in evolved aaRS variants, as compared with the WT *Methanocaldococcus jannaschii* tyrosyl-tRNA synthetase (MjTyrRS) sequence. In addition to the indicated mutations, all mutants also harbor the R257G and D286R mutations, which have been shown to improve tRNA binding.

| | Position | | | | | | | | | Name in |
|---|---|---|---|---|---|---|---|---|---|---|
| Annotation | 32 | 65 | 107 | 108 | 109 | 158 | 159 | 162 | 167 | FIG. 1B |
| WT-MjTyrRS | Y | L | E | F | Q | D | I | L | A | |
| AzoRS-1 | G | V | E | F | Q | G | Y | S | F | Mut 2 |
| AzoRS-2 | L | V | S | V | S | G | Y | S | F | Mut 3 |
| AzoRS-3 | L | V | N | V | L | G | Y | S | F | Mut 4 |
| AzoRS-4 | G | V | E | F | Q | G | Y | R | A | Mut 7 |

Example 5: ELPs with a UV-Light-Responsive Phase-Separation Behavior

While the above-mentioned ELP-GFP fusion proteins are valuable reporters for assessing the efficiency and ability of the aaRSs to incorporate multiple uAA instances, their transition temperature (Tt) is either above (in the form of GFP-fused proteins) or below (as unfused proteins) the typical temperature range (10-90° C.) used for Tt analysis and characterization. Therefore, a new set of ELP variants was designed to analyze the effect of azobenzene incorporation on the ELP Tt. The design was based on previously described hydrophilic ELPs which have a high Tt (>90° C. for a 25 μM solution) and are composed of glycine and alanine amino acids alternating in the X-guest residue position. These ELPs were selected as hosts for azobenzene incorporation since the hydrophobic azobenzene molecule was expected to dramatically reduce the Tt when incorporated in multiple sites in the ELPs. To analyze the effect of varying the number of azobenzene groups per ELP, four ELP genes were designed, each containing 60 pentapeptides and either 0, 2, 6, or 10 TAG codons (for azobenzene incorporation) distributed equally along the guest residue of the ELP; these ELP genes were termed $ELP_{60}$WT, $ELP_{60}$(2TAG), $ELP_{60}$(6TAG), and $ELP_{60}$(10TAG), respectively (Table 1). Proteins expressed from the above-mentioned ELP genes are named according to the number and identity of the amino acid incorporated in the TAG codons. For example, $ELP_{60}$(1×10) is the protein product of the $ELP_{60}$(10TAG) gene, wherein 1 was incorporated in 10 encoded TAG codons.

Figure 11:
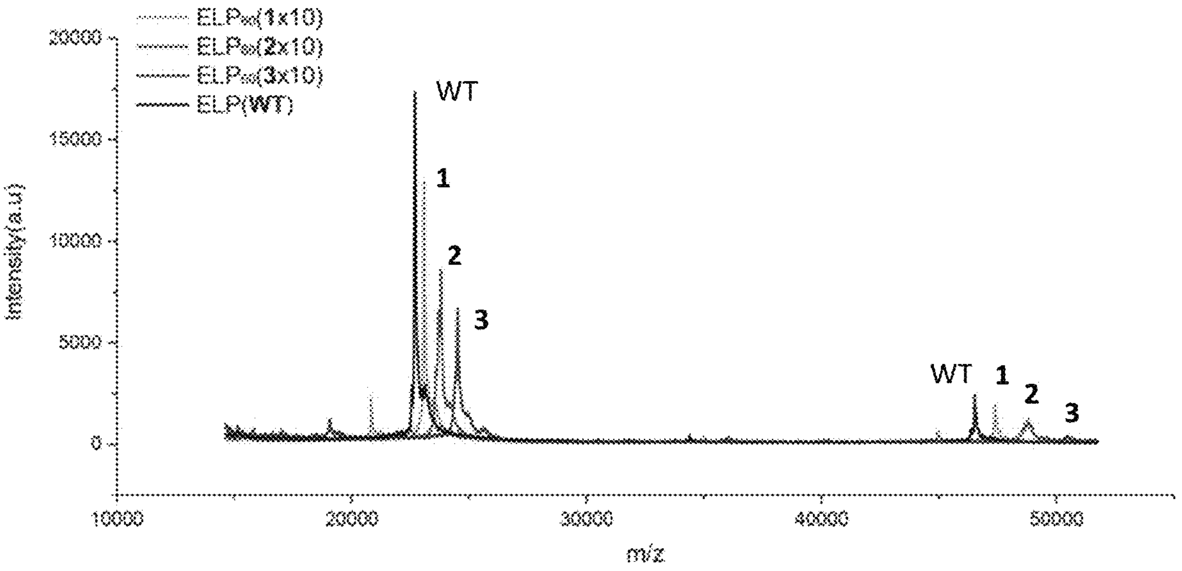
FIG. 11: MALDI-TOF analysis of ELP60(WT) [expected: 22,760.4, found: 22726.03], ELP60(2×1) [expected: 23,148.87, found: 23083.17], ELP60(6×1) [expected: 23,841.65, found: 23793.87], and ELP60(10×1) [expected: 24,562.47 found: 24519.49].

The $ELP_{60}$ protein series was first produced in the C321.ΔRF1 strain by using AzoRS-4 and azobenzene-uAA 1. To determine protein yields, small batches of $ELP_{60}$(1×2), $ELP_{60}$(1×6), and $ELP_{60}$(1×10) were purified, and the protein yields were 35.69±3.69, 22.9±1.27, and 24.34±1.69 mg $L^{-1}$, respectively, as compared with 39.72±0.68 mg $L^{-1}$ of $ELP_{60}$ (WT). The accuracy of incorporating 1 was evaluated by intact mass-spectrometry (MS) (FIG. 11), and we also analyzed tryptic fragments of the MS-optimized reporter protein $ELP_{60}(10TAG)_{MS}$ (Table 1) expressed with 1 (i.e., $ELP_{60}(1\times10)_{MS}$) by liquid chromatography-MS (LC-MS), which identifies and assesses the extent of natural amino acid misincorporation more accurately than intact MS. The incorporation of 1 by AzoRS-4 was detected in ~97% of the total ions, as compared with ~22% detected by AzoRS (Tables 4-6).

Tables 4-7. Sequence and signal intensities of peptides identified LC-MS of tryptic fragments. X denoted the azobenzene-uAA.

TABLE 4

$ELP_{60}(10x1)_{Ms}$, expressed by AzoRS in the C321.ΔRF1 strain.

| Sequence (SEQ ID NO:) | Instances of peptide sequenced | % of peptides | MH+ [Da] | ΔM [ppm] | XCorr |
|---|---|---|---|---|---|
| VPGGGVPGXGVPGGGK (44) | 1 | 21.5 | 1442.756 | 1.52 | 3.35 |
| VPGGGVPGQGVPGGGK (45) | 2 | 35.4 | 1319.707 | 0.09 | 3.25 |
| VPGGGVPGPGVPGGGK (46) | 2 | 2.5 | 1288.7 | -0.9 | 2.23 |
| VPGGGVPGYGVPGGGK (47) | 6 | 7.6 | 1354.71 | -1.07 | 3.68 |

TABLE 4-continued

| ELP$_{60}$(10x1)$_{Ms}$, expressed by AzoRS in the C321.ΔRF1 strain. | | | | | |
|---|---|---|---|---|---|
| Sequence (SEQ ID NO:) | Instances of peptide sequenced | % of peptides | MH+ [Da] | ΔM [ppm] | XCorr |
| VPGGGVPGLGVPGGGK (48) | 2 | 30.4 | 1304.732 | 0.2 | 2.89 |
| VPGGGVPGFGVPGGGK (49) | 2 | 2.5 | 1338.714 | -2.07 | 2.68 |

TABLE 5

| ELP$_{60}$(10x1)$_{Ms}$, expressed by AzoRS-4 in the C321.ΔRF1 strain. | | | | | |
|---|---|---|---|---|---|
| Sequence (SEQ ID NO:) | Instances of peptide sequenced | % of peptides | MH+ [Da] | ΔM [ppm] | XCorr |
| VPGGGVPGXGVPGGGK (50) | 16 | 97.0 | 1442.755 | 0.84 | 3.03 |
| VPGGGVPGQGVPGGGK (51) | 5 | 3.0 | 1596.81 | -1.95 | 2.07 |

TABLE 6

| ELP$_{60}$(10x2)$_{MS}$, expressed by AzoRS-4 in the C321.ΔRF1 strain. | | | | | |
|---|---|---|---|---|---|
| Sequence (SEQ ID NO:) | Instances of peptide sequenced | % of peptides | MH+ [Da] | ΔM [ppm] | XCorr |
| VPGGGVPGZGVPGGGK (50) | 3 | 97.4 | 1496.726 | 0.49 | 3.41 |
| VPGGGVPGYGVPGGGK (52) | 1 | 2.6 | 1354.71 | -0.8 | 2.01 |

TABLE 7

| ELP$_{60}$(10x3)$_{Ms}$, expressed by AzoRS-4 in the C321.ΔRF1 strain. | | | | | |
|---|---|---|---|---|---|
| Sequence (SEQ ID NO:) | Instances of peptide | % of peptides | MH+ [Da] | ΔM [ppm] | XCorr |
| VPGGGVPGXGVPGGGK (44) | 64 | 82.1 | 1514.71 | -2.34 | 3.54 |
| VPGGGVPGQGVPGGGK (45) | 2 | 2.6 | 1319.70 | -0.28 | 3.45 |
| VPGGGVPGPGVPGGGK (46) | 3 | 3.8 | 1288.69 | -1.75 | 3.32 |
| VPGGGVPGLGVPGGGK (48) | 4 | 5.1 | 1304.73 | -1.39 | 3.31 |
| VPGGGVPGFGVPGGGK (49) | 2 | 2.6 | 1338.71 | -2.16 | 3.24 |
| VPGGGVPGYGVPGGGK (47) | 3 | 3.8 | 1354.71 | 0.19 | 3.24 |

Figure 12:
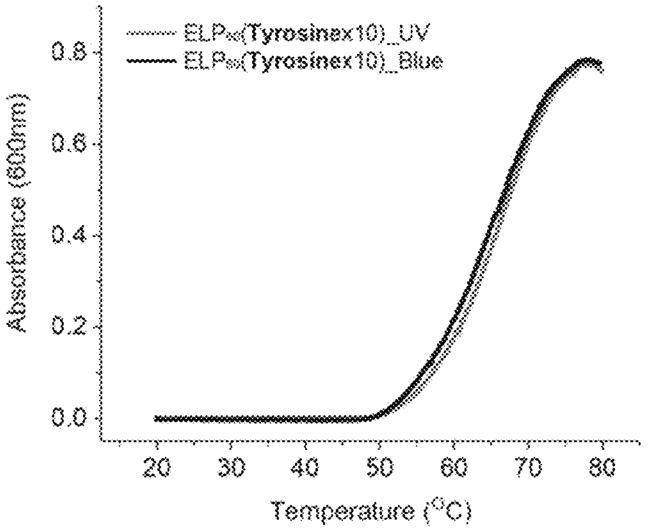
FIG. 12: Turbidity profile, as a function of temperature and light irradiation for $ELP_{60}$(tyrosine×10), 25 μM solution in water.
Figure 13A:
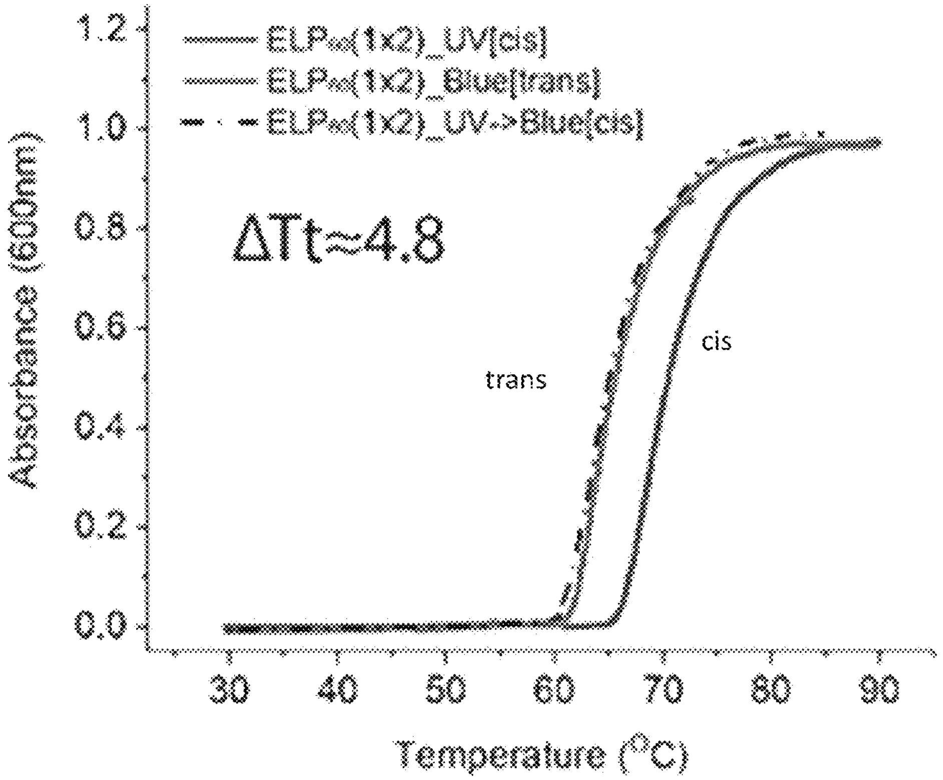
FIG. 13A-R: Characterization of the light-responsive properties of ELPs containing multiple instances of azobenzene-uAA 1. (13A-C) Turbidity profiles as a function of temperature and light irradiation for ELPs (25 μM solutions in water) containing either (13A) 2 (supplemented with 1 M NaCl), (13B) 6, or (13C) 10 instances of 1. (13D-F) CD spectra of light-irradiated ELPs (7.5 μM solutions in water) containing either (13D) 2, (13E) 6, or (13F) 10 instances of 1 at 10° C. or 30° C. (13G-H) Turbidity profiles as a function of the duration of irradiation with either (13G) UV or (13H) blue-light for ELPs containing 10 instances of 1 (25 μM solutions in water). (13I) Reversibility of the light-mediated transition (600 nm), and of azobenzene isomerization (325 nm), over multiple cycles of 30 s illumination of ELPs (25 μM solutions in water) containing 10 instances of azobenzene-uAA 1 at 26° C. (13J-K) CD spectra of (13J) ELP60 (tyrosine×10) and (13K) ELP60(benzophenone×10), both as 7.5 μM solutions in water, tested at 10° C. or 30° C. (13L-N) Turbidity profiles as a function of temperature and light irradiation for ELP60(1×10) at concentrations of (13L) 12.5 μM, (13M) 25 μM, or (13N) 50 μM (C) in water. (13O) Turbidity profiles (heating and cooling) of light-irradiated ELP60(1×10), 25 μM in water. (13P-R) UV-vis spectra of light-irradiated ELPs containing 10 instances of azobenzene-uAA (13P) 1, (13Q) 2, or (13R) 3. Insets show the red-shifted band separation for azobenzene-uAAs 2 and 3.
Figure 13B:
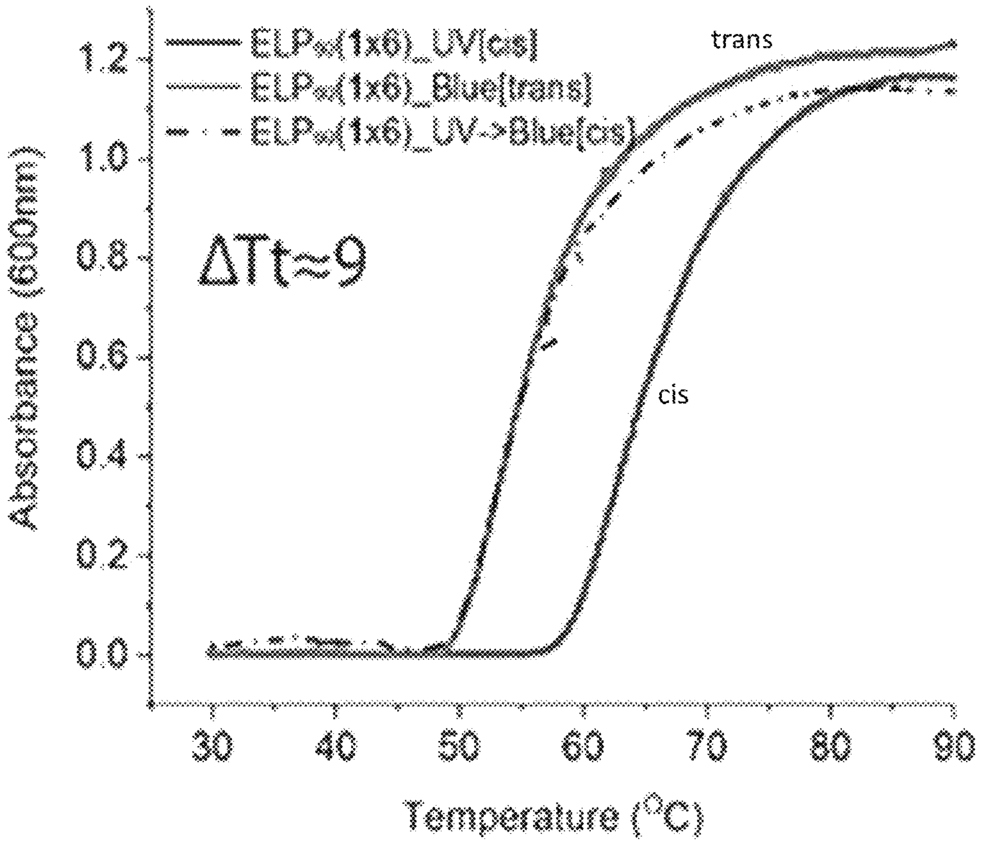
Figure 13C:
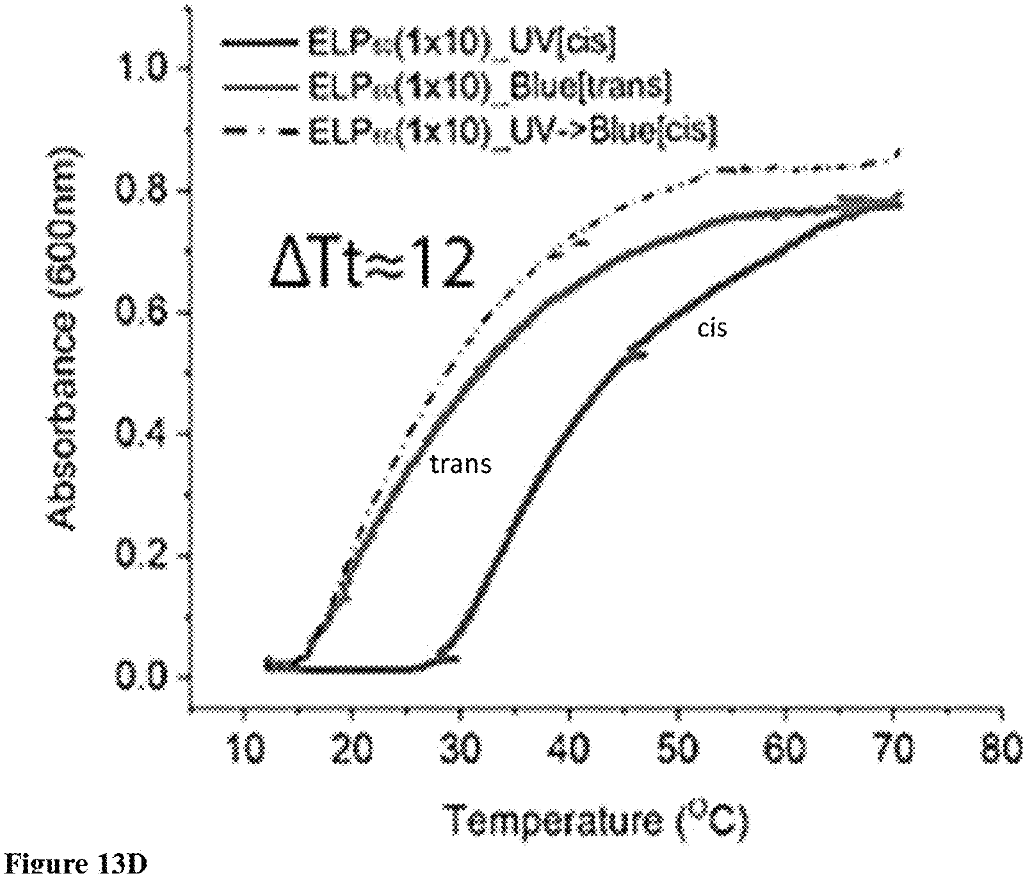
Figure 13D:
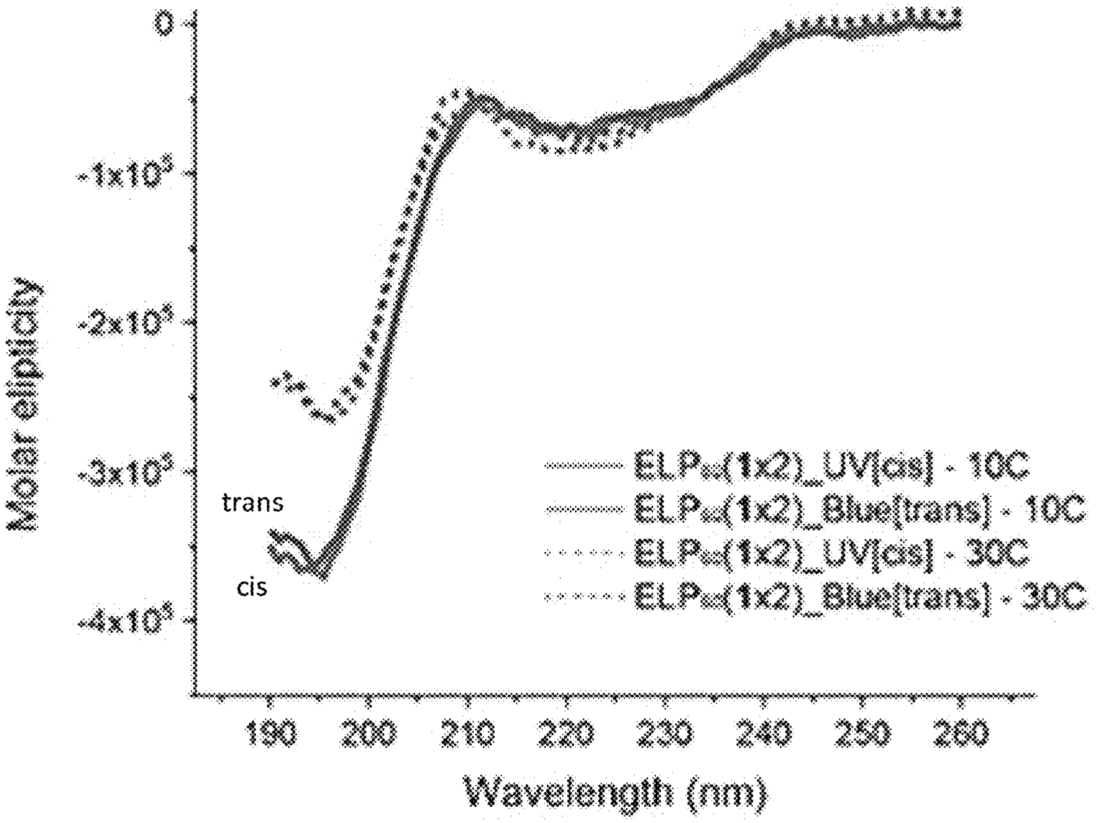
Figure 13E:
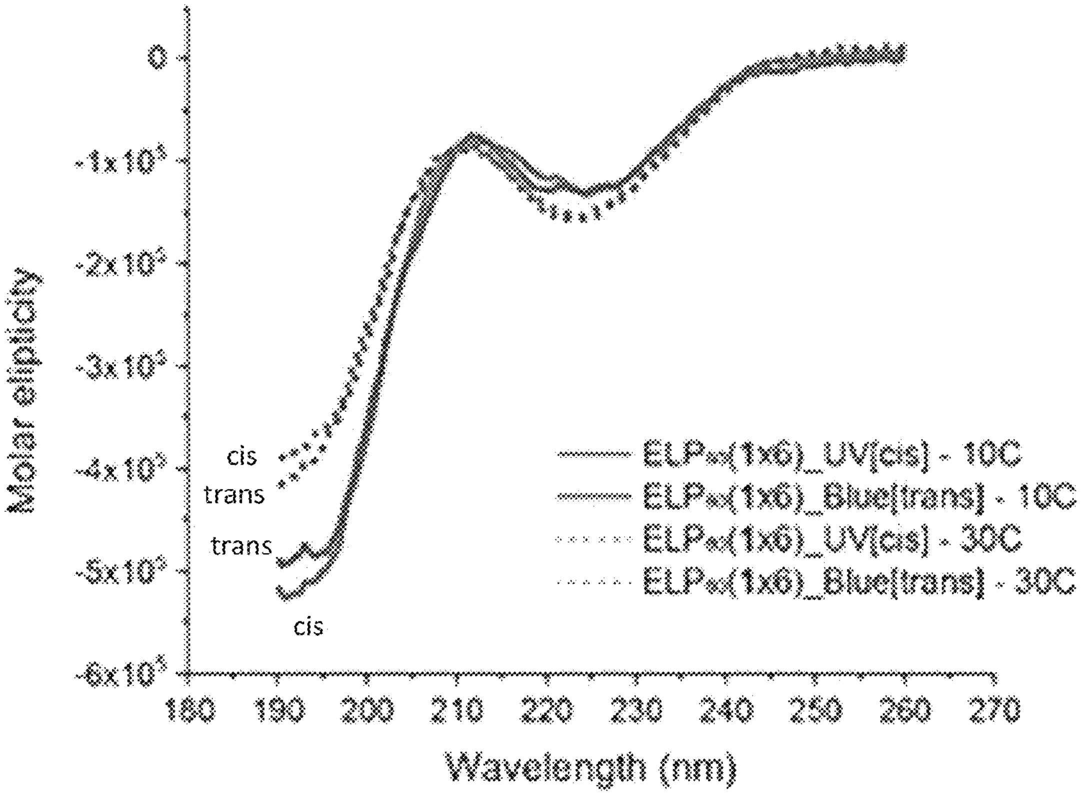
Figure 13F:
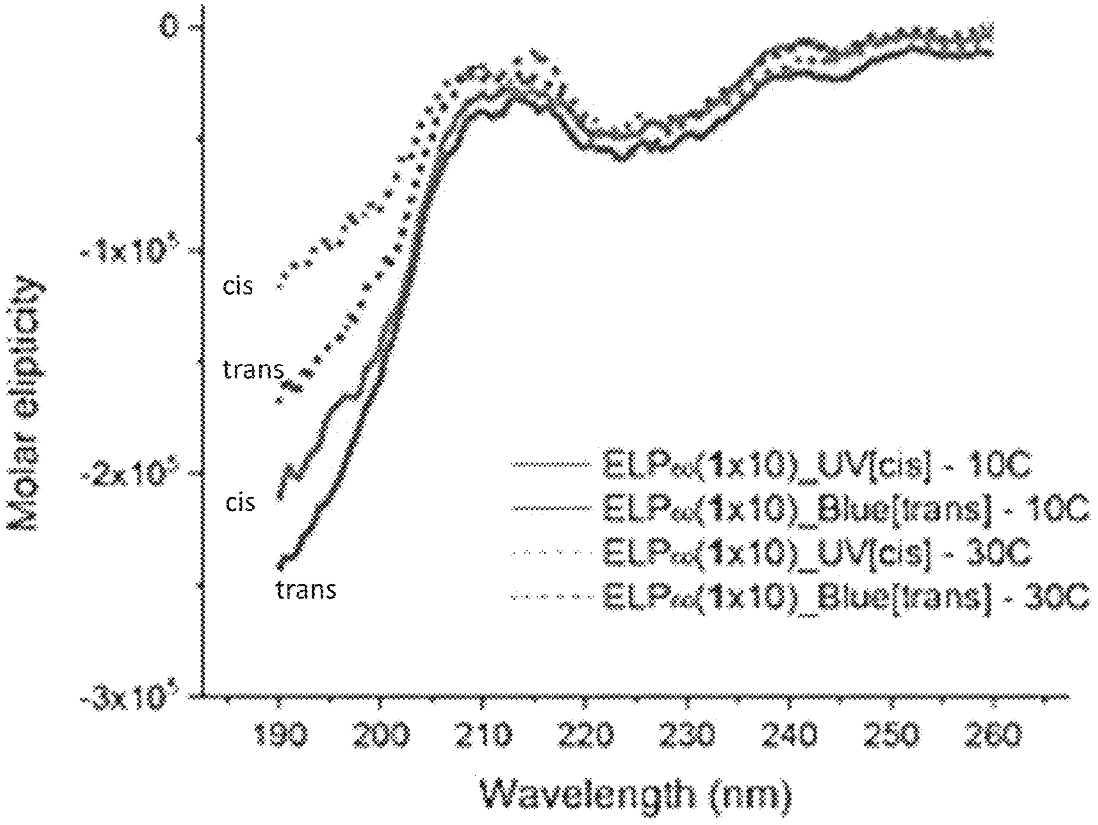
Figure 13G:
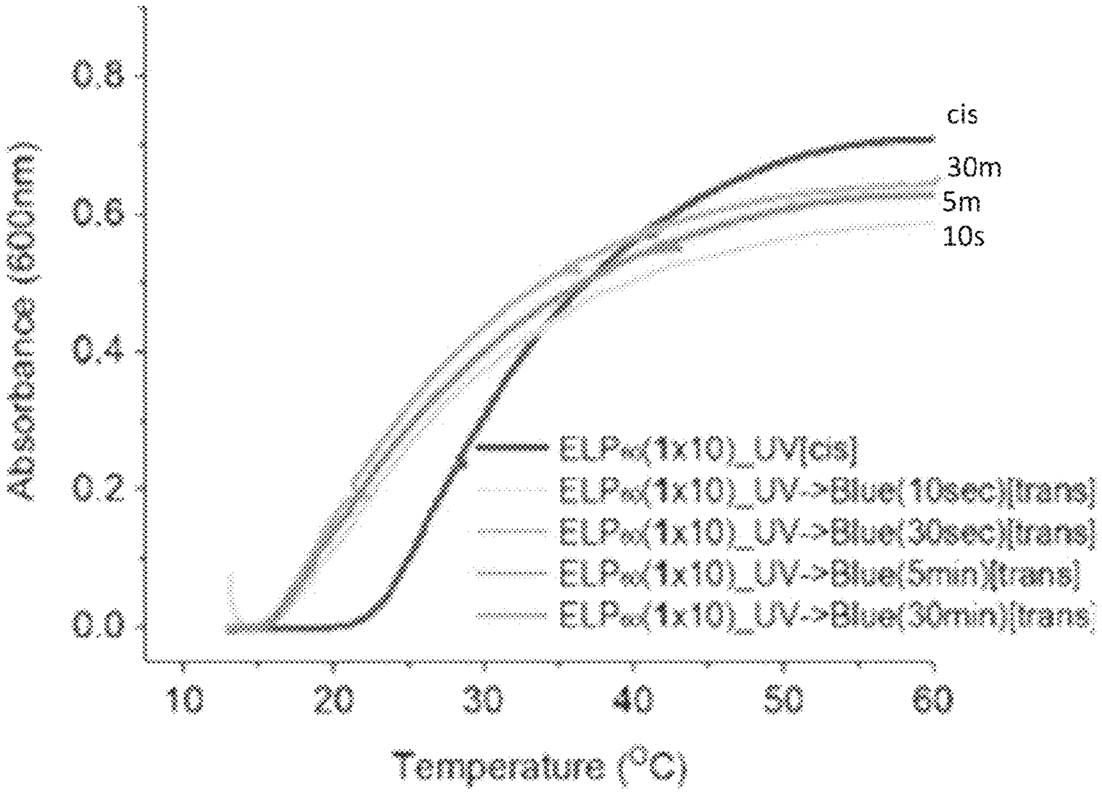
Figure 13H:
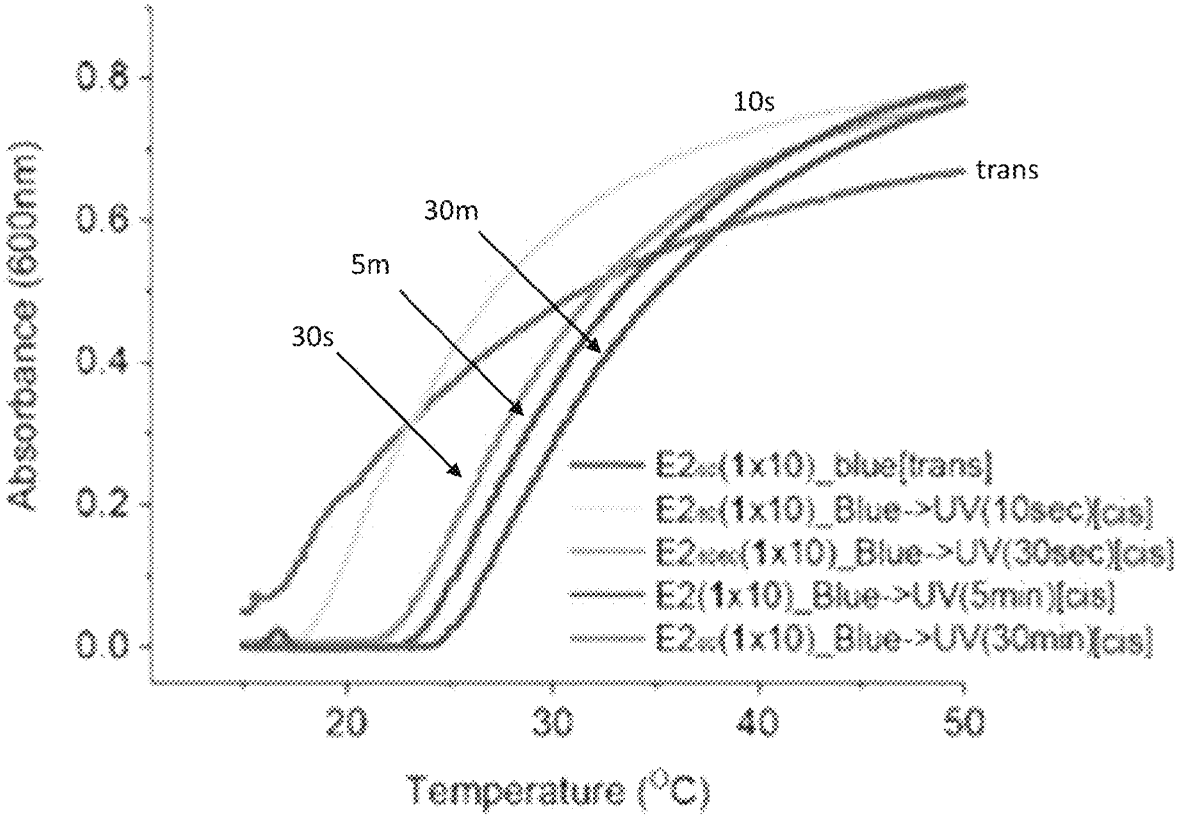
Figure 13I:
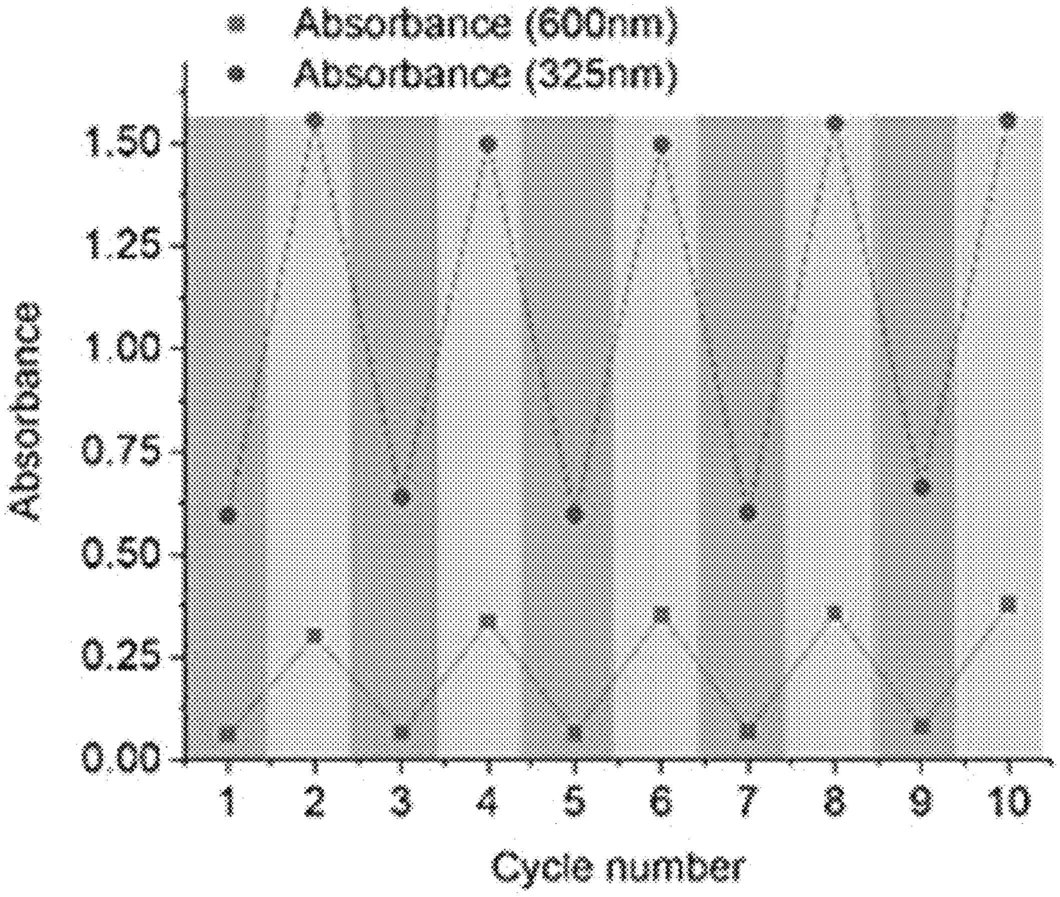
Figure 13J:
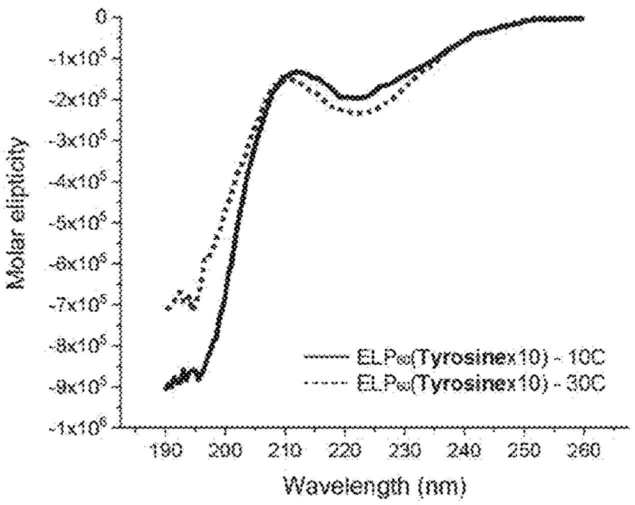
Figure 13K:
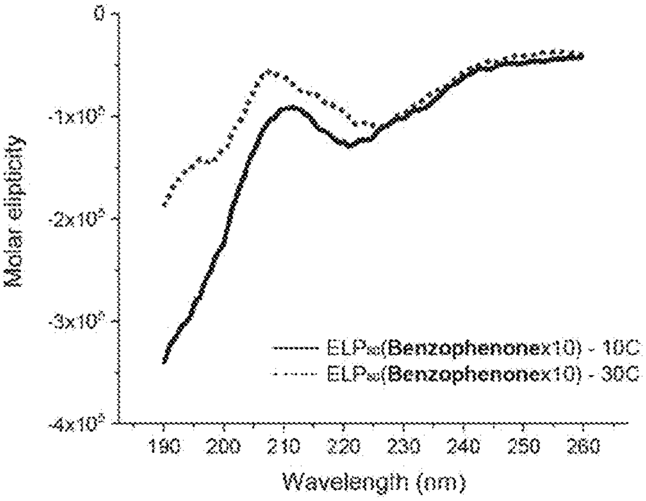
Figure 13L:
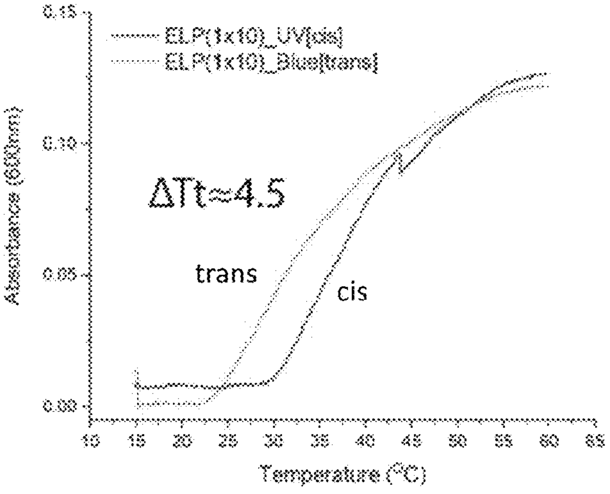
Figure 13M:
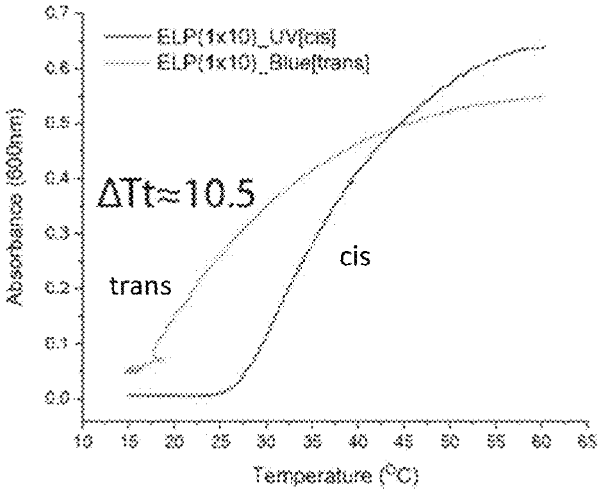
Figure 13N:
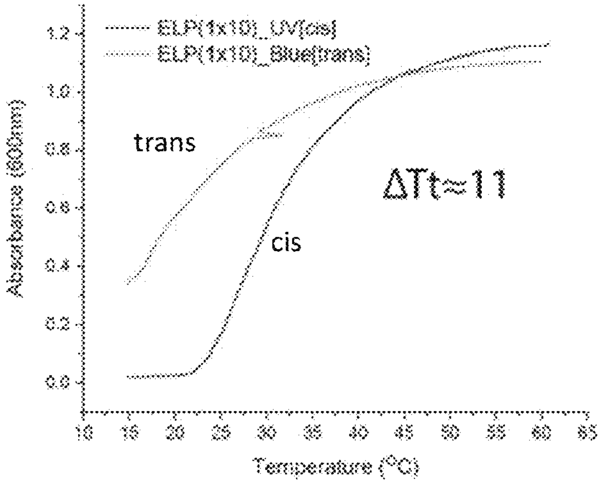
Figure 13O:
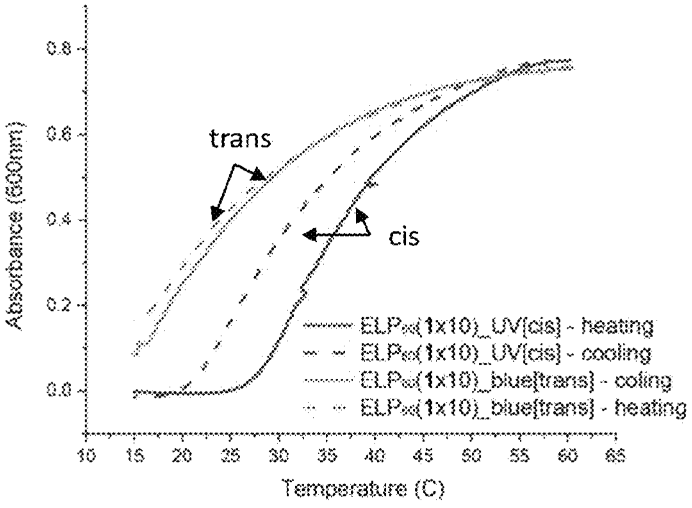

To determine the ability of a light-mediated isomerization of 1 to engender a difference in the Tt of the ELP (indicated as ΔTt$_{cis/trans}$), the ELPs were irradiated at 365 nm or 405 nm to induce isomerization to the cis (more hydrophilic) or trans (more hydrophobic) configuration, respectively. As expected, ELPs bearing mostly the cis isomers exhibited a higher Tt than ELPs bearing mostly the trans isomers. The ΔTt$_{cis/trans}$ induced by the isomerization process increased with the number of incorporated instances of 1, from zero [for the control protein ELP$_{60}$(tyrosine×10); FIG. 12] to ~12° C. for ELP$_{60}$(1×10) (FIG. 13A-C). It is also evident that the Tt of the ELPs decreases with increasing azobenzene content. Next, the secondary structure of light-irradiated ELPs was examined by using circular dichroism (CD) spectroscopy at various temperatures. All ELPs—including the control ELPs—showed the characteristic disordered negative peak at around ~190 nm, which decreased in magnitude as the temperature increased (FIG. 13D-F). Notably, the magnitude of the negative peak was greater in the control ELP$_{60}$(tyrosine×10) than in ELPs containing 1, and it was similar in the control ELP$_{60}$(benzophenone×10), which contains an uAA with two aromatic rings, and in ELP$_{60}$(1×10) (FIG. 13J-K). The effect of isomerization was also evident in the CD spectra and increased with increasing numbers of 1 incorporated per ELP chain. The irradiation time required to induce the change in the Tt for ELP$_{60}$(1×10), which showed the largest ΔTt$_{cis/trans}$, was further investigated. Under these experimental conditions, 30 s of irradiation with blue or UV light were sufficient to generate ~90% and ~60%, respectively, of the maximum ΔTt$_{cis/trans}$ (defined as the $\Delta Tt_{cis/trans}$ observed after 30 min of irradiation) in this ELP (FIG. 13G-H). In addition, increasing the concentration of $ELP_{60}(1\times10)$ (from 12.5 μM to 50 μM) also increased the observed $\Delta Tt_{cis/trans}$ (FIG. 13L-N). Interestingly, ELPs bearing cis isomers of 1, but not those bearing the trans isomer, exhibited a moderate thermal hysteresis, i.e., the Tt observed when heating the ELP solution was lower from that observed while cooling it (FIG. 130). The OD changes in the ELP60(1×10) solution were nearly identical throughout 10 successive 30 second- or 3-minute irradiation cycles (FIG. 13I), indicating that the effect of isomerization on the Tt was reversible throughout multiple (and short) irradiation cycles. Finally, we confirmed that light irradiation indeed induced the isomerization of 1 within the ELP by examining the UV-vis spectrum of ELP(1×10) after light irradiation. Indeed, the characteristic peaks associated with the cis and trans isomers of 1 were clearly visible (FIG. 13P-R) and reversible throughout 10 successive irradiation cycles (FIG. 13I).

There are two previous studies in which ELPs containing 1 (or any azobenzene) have been produced, in both cases by the polymerization of chemically synthesized peptides containing various quantities of 1 in the X-guest residue. In "Photomodulation of the inverse temperature transition of a modified elastin poly(pentapeptide)", Strzegowski, et al., *Journal of the American Chemical Society* 1994, 116, 813-814, an ELP was synthesized with the sequence $(VPGXG)_n$, in which the mole fraction of X was 68% valine (V) and 32% azobenzene and n>120. This ELP exhibited a $\Delta Tt_{cis/trans}$ of 10° C. In "Spiropyran derivative of an elastin-like bielastic polymer: photoresponsive molecule machine to convert sunlight into mechanical work", Alonso et al., *Macromolecules* 2001, 34, 8072-8077, ELP polymers were chemically synthesized and polymerized with the sequence $[f_V(VPGVG), f_X(VPGXG)]_n$, where X represents an azobenzene-bearing amino acid and fv and fx represent the mole-fraction of each pentapeptide. This study also demonstrated that the ELP Tt can be manipulated by triggering the cis-trans isomerization of the azobenzene groups, with a $\Delta Tt_{cis/trans}$ 0.5 or 5° C. for ELPs with a 5% or 15% mole fraction of azobenzene incorporated in the X position, respectively. However, the molecular weight distribution of these ELPs was not reported and only the VPGVG motif was explored. In contrast, the incorporation of 1 by the evolved aaRSs disclosed herein enabled the precise production of ELPs bearing various numbers of 1, allowing us to evaluate the effect of increasing azobenzene incorporation on the Tt of the ELP by comparing it across ELPs comprising exactly 60 pentapeptides for each construct. The findings presented herein demonstrate that the incorporation of 1 into more hydrophilic ELPs, at mole fractions ranging between 3.3% for $ELP_{60}(1\times2)$ to 16.7% for $ELP_{60}(1\times10)$, can generate a Tt difference of ~5-12° C. (when examined at 25 μM). These findings suggest that the natural amino acids incorporated in the remaining X-guest residue positions may also affect the $\Delta Tt_{cis/trans}$ generated upon azobenzene isomerization. Thus, the evolved aaRSs described in this study, which permit the precise positioning of azobenzene units alongside other, natural amino acids in various ELP and ELP-inspired sequences, will facilitate the examination of additional sequence determinants for encoding light-responsiveness in ELPs.

Figure 13P:
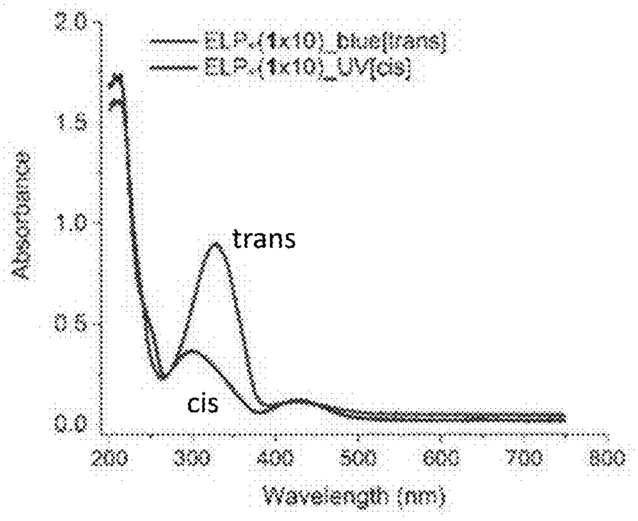
Figure 13Q:
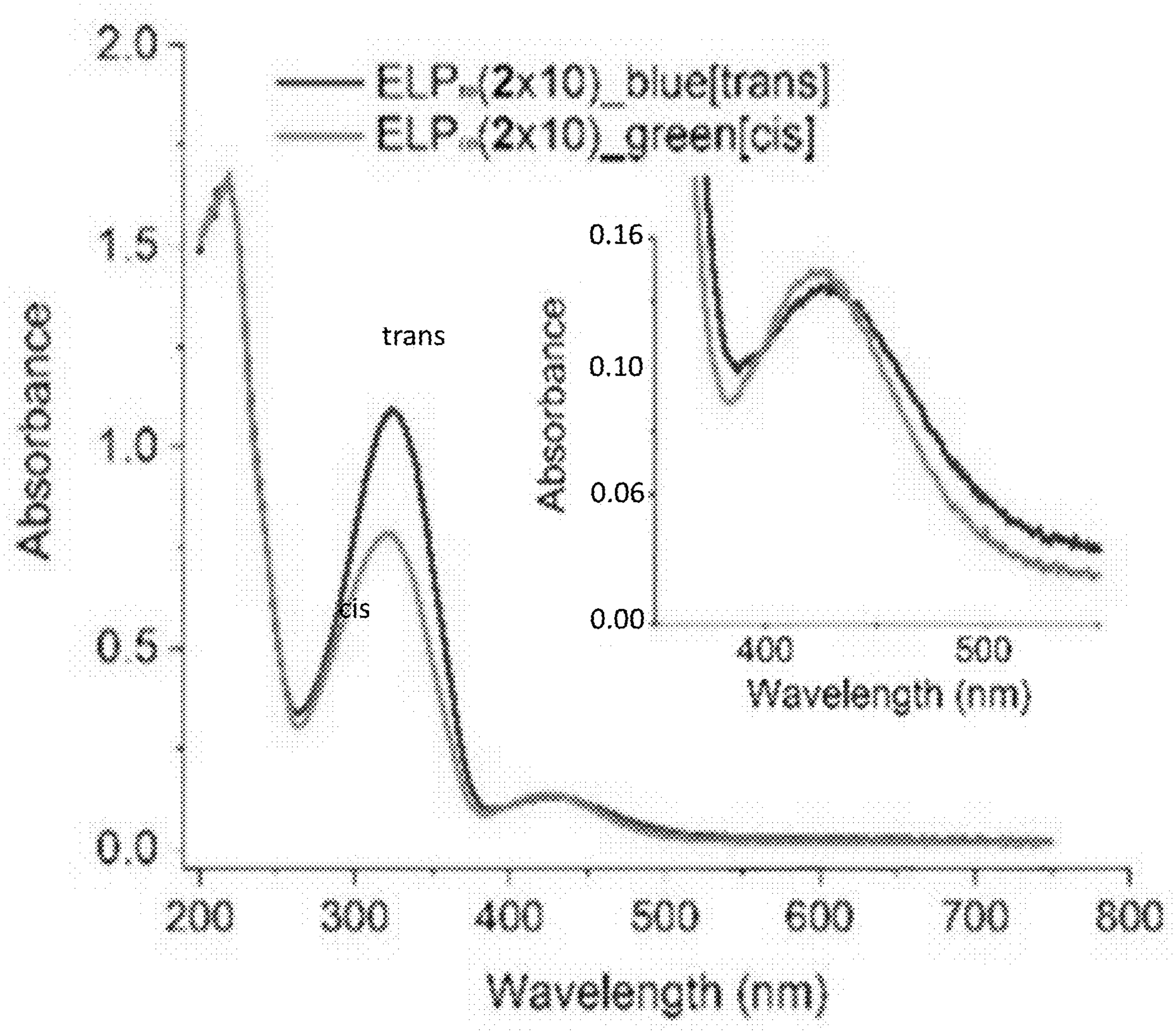
Figure 13R:
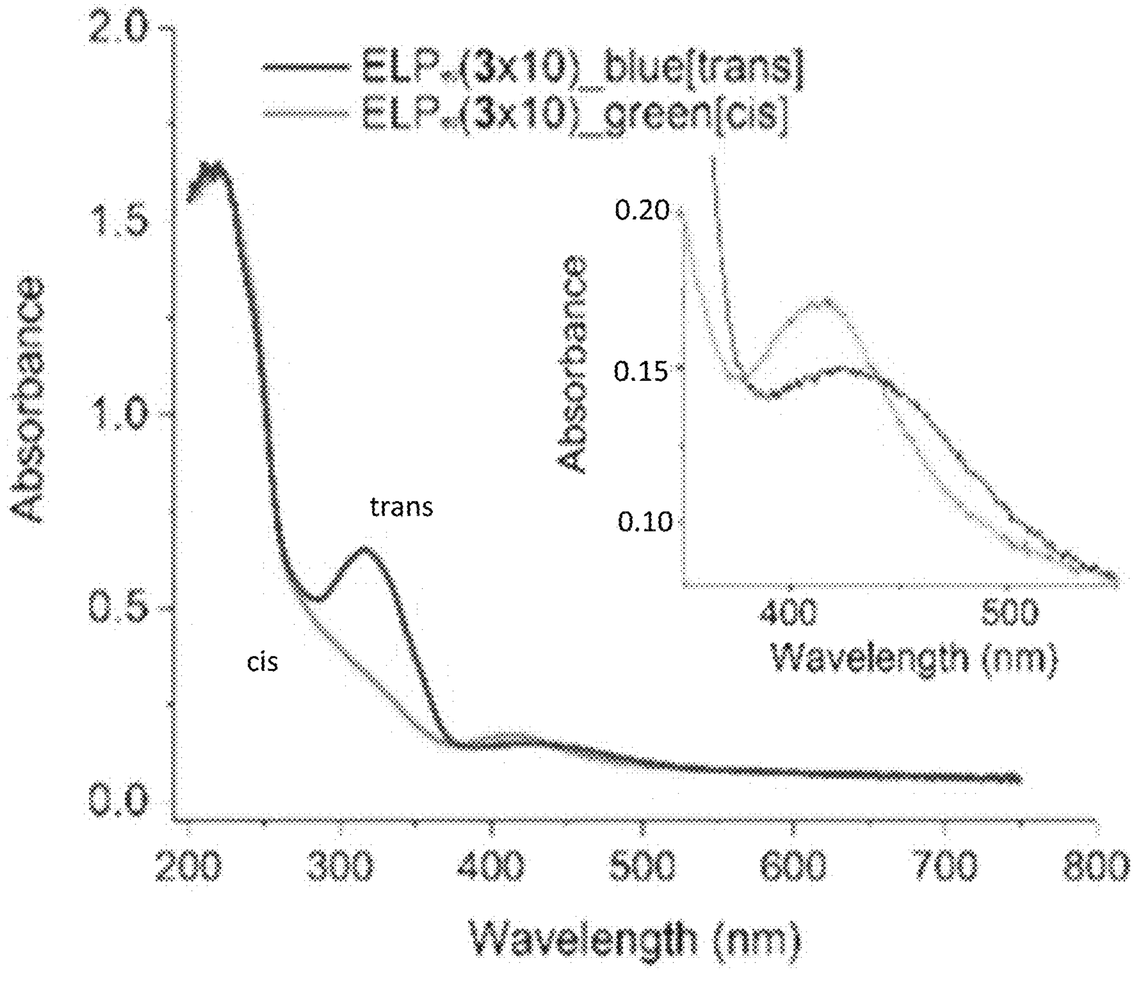
Figure 14A:
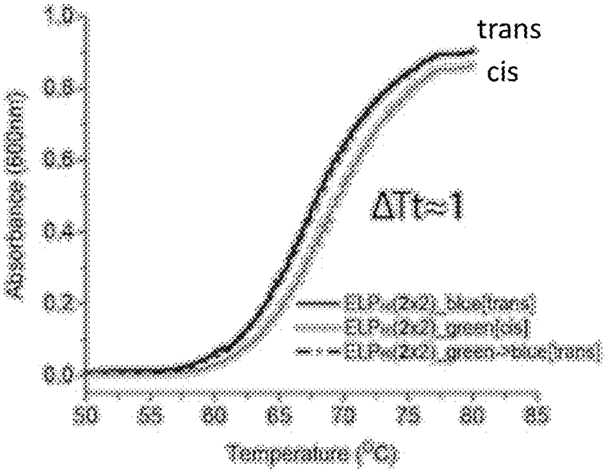
FIGS. 14A-L: Characterization of the light-responsive properties of ELP containing multiple instances of azobenzene-uAA 2 (25 μM solutions in water, unless otherwise indicated). (14A-C) Turbidity profiles as a function of temperature and light irradiation for ELPs containing either (14A) 2 (supplemented with 1 M NaCl), (14B) 6, or (14C) 10 instances of 2. (14D-E) Turbidity profiles as a function of the duration of irradiation with either (14D) blue or (14E) green light for ELPs containing 10 instances of 2. (14F) Reversibility of the light-mediated transition (600 nm), and azobenzene isomerization (340 nm), over (first) five cycles of 5 min and then 5 cycles of 30 s illumination of ELPs containing 10 instances of azobenzene-uAA 2 at 24° C. (14G-I) Turbidity profiles as a function of temperature and light irradiation for ELP60(2×10) at concentrations of (14G) 12.5 μM, (14H) 25 μM, or (14I) 50 μM in water. (14J-L) Comparison of the CD spectra of (14J) ELP60(1×10), (14K) ELP60(2×10), and (14L) ELP60(3×10), all 7.5 μM solutions in water, as a function of light irradiation at 10° C. or 30° C.
Figure 14B:
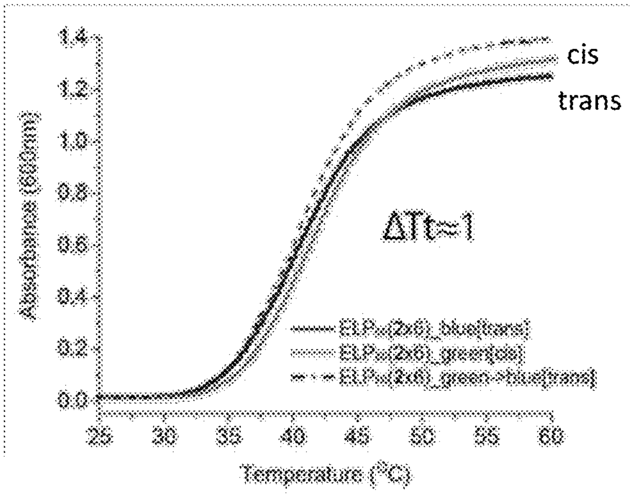
Figure 14C:
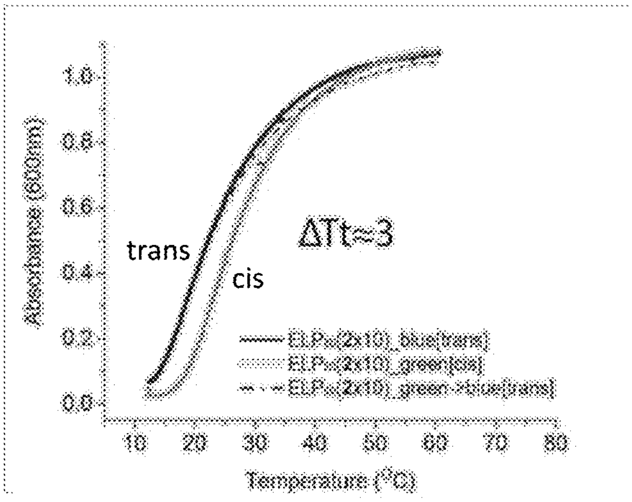
Figure 14D:
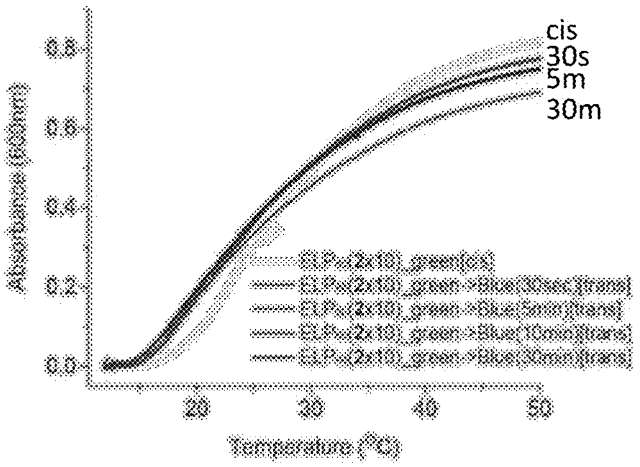
Figure 14E:
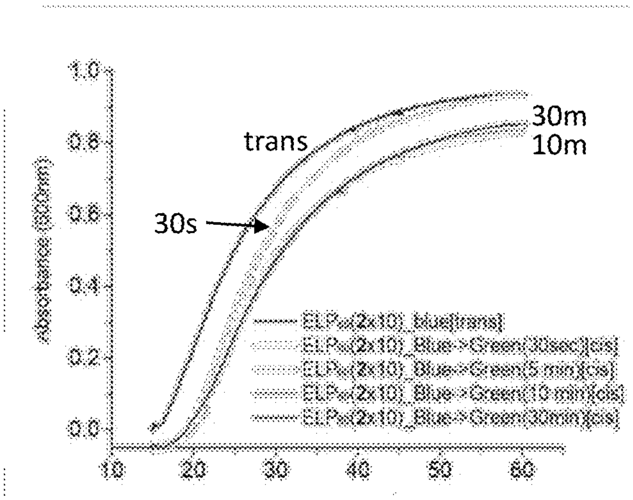
Figure 14F:
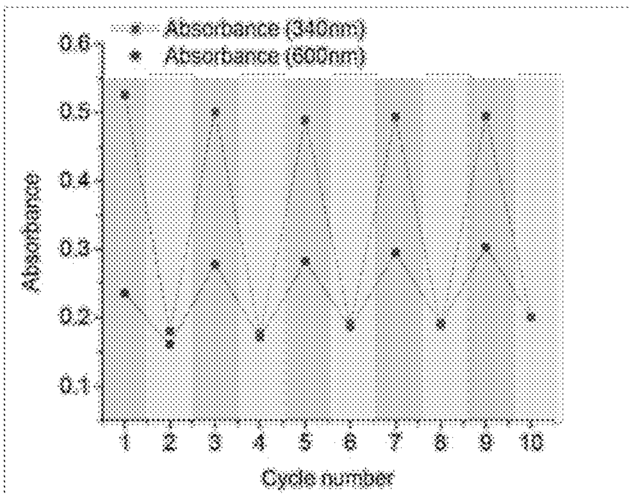
Figure 14G:
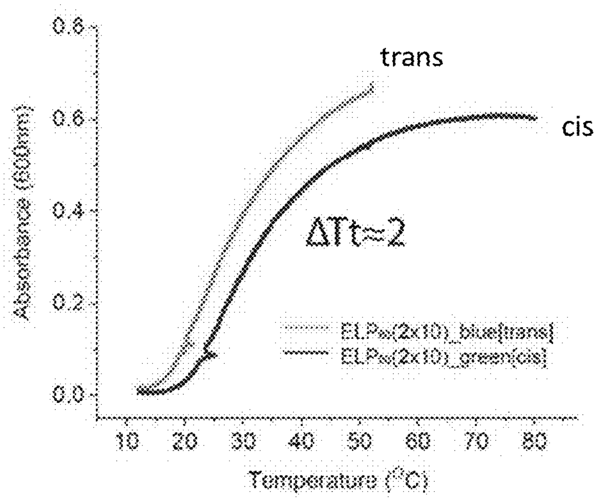
Figure 14H:
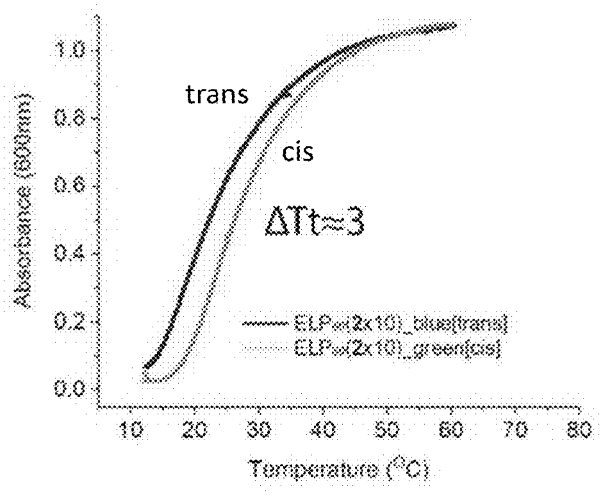
Figure 14I:
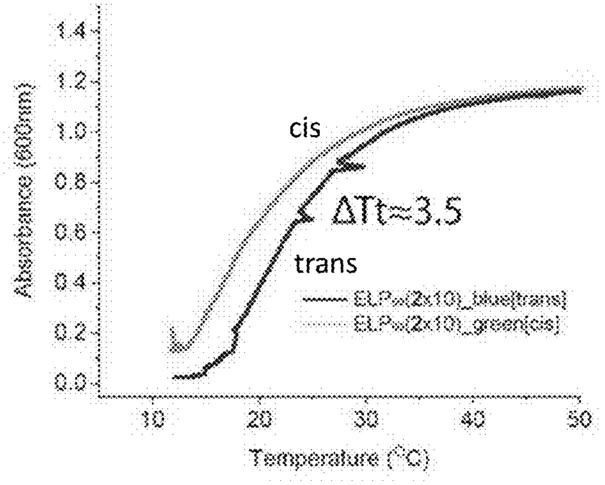
Figure 14J:
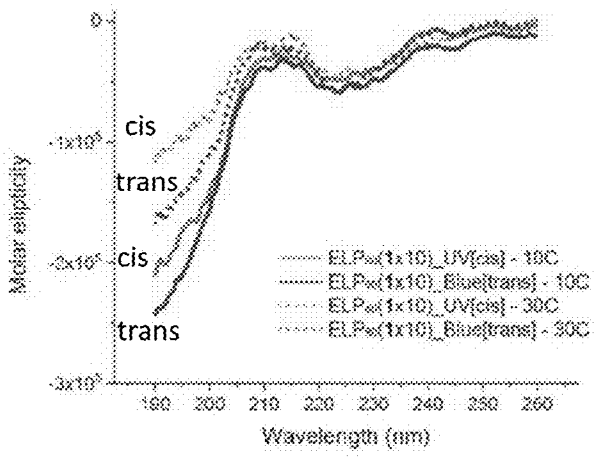
Figure 14K:
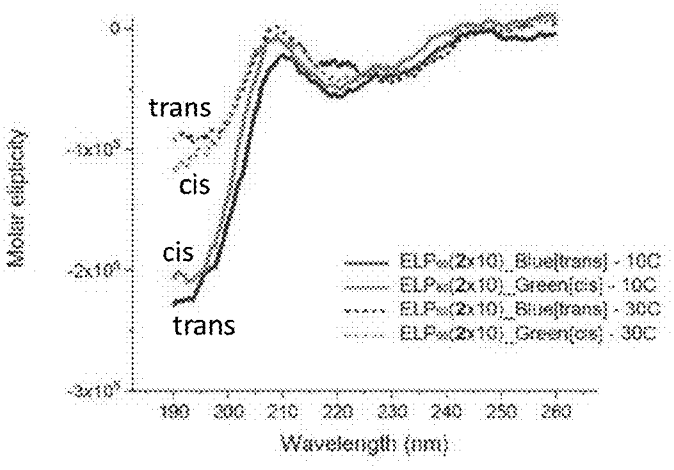
Figure 14L:
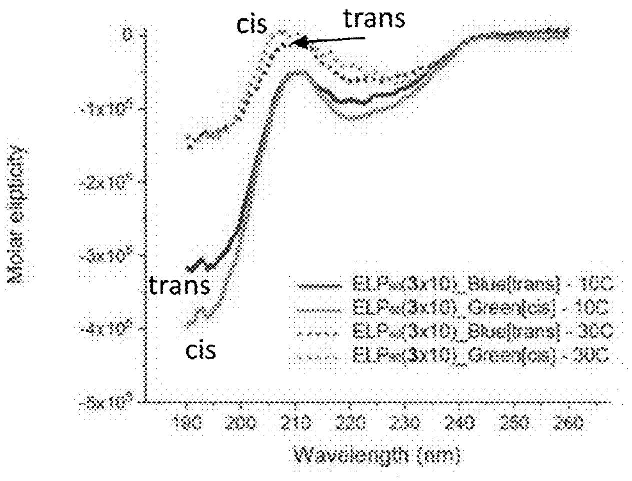

Example 6: Producing ELPs with a Visible-Light-Responsive Phase-Separation Behavior Since UV light is less preferable than visible light for biological applications, the effects of azobenzene substituents, previously shown to permit isomerization with visible light, on the ELP $\Delta Tt_{cis/trans}$ were examined next. To this end, ELPs (as described above) were produced containing the visible light-responsive azobenzene-uAAs 2 and 3, using AzoRS-4 in the C321.ΔRF1 strain. The protein yields of $ELP_{60}(2\times10)$ and $ELP_{60}(3\times10)$ were 10.7±0.44 and 2.63±0.77 mg $L^{-1}$, respectively, as determined by small-batch expression. The fidelity of incorporation was assessed by the LC-MS of tryptic fragments of $ELP_{60}(10TAG)_{MS}$, expressed as $ELP_{60}(2\times10)_{MS}$ and $ELP_{60}(3\times10)_{MS}$ (~97% of the total ions for 2 and ~82% of the total ions for 3; Tables 6-7). The visible-light irradiation of 2, as compared with 1, produces lower quantities of each isomer in the photostationary state (PSS) (FIG. 9B). Nevertheless, since the ELP phase transition involves both intra and inter-chain interactions, and since multiple instances of 2 are incorporated per ELP chain, it was hypothesized that the isomerization of even a small majority of 2 would suffice to change the overall ELP hydrophobicity and, therefore, its Tt upon isomerization. Indeed, the light-irradiation of $ELP_{60}(2\times2)$, $ELP_{60}(2\times6)$, and $ELP_{60}(2\times10)$ produced a more modest—but reproducible—$\Delta Tt_{cis/trans}$ (namely, a difference of between ~1° C. and ~3° C. for a 25 μM solution) upon light irradiation (FIG. 14A-C), which was also slightly affected by ELP concentration (FIG. 14G-I), which can be attributed to the lower PSS composition of 2 compared with 1. Nevertheless, a 30 s irradiation was sufficient to induce ~75% of the maximum $\Delta Tt_{cis/trans}$ for $ELP_{60}(2\times10)$ (FIG. 4D-E). The effect of isomerization on the Tt was reversible throughout 10 successive irradiation cycles (FIG. 14F) and a light-induced isomerization was clearly visible by the UV-vis spectrum of the visible-light irradiated $ELP_{60}(2\times10)$ (FIG. 13P-R). The CD signature of $ELP_{60}(2\times10)$ confirmed its disordered conformation, albeit with smaller variations in the magnitude of the negative peak (around 190 nm) between ELPs bearing mostly cis or mostly trans isomers, as compared with $ELP_{60}(1\times10)$ (FIG. 14J-L).

Figure 15:
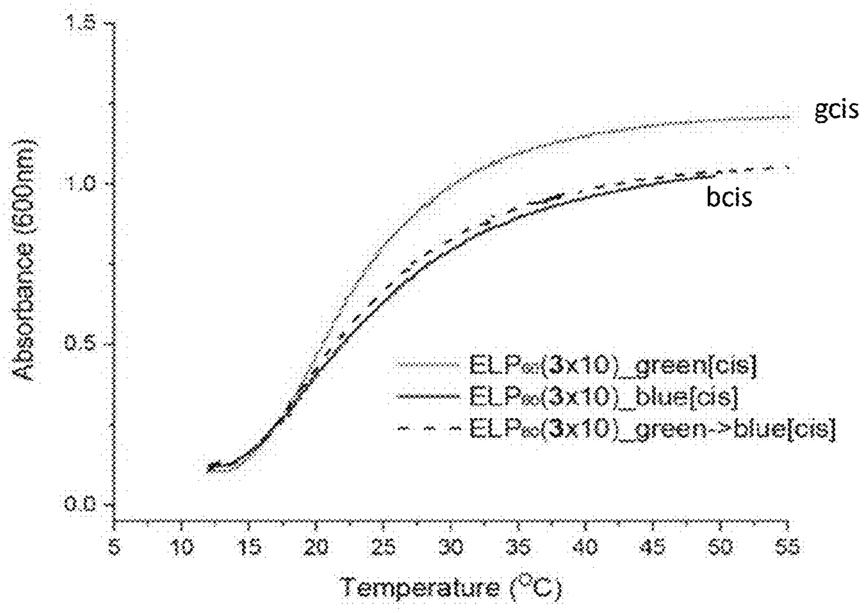
FIG. 15: Turbidity profile as a function of temperature and light irradiation for ELP60(3×10) at concentration of 12.5 μM.

Next, the light-responsive properties of ELPs bearing multiple instances of 3 were examined. These ELPs have excellent photoisomerization efficiencies, reaching PSS compositions of 91% and 84% in the cis and trans configurations, respectively (FIG. 9B). Surprisingly, the visible-light irradiation of $ELP_{60}(3\times10)$ produced the smallest effect on the ELP Tt (~0° C. for a 12.5 μM solution) of all of the examined azobenzene-uAAs (FIG. 15), and the incorporation of 3 appeared to decrease the ELP Tt to a greater extent than the incorporation of 1 or 2 (which prevented analysis of $ELP_{60}(3\times10)$ and $ELP_{60}(3\times6)$ at 25 μM). This finding was apparently unrelated to the PSS ratios, as an efficient isomerization was clearly visible by the UV-vis spectrum of the light-irradiated $ELP_{60}(3\times10)$ (FIG. 13P-R). The CD signature of $ELP_{60}(3\times10)$ also revealed that the magnitude of the negative peak observed around 190 nm was different between ELPs bearing mostly cis or mostly trans isomers, and these differences were of a similar extent to those observed in $ELP_{60}(1\times10)$ at 10° C. (FIG. 14J-L).

Figure 16A:
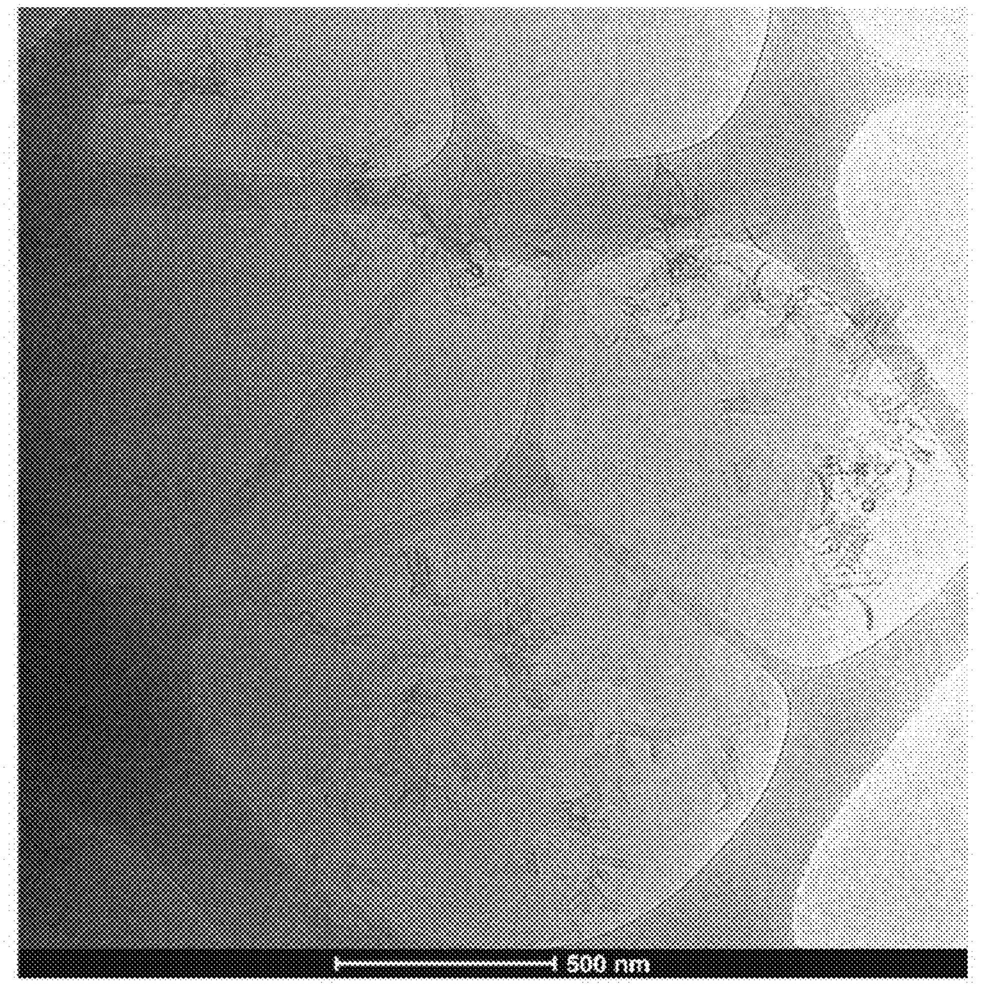
FIGS. 16A-16V: (16A-B) Cryo-TEM images of self-assembled molecules of 1 isomerized to the (16A) trans or (16B) cis conformations. (16C-J) Dynamic light scattering analysis of ELPs containing (16C) 10 instances of tyrosine, (16D) 10 instances of a benzophenone-bearing uAA, (16E) 2 instances of 1, irradiated with blue light, (16F) 2 instances of 1, irradiated with UV light, (16G) 6 instances of 1, irradiated with blue light, (16H) 6 instances of 1, irradiated with UV light, (16I) 10 instances of 1, irradiated with blue light, (16J) 10 instances of 1, irradiated with UV light. (16K-P) Dynamic light scattering analysis of ELPs containing (16K) 2 instances of 2, irradiated with blue light, (16L) 2 instances of 2, irradiated with green light, (16M) 6 instances of 2, irradiated with blue light, (16N) 6 instances of 2, irradiated with green light, (16O) 10 instances of 2, irradiated with blue light, (16P) 10 instances of 2, irradiated with green light. (16Q-V) Dynamic light scattering analysis of ELPs containing (16Q) 2 instances of 3, irradiated with blue light, (16R) 2 instances of 3, irradiated with green light, (16S) 6 instances of 3, irradiated with blue light, (16T) 6 instances of 3, irradiated with green light, (16U) 10 instances of 3, irradiated with blue light, (16V) 10 instances of 3, irradiated with green light.
Figure 16B:
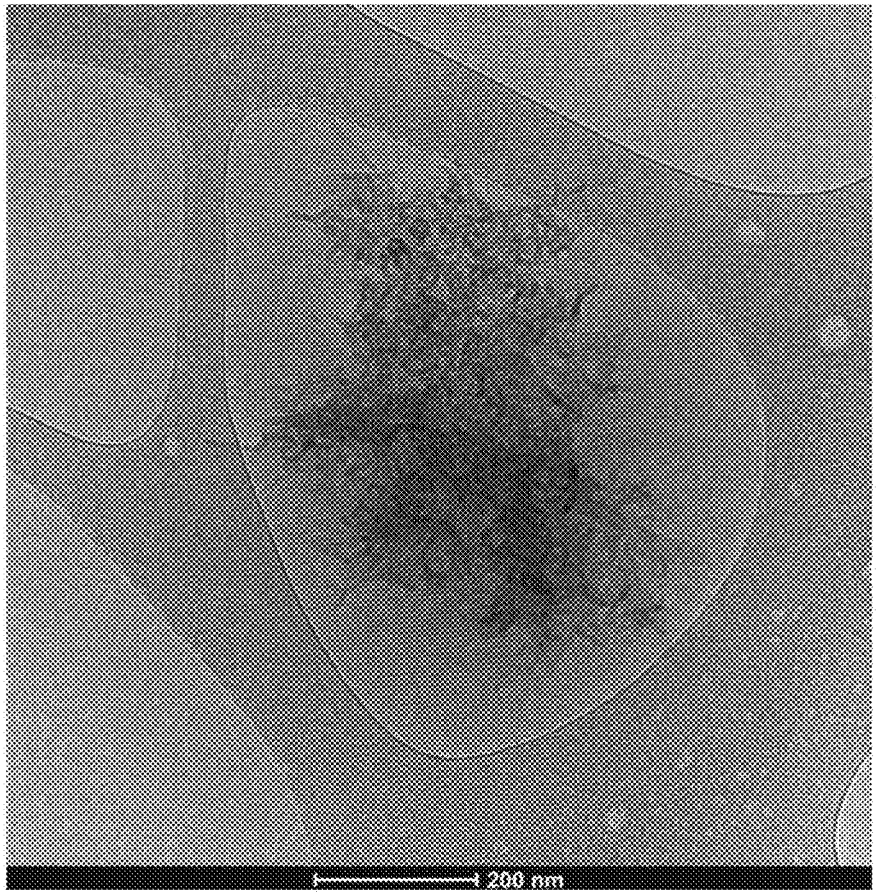
Figure 16C:
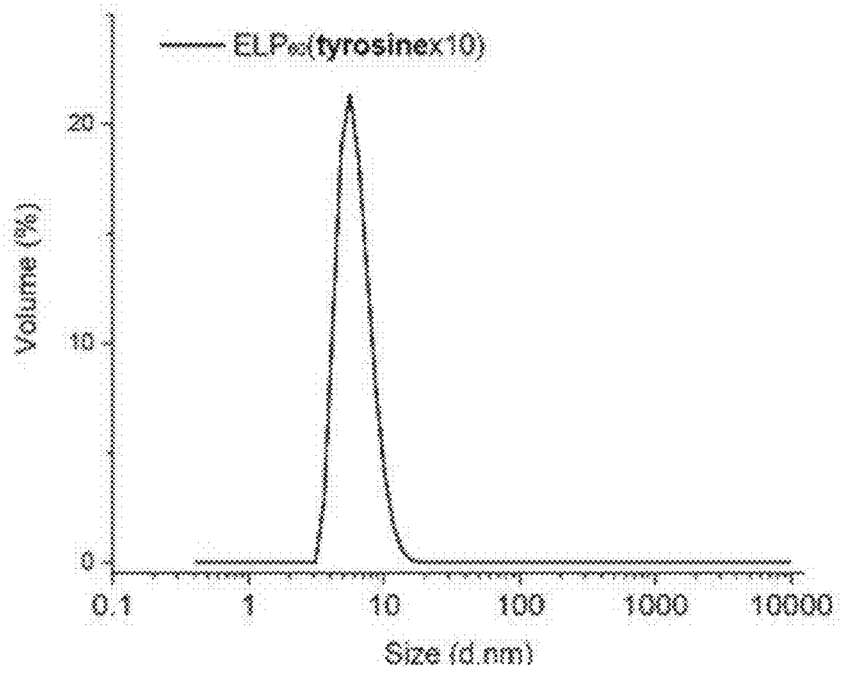
Figure 16D:
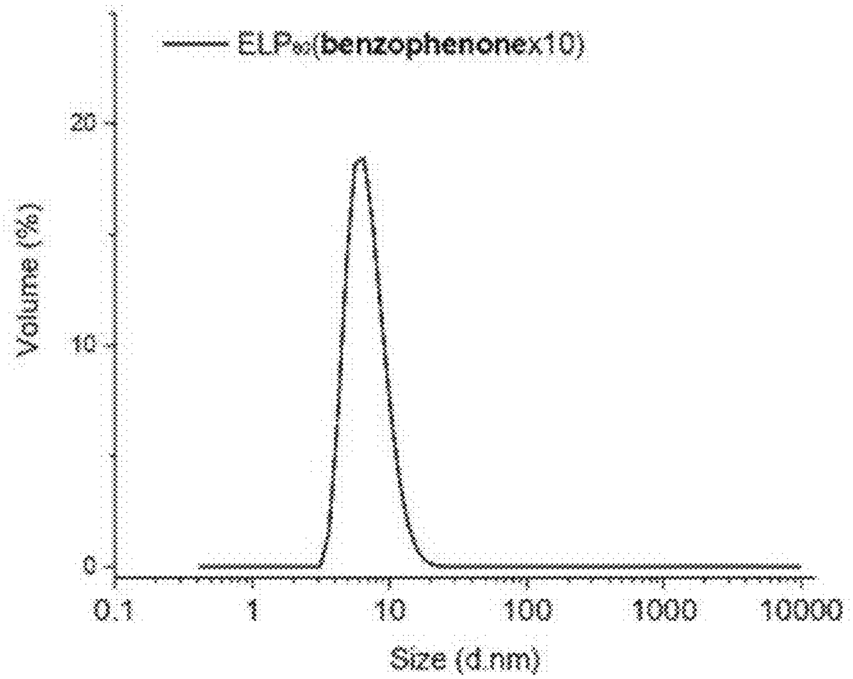
Figure 16E:
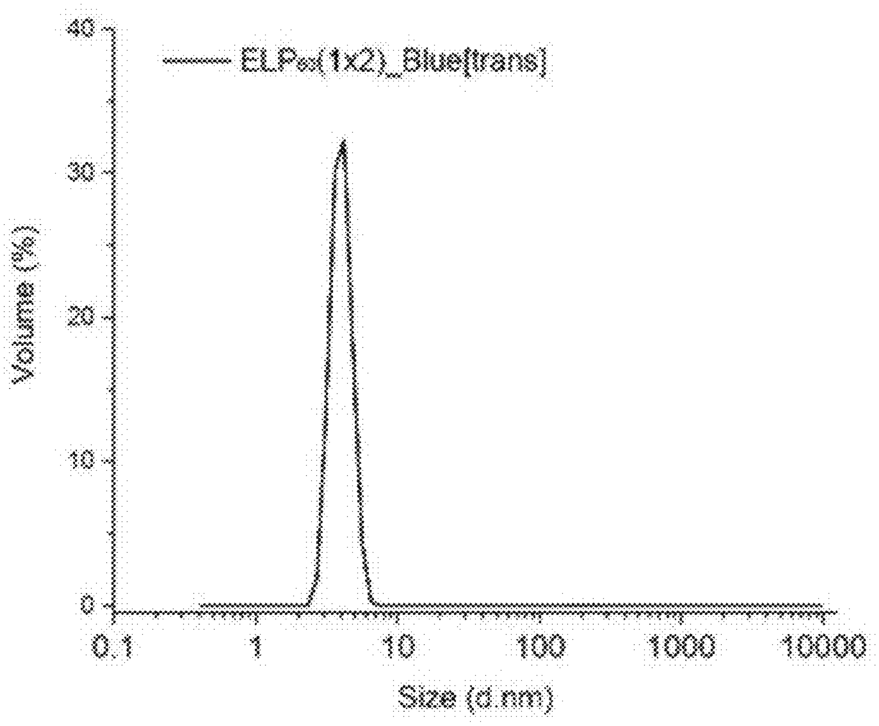
Figure 16F:
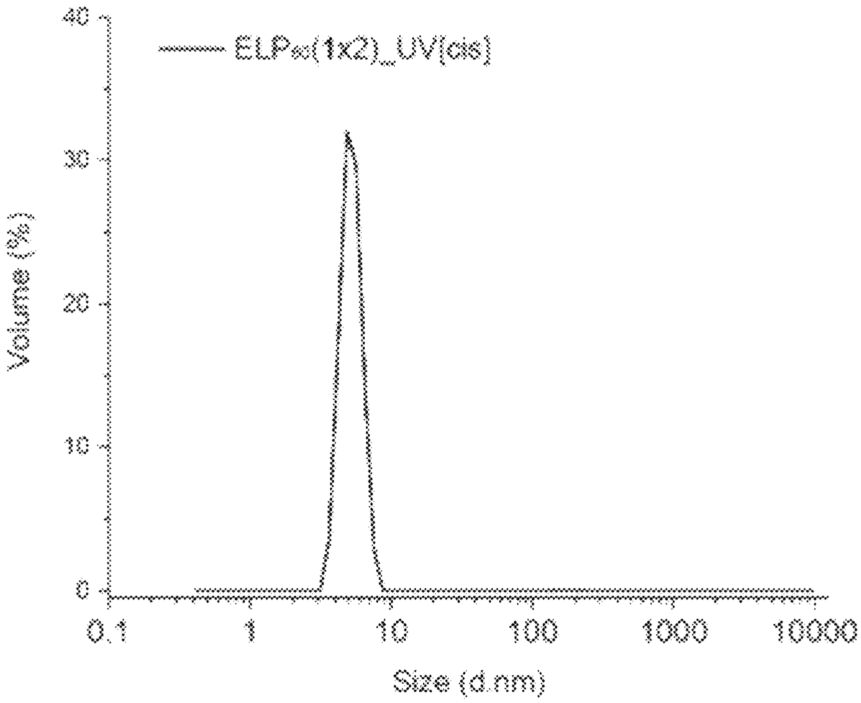
Figure 16G:
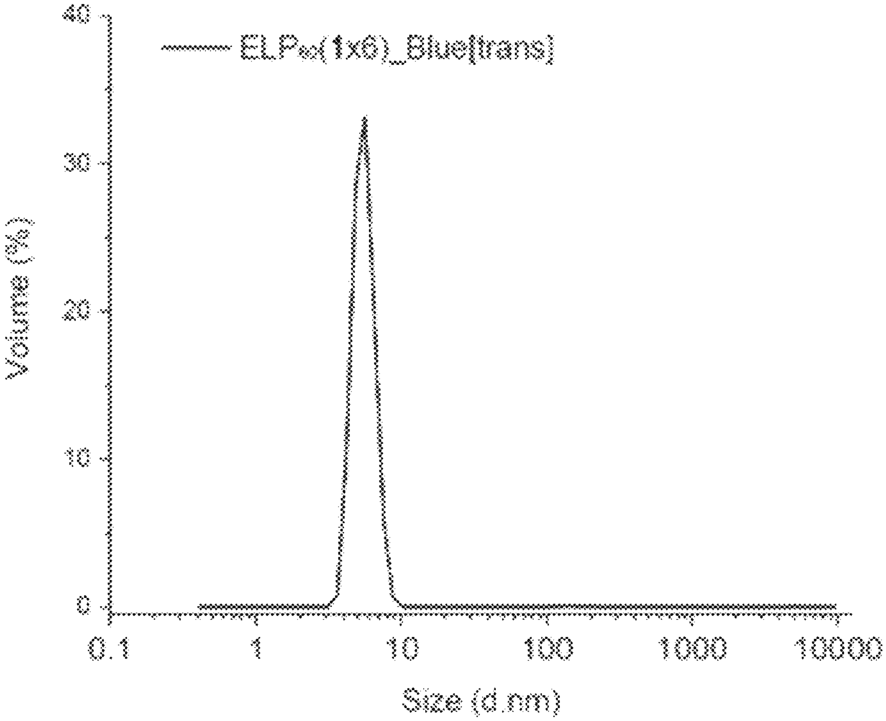
Figure 16H:
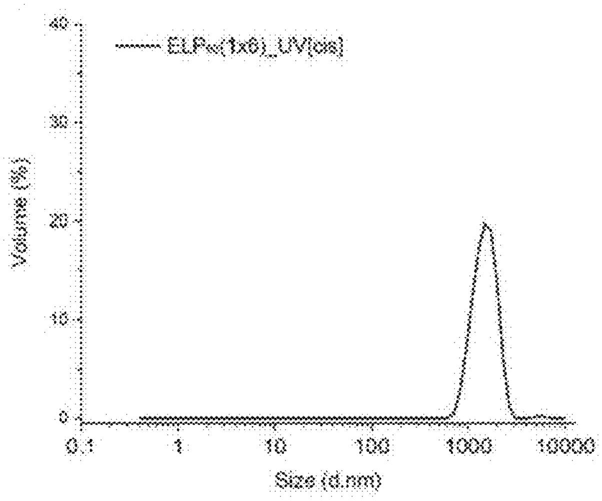
Figure 16I:
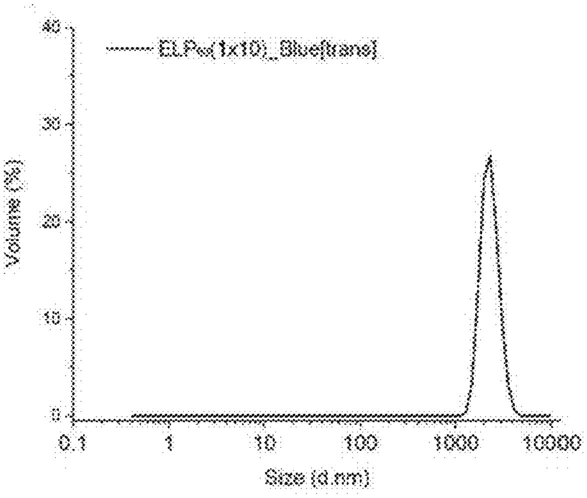
Figure 16J:
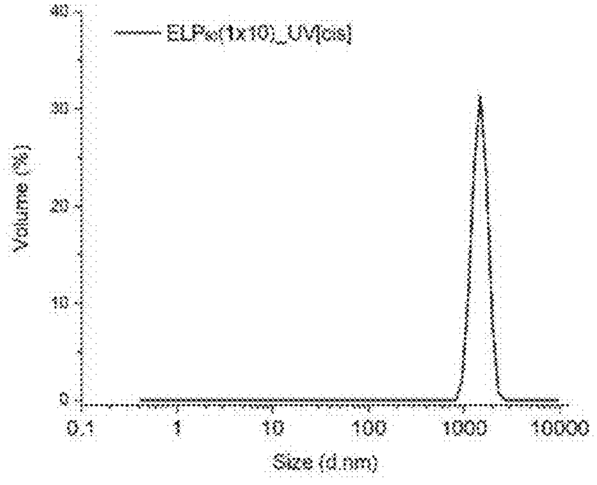
Figure 16K:
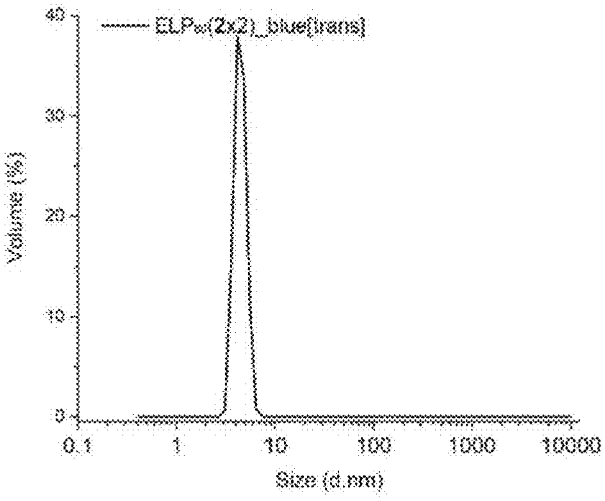
Figure 16L:
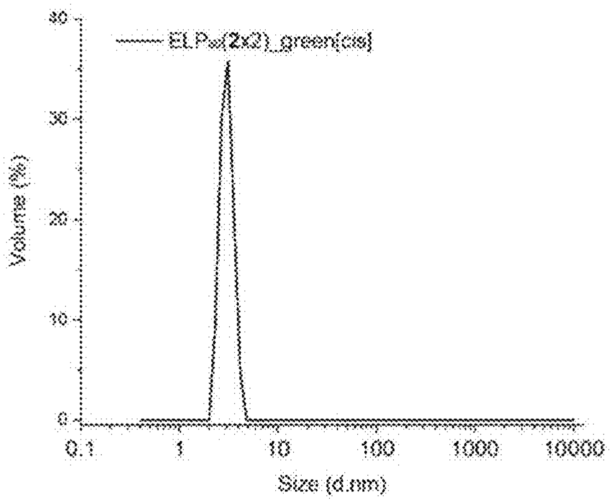
Figure 16M:
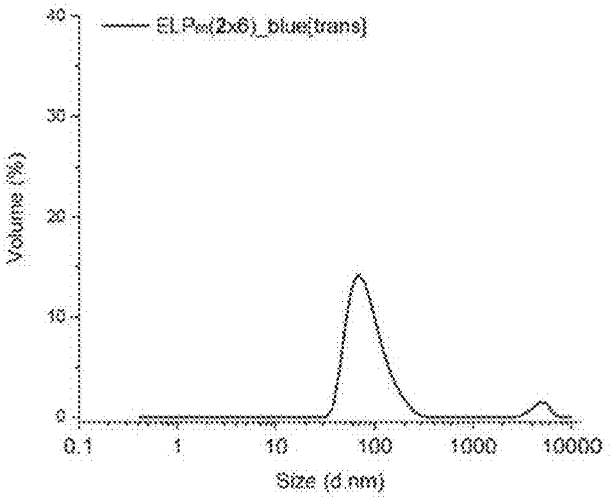
Figure 16N:
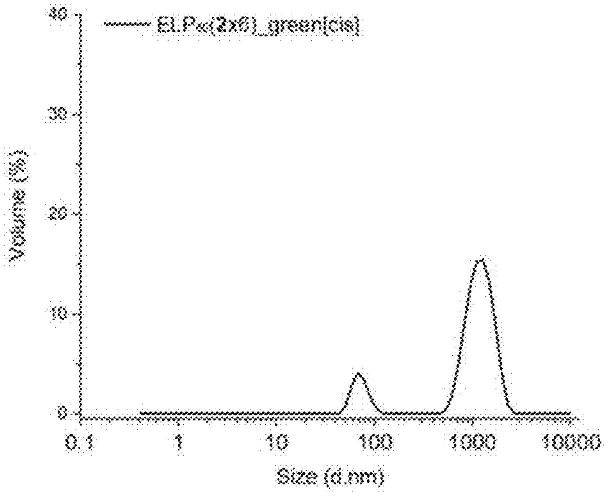
Figure 16O:
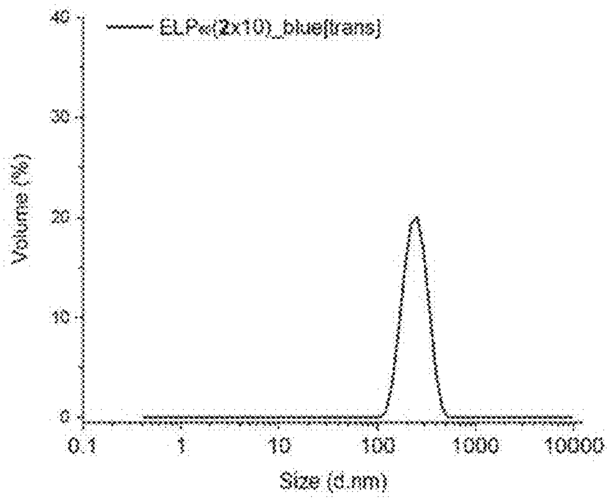
Figure 16P:
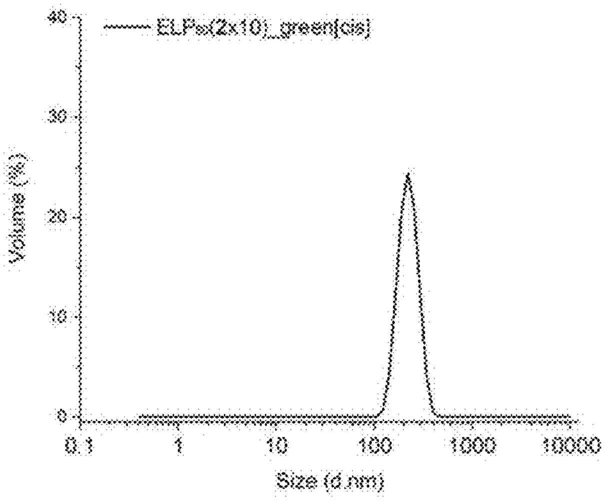
Figure 16Q:
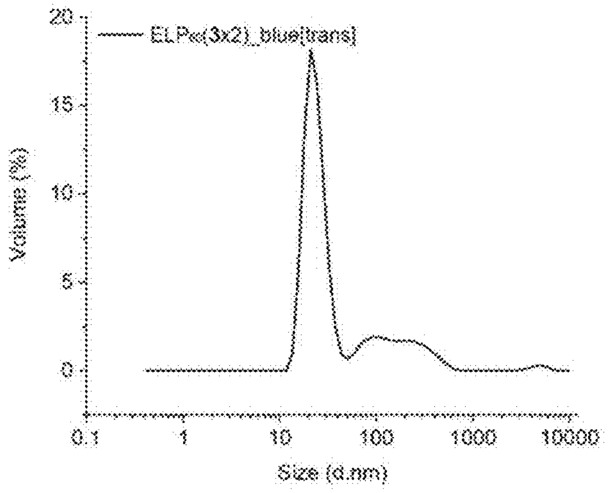
Figure 16R:
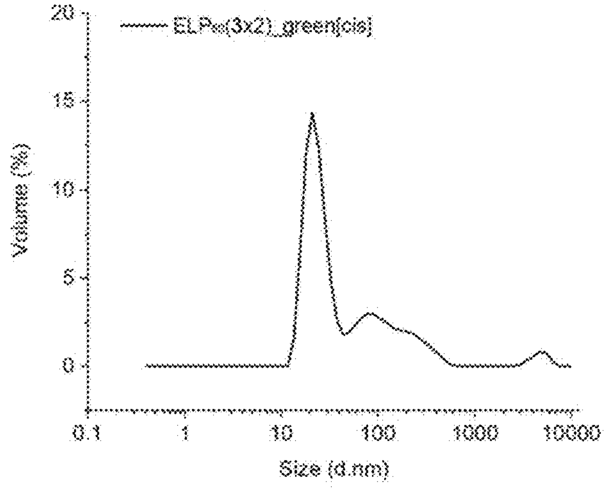
Figure 16S:
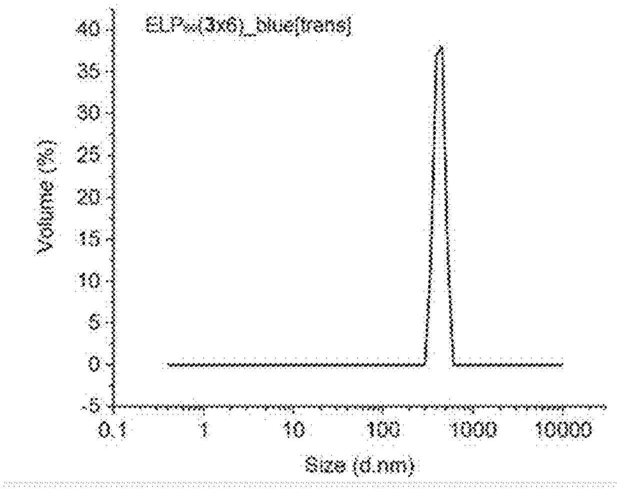
Figure 16T:
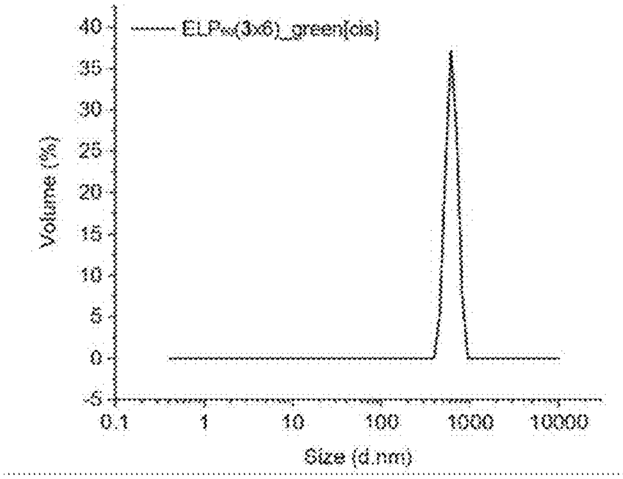
Figure 16U:
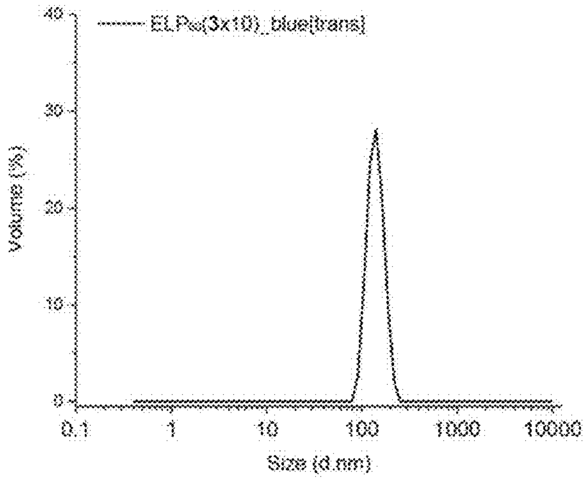
Figure 16V:
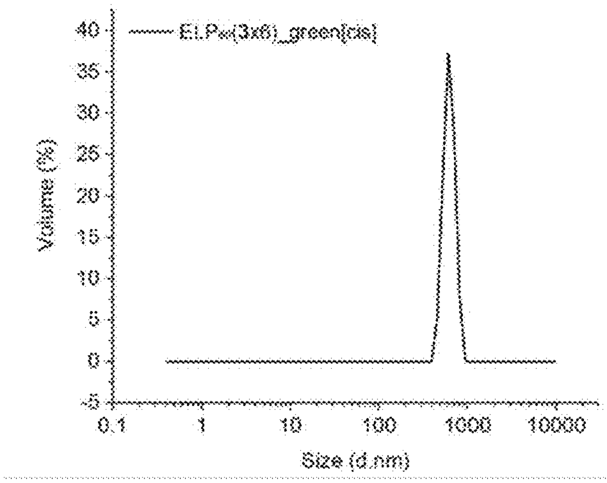

Azobenzene molecules are known to self-assemble and stimulate the self-assembly of various azobenzene conjugates. Therefore, it was hypothesized that azobenzene molecules also engender ELP self-assembly, which, in turn, may affect the local ELP concentration and, therefore, its Tt. Indeed, even when present as an amino acid side-chain, molecule 1 clearly self-assembled, in both the cis and trans configurations, and in different geometries depending on the isomerization state (FIG. 16A-B). To examine the effects of azobenzene properties and content on ELP self-assembly, first a dynamic light-scattering (DLS) analysis of all azobenzene-containing ELPs and of control ELPs containing 10 instances of tyrosine or benzophenone-bearing uAAs was performed. While ELPs bearing either 6 or 10 azobenzene-uAAs assembled into structures as large as a few hundred nanometers, ELPs bearing only two instances of azobenzene-uAAs 1 or 2 did not appear to self-assemble (control ELPs containing 10 instances of tyrosine or benzophenone-bearing uAAs also did not appear to assemble). In contrast, ELPs bearing only two instances of 3 did appear to self-assemble (FIG. 16A-V). To examine the geometries of the self-assembled nanostructures, we imaged $ELP_{60}(1\times10)$, $ELP_{60}(2\times10)$, and $ELP_{60}(3\times10)$ by cryo-transmission electron microscopy (cryo-TEM). All azobenzene-ELPs self-assembled into thin sheets, but $ELP_{60}(2\times10)$ and $ELP_{60}(3\times10)$ also formed clusters of aggregates. Notably, the number of aggregates of $ELP_{60}(3\times10)$ was higher than the number of self-assembled sheets and much higher than the number of $ELP_{60}(2\times10)$ aggregates (FIG. 17A-F). The control $ELP_{60}$ (tyrosine×10) did not show a self-assembly behavior (not shown). These findings raise the possibility that the somewhat different geometries and the greater self-assembly/aggregation tendency of $ELP_{60}(3\times10)$ structures increase the local concentrations of these ELPs and, thereby, decrease their Tt and eliminate Tt differences in the cis- and trans-azobenzene isomerization state. Additionally, the ability of 3 to engender light-responsiveness and promote self-assembly may be attributed to the non-planar geometry of the trans configuration of 3, as it has been reported that changes in hydrogel elasticity were more modest when using the azobenzene side-chain of 3 than when using the azobenzene side-chain of 1, presumably because the trans configuration of 3 deviates significantly from planarity, which weakens its π-stacking ability.

Genetically encoding various azobenzene-uAAs has allowed the comparison of ELPs of identical sequences and molecular weights while varying only the type of the incorporated azobenzene. Thereby, additional factors were identified related to the properties of azobenzene (derived from their substituent pattern), which may affect the self-assembly and phase-transition behavior of azobenzene-containing ELPs.

Figure 18A:
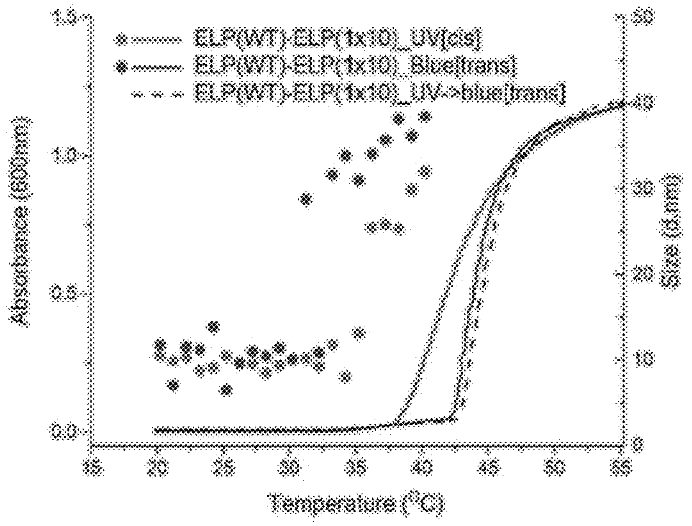
FIGS. 18A-N: Characterization of the self-assembly of diblock ELPs as a function of temperature and azobenzene isomerization. (18A) Turbidity profiles (solid lines) as a function of temperature and light irradiation for $ELP_{60}$(WT)-$ELP_{60}$(1×10); dots indicate particle size, as determined by DLS. (18B) Reversibility of the light-mediated self-assembly of $ELP_{60}$(WT)-$ELP_{60}$(1×10), over ten cycles of 30 s illumination (25 μM solutions in water) at 25° C. (18C-F) Cryo-TEM images of (18C-D) blue- or (18E-F) UV-light irradiated $ELP_{60}$(WT)-$ELP_{60}$(1×10). (18G) Turbidity profiles (solid lines) as a function of temperature and light irradiation for ELP60(WT)-ELP60(2×10); dots indicate particle size, as determined by DLS. (18H) Turbidity profiles (solid lines) as a function of temperature and light irradiation for ELP60(WT)-ELP60(2×10); dots indicate particle size, as determined by DLS. (18I-L) Cryo-TEM images of the self-assembly of ELP60(WT)-ELP60(2×10 irradiated with (18I-J) blue or (18K-L) green light. (18M-N) Dynamic light scattering analysis of (18M) ELP60(WT)-ELP60(1×10) and (18N) ELP60(WT)-ELP60(2×10) as a function of light-irradiation, analyzed at 38° C.
Figure 18B:
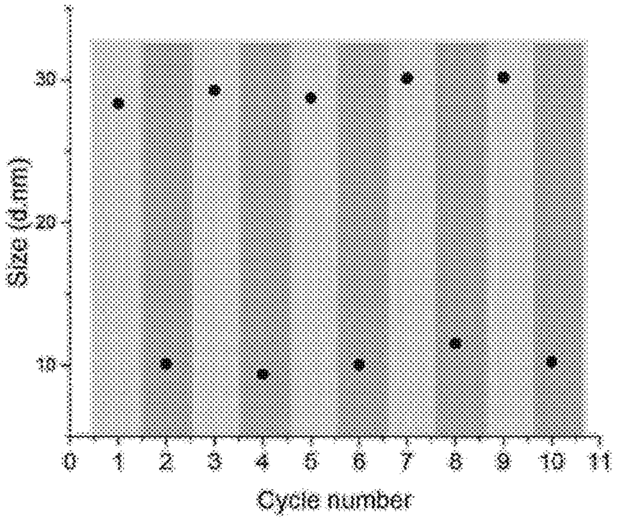
Figure 18C:
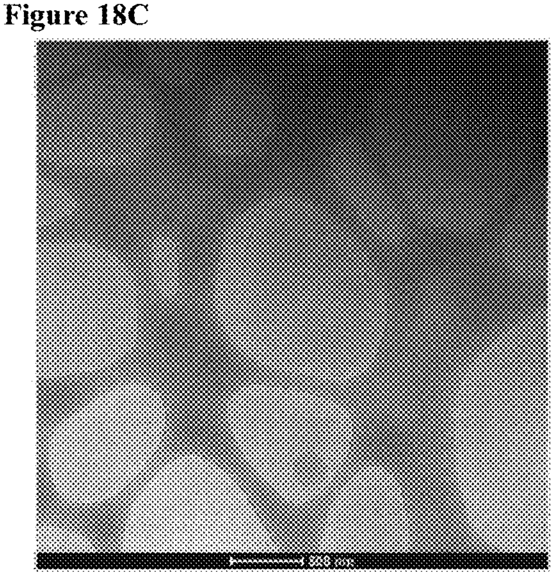
Figure 18D:
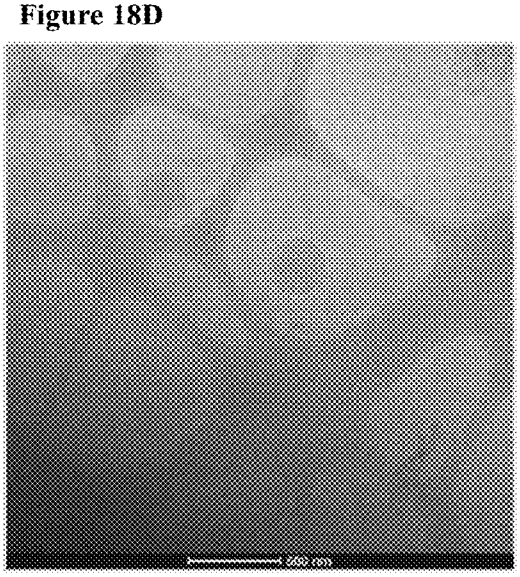
Figure 18E:
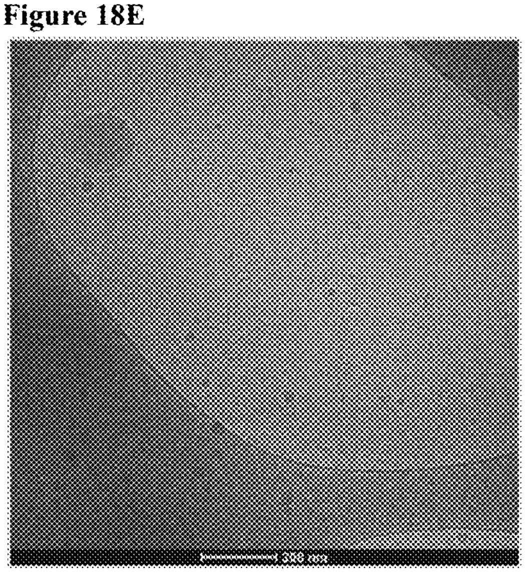
Figure 18F:
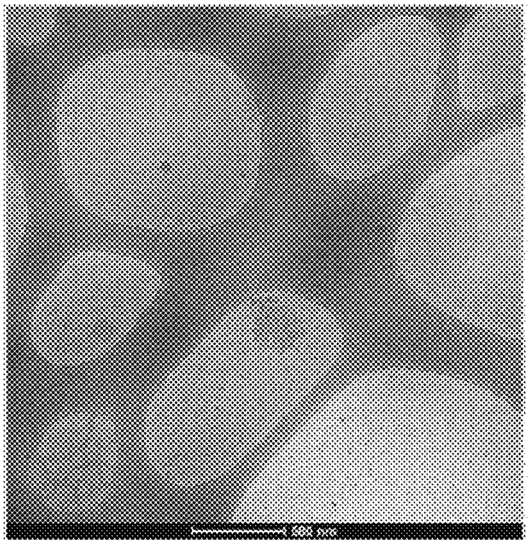
Figure 18G:
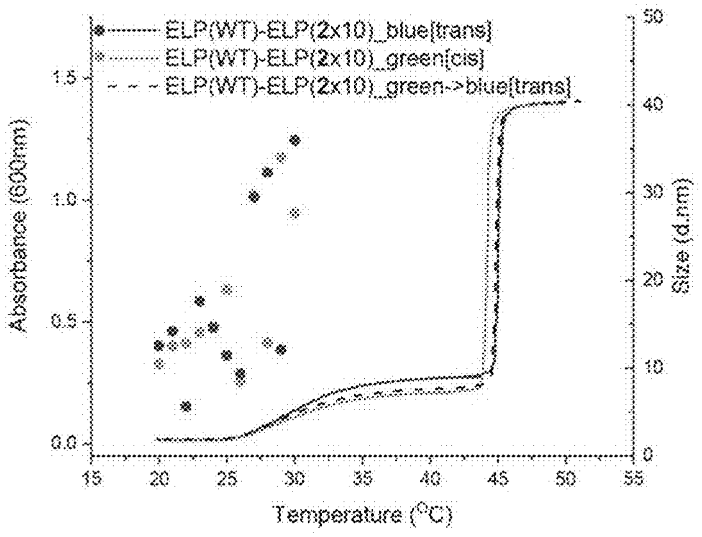
Figure 18H:
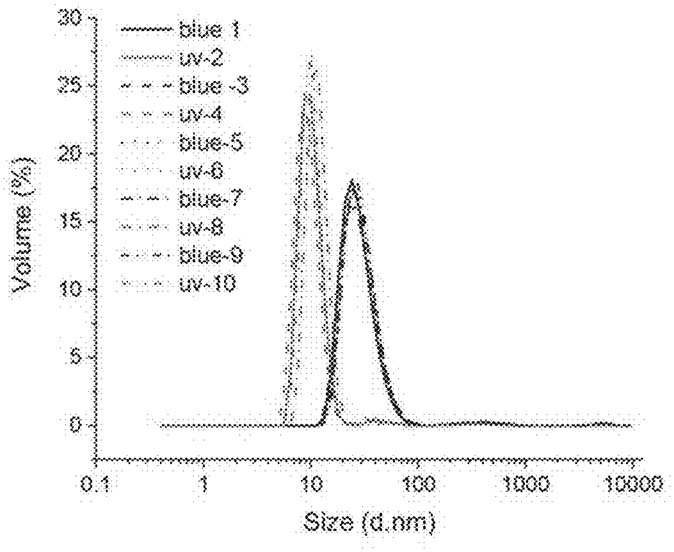
Figure 18I:
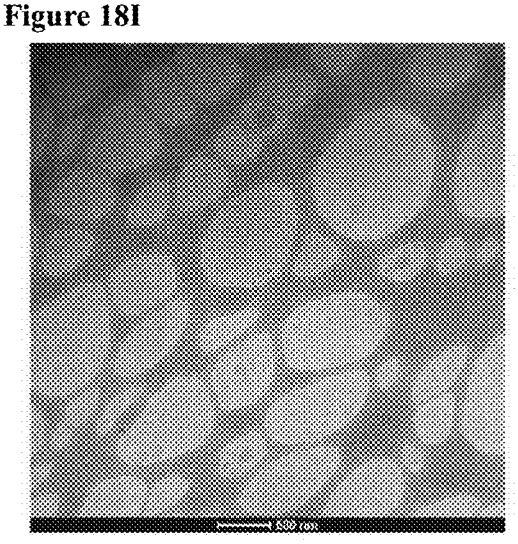
Figure 18J:
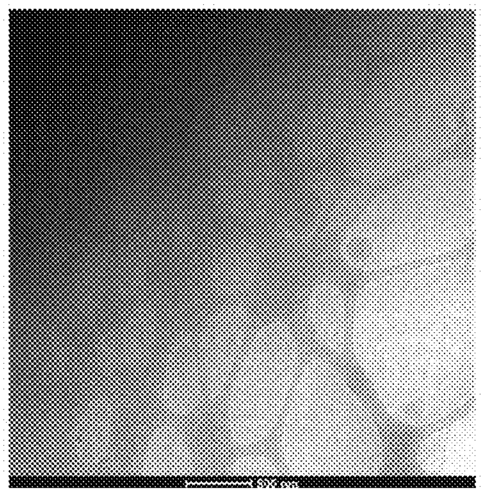
Figure 18K:
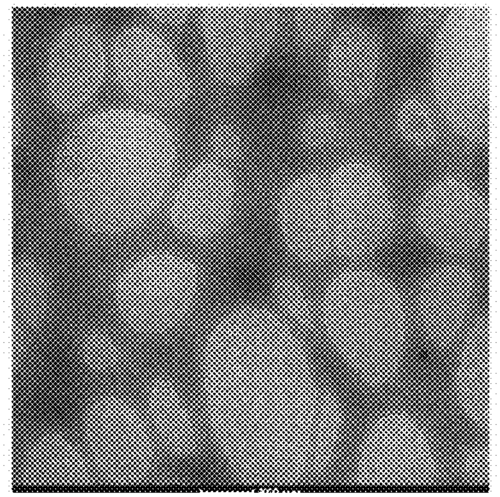
Figure 18L:
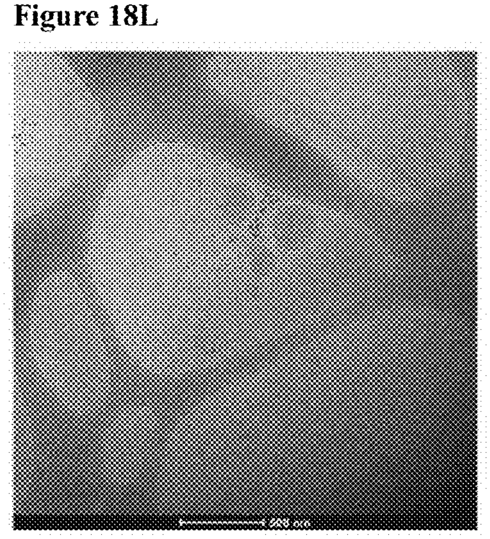
Figure 18M:
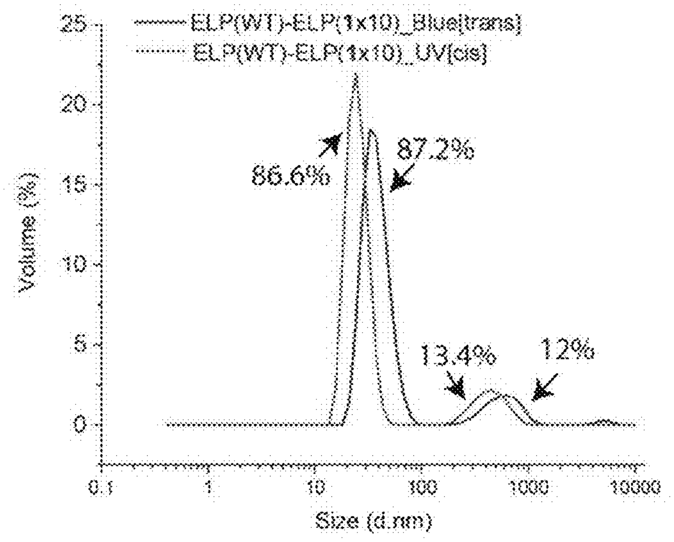
Figure 18N:
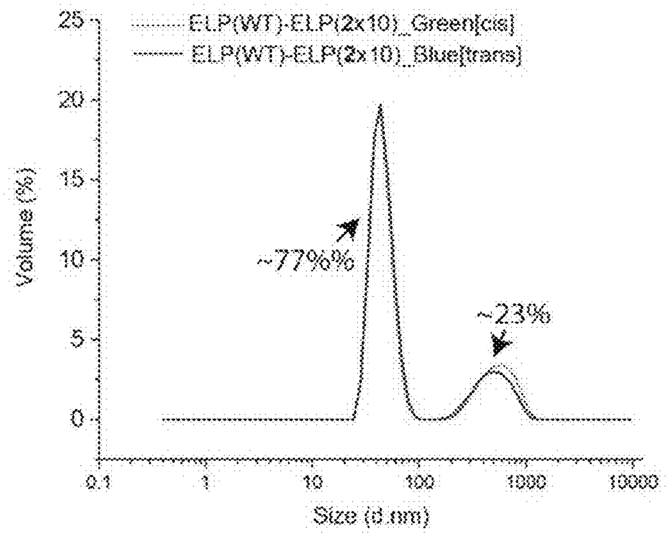
Figure 19A:
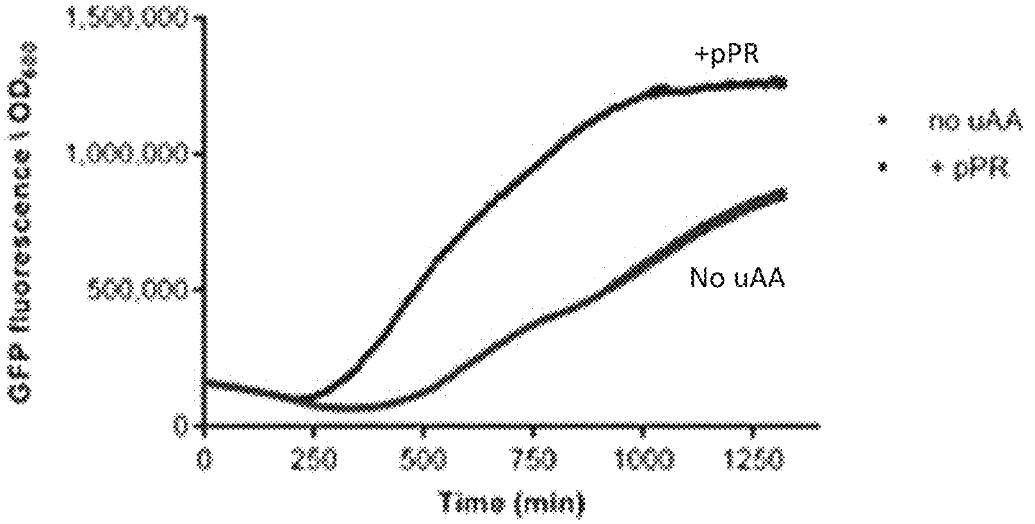
FIGS. 19A-D: Kinetic analysis of GFP production by aaRS variants expressed on plasmids. Time course analysis of (19A) GFP(3TAG) expression by Mut1-RS, (19B) GFP (3TAG) expression by Mut2-RS, (19C) ELP(10TAG)-GFP expression by Mut1-RS and (19D) ELP(10TAG)-GFP expression by Mut2-RS, expressed on multi-copy plasmids in the presence of pPR or with no uAA. n=3; Error bars, mean±s.d.
Figure 19B:
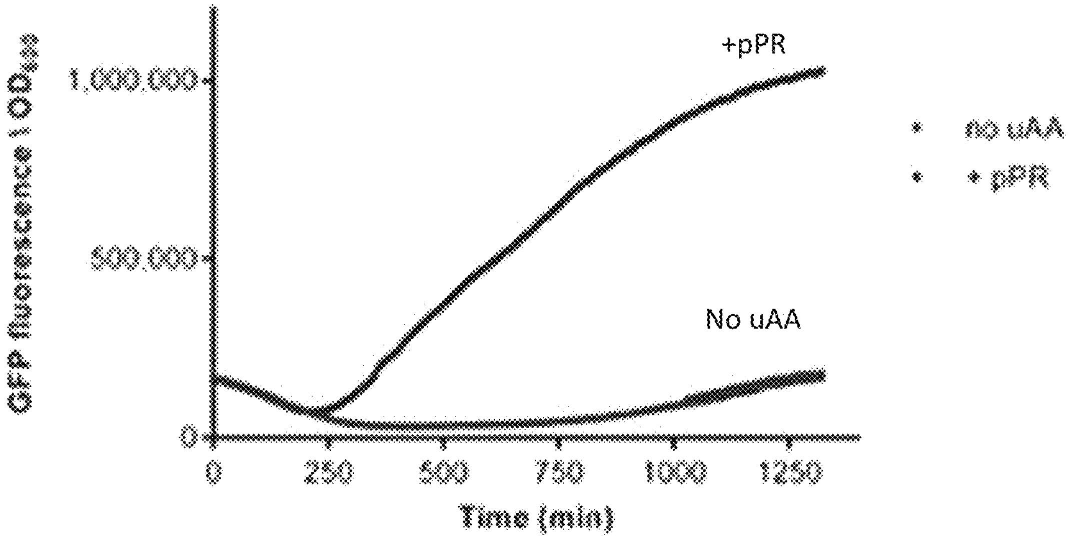
Figure 19C:
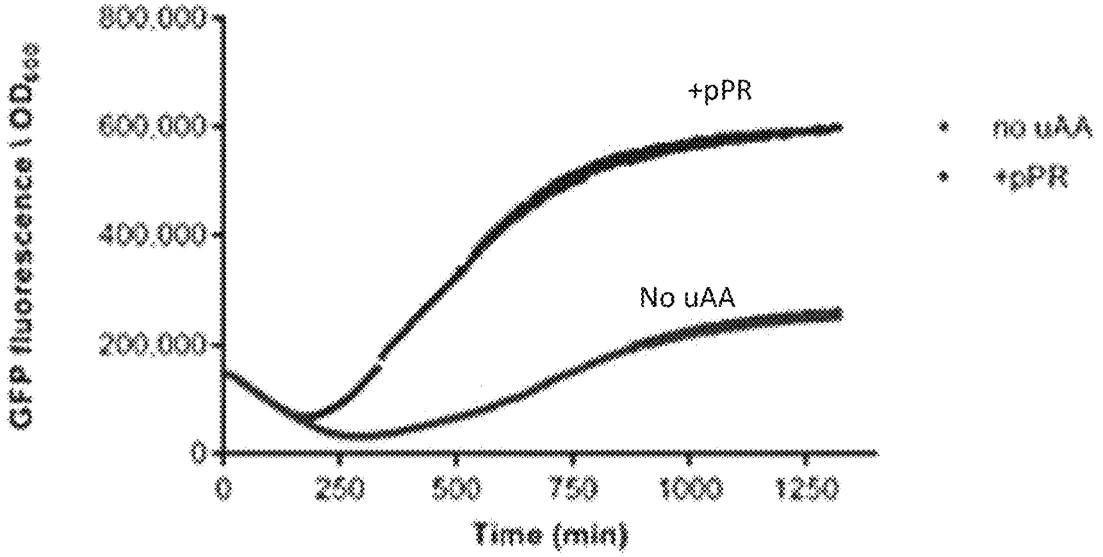
Figure 19D:
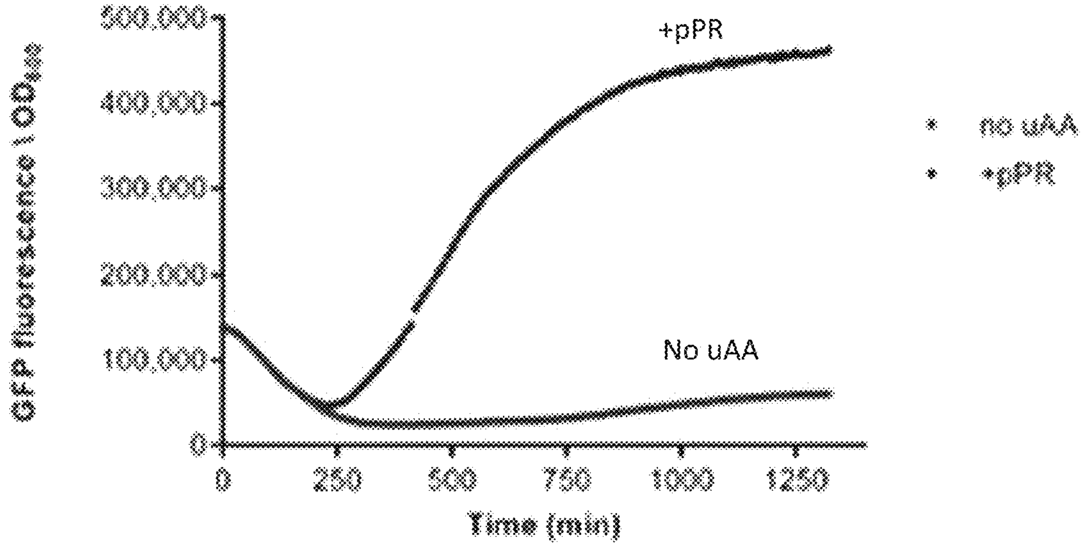
Figure 20:
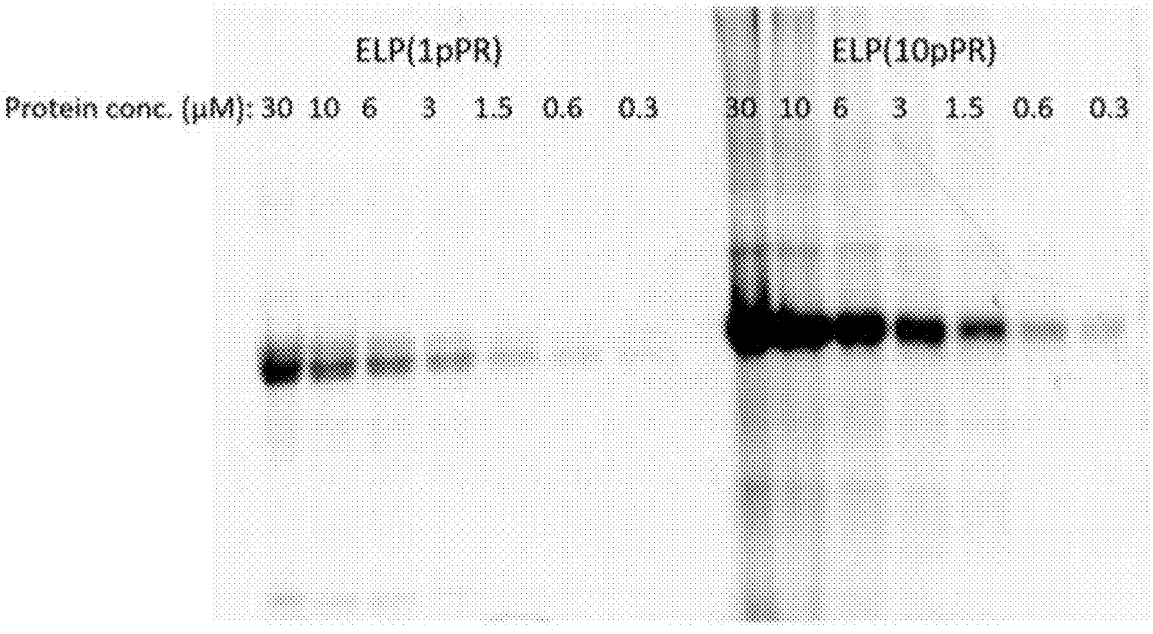
FIG. 20: Post-purification fluorescent labeling of ELPs. In-gel fluorescence analysis of ELPs containing 1 or 10 instances of pPR, conjugated to TAMRA-azide, at varied protein concentrations. ELP(10pPR) (right) shows improved signals and reduced limit of detection for proteins as compared with only a single pPR residue (ELP(1pPR), right).
Figure 21:
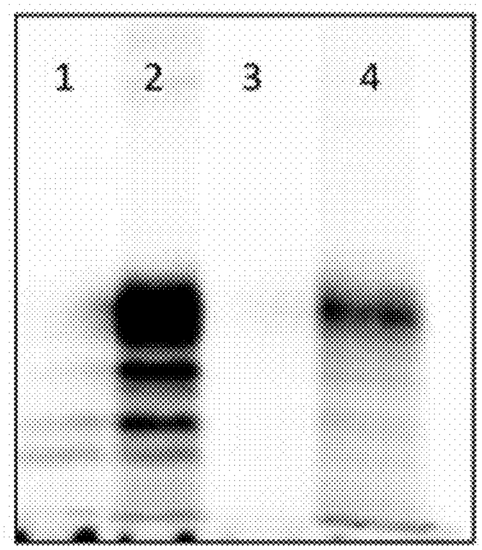
FIG. 21: In vitro TAMRA labeling of ELP(10pPR) in non-recoded BL21 strain and in the GRO. Proteins were expressed in either BL21 by the (1) parent or (2) Mut1-RS, or in the GRO by (3) parent pPR-RS or (4) Mut1-RS. Typhoon imaging at 532 nm.
Figure 22A:
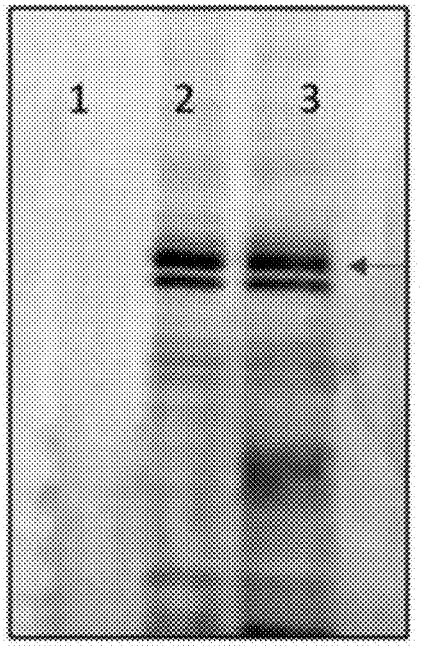
FIGS. 22A-B: Staining of the OTS through conjugation of pPR to TAMRA. (22A) In-vivo, or (22B) in-vitro fluorescent labeling of cells harboring Mut1-RS plasmid (1) without or (2) with induction of the OTS, or (3) cells harboring both Mut1-RS and ELP(10pPR) plasmids. Double-band (marked by red arrow) is detected when OTS in induced, suggesting these bands represent the aminoacylated aaRS and aminoacylated aaRS-tRNA complex.
Figure 22B:
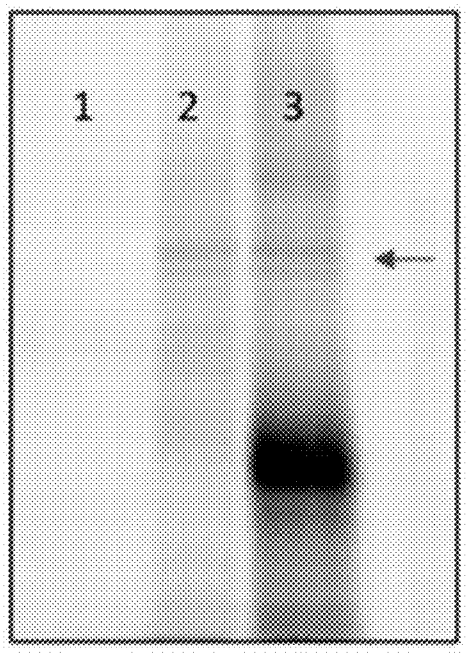

Example 7: Producing ELP Diblock Copolymers with a Light-Responsive Self-Assembly Behavior Numerous studies demonstrated that the genetic fusion of two or more ELP blocks of varying hydrophilicities can generate self-assembled nanostructures with various geometries. Building on this knowledge, self-assembling ELPs composed of a hydrophilic block and a hydrophobic block were designed, namely without and with azobenzene-uAAs, respectively. It was hypothesized that the change in the hydrophobicity of the azobenzene-uAAs upon isomerization would also modulate nanostructure assembly. The design was based on previously characterized ELP diblock copolymers that were shown to self-assemble to form spherical micelles at ratios between 1:2 and 2:1 of the hydrophilic:hydrophobic ELP blocks. An ELP fusion protein, termed $ELP_{60}$(WT)-$ELP_{60}$(10TAG), consisting of the gene for $ELP_{60}$(WT) (the hydrophilic block) fused at the genetic level to the gene for $ELP_{60}$(10TAG) (the hydrophobic block) was generating, thus setting a 1:1 hydrophilic:hydrophobic block ratio. $ELP_{60}$(WT)-$ELP_{60}(1\times10)$ and $ELP_{60}$(WT)-$ELP_{60}(2\times10)$ were then expressed and their light-responsive self-assembly behavior characterized using UV-vis spectrometry and DLS. It was previously hypothesized that the diblock ELP assembly into nanostructures is due to the transition of the hydrophobic block, which is visible as a slight increase in the optical density of the solution at temperatures below the Tt, as was also apparent for $ELP_{60}$(WT)-$ELP_{60}(1\times10)$ and $ELP_{60}$(WT)-$ELP_{60}(2\times10)$ (FIG. 18A, solid lines, FIG. 18G). The DLS confirmed the formation of self-assembled nanostructures for all proteins and the light-dependent assembly of these structures, with a $\Delta T_{SELF\text{-}ASSEMBLY}$ of ~5 for $ELP_{60}$(WT)-$ELP_{60}(1\times10)$ and of ~1° C. for $ELP_{60}$(WT)-$ELP_{60}(2\times10)$ (FIG. 18A, colored dots, FIG. 18G). Thus, it appears that identical azobenzene-bearing ELPs (i.e., $ELP_{60}(1\times10)$ and $ELP_{60}(2\times10)$) generate a larger ΔTt of mono-block phase transition than a $\Delta T_{SELF\text{-}ASSEMBLY}$ as hydrophobic segments in diblock ELPs. Notably, while nanostructures of ~25-45 nm were the predominant species observed in all proteins, small amounts (~2% by volume at the onset of micelle formation) of larger nanostructures (a several hundred nm) appeared to form as well, and their proportion increased with increasing temperatures (up to ~15% or 25% for $ELP_{60}$(WT)-$ELP_{60}(1\times10)$ and of ~1° C. for $ELP_{60}$(WT)-$ELP_{60}(2\times10)$, respectively, at 40° C.). Nevertheless, we were again able to confirm the reversibility of the isothermal light-mediated self-assembly of $ELP_{60}$(WT)-$ELP_{60}(1\times10)$ during 10 successive irradiation cycles of only 30 s each, which generated populations of >95% monomer or self-assembled nanostructures by azobenzene isomerization (FIG. 18B, 18H).

Figure 17A:
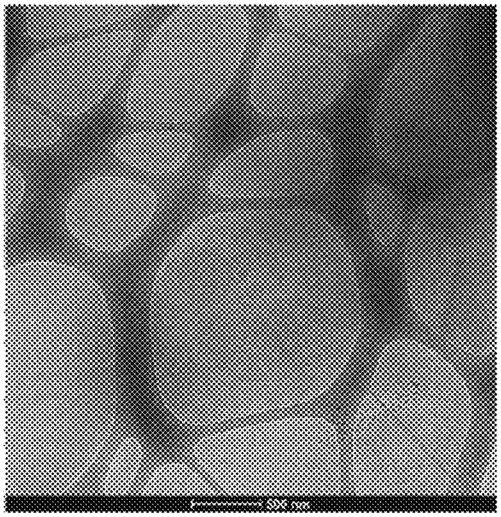
FIGS. 17A-F: Cryo-TEM images of the self-assembly of ELPs containing 10 instances of either 1 irradiated with (17A) blue or (17B) uv light, 2 irradiated with (17C) blue or (17D) green light, or 3 irradiated with (17E) blue or (17F) green light.
Figure 17B:
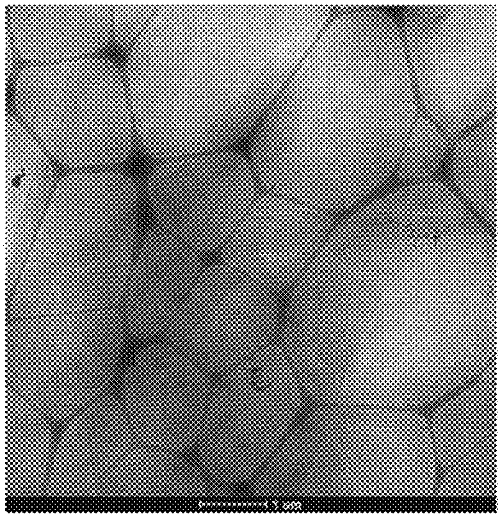
Figure 17C:
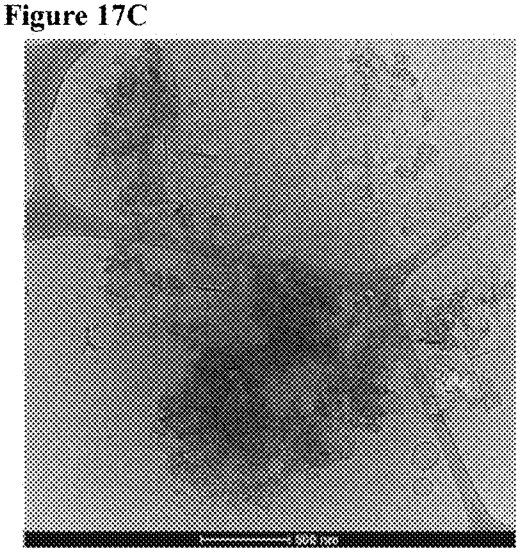
Figure 17D:
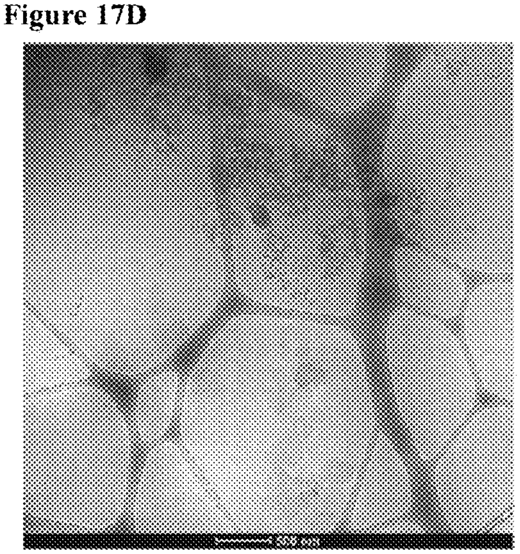
Figure 17E:
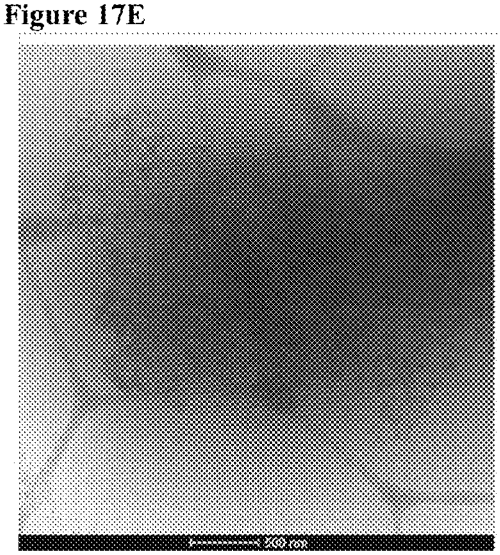
Figure 17F:
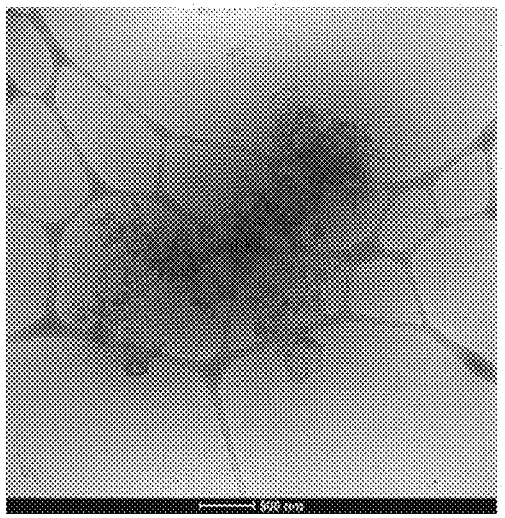

Surprisingly, while diblocks bearing the more hydrophilic cis isomers were expected to demonstrate a higher Tt than that of diblocks bearing the more hydrophobic trans isomers, the opposite was observed: the $\Delta Tt_{cis/trans}$ was ~-5° C. and ~-1° C. for $ELP_{60}$(WT)-$ELP_{60}(1\times10)$ and $ELP_{60}$(WT)-$ELP_{60}(2\times10)$, respectively. This finding suggests that the architecture and, accordingly, the properties of the self-assembled nanostructures depend on the azobenzene isomerization state. The DLS analysis also suggests that nanostructures assembled from the trans-$ELP_{60}$(WT)-$ELP_{60}(1\times10)$ were slightly (~5-10 nm) but consistently larger than those assembled from the cis-$ELP_{60}$(WT)-$ELP_{60}(1\times10)$ (FIG. 17A). To examine the self-assembled structures and how they differ upon irradiation, both the cis and trans configurations of the self-assembled $ELP_{60}$(WT)-$ELP_{60}(1\times10)$ and $ELP_{60}$(WT)-$ELP_{60}(2\times10)$ were examined by cryo-TEM at 38° C., a temperature in all constructs self-assembled. It was found that both spherical nanostructures of ~100-200 nm (similar in appearance to the spherical micelles generated by other ELP diblocks) and larger (several hundred nm), sheet-like structures were present in all samples, however spherical structures were rare in the cis-$ELP_{60}$(WT)-$ELP_{60}(1\times10)$ and were less symmetrical (tear-drop shaped). In addition, aggregate clusters of ~100-200 nm diameter were apparent in the cis-$ELP_{60}$(WT)-$ELP_{60}(1\times10)$ but were rare in the trans-$ELP_{60}$(WT)-$ELP_{60}(1\times10)$ sample (FIG. 18C-D, 18I-N). Thus, it is plausible that the isomerization of 1 affected not only the critical self-assembly temperature (thus generating a $\Delta T_{SELF\text{-}ASSEMBLY}$) but also the morphology of the self-assembled nanostructures across the entire self-assembly temperature range. In contrast, the light irradiation of 2 generated a more modest response, reflected both in the $\Delta T_{SELF\text{-}ASSEMBLY}$ and in the indistinguishable morphologies of the nanostructures generated by mostly-cis or mostly-trans ELP diblock. Numerous studies demonstrated the design of ELP block-copolymers that self-assembled into a wide variety of geometries, both in vitro and inside cells. However, this is the first demonstration that previously established guidelines for thermal ELP assembly can be employed to generate light-responsive formation of nanostructures. These results indicate that, by genetically encoding azobenzene-uAAs in multi-block ELP polymers, engineering light-responsive self-assembly or change in structural properties of additional geometries can be informed by previously described guiding principles for generating such assemblies.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A mutant aminoacyl-tRNA synthetase (aaRS) comprising an amino acid sequence of an aaRS with at least 85% sequence identity to SEQ ID NO: 1 and comprising:

a) aspartic acid 158 mutated to glycine; isoleucine 159 mutated to tyrosine; and leucine 162 mutated to serine or leucine 162 mutated to arginine;

b) aspartic acid 158 mutated to glycine; isoleucine 159 mutated to tyrosine; leucine 162 mutated to serine or leucine 162 mutated to arginine; and alanine 167 mutated to phenylalanine;

c) aspartic acid 158 mutated to glycine; isoleucine 159 mutated to tyrosine; leucine 162 mutated to serine or leucine 162 mutated to arginine and tyrosine 32 mutated to leucine or tyrosine 32 mutated to glycine;

d) aspartic acid 158 mutated to glycine; isoleucine 159 mutated to tyrosine; leucine 162 mutated to serine or leucine 162 mutated to arginine; alanine 167 mutated to phenylalanine; and tyrosine 32 mutated to leucine or tyrosine 32 mutated to glycine;

e) aspartic acid 158 mutated to glycine; isoleucine 159 mutated to tyrosine; leucine 162 mutated to serine or leucine 162 mutated to arginine; and leucine 65 mutated to valine or leucine 65 mutated to glycine;

f) aspartic acid 158 mutated to glycine; isoleucine 159 mutated to tyrosine; leucine 162 mutated to serine or leucine 162 mutated to arginine; alanine 167 mutated to phenylalanine; and leucine 65 mutated to valine or leucine 65 mutated to glycine;

g) aspartic acid 158 mutated to glycine; isoleucine 159 mutated to tyrosine; leucine 162 mutated to serine or leucine 162 mutated to arginine; tyrosine 32 mutated to leucine or tyrosine 32 mutated to glycine; and leucine 65 mutated to valine or leucine 65 mutated to glycine; or h) aspartic acid 158 mutated to glycine; isoleucine 159 mutated to tyrosine; leucine 162 mutated to serine or leucine 162 mutated to arginine; alanine 167 mutated to phenylalanine; tyrosine 32 mutated to leucine or tyrosine 32 mutated to glycine; and leucine 65 mutated to valine or leucine 65 mutated to glycine.

2. The mutant aaRS of claim 1, wherein at least 85% identity is at least 95% identity.

3. The mutant aaRS of claim 1, wherein said mutant is selected from the group consisting of:

a) a mutant comprising tyrosine 32 mutated to leucine, lysine 65 mutated to valine; aspartic acid 158 mutated to glycine; isoleucine 159 mutated to tyrosine; leucine 162 mutated to serine; and alanine 167 mutated to phenylalanine;

b) a mutant comprising tyrosine 32 mutated to glycine, lysine 65 mutated to valine; aspartic acid 158 mutated to glycine; isoleucine 159 mutated to tyrosine; leucine 162 mutated to serine; and alanine 167 mutated to phenylalanine;

c) a mutant comprising tyrosine 32 mutated to leucine, lysine 65 mutated to valine; glutamic acid 107 mutated to serine, phenylalanine 108 mutated to valine, glutamine 109 mutated to serine; aspartic acid 158 mutated to glycine; isoleucine 159 mutated to tyrosine; leucine 162 mutated to serine; and alanine 167 mutated to phenylalanine;

d) a mutant comprising tyrosine 32 mutated to leucine, lysine 65 mutated to valine; glutamic acid 107 mutated to asparagine, phenylalanine 108 mutated to valine, glutamine 109 mutated to leucine; aspartic acid 158 mutated to glycine; isoleucine 159 mutated to tyrosine; leucine 162 mutated to serine; and alanine 167 mutated to phenylalanine;

e) a mutant comprising tyrosine 32 mutated to leucine, lysine 65 mutated to valine; glutamic acid 107 mutated to aspartic acid, aspartic acid 158 mutated to glycine; isoleucine 159 mutated to tyrosine; leucine 162 mutated to serine; and alanine 167 mutated to phenylalanine;

f) a mutant comprising tyrosine 32 mutated to leucine, lysine 65 mutated to valine; glutamic acid 107 mutated to serine, phenylalanine 108 mutated to valine, glutamine 109 mutated to cysteine; aspartic acid 158 mutated to glycine; isoleucine 159 mutated to tyrosine; leucine 162 mutated to serine; and alanine 167 mutated to phenylalanine;

g) a mutant comprising tyrosine 32 mutated to leucine, lysine 65 mutated to valine; aspartic acid 158 mutated to glycine; isoleucine 159 mutated to tyrosine; and leucine 162 mutated to arginine; and h) a mutant comprising tyrosine 32 mutated to leucine, lysine 65 mutated to glycine; glutamic acid 107 mutated to aspartic acid, phenylalanine 108 mutated to arginine, glutamine 109 mutated to methionine; aspartic acid 158 mutated to glycine; isoleucine 159 mutated to tyrosine; leucine 162 mutated to serine; and alanine 167 mutated to phenylalanine.

4. The mutant aaRS of claim 1, wherein said mutant comprises an amino acid sequence selected from: SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19.

5. A nucleic acid molecule comprising a coding region encoding the mutant aaRS of claim 1.

6. The nucleic acid molecule of claim 5, wherein said coding region comprises a nucleic acid sequence selected from SEQ ID NO: 20, SEQ ID NO: 21, SEQ ID NO: 22, SEQ ID NO: 23, SEQ ID NO: 24; SEQ ID NO: 25, SEQ ID NO: 26, and SEQ ID NO: 27.

7. The nucleic acid molecule of claim 5, wherein said coding region is operably linked to at least one regulatory element configured to express said coding region in a target cell.

8. An orthogonal translation system, comprising, a) a mutant aaRS of claim 1, and b) an orthogonal tRNA compatible with said mutant aaRS and comprising an anticodon that corresponds to a stop codon, optionally wherein said stop codon is a TAG stop codon.

9. The orthogonal translation system of claim 8, further comprising:

a) a non-standard amino acid (nsAA) recognized by said mutant aaRS;

b) a modified phenylalanine recognized by said mutant aaRS;

c) a 4-propargyloxy-L-phenylalanine (pPR) recognized by said mutant aaRS d) an unnatural amino acid (uAA) recognized by said mutant aaRS;

e) an unnatural amino acid (uAA) comprising an azobenzene group recognized by said mutant aaRS;

f) a biorthogonal chemical moiety recognized by said mutant aaRS; or g) at least one of a phenylalanine-4'-azobenzene (AzoPhe) amino acid, a tri-fluorinated azobenzene (Azo3F) amino acid, and a tetra-ortho-fluorinated azobenzene (Azo4F) amino acid recognized by said mutant aaRS.

10. A cell comprising an orthogonal translation system of claim 8.

11. The cell of claim 10, further comprising an expression vector comprising an open reading frame (ORF), wherein said ORF a) comprises at least one of said stop codons;

b) comprises a plurality of said stop codons;

c) comprises at least 10 of said stop codons;

d) is operatively linked to at least one regulatory element capable of inducing expression of said ORF within said cell; or e) a combination thereof.

12. A method of producing a light-responsive protein comprising a nsAA, the method comprising introducing into a cell an expression vector comprising an open reading frame encoding said protein wherein said open reading frame comprises a stop codon, wherein said cell comprises an orthogonal translation system of claim 8.

13. The method of claim 12 for labeling said protein, the method further comprising converting said nsAA into a detectably labeled amino acid, optionally wherein said converting comprises addition of a detectable moiety by Click chemistry.

14. A variant of a protein comprising SEQ ID NO: 1, wherein the variant comprises an amino acid sequence that is at least 95% identical to SEQ ID NO: 1 comprising a) aspartic acid 158 mutated to glycine; isoleucine 159 mutated to tyrosine; and leucine 162 mutated to serine or leucine 162 mutated to arginine;

b) aspartic acid 158 mutated to glycine; isoleucine 159 mutated to tyrosine; leucine 162 mutated to serine or leucine 162 mutated to arginine; and alanine 167 mutated to phenylalanine;

c) aspartic acid 158 mutated to glycine; isoleucine 159 mutated to tyrosine; leucine 162 mutated to serine or leucine 162 mutated to arginine and tyrosine 32 mutated to leucine or tyrosine 32 mutated to glycine;

d) aspartic acid 158 mutated to glycine; isoleucine 159 mutated to tyrosine; leucine 162 mutated to serine or leucine 162 mutated to arginine; alanine 167 mutated to phenylalanine; and tyrosine 32 mutated to leucine or tyrosine 32 mutated to glycine;

e) aspartic acid 158 mutated to glycine; isoleucine 159 mutated to tyrosine; leucine 162 mutated to serine or leucine 162 mutated to arginine; and leucine 65 mutated to valine or leucine 65 mutated to glycine;

f) aspartic acid 158 mutated to glycine; isoleucine 159 mutated to tyrosine; leucine 162 mutated to serine or leucine 162 mutated to arginine; alanine 167 mutated to phenylalanine; and leucine 65 mutated to valine or leucine 65 mutated to glycine;

g) aspartic acid 158 mutated to glycine; isoleucine 159 mutated to tyrosine; leucine 162 mutated to serine or leucine 162 mutated to arginine; tyrosine 32 mutated to leucine or tyrosine 32 mutated to glycine; and leucine 65 mutated to valine or leucine 65 mutated to glycine; or h) aspartic acid 158 mutated to glycine; isoleucine 159 mutated to tyrosine; leucine 162 mutated to serine or leucine 162 mutated to arginine; alanine 167 mutated to phenylalanine; tyrosine 32 mutated to leucine or tyrosine 32 mutated to glycine; and leucine 65 mutated to valine or leucine 65 mutated to glycine.

15. The variant of claim 14, wherein said mutant is selected from the group consisting of:

a) a mutant comprising tyrosine 32 mutated to leucine, lysine 65 mutated to valine; aspartic acid 158 mutated to glycine; isoleucine 159 mutated to tyrosine; leucine 162 mutated to serine; and alanine 167 mutated to phenylalanine;

b) a mutant comprising tyrosine 32 mutated to glycine, lysine 65 mutated to valine; aspartic acid 158 mutated to glycine; isoleucine 159 mutated to tyrosine; leucine 162 mutated to serine; and alanine 167 mutated to phenylalanine;

c) a mutant comprising tyrosine 32 mutated to leucine, lysine 65 mutated to valine; glutamic acid 107 mutated to serine, phenylalanine 108 mutated to valine, glutamine 109 mutated to serine; aspartic acid 158 mutated to glycine; isoleucine 159 mutated to tyrosine; leucine 162 mutated to serine; and alanine 167 mutated to phenylalanine;

d) a mutant comprising tyrosine 32 mutated to leucine, lysine 65 mutated to valine; glutamic acid 107 mutated to asparagine, phenylalanine 108 mutated to valine, glutamine 109 mutated to leucine; aspartic acid 158 mutated to glycine; isoleucine 159 mutated to tyrosine; leucine 162 mutated to serine; and alanine 167 mutated to phenylalanine;

e) a mutant comprising tyrosine 32 mutated to leucine, lysine 65 mutated to valine; glutamic acid 107 mutated to aspartic acid, aspartic acid 158 mutated to glycine; isoleucine 159 mutated to tyrosine; leucine 162 mutated to serine; and alanine 167 mutated to phenylalanine;

f) a mutant comprising tyrosine 32 mutated to leucine, lysine 65 mutated to valine; glutamic acid 107 mutated to serine, phenylalanine 108 mutated to valine, glutamine 109 mutated to cysteine; aspartic acid 158 mutated to glycine; isoleucine 159 mutated to tyrosine; leucine 162 mutated to serine; and alanine 167 mutated to phenylalanine;

g) a mutant comprising tyrosine 32 mutated to leucine, lysine 65 mutated to valine; aspartic acid 158 mutated to glycine; isoleucine 159 mutated to tyrosine; and leucine 162 mutated to arginine; and h) a mutant comprising tyrosine 32 mutated to leucine, lysine 65 mutated to glycine; glutamic acid 107 mutated to aspartic acid, phenylalanine 108 mutated to arginine, glutamine 109 mutated to methionine; aspartic acid 158 mutated to glycine; isoleucine 159 mutated to tyrosine; leucine 162 mutated to serine; and alanine 167 mutated to phenylalanine.

16. A nucleic acid molecule comprising a coding region encoding the variant of claim 14.

17. The nucleic acid molecule of claim 16, wherein said coding region is operably linked to at least one regulatory element configured to express said coding region in a target cell.

18. A cell comprising the variant of claim 14.

* * * * *